US010822612B2

(12) United States Patent
Schommer et al.

(10) Patent No.: US 10,822,612 B2
(45) Date of Patent: Nov. 3, 2020

(54) CHIMERIC PROTEINS WHICH ENHANCE THE ACTIVITY OF DNA BINDING DOMAINS (DBD) AND TRANSCRIPTION FACTORS IN PLANTS

(71) Applicants: CONSEJO NACIONAL DE INVESTIGACIONES CIENTÍFICAS Y TÉCNICAS (CONICET), Ciudad Autónoma de Buenos Aires (AR); UNIVERSIDAD NACIONAL DE ROSARIO, Rosario Pcia. de Santa Fe (AR)

(72) Inventors: Carla Schommer, Rosario (AR); Javier Palatnik, Rosario (AR); Juan Manuel Debernardi, Colón (AR); Ramiro Esteban Rodriguez Virasoro, Rosario (AR)

(73) Assignees: CONSEJO NACIONAL DE INVESTIGACIONES CIENTÍFICAS Y TÉCNICAS (CONICET), Buenos Aires (AR); UNIVERSIDAD NACIONAL DE ROSARIO, Santa Fe (AR)

( * ) Notice: Subject to any disclaimer, the term of this patent is extended or adjusted under 35 U.S.C. 154(b) by 219 days.

(21) Appl. No.: 15/537,047

(22) PCT Filed: Dec. 16, 2015

(86) PCT No.: PCT/IB2015/059696
§ 371 (c)(1),
(2) Date: Jun. 16, 2017

(87) PCT Pub. No.: WO2016/098027
PCT Pub. Date: Jun. 23, 2016

(65) Prior Publication Data
US 2017/0362601 A1 Dec. 21, 2017

Related U.S. Application Data

(60) Provisional application No. 62/093,167, filed on Dec. 17, 2014.

(51) Int. Cl.
C12N 15/82 (2006.01)
C07K 14/415 (2006.01)

(52) U.S. Cl.
CPC ........ C12N 15/8216 (2013.01); C07K 14/415 (2013.01); C12N 15/8242 (2013.01); C12N 15/8261 (2013.01); C07K 2319/00 (2013.01); C07K 2319/80 (2013.01); Y02A 40/146 (2018.01)

(58) Field of Classification Search
None
See application file for complete search history.

(56) References Cited

U.S. PATENT DOCUMENTS

2011/0061133 A1* 3/2011 Reuzeau .............. C07K 14/415
800/290

FOREIGN PATENT DOCUMENTS

WO  WO 2012/153267 A1  11/2012

OTHER PUBLICATIONS

Century et al., "Regulating the Regulators: the Future Prospects for Transcription-Factor-Based Agricultural Biotechnology Products," Plant Physiology, vol. 147, No. 1, May 2008, pp. 20-29.
Debernardi et al., "Functional Specialization of the Plant miR396 Regulatory Network Through Distinct microRNA-Target Interactions," PLoS Genet, vol. 8, Issue 1, e1002419, Jan. 5, 2012, pp. 1-14.
Debernardi et al., "Post-Transcriptional Control of GRF Transcription Factors by microRNA miR396 and GIF Co-Activator Affects Leaf Size and Longevity," The Plant Journal, vol. 79, 2014 (published online Jun. 2, 2014), pp. 413-426.
Doebley et al., "The Evolution of Apical Dominance in Maize," Nature, vol. 386, No. 6624, Apr. 3, 1997, pp. 485-488.
Gonzalez et al., "David and Goliath: What Can the Tiny Weed Arabidopsis Teach Us to Improve Biomass Production in Crops?" Current Opinion in Plant Biology, vol. 12, No. 2, 2009 (published online Dec. 30, 2008), pp. 157-164.
Gonzalez et al., "Increased Leaf Size: Different Means to an End," Plant Physiology, vol. 153, No. 3, Jul. 2010, pp. 1261-1279.
Hake et al., "The Role of Knox Genes in Plant Development," Annu Rev Cell Dev Biol, vol. 20, 2004 (published online Jun. 16, 2004), pp. 125-151 (29 pages total).
Horiguchi et al., "The Transcription Factor AtGRF5 and the Transcription Coactivator AN3 Regulate Cell Proliferation in Leaf Primordia of Arabidopsis thaliana," Plant Journal, vol. 43, No. 1, 2005, pp. 68-78.

(Continued)

Primary Examiner — Elizabeth F McElwain
(74) Attorney, Agent, or Firm — Birch, Stewart, Kolasch & Birch, LLP

(57) ABSTRACT

The present invention relates to a method of enhancing the activity of a transcription factor in a plant comprising expressing in said plant a chimeric protein comprising a GIF moiety comprising a GIF domain or fragment thereof, and a DNA binding domain (DBD) moiety. The chimeric proteins comprise a GIF moiety comprising a GIF domain or fragment thereof, or a polypeptide with an amino acid sequence having at least 85%, preferably at least 90%, even more preferably at least 95% sequence identity to the amino acid sequence of a GIF domain or fragment thereof; and a DBD moiety comprising the DBD or plant transcription factor whose activity enhancement is intended, or a binding protein which is capable of forming a tertiary complex with the DBD or transcription factor whose activity modification and/or enhancement is intended. The invention also relates to polynucleotides and polypeptides useful in the method of the invention.

1 Claim, 14 Drawing Sheets
Specification includes a Sequence Listing.

(56) References Cited

OTHER PUBLICATIONS

Ikeda et al., "Genes Offering the Potential for Designing Yield-Related Traits in Rice," Current Opinion in Plant Biology, vol. 16, No. 2, 2013 (published online Mar. 1, 2013), pp. 213-220.
International Search Report and Written Opinion of the International Searching Authority (Forms PCT/ISA/220, PCT/ISA/210 and PCT/ISA/237) for International Application No. PCT/IB2015/059696, dated Apr. 11, 2016.
Jarvis et al., "An *Arabidopsis* Mutant Defective in the Plastid General Protein Import Apparatus," Science, vol. 282, No. 5386, Oct. 2, 1998, pp. 100-103.
Jirschitzka et al., "Learning From Nature: New Approaches to the Metabolic Engineering of Plant Defense Pathways," Current Opinion in Biotechnology, vol. 24, No. 2, 2013 (published online Nov. 7, 2012), pp. 320-328.
Kim et al., "A Transcriptional Coactivator, AtGIF1, is Involved in Regulating Leaf Growth and Morphology in *Arabidopsis*," Proc Natl Acad Sci USA, vol. 101, No. 36, Sep. 7, 2004, pp. 13374-13379.
Kim et al., "*Arabidopsis* Growth-Regulating Factor7 Functions as a Transcriptional Repressor of Abscisic Acid- and Osmotic Stress-Responsive Genes, Including DREB2A," Plant Cell, vol. 24, No. 8, Aug. 31, 2012, pp. 3393-3405 (14 pages total).
Kim et al., "Growth-Regulating FACTOR4 of *Arabidopsis thaliana* is Required for Development of Leaves, Cotyledons, and Shoot Apical Meristem," Journal of Plant Biology, vol. 49, No. 6, Dec. 2006, pp. 463-468.
Kim et al., "The AtGRF Family of Putative Transcription Factors is Involved in Leaf and Cotyledon Growth in *Arabidopsis*," Plant Journal, vol. 36, No. 1, 2003, pp. 94-104.
Kosugi et al., "PCF1 and PCF2 Specifically Bind to cis Elements in the Rice Proliferating Cell Nuclear Antigen Gene," Plant Cell, vol. 9, No. 9, Sep. 1997, pp. 1607-1619 (14 pages total).
Lee et al., "The *Arabidopsis* GRF-Interacting Factor Gene Family Performs an Overlapping Function in Determining Organ Size as Well as Multiple Developmental Properties," Plant Physiology, vol. 151, Oct. 2009 (published Jul. 31, 2009), pp. 655-668.

Liu et al., "Ectopic Expression of miR396 Suppresses GRF Target Gene Expression and Alters Leaf Growth in *Arabidopsis*," Physiologia Plantarum, vol. 136, No. 2, 2009, pp. 223-236.
Luo et al., "Origin of Floral Asymmetry in Antirrhinum," Nature, vol. 383, No. 6603, Oct. 31, 1996, pp. 794-799.
Murashige et al., "A Revised Medium for Rapid Growth and Bio Assays with Tobacco Tissue Cultures," Physiologia Plantarum, vol. 15, No. 3, 1962, pp. 473-497 (26 pages total).
Palatnik et al., "Control of Leaf Morphogenesis by microRNAs," Nature, vol. 425, No. 6955, Sep. 18, 2003 (published online Aug. 20, 2003), pp. 257-263.
Pulido et al., "Co-Ordination of Developmental Processes by Small RNAs During Leaf Development," Journal of Experimental Botany, vol. 61, No. 5, 2010 (Advance Access publication Jan. 22, 2010), pp. 1277-1291.
Rodriguez et al., "Control of Cell Proliferation in *Arabidopsis thaliana* by microRNA miR396," Development, vol. 137, No. 1, 2010, pp. 103-112.
Rubio-Somoza et al., "MicroRNA Networks and Developmental Plasticity in Plants," Trends in Plant Science, vol. 16, No. 5, May 2011, pp. 258-264.
Tsiantis et al., "Comparative Plant Development: the Time of the Leaf?" Nature Reviews Genetics, vol. 4, No. 3, Mar. 2003, pp. 169-180 (13 pages total).
Van Camp, "Yield Enhancement Genes: Seeds for Growth," Current Opinion in Biotechnology, vol. 16, No. 2, 2005 (published online Mar. 9, 2005), pp. 147-153.
Van Der Knaap et al., "A Novel Gibberellin-Induced Gene from Rice and its Potential Regulatory Role in Stem Growth," Plant Physiology, vol. 122, No. 3, Mar. 2000, pp. 695-704.
Vercruyssen et al., "ANGUSTIFOLIA3 Binds to SWI/SNF Chromatin Remodeling Complexes to Regulate Transcription During Arabidopsis Leaf Development," Plant Cell, vol. 26, No. 1, Jan. 2014, pp. 210-229.
Wang et al., "miR396-Targeted AtGRF Transcription Factors are Required for Coordination of Cell Division and Differentiation During Leaf Development in *Arabidopsis*," Journal of Experimental Botany, vol. 62, No. 2, 2011 (Advance Access publication Oct. 29, 2010), pp. 761-773.

\* cited by examiner

SEQUENCE LISTING

```
<160> NUMBER OF SEQ ID NOS: 61

<210> SEQ ID NO 1
<211> LENGTH: 210
<212> TYPE: PRT
<213> ORGANISM: Arabidopsis thaliana

<400> SEQUENCE: 1

Met Gln Gln His Leu Met Gln Met Gln Pro Met Met Ala Gly Tyr Tyr
1               5                   10                  15

Pro Ser Asn Val Thr Ser Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Arg Asn Leu Met Tyr
    50                  55                  60

Leu Ala Ala Ile Ala Asp Ser Gln Pro Gln Pro Pro Ser Val His Ser
65                  70                  75                  80

Gln Tyr Gly Ser Ala Gly Gly Gly Met Ile Gln Gly Glu Gly Gly Ser
                85                  90                  95

His Tyr Leu Gln Gln Gln Gln Ala Thr Gln Gln Gln Gln Met Thr Gln
            100                 105                 110

Gln Ser Leu Met Ala Ala Arg Ser Ser Met Leu Tyr Ala Gln Gln Gln
        115                 120                 125

Gln Gln Gln Gln Pro Tyr Ala Thr Leu Gln His Gln Gln Leu His His
    130                 135                 140

Ser Gln Leu Gly Met Ser Ser Ser Ser Gly Gly Gly Gly Ser Ser Gly
145                 150                 155                 160

Leu His Ile Leu Gln Gly Glu Ala Gly Gly Phe His Asp Phe Gly Arg
                165                 170                 175

Gly Lys Pro Glu Met Gly Ser Gly Gly Gly Gly Glu Gly Arg Gly Gly
            180                 185                 190

Ser Ser Gly Asp Gly Gly Glu Thr Leu Tyr Leu Lys Ser Ser Asp Asp
        195                 200                 205

Gly Asn
    210

<210> SEQ ID NO 2
<211> LENGTH: 633
<212> TYPE: DNA
<213> ORGANISM: Arabidopsis thaliana

<400> SEQUENCE: 2
atgcaacagc acctgatgca gatgcagccc atgatggctg gttactaccc cagcaatgtt     60
```

```
acctctgatc atatccaaca gtacttggac gaaaacaaat cgttgattct gaagattgtt      120
gagtctcaaa actctggaaa gcttagcgaa tgcgccgaga atcaagcaag gcttcaacgc      180
aacctaatgt acctagctgc aatagcagat tctcagcctc agccaccaag tgtgcatagc      240
cagtatggat ctgctggtgg tgggatgatt cagggagaag gagggtcaca ctatttgcag      300
cagcaacaag cgactcaaca gcaacagatg actcagcagt ctctaatggc ggctcgatct      360
tcaatgttgt atgctcagca acagcagcag cagcagcctt acgcgacgct tcagcatcag      420
caattgcacc atagccagct tggaatgagc tcgagcagcg gaggaggagg aagcagtggt      480
ctccatatcc ttcagggaga ggctggtggg tttcatgatt ttggccgtgg gaagccggaa      540
atgggaagtg gtggtggcgg tgaaggcaga ggaggaagtt cagggatgg tggagaaacc       600 ctttacttga aatcatcaga tgatgggaat tga                                   633
```

<210> SEQ ID NO 3
<211> LENGTH: 75
<212> TYPE: PRT
<213> ORGANISM: Arabidopsis thaliana

<400> SEQUENCE: 3

```
Met Gln Gln His Leu Met Gln Met Gln Pro Met Met Ala Gly Tyr Tyr
1               5                  10                  15

Pro Ser Asn Val Thr Ser Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Arg Asn Leu Met Tyr
    50                  55                  60

Leu Ala Ala Ile Ala Asp Ser Gln Pro Gln
65                  70                  75
```

<210> SEQ ID NO 4
<211> LENGTH: 111
<212> TYPE: PRT
<213> ORGANISM: Arabidopsis thaliana

<400> SEQUENCE: 4

```
Met Gln Gln His Leu Met Gln Met Gln Pro Met Met Ala Gly Tyr Tyr
1               5                  10                  15

Pro Ser Asn Val Thr Ser Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ala Arg Leu Gln Arg Asn Leu Met Tyr
    50                  55                  60

Leu Ala Ala Ile Ala Asp Ser Gln Pro Gln Pro Ser Val His Ser
65                  70                  75                  80

Gln Tyr Gly Ser Ala Gly Gly Gly Met Ile Gln Gly Glu Gly Gly Ser
            85                  90                  95

His Tyr Leu Gln Gln Gln Gln Ala Thr Gln Gln Gln Met Thr
            100                 105                 110
```

<210> SEQ ID NO 5
<211> LENGTH: 59
<212> TYPE: PRT
<213> ORGANISM: Arabidopsis thaliana

<400> SEQUENCE: 5

Pro Ser Asn Val Thr Ser Asp His Ile Gln Gln Tyr Leu Asp Glu Asn
1               5                   10                  15

Lys Ser Leu Ile Leu Lys Ile Val Glu Ser Gln Asn Ser Gly Lys Leu
            20                  25                  30

Ser Glu Cys Ala Glu Asn Gln Ala Arg Leu Gln Arg Asn Leu Met Tyr
        35                  40                  45

Leu Ala Ala Ile Ala Asp Ser Gln Pro Gln Pro
    50                  55

<210> SEQ ID NO 6
<211> LENGTH: 95
<212> TYPE: PRT
<213> ORGANISM: Arabidopsis thaliana

<400> SEQUENCE: 6

Pro Ser Asn Val Thr Ser Asp His Ile Gln Gln Tyr Leu Asp Glu Asn
1               5                   10                  15

Lys Ser Leu Ile Leu Lys Ile Val Glu Ser Gln Asn Ser Gly Lys Leu
            20                  25                  30

Ser Glu Cys Ala Glu Asn Gln Ala Arg Leu Gln Arg Asn Leu Met Tyr
        35                  40                  45

Leu Ala Ala Ile Ala Asp Ser Gln Pro Gln Pro Pro Ser Val His Ser
    50                  55                  60

Gln Tyr Gly Ser Ala Gly Gly Met Ile Gln Gly Glu Gly Gly Ser
65                  70                  75                  80

His Tyr Leu Gln Gln Gln Gln Ala Thr Gln Gln Gln Met Thr
            85                  90                  95

<210> SEQ ID NO 7
<211> LENGTH: 194
<212> TYPE: PRT
<213> ORGANISM: Arabidopsis thaliana

<400> SEQUENCE: 7

Pro Ser Asn Val Thr Ser Asp His Ile Gln Gln Tyr Leu Asp Glu Asn
1               5                   10                  15

Lys Ser Leu Ile Leu Lys Ile Val Glu Ser Gln Asn Ser Gly Lys Leu
            20                  25                  30

Ser Glu Cys Ala Glu Asn Gln Ala Arg Leu Gln Arg Asn Leu Met Tyr
        35                  40                  45

Leu Ala Ala Ile Ala Asp Ser Gln Pro Gln Pro Pro Ser Val His Ser
    50                  55                  60

Gln Tyr Gly Ser Ala Gly Gly Met Ile Gln Gly Glu Gly Gly Ser
65                  70                  75                  80

His Tyr Leu Gln Gln Gln Gln Ala Thr Gln Gln Gln Met Thr Gln
            85                  90                  95

Gln Ser Leu Met Ala Ala Arg Ser Ser Met Leu Tyr Ala Gln Gln
                100                 105                 110

Gln Gln Gln Gln Pro Tyr Ala Thr Leu Gln His Gln Leu His His
            115                 120                 125

Ser Gln Leu Gly Met Ser Ser Ser Gly Gly Gly Ser Ser Gly
                130                 135                 140

Leu His Ile Leu Gln Gly Glu Ala Gly Gly Phe His Asp Phe Gly Arg
145                 150                 155                 160

Gly Lys Pro Glu Met Gly Ser Gly Gly Gly Glu Gly Arg Gly Gly

```
            165                 170                 175

Ser Ser Gly Asp Gly Gly Glu Thr Leu Tyr Leu Lys Ser Ser Asp Asp
            180                 185                 190

Gly Asn

<210> SEQ ID NO 8
<211> LENGTH: 138
<212> TYPE: PRT
<213> ORGANISM: Arabidopsis thaliana

<400> SEQUENCE: 8

Pro Gln Pro Pro Ser Val His Ser Gln Tyr Gly Ser Ala Gly Gly Gly
1               5                   10                  15

Met Ile Gln Gly Glu Gly Gly Ser His Tyr Leu Gln Gln Gln Gln Ala
            20                  25                  30

Thr Gln Gln Gln Gln Met Thr Gln Gln Ser Leu Met Ala Ala Arg Ser
        35                  40                  45

Ser Met Leu Tyr Ala Gln Gln Gln Gln Gln Gln Pro Tyr Ala Thr
    50                  55                  60

Leu Gln His Gln Gln Leu His His Ser Gln Leu Gly Met Ser Ser Ser
65                  70                  75                  80

Ser Gly Gly Gly Gly Ser Ser Gly Leu His Ile Leu Gln Gly Glu Ala
                85                  90                  95

Gly Gly Phe His Asp Phe Gly Arg Gly Lys Pro Glu Met Gly Ser Gly
            100                 105                 110

Gly Gly Gly Glu Gly Arg Gly Gly Ser Ser Gly Asp Gly Gly Glu Thr
        115                 120                 125

Leu Tyr Leu Lys Ser Ser Asp Asp Gly Asn
    130                 135

<210> SEQ ID NO 9
<211> LENGTH: 102
<212> TYPE: PRT
<213> ORGANISM: Arabidopsis thaliana

<400> SEQUENCE: 9

Gln Met Thr Gln Gln Ser Leu Met Ala Ala Arg Ser Ser Met Leu Tyr
1               5                   10                  15

Ala Gln Gln Gln Gln Gln Gln Pro Tyr Ala Thr Leu Gln His Gln
            20                  25                  30

Gln Leu His His Ser Gln Leu Gly Met Ser Ser Ser Ser Gly Gly Gly
        35                  40                  45

Gly Ser Ser Gly Leu His Ile Leu Gln Gly Glu Ala Gly Gly Phe His
    50                  55                  60

Asp Phe Gly Arg Gly Lys Pro Glu Met Gly Ser Gly Gly Gly Gly Glu
65                  70                  75                  80

Gly Arg Gly Gly Ser Ser Gly Asp Gly Gly Glu Thr Leu Tyr Leu Lys
                85                  90                  95

Ser Ser Asp Asp Gly Asn
            100

<210> SEQ ID NO 10
<211> LENGTH: 398
<212> TYPE: PRT
<213> ORGANISM: Arabidopsis thaliana

<400> SEQUENCE: 10
```

Met Asp Leu Gln Leu Lys Gln Trp Arg Ser Gln Gln Gln Gln His
1               5                   10                  15

Gln Thr Glu Ser Glu Glu Gln Pro Ser Ala Ala Lys Ile Pro Lys His
            20                  25                  30

Val Phe Asp Gln Ile His Ser His Thr Ala Thr Ser Thr Ala Leu Pro
        35                  40                  45

Leu Phe Thr Pro Glu Pro Thr Ser Ser Lys Leu Ser Ser Leu Ser Pro
    50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Pro Ile Lys Lys Ser
            100                 105                 110

Leu Leu His Leu Ser Pro Ser Tyr Phe Leu His His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
                165                 170                 175

Arg Gly Arg Asn Arg Ser Arg Lys Pro Val Glu Thr Pro Thr Thr Val
            180                 185                 190

Asn Ala Thr Ala Thr Ser Met Ala Ser Ser Val Ala Ala Ala Ala Thr
        195                 200                 205

Thr Thr Thr Ala Thr Thr Thr Ser Thr Phe Ala Phe Gly Gly Gly Gly
    210                 215                 220

Gly Ser Glu Glu Val Val Gly Gln Gly Gly Ser Phe Phe Ser Gly
225                 230                 235                 240

Ser Ser Asn Ser Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
        275                 280                 285

Arg Pro Phe Phe Asp Asp Trp Pro Arg Ser Ser Leu Gln Glu Ala Asp
    290                 295                 300

Asn Ser Ser Ser Pro Met Ser Ser Ala Thr Cys Leu Ser Ile Ser Met
305                 310                 315                 320

Pro Gly Asn Ser Ser Ser Asp Val Ser Leu Lys Leu Ser Thr Gly Asn
                325                 330                 335

Glu Glu Gly Ala Arg Ser Asn Asn Asn Gly Arg Asp Gln Gln Asn Met
            340                 345                 350

Ser Trp Trp Ser Gly Gly Gly Ser Asn His His His Asn Met Gly
        355                 360                 365

Gly Pro Leu Ala Glu Ala Leu Arg Ser Ser Ser Ser Ser Pro Thr
    370                 375                 380

Ser Val Leu His Gln Leu Gly Val Ser Thr Gln Ala Phe His
385                 390                 395

<210> SEQ ID NO 11
<211> LENGTH: 2318
<212> TYPE: DNA

<213> ORGANISM: Arabidopsis thaliana

<400> SEQUENCE: 11

| | | | | | |
|---|---|---|---|---|---|
| atggatttgc | aactgaaaca | atggagaagc | cagcagcagc | aacaacatca | gacagagtca | 60 |
| gaagaacaac | cttctgcagc | taagatacca | aaacatgtct | ttgaccagat | tcattctcac | 120 |
| actgcaactt | ctactgctct | tcctctcttt | acccctgagc | ctacttcttc | taaactctcc | 180 |
| tctttgtctc | ctgattcttc | ctccaggttc | cccagtgagt | cttttcttcc | tcttatctta | 240 |
| tctttcttga | taaagaatta | gacttttcat | tcatatagtt | tgtgtttaat | tgattttgat | 300 |
| tccttttgt | agagatgggg | agcttcttta | gctgggcaca | gtggcaagaa | cttgaactac | 360 |
| aagctctgat | ctacaggtac | atgttggctg | gtgctgctgt | tcctcaggag | ctccttttac | 420 |
| caatcaagaa | aagccttctc | catctatctc | cttcctactt | tcttcaccat | cctcttcaac | 480 |
| acctacctca | ttaccaacct | gcttgtgagt | ctcgagaaca | gtcttcatct | atctattttt | 540 |
| taaatataaa | tgggttttgt | gctactggtg | ttggagttgt | gttcccaaga | tccagacttt | 600 |
| caatattagt | atattatctc | gttttgccaa | tcttgaagat | ctaaacatgt | gtgaatggga | 660 |
| ttaagtagga | ttagaatctt | gttattgatc | tgatatgtga | tatgaatgtt | gaaaacaggg | 720 |
| tatttgggaa | gggcagcgat | ggatcctgag | ccaggcagat | gcaggagaac | ggatggtaag | 780 |
| aagtggagat | gttcaagaga | cgtcttcgct | ggccacaagt | attgcgagcg | ccacatgcac | 840 |
| cgtggccgca | accgttcaag | aaagcctgtg | gaaactccaa | ccaccgtcaa | tgcaactgcc | 900 |
| acgtccatgg | cttcatcagt | agcagccgca | gccaccacta | caacagcaac | aacaacatct | 960 |
| acgtttgctt | tggtggtgg | tggtggtagt | gaggaagtgg | ttggtcaagg | aggatctttc | 1020 |
| ttcttctctg | gctcttctaa | ctcttcatct | gaacttctcc | accttagtca | aaggtaataa | 1080 |
| aaagaaactg | tttttttttc | tcttaggtct | gtctgtttta | gctgttgaac | tttatggtca | 1140 |
| aaacattaaa | cttaaacaca | ttgactttt | tatttcttta | gtgttgagcc | aataagattc | 1200 |
| atggttgaga | tttagacaa | ttgttttgaa | taataatgaa | atcgatttaa | agcaatactg | 1260 |
| attcttgatt | tattagtatg | aagtatgaac | taatgatata | cacaacttgg | tttgtatgtt | 1320 |
| catagcgatg | ttgtgaagag | aggggtaatg | ttggaaattg | agagacacat | ccttatcatt | 1380 |
| ttagggttgg | ttggtttgtt | tgtttgttga | attatgagtt | tgatttcatt | gtgaaaatat | 1440 |
| ctttctttct | tttttcttat | tgtgttgaga | gataatgata | acattggatt | tgatagaatc | 1500 |
| tataatttga | agctaggtgt | gagacttttc | aaacagagaa | aatagaaaga | gagagaaatg | 1560 |
| gtaggacctt | agtgaaagct | gacccatata | tgtctcatat | cttgcagaaa | agttaaagct | 1620 |
| tttagattct | tctgcaccca | cctcccctat | ccacacacaa | cacatgatat | acaaaacact | 1680 |
| cactttataa | ttctatttct | atttactgct | taatcaattc | ttataaaacc | cacattaaaa | 1740 |
| ggtacttta | aagcctataa | actaatataa | aggctactac | tgtctgcaac | tttgttgttg | 1800 |
| aagcctaaat | gtggtttctc | ttttgacaaa | ttattgcttt | tgtgctttgt | tttcaccaat | 1860 |
| gagatgtgga | ttctgttaac | agttgttcgg | agatgaagca | agaaagcaac | aacatgaaca | 1920 |
| acaagaggcc | atacgagtcc | cacatcggat | tcagtaacaa | cagatcagat | ggaggacaca | 1980 |
| tcctgaggcc | cttctttgac | gattggcctc | gttcttcgct | ccaagaagct | gacaatagtt | 2040 |
| caagccccat | gagctcagcc | acttgtctct | ccatctccat | gcccgggaac | tcttcctcag | 2100 |
| acgtctctct | gaagctgtcc | acaggcaacg | aagagggagc | ccggagcaac | aacaatggga | 2160 |
| gagatcagca | aaacatgagc | tggtggagcg | gtggaggttc | caaccaccat | catcacaaca | 2220 |
| tgggcggacc | attggccgaa | gccctgagat | cttcttcctc | atcttcccca | accagtgttc | 2280 | tccatcagct tggtgtctcg acacaagcct ttcattga                    2318

<210> SEQ ID NO 12
<211> LENGTH: 634
<212> TYPE: PRT
<213> ORGANISM: Artificial Sequence
<220> FEATURE:
<223> OTHER INFORMATION: Chimaera GRF3-GFP

<400> SEQUENCE: 12

Met Asp Leu Gln Leu Lys Gln Trp Arg Ser Gln Gln Gln Gln His
1               5                   10                  15

Gln Thr Glu Ser Glu Glu Gln Pro Ser Ala Ala Lys Ile Pro Lys His
            20                  25                  30

Val Phe Asp Gln Ile His Ser His Thr Ala Thr Ser Thr Ala Leu Pro
        35                  40                  45

Leu Phe Thr Pro Glu Pro Thr Ser Ser Lys Leu Ser Ser Leu Ser Pro
    50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Leu Pro Ile Lys Lys Ser
            100                 105                 110

Leu Leu His Leu Ser Pro Ser Tyr Phe Leu His His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
                165                 170                 175

Arg Gly Arg Asn Arg Ser Arg Lys Pro Val Glu Thr Pro Thr Thr Val
            180                 185                 190

Asn Ala Thr Ala Thr Ser Met Ala Ser Val Ala Ala Ala Ala Thr
        195                 200                 205

Thr Thr Thr Ala Thr Thr Thr Ser Thr Phe Ala Phe Gly Gly Gly Gly
    210                 215                 220

Gly Ser Glu Glu Val Val Gly Gln Gly Gly Ser Phe Phe Phe Ser Gly
225                 230                 235                 240

Ser Ser Asn Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
        275                 280                 285

Arg Pro Phe Phe Asp Asp Trp Pro Arg Ser Ser Leu Gln Glu Ala Asp
    290                 295                 300

Asn Ser Ser Ser Pro Met Ser Ser Ala Thr Cys Leu Ser Ile Ser Met
305                 310                 315                 320

Pro Gly Asn Ser Ser Ser Asp Val Ser Leu Lys Leu Ser Thr Gly Asn
                325                 330                 335

Glu Glu Gly Ala Arg Ser Asn Asn Asn Gly Arg Asp Gln Gln Asn Met
            340                 345                 350

| | | | | | | | | | | | |
|---|---|---|---|---|---|---|---|---|---|---|---|
|Ser|Trp|Trp|Ser|Gly|Gly|Gly|Ser|Asn|His|His|His|Asn|Met|Gly|
| |355| | | | |360| | | | |365| | | |

Ser Trp Trp Ser Gly Gly Gly Ser Asn His His His Asn Met Gly
            355                 360                 365

Gly Pro Leu Ala Glu Ala Leu Arg Ser Ser Ser Ser Pro Thr
    370              375              380

Ser Val Leu His Gln Leu Gly Val Ser Thr Gln Ala Phe His Val Asp
385             390                 395                 400

Asp Leu Thr Ser Lys Gly Glu Leu Phe Thr Gly Val Asp Gly Asp
            405             410                 415

Val Asn Gly His Lys Phe Ser Val Ser Gly Glu Gly Glu Gly Asp Ala
            420             425                 430

Thr Tyr Gly Lys Leu Thr Leu Lys Phe Ile Cys Thr Thr Gly Lys Leu
            435             440                 445

Pro Val Pro Trp Pro Thr Leu Val Thr Thr Phe Ser Tyr Gly Val Gln
    450              455                  460

Cys Phe Ser Arg Tyr Pro Asp His Met Lys Arg His Asp Phe Phe Lys
465             470              475                  480

Ser Ala Met Pro Glu Gly Tyr Val Gln Glu Arg Thr Ile Phe Phe Lys
                485             490                  495

Asp Asp Gly Asn Tyr Lys Thr Arg Ala Glu Val Lys Phe Glu Gly Asp
            500             505                  510

Thr Leu Val Asn Arg Ile Glu Leu Lys Gly Ile Asp Phe Lys Glu Asp
            515             520                  525

Gly Asn Ile Leu Gly His Lys Leu Glu Tyr Asn Tyr Asn Ser His Asn
    530              535              540

Val Tyr Ile Met Ala Asp Lys Gln Lys Asn Gly Ile Lys Ala Asn Phe
545             550                  555                  560

Lys Thr Arg His Asn Ile Glu Asp Gly Gly Val Gln Leu Ala Asp His
                565             570                  575

Tyr Gln Gln Asn Thr Pro Ile Gly Asp Gly Pro Val Leu Leu Pro Asp
            580             585                  590

Asn His Tyr Leu Ser Thr Gln Ser Ala Leu Ser Lys Asp Pro Asn Glu
            595             600                  605

Lys Arg Asp His Met Val Leu Leu Glu Phe Val Thr Ala Ala Gly Ile
    610              615              620

Thr His Gly Met Asp Glu Leu Tyr Lys Ala
625                 630

<210> SEQ ID NO 13
<211> LENGTH: 3026
<212> TYPE: DNA
<213> ORGANISM: Artificial Sequence
<220> FEATURE:
<223> OTHER INFORMATION: Chimarea GRF3-GFP

<400> SEQUENCE: 13

```
atggatttgc aactgaaaca atggagaagc cagcagcagc aacaacatca gacagagtca      60
gaagaacaac cttctgcagc taagatacca aaacatgtct tgaccagat tcattctcac     120 actgcaactt ctactgctct cctctctttt acccctgagc ctacttcttc taaactctcc     180
tctttgtctc ctgattcttc ctccaggttc cccagtgagt ctttcttcc tcttatctta     240 tctttcttga taaagaatta gacttttcat tcatatagtt tgtgtttaat tgattttgat     300
tcctttttgt agagatgggg agcttcttta gctgggcaca gtgcaagaa cttgaactac     360 aagctctgat ctacaggtac atgttggctg gtgctgctgt tcctcaggag ctccttttac     420
caatcaagaa aagccttctc catctatctc cttcctactt tcttcaccat cctcttcaac     480
```

```
acctacctca ttaccaacct gcttgtgagt ctcgagaaca gtcttcatct atctattttt    540
taaatataaa tgggttttgt gctactggtg ttggagttgt gttcccaaga tccagacttt    600
caatattagt atattatctc gttttgccaa tcttgaagat ctaaacatgt gtgaatggga    660
ttaagtagga ttagaatctt gttattgatc tgatatgtga tatgaatgtt gaaaacaggg    720
tatttgggaa gggcagcgat ggatcctgag ccaggcagat gcaggagaac ggatggtaag    780
aagtggagat gttcaagaga cgtcttcgct ggccacaagt attgcgagcg ccacatgcac    840
cgtggccgca accgttcaag aaagcctgtg gaaactccaa ccaccgtcaa tgcaactgcc    900
acgtccatgg cttcatcagt agcagccgca gccaccacta acagcaac aacaacatct    960 acgtttgctt ttggtggtgg tggtggtagt gaggaagtgg ttggtcaagg aggatctttc    1020
ttcttctctg gctcttctaa ctcttcatct gaacttctcc accttagtca aggtaataa    1080 aaagaaactg ttttttttc tcttaggtct gtctgtttta gctgttgaac tttatggtca    1140
aaacattaaa cttaaacaca ttgactttt tatttcttta gtgttgagcc aataagattc    1200
atggttgaga ttttagacaa ttgttttgaa taataatgaa atcgatttaa agcaatactg    1260
attcttgatt tattagtatg aagtatgaac taatgatata cacaacttgg tttgtatgtt    1320
catagcgatg ttgtgaagag aggggtaatg ttggaaattg agagacacat ccttatcatt    1380
ttagggttgg ttggtttgtt tgtttgttga attatgagtt tgattcatt gtgaaaatat    1440 ctttctttct tttttcttat tgtgttgaga gataatgata acattggatt tgatagaatc    1500
tataatttga agctaggtgt gagactttc aaacagagaa aatagaaaga gagagaaatg    1560
gtaggacctt agtgaaagct gacccatata tgtctcatat cttgcagaaa agttaaagct    1620
tttagattct tctgcaccca cctcccctat ccacacacaa cacatgatat acaaaacact    1680
cactttataa ttctatttct atttactgct taatcaattc ttataaaacc cacattaaaa    1740 ggtacttta aagcctataa actaatataa aggctactac tgtctgcaac tttgttgttg    1800
aagcctaaat gtggtttctc ttttgacaaa ttattgcttt tgtgctttgt tttccccat    1860 gagatgtgga ttctgttaac agttgttcgg agatgaagca agaaagcaac acatgaaca    1920 acaagaggcc atacgagtcc cacatcggat tcagtaacaa cagatcagat ggaggacaca    1980
tcctgaggcc cttctttgac gattggcctc gttcttcgct ccaagaagct gacaatagtt    2040
caagccccat gagctcagcc acttgtctct ccatctccat gcccgggaac tcttcctcag    2100
acgtctctct gaagctgtcc acaggcaacg aagagggagc ccggagcaac aacaatggga    2160
gagatcagca aaacatgagc tggtggagcg gtggaggttc caaccaccat catcacaaca    2220
tgggcggacc attggccgaa gccctgagat cttcttcctc atcttcccca accagtgttc    2280
tccatcagct tggtgtctcg acacaagcct ttcatgtcga cgatctgact agtaaaggag    2340 aagaacttt cactggagta gatggtgatg ttaatgggca caaattttct gtcagtggag    2400
agggtgaagg tgatgcaaca tacggaaaac ttacccttaa atttatttgc actactggaa    2460
aactacctgt tccgtggcca acacttgtca ctactttctc ttatggtgtt caatgctttt    2520 caagatacccc agatcatatg aagcggcacg acttcttcaa gagcgccatg cctgagggat    2580
acgtgcagga gaggaccatc ttcttcaagg acgacggaac ctacaagaca cgtgctgaag    2640
tcaagtttga gggagacacc ctcgtcaaca ggatcgagct taagggaatc gatttcaagg    2700
aggacggaaa catcctcggc cacaagttgg aatacaacta caactcccac aacgtataca    2760
tcatggccga caagcaaaag aacggcatca agccaacttt caagacccgc cacaacatcg    2820
```

```
aagacggcgg cgtgcaactc gctgatcatt atcaacaaaa tactccaatt ggcgatggcc    2880
ctgtcctttt accagacaac cattacctgt ccacacaatc tgcccttccg aaagatccca    2940
acgaaaagag agaccacatg gtccttcttg agtttgtaac agctgctggg attacacatg    3000
gcatggatga actatacaaa gcttga                                         3026
```

<210> SEQ ID NO 14
<211> LENGTH: 14133
<212> TYPE: DNA
<213> ORGANISM: Artificial Sequence
<220> FEATURE:
<223> OTHER INFORMATION: Binary vector pJD104 for expression of chimeric protein GRF3-GPF.

<400> SEQUENCE: 14

```
ttgatcccga ggggaaccct gtggttggca tgcacataca aatggacgaa cggataaacc      60
ttttcacgcc cttttaaata tccgttattc taataaacgc tcttttctct taggtttacc     120
cgccaatata tcctgtcaaa cactgatagt ttaaactgaa ggcgggaaac gacaatctga     180
tccaagctca agctgctcta gccaatacgc aaaccgcctc tccccgcgcg ttggccgatt     240
cattaatgca gctggcacga caggtttccc gactggaaag cgggcagtga gcgcaacgca     300
attaatgtga gttagctcac tcattaggca ccccaggctt tacactttat gcttccggct     360
cgtatgttgt gtggaattgt gagcggataa caatttcaca caggaaacag ctatgaccat     420
gattacgaat tgaaaacgca ggcccattta catcctccaa acaaaagaa gcaatagaat      480 ccggaactga attaaaaaca tacaaaccaa gaggtaaaga aaacgcatag ttagctaacc     540
cgtccgcaag acgattgacc tccctataca cgtgagaaat acggactaac cagtcccttg     600
atatgaagcc ataacacaaa cgtagtagga aagatagagg atgagaatcc ggtatccctg     660
tctgtaaaaa cccaaccacg atcttcgaat ccacttccag ctcaaggcgt gttattcctt     720
gctcccagac tatgtgtaac ccatagtaga gtccccacaa ctctgctagt ggcgctgaac     780
agatttcgat attcaaagca aaaaccccaa cccagttctc gttcccatca cgcaccgcac     840
ctcccgctgc tgctaacccg ggattctctc tcgaggctcc atccatgttc aactagcctg     900
atgaatttat taaactcatg tttccatttt ttttcccacc agttatgtta gtttgattaa     960 ttttcagtc aatttggca taacgcttta aataattat atcaaataa tattttcagt       1020 ttttctgcaa cagattcatt ccaccaagaa ttcagccgat tctacccgaa ttaatattac    1080
cattttcgga ctagatctat gaacgaaggt acaaaattaa tcagttaaaa agaaaatag    1140 agtggcaagt actacatcta gtgccgtatg atatgataat ataggaacct aaacgaattt    1200
tatactaatt caatttaaa agtagttagg tttgtcacaa atgcaaatta caattatat     1260 cgacgtaacg cttactcatt aaataatcta aattacttgg ttaaaagact aattaaatat    1320
tcttaacaag taggcttttg ttttcattat aaaacaaatt aaaaagctat actaatataa    1380
aaatggagat tggtatttcc aaagcagcaa agacagaaaa actgcaggtt attatctctc    1440
catcttcatc ttgcagagtg gttctttctg gttttctga cttgcttttc atttttttat     1500
tgatacaaat gttaaaccaa ttatttaaa tagtctttga gattaatgaa gagagatttg    1560
tgaacacaat taataaagag ttatactata gtagtagtct ttttactgt atagtatttt    1620 ctccccgcat ctgtcttgtc tcactgtctt tttctcgcaa gtctctctat taaaaacctc    1680
tttccctcta ctctgtcctt tctctctctg cagaagaagc tcagatacag aaactgacta    1740
ccaagaacaa agcttttcc ttcgagcaaa gaaagttctt ttttcttttc ttttgctctt    1800
```

```
cgtaacccaa ccaacaagac tttcataagc tattaaatca gaaccctgga agacaaaaaa   1860
ggggaaaaac cattatcctt aaagtaacca acacttctct ctctctttct tcaggtacca   1920
tggatttgca actgaaacaa tggagaagcc agcagcagca acaacatcag acagagtcag   1980
aagaacaacc ttctgcagct aagataccaa acatgtcttt tgaccagatt cattctcaca   2040
ctgcaacttc tactgctctt cctctcttta ccccctgagcc tacttcttct aaactctcct   2100
ctttgtctcc tgattcttcc tccaggttcc ccagtgagtc ttttcttcct cttatcttat   2160
ctttcttgat aaagaattag acttttcatt catatagttt gtgtttaatt gattttgatt   2220 ccttttgta gagatgggga gcttctttag ctgggcacag tggcaagaac ttgaactaca   2280
agctctgatc tacaggtaca tgttggctgg tgctgctgtt cctcaggagc tccttttacc   2340
aatcaagaaa agccttctcc atctatctcc ttcctacttt cttcaccatc ctcttcaaca   2400
cctacctcat taccaacctg cttgtgagtc tcgagaacag tcttcatcta tctatttttt   2460
aaatataaat gggttttgtg ctactggtgt tggagttgtg ttcccaagat ccagactttc   2520
aatattagta tattatctcg ttttgccaat cttgaagatc taaacatgtg tgaatgggat   2580
taagtaggat tagaatcttg ttattgatct gatatgtgat atgaatgttg aaaacagggt   2640
atttgggaag ggcagcgatg gatcctgagc caggcagatg caggagaacg gatggtaaga   2700
agtggagatg ttcaagagac gtcttcgctg gccacaagta ttgcgagcgc cacatgcacc   2760
gtggccgcaa ccgttcaaga aagcctgtgg aaactccaac caccgtcaat gcaactgcca   2820
cgtccatggc ttcatcagta gcagccgcag ccaccactac aacagcaaca acaacatcta   2880
cgtttgcttt tggtggtggt ggtggtagtg aggaagtggt tggtcaagga ggatctttct   2940
tcttctctgg ctcttctaac tcttcatctg aacttctcca ccttagtcaa aggtaataaa   3000
aagaaactgt tttttttttct cttaggtctg tctgttttag ctgttgaact ttatggtcaa   3060
aacattaaac ttaaacacat tgactttttt atttctttag tgttgagcca ataagattca   3120
tggttgagat tttagacaat tgttttgaat aataatgaaa tcgatttaaa gcaatactga   3180
ttcttgattt attagtatga agtatgaact aatgatatac acaacttggt ttgtatgttc   3240
atagcgatgt tgtgaagaga ggggtaatgt tggaaattga gagacacatc cttatcattt   3300
tagggttggt tggtttgttt gtttgttgaa ttatgagttt gatttcattg tgaaaatatc   3360
tttctttctt ttttcttatt gtgttgagag ataatgataa cattggattt gatagaatct   3420
ataatttgaa gctaggtgtg agacttttca aacagagaaa atagaaagag agagaaatgg   3480 taggaccttta gtgaaagctg acccatatat gtctcatatc ttgcagaaaa gttaaagctt   3540
ttagattctt ctgcacccac ctcccctatc cacacacaac acatgatata caaaacactc   3600
actttataat tctatttcta tttactgctt aatcaattct tataaaaccc acattaaaag   3660
gtacttttaa agcctataaa ctaatataaa ggctactact gtctgcaact tgttgttga   3720 agcctaaatg tggtttctct tttgacaaat tattgctttt gtgctttgtt ttcaccaatg   3780
agatgtggat tctgttaaca gttgttcgga gatgaagcaa gaaagcaaca acatgaacaa   3840
caagaggcca tacgagtccc acatcggatt cagtaacaac agatcagatg gaggacacat   3900
cctgaggccc ttctttgacg attggcctcg ttcttcgctc caagaagctg acaatagttc   3960
aagccccatg agctcagcca cttgtctctc catctccatg cccgggaact cttcctcaga   4020
cgtctctctg aagctgtcca caggcaacga agagggagcc cggagcaaca acaatgggag   4080
agatcagcaa aacatgagct ggtggagcgg tggaggttcc aaccaccatc atcacaacat   4140
gggcggacca ttggccgaag ccctgagatc ttcttcctca tcttccccaa ccagtgttct   4200
```

```
ccatcagctt ggtgtctcga cacaagcctt tcatgtcgac gatctgacta gtaaaggaga    4260 agaactttc  actggagtag atggtgatgt taatgggcac aaattttctg tcagtggaga    4320
gggtgaaggt gatgcaacat acggaaaact taccttaaa  tttatttgca ctactggaaa    4380
actacctgtt ccgtggccaa cacttgtcac tactttctct tatggtgttc aatgcttttc    4440
aagataccca gatcatatga agcggcacga cttcttcaag agcgccatgc ctgagggata    4500
cgtgcaggag aggaccatct tcttcaagga cgacgggaac tacaagacac gtgctgaagt    4560
caagtttgag ggagacaccc tcgtcaacag gatcgagctt aagggaatcg atttcaagga    4620
ggacggaaac atcctcggcc acaagttgga atacaactac aactcccaca cgtatacat    4680 catggccgac aagcaaaaga cggcatcaa  agccaacttc aagacccgcc acaacatcga    4740
agacggcggt gtgcaactcg ctgatcatta tcaacaaaat actccaattg gcgatggccc    4800
tgtcctttta ccagacaacc attacctgtc cacacaatct gccctttcga agatcccaa    4860 cgaaaagaga gaccacatgg tccttcttga gtttgtaaca gctgctggga ttacacatgg    4920
catggatgaa ctatacaaag cttgactgca gagctttcgt tcgtatcatc ggtttcgaca    4980
acgttcgtca agttcaatgc atcagtttca ttgcgcacac accagaatcc tactgagttc    5040
gagtattatg gcattgggaa acatgttttt cttgtaccat ttgttgtgct tgtaatttac    5100 tgtgttttt  attcggtttt cgctatcgaa ctgtgaaatg gaatggatg  gagaagagtt    5160 aatgaatgat atggtccttt tgttcattct caaattaata ttatttgttt tttctcttat    5220
ttgttgtgtg ttgaatttga aaatataaga gatatgcaaa catttttgttt tgagtaaaaa    5280 tgtgtcaaat cgtggcctct aatgaccgaa gttaatatga ggagtaaaac acttgtagtt    5340
gtaccattat gcttattcac taggcaacaa atatattttc agacctagaa aagctgcaaa    5400
tgttactgaa tacaagtatg tcctcttgtg ttttagacat ttatgaactt tcctttatgt    5460
aattttccag aatccttgtc agattctaat cattgcttta taattatagt tatactcatg    5520
gatttgtagt tgagtatgaa aatatttttt aatgcattt  atgacttgcc aattgattga    5580
caacatgcat caatcgaagc ttggcactgg ccgtcgtttt acaacgtcgt gactgggaaa    5640
accctggcgt tacccaactt aatcgccttg cagcacatcc cccttcgcc  agctggcgta    5700 atagcgaaga ggcccgcacc gatcgcccct cccaacagtt gcgcagcctg aatggcgaat    5760
gctagagcag cttgccaaca tggtggagca cgacactctc gtctactcca agaatatcaa    5820
agatacagtc tcagaagacc aaagggctat tgagactttt caacaaaggg taatatcggg    5880
aaacctcctc ggattccatt gcccagctat ctgtcacttc atcaaaagga cagtagaaaa    5940
ggaaggtggc acctacaaat gccatcattg cgataaagga aaggctatcg ttcaagatgc    6000
ctctgccgac agtggtccca agatggaccc cacccacg  aggagcatcg tggaaaaaga    6060
agacgttcca accacgtctt caaagcaagt ggattgatgt gataacatgg tggagcacga    6120
cactctcgtc tactccaaga atatcaaaga tacagtctca aagaccaaa  gggctattga    6180 gacttttcaa caagggtaa  tatcgggaaa cctcctcgga ttccattgcc cagctatctg    6240
tcacttcatc aaaaggacag tagaaaagga aggtggcacc tacaaatgcc atcattgcga    6300
taaaggaaag gctatcgttc aagatgcctc tgccgacagt ggtcccaaag atggaccccc    6360
acccacgagg agcatcgtgg aaaaagaaga cgttccaacc acgtcttcaa agcaagtgga    6420
ttgatgtgat atctccactg acgtaaggga tgacgcacaa tcccactatc cttcgcaaga    6480
cccttcctct atataaggaa gttcatttca tttggagagg acacgctgaa atcaccagtc    6540
```

```
tctctctaca aatctatctc tctcgattcg cagatctgtc gatcgaccat ggggattgaa    6600
caagatggat tgcacgcagg ttctccggcc gcttgggtgg agaggctatt cggctatgac    6660
tgggcacaac agacaatcgg ctgctctgat gccgccgtgt tccggctgtc agcgcagggg    6720
cgcccggttc ttttgtcaa gaccgacctg tccggtgccc tgaatgaact ccaggacgag    6780
gcagcgcggc tatcgtggct ggccacgacg ggcgttcctt gcgcagctgt gctcgacgtt    6840
gtcactgaag cgggaaggga ctggctgcta ttgggcgaag tgccggggca ggatctcctg    6900
tcatctcacc ttgctcctgc cgagaaagta tccatcatgg ctgatgcaat gcggcggctg    6960
catacgcttg atccggctac ctgcccattc gaccaccaag cgaaacatcg catcgagcga    7020
gcacgtactc ggatggaagc cggtcttgtc gatcaggatg atctggacga agagcatcag    7080
gggctcgcgc cagccgaact gttcgccagg ctcaaggcgc gcatgcccga cggcgaggat    7140
ctcgtcgtga cacatggcga tgcctgcttg ccgaatatca tggtggaaaa tggccgcttt    7200
tctggattca tcgactgtgg ccggctgggt gtggcggacc gctatcagga catagcgttg    7260
gctacccgtg atattgctga agagcttggc ggcgaatggg ctgaccgctt cctcgtgctt    7320
tacggtatcg ccgctcccga ttcgcagcgc atcgccttct atcgccttct tgacgagttc    7380
ttctgagcgg gactctgggg ttcggatcga tcctctagct agagtcgatc gacatcgagt    7440
ttctccataa taatgtgtga gtagttccca gataagggaa ttagggttct tatagggttt    7500
cgctcacgtg ttgagcatat aagaaaccct tagtatgtat ttgtatttgt aaaatacttc    7560
tatcaataaa atttctaatt cctaaaacca aaatccagta ctaaaatcca gatcacctaa    7620
agtccctata gatcccccga attaattcgg cgttaattca gtacattaaa aacgtccgca    7680
atgtgttatt aagttgtcta agcgtcaatt tgtttacacc acaatatatc ctgccaccag    7740
ccagccaaca gctccccgac cggcagctcg gcacaaaatc accactcgat acaggcagcc    7800
catcagtccg ggacggcgtc agcgggagag ccgttgtaag gcggcagact tgctcatgt    7860
taccgatgct attcggaaga acggcaacta agctgccggg tttgaaacac ggatgatctc    7920
gcggagggta gcatgttgat tgtaacgatg acagagcgtt gctgcctgtg atcaattcgg    7980
gcacgaaccc agtggacata agcctcgttc ggttcgtaag ctgtaatgca agtagcgtaa    8040
ctgccgtcac gcaactggtc cagaaccttg accgaacgca gcggtggtaa cggcgcagtg    8100
gcggttttca tggcttcttg ttatgacatg ttttttggg gtacagtcta tgcctcgggc    8160
atccaagcag caagcgcgtt acgccgtggg tcgatgtttg atgttatgga gcagcaacga    8220
tgttacgcag cagggcagtc gccctaaaac aaagttaaac atcatggggg aagcggtgat    8280
cgccgaagta tcgactcaac tatcagaggt agttggcgtc atcgagcgcc atctcgaacc    8340
gacgttgctg gccgtacatt tgtacggctc cgcagtggat ggcggcctga agccacacag    8400
tgatattgat ttgctggtta cggtgaccgt aaggcttgat gaaacaacgc ggcgagcttt    8460
gatcaacgac cttttggaaa cttcggcttc ccctggagag agcgagattc tccgcgctgt    8520
agaagtcacc attgttgtgc acgacgacat cattccgtgg cgttatccag ctaagcgcga    8580
actgcaattt ggagaatggc agcgcaatga cattcttgca ggtatcttcg agccagccac    8640
gatcgacatt gatctggcta tcttgctgac aaaagcaaga gaacatagcg ttgccttggt    8700
aggtccagcg gcggaggaac tctttgatcc ggttcctgaa caggatctat ttgaggcgct    8760
aaatgaaacc ttaacgctat ggaactcgcc gcccgactgg gctggcgatg agcgaaatgt    8820
agtgcttacg ttgtcccgca tttggtacag cgcagtaacc ggcaaaatcg cgccgaagga    8880
tgtcgctgcc gactgggcaa tggagcgcct gccggcccag tatcagcccg tcatacttga    8940
```

```
agctagacag gcttatcttg gacaagaaga agatcgcttg gcctcgcgcg cagatcagtt      9000
ggaagaattt gtccactacg tgaaaggcga gatcaccaag gtagtcggca ataatgtct       9060 agctagaaat tcgttcaagc cgacgccgct tcgccggcgt taactcaagc gattagatgc      9120
actaagcaca taattgctca cagccaaact atcaggtcaa gtctgctttt attatttta      9180 agcgtgcata ataagcccta cacaaattgg gagatatatc atgcatgacc aaaatcccett    9240 aacgtgagtt ttcgttccac tgagcgtcag accccgtaga aaagatcaaa ggatcttctt     9300
gagatccttt ttttctgcgc gtaatctgct gcttgcaaac aaaaaaacca ccgctaccag     9360
cggtggtttg tttgccggat caagagctac caactctttt tccgaaggta actggcttca     9420
gcagagcgca gataccaaat actgtccttc tagtgtagcc gtagttaggc caccacttca     9480
agaactctgt agcaccgcct acatacccg ctctgctaat cctgttacca gtggctgctg      9540
ccagtggcga taagtcgtgt cttaccgggt tggactcaag acgatagtta ccggataagg     9600
cgcagcggtc gggctgaacg gggggttcgt gcacacagcc cagcttggag cgaacgacct     9660
acaccgaact gagataccta cagcgtgagc tatgagaaag cgccacgctt cccgaaggga     9720
gaaaggcgga caggtatccg gtaagcggca gggtcggaac aggagagcgc acgagggagc     9780 ttccagggg aaacgcctgg tatctttata gtcctgtcgg gtttcgccac ctctgacttg      9840
agcgtcgatt tttgtgatgc tcgtcagggg gcggagcct atggaaaaac gccagcaacg      9900 cggcctttt acggttcctg gccttttgct ggccttttgc tcacatgttc tttcctgcgt      9960
tatcccctga ttctgtggat aaccgtatta ccgcctttga gtgagctgat accgctcgcc    10020
gcagccgaac gaccgagcgc agcgagtcag tgagcgagga agcggaagag cgcctgatgc    10080
ggtattttct ccttacgcat ctgtgcggta tttcacaccg catatggtgc actctcagta    10140
caatctgctc tgatgccgca tagttaagcc agtatacact ccgctatcgc tacgtgactg    10200
ggtcatggct gcgccccgac acccgccaac acccgctgac gcgccctgac gggcttgtct    10260
gctcccggca tccgcttaca gacaagctgt gaccgtctcc gggagctgca tgtgtcagag    10320
gttttcaccg tcatcaccga aacgcgcgag gcagggtgcc ttgatgtggg cgccggcggt    10380
cgagtggcga cggcgcggct tgtccgcgcc ctggtagatt gcctggccgt aggccagcca    10440
tttttgagcg gccagcggcc gcgataggcc gacgcgaagc ggcggggcgt agggagcgca    10500
gcgaccgaag ggtaggcgct ttttgcagct cttcggctgt gcgctggcca gacagttatg    10560
cacaggccag gcgggtttta agagtttta taagttttaa agagttttag gcggaaaaat     10620 cgccttttt ctcttttata tcagtcactt acatgtgtga ccggtcccca atgtacggct     10680
ttgggttccc aatgtacggg ttccggttcc caatgtacgg ctttgggttc ccaatgtacg    10740
tgctatccac aggaaagaga cctttttcgac cttttttcccc tgctagggca atttgcccta   10800
gcatctgctc cgtacattag gaaccggcgg atgcttcgcc ctcgatcagg ttgcggtagc    10860
gcatgactag gatcgggcca gcctgccccg cctcctcctt caaatcgtac tccggcaggt    10920
catttgaccc gatcagcttg cgcacggtga aacagaactt cttgaactct ccggcgctgc    10980
cactgcgttc gtagatcgtc ttgaacaacc atctggcttc tgccttgcct gcggcgcggc    11040
gtgccaggcg gtagagaaaa cggccgatgc cgggatcgat caaaaagtaa tcggggtgaa    11100
ccgtcagcac gtccgggttc ttgccttctg tgatctcgcg gtacatccaa tcagctagct    11160
cgatctcgat gtactccggc cgcccggttt cgctctttac gatcttgtag cggctaatca    11220
aggcttcacc ctcggatacc gtcaccaggc ggccgttctt ggccttcttc gtacgctgca    11280
```

```
tggcaacgtg cgtggtgttt aaccgaatgc aggtttctac caggtcgtct ttctgctttc   11340
cgccatcggc tcgccggcag aacttgagta cgtccgcaac gtgtggacgg aacacgcggc   11400
cgggcttgtc tcccttccct tcccggtatc ggttcatgga ttcggttaga tgggaaaccg   11460
ccatcagtac caggtcgtaa tcccacacac tggccatgcc ggccggccct gcggaaacct   11520
ctacgtgccc gtctggaagc tcgtagcgga tcacctcgcc agtcgtcgg tcacgcttcg    11580 acagacggaa aacggccacg tccatgatgc tgcgactatc gcgggtgccc acgtcataga   11640
gcatcggaac gaaaaaatct ggttgctcgt cgcccttggg cggcttccta atcgacggcg   11700
caccggctgc cggcggttgc cgggattctt tgcggattcg atcagcggcc gcttgccacg   11760
attcaccggg gcgtgcttct gcctcgatgc gttgccgctg ggcggcctgc gcggccttca   11820
acttctccac caggtcatca cccagcgccg cgccgatttg taccgggccg gatggtttgc   11880
gaccgtcacg ccgattcctc gggcttgggg gttccagtgc cattgcaggg ccggcagaca   11940
acccagccgc ttacgcctgg ccaaccgccc gttcctccac acatggggca ttccacggcg   12000
tcggtgcctg gttgttcttg attttccatg ccgcctcctt tagccgctaa aattcatcta   12060
ctcatttatt catttgctca tttactctgg tagctgcgcg atgtattcag atagcagctc   12120
ggtaatggtc ttgccttggc gtaccgcgta catcttcagc ttggtgtgat cctccgccgg   12180
caactgaaag ttgacccgct tcatggctgg cgtgtctgcc aggctggcca acgttgcagc   12240
cttgctgctg cgtgcgctcg gacgccggc acttagcgtg tttgtgcttt tgctcatttt    12300
ctctttacct cattaactca aatgagtttt gatttaattt cagcggccag cgcctggacc   12360
tcgcgggcag cgtcgccctc gggttctgat tcaagaacgg ttgtgccggc ggcggcagtg   12420
cctgggtagc tcacgcgctg cgtgatacgg gactcaagaa tgggcagctc gtacccggcc   12480
agcgcctcgg caacctcacc gccgatgcgc gtgcctttga tcgccgcgca cacgacaaag   12540
gccgcttgta gccttccatc cgtgacctca atgcgctgct taaccagctc caccaggtcg   12600
gcggtggccc atatgtcgta agggcttggc tgcaccggaa tcagcacgaa gtcggctgcc   12660
ttgatcgcgg acacagccaa gtccgccgcc tggggcgctc cgtcgatcac tacgaagtcg   12720
cgccggccga tggccttcac gtcgcggtca atcgtcgggc ggtcgatgcc gacaacggtt   12780
agcggttgat cttcccgcac ggccgcccaa tcgcgggcac tgccctgggg atcggaatcg   12840
actaacagaa catcggcccc ggcgagttgc agggcgcggg ctagatgggt tgcgatggtc   12900
gtcttgcctg acccgccttt ctggttaagt acagcgataa ccttcatgcg ttcccccttgc  12960 gtatttgttt atttactcat cgcatcatat acgcagcgac cgcatgacgc aagctgtttt   13020
actcaaatac acatcacctt tttagacggc ggcgctcggt ttcttcagcg ccaagctgg    13080 ccggccaggc cgccagcttg gcatcagaca aacggccag gatttcatgc agccgcacgg    13140
ttgagacgtg cgcgggcggc tcgaacacgt acccggccgc gatcatctcc gcctcgatct   13200
cttcggtaat gaaaaacggt tcgtcctggc cgtcctggtg cggtttcatg cttgttcctc   13260
ttggcgttca ttctcggcgg ccgccagggc gtcggcctcg tcaatgcgt cctcacggaa    13320 ggcaccgcgc cgcctggcct cggtgggcgt cacttcctcg ctgcgctcaa gtgcgcggta   13380
cagggtcgag cgatgcacgc caagcagtgc agccgcctct ttcacggtgc ggccttcctg   13440
gtcgatcagc tcgcgggcgt gcgcgatctg tgccggggtg agggtagggc gggggccaaa   13500
cttcacgcct cgggccttgg cggcctcgcg cccgctccgg gtgcggtcga tgattaggga   13560
acgctcgaac tcgcaatgc cggcgaacac ggtcaacacc atgcggccgg ccggcgtggt    13620
ggtgtcggcc cacggctctg ccaggctacg caggcccgcg ccggcctcct ggatgcgctc   13680
```

```
ggcaatgtcc agtaggtcgc gggtgctgcg ggccaggcgg tctagcctgg tcactgtcac    13740
aacgtcgcca gggcgtaggt ggtcaagcat cctggccagc tccgggcggt cgcgcctggt    13800
gccggtgatc ttctcggaaa acagcttggt gcagccggcc gcgtgcagtt cggcccgttg    13860
gttggtcaag tcctggtcgt cggtgctgac gcgggcatag cccagcaggc cagcggcggc    13920
gctcttgttc atggcgtaat gtctccggtt ctagtcgcaa gtattctact ttatgcgact    13980
aaaacacgcg acaagaaaac gccaggaaaa gggcagggcg gcagcctgtc gcgtaactta    14040
ggacttgtgc gacatgtcgt tttcagaaga cggctgcact gaacgtcaga agccgactgc    14100
actatagcag cggaggggtt ggatcaaagt act                                 14133
```

<210> SEQ ID NO 15
<211> LENGTH: 634
<212> TYPE: PRT
<213> ORGANISM: Artificial Sequence
<220> FEATURE:
<223> OTHER INFORMATION: Chimaera rGRF3-GFP

<400> SEQUENCE: 15

```
Met Asp Leu Gln Leu Lys Gln Trp Arg Ser Gln Gln Gln Gln His
1               5                   10                  15

Gln Thr Glu Ser Glu Glu Gln Pro Ala Ala Lys Ile Pro Lys His
                20                  25                  30

Val Phe Asp Gln Ile His Ser His Thr Ala Thr Ser Thr Ala Leu Pro
            35                  40                  45

Leu Phe Thr Pro Glu Pro Thr Ser Ser Lys Leu Ser Ser Leu Ser Pro
        50                  55                  60

Asp Ser Ser Ser Arg Phe Pro Lys Met Gly Ser Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Pro Ile Lys Lys Ser
            100                 105                 110

Leu Leu His Leu Ser Pro Ser Tyr Phe Leu His His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
                165                 170                 175

Arg Gly Arg Asn Arg Ser Arg Lys Pro Val Glu Thr Pro Thr Thr Val
            180                 185                 190

Asn Ala Thr Ala Thr Ser Met Ala Ser Ser Val Ala Ala Ala Ala Thr
        195                 200                 205

Thr Thr Thr Ala Thr Thr Thr Ser Thr Phe Ala Phe Gly Gly Gly Gly
    210                 215                 220

Gly Ser Glu Glu Val Val Gly Gln Gly Gly Ser Phe Phe Ser Gly
225                 230                 235                 240

Ser Ser Asn Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
```

```
                275                 280                 285
Arg Pro Phe Phe Asp Asp Trp Pro Arg Ser Ser Leu Gln Glu Ala Asp
    290                 295                 300

Asn Ser Ser Ser Pro Met Ser Ser Ala Thr Cys Leu Ser Ile Ser Met
305                 310                 315                 320

Pro Gly Asn Ser Ser Asp Val Ser Leu Lys Leu Ser Thr Gly Asn
                325                 330                 335

Glu Glu Gly Ala Arg Ser Asn Asn Asn Gly Arg Asp Gln Gln Asn Met
            340                 345                 350

Ser Trp Trp Ser Gly Gly Ser Asn His His His Asn Met Gly
        355                 360                 365

Gly Pro Leu Ala Glu Ala Leu Arg Ser Ser Ser Ser Ser Pro Thr
    370                 375                 380

Ser Val Leu His Gln Leu Gly Val Ser Thr Gln Ala Phe His Val Asp
385                 390                 395                 400

Asp Leu Thr Ser Lys Gly Glu Glu Leu Phe Thr Gly Val Asp Gly Asp
                405                 410                 415

Val Asn Gly His Lys Phe Ser Val Ser Gly Glu Gly Glu Gly Asp Ala
            420                 425                 430

Thr Tyr Gly Lys Leu Thr Leu Lys Phe Ile Cys Thr Thr Gly Lys Leu
        435                 440                 445

Pro Val Pro Trp Pro Thr Leu Val Thr Thr Phe Ser Tyr Gly Val Gln
    450                 455                 460

Cys Phe Ser Arg Tyr Pro Asp His Met Lys Arg His Asp Phe Phe Lys
465                 470                 475                 480

Ser Ala Met Pro Glu Gly Tyr Val Gln Glu Arg Thr Ile Phe Phe Lys
                485                 490                 495

Asp Asp Gly Asn Tyr Lys Thr Arg Ala Glu Val Lys Phe Glu Gly Asp
            500                 505                 510

Thr Leu Val Asn Arg Ile Glu Leu Lys Gly Ile Asp Phe Lys Glu Asp
        515                 520                 525

Gly Asn Ile Leu Gly His Lys Leu Glu Tyr Asn Tyr Asn Ser His Asn
    530                 535                 540

Val Tyr Ile Met Ala Asp Lys Gln Lys Asn Gly Ile Lys Ala Asn Phe
545                 550                 555                 560

Lys Thr Arg His Asn Ile Glu Asp Gly Gly Val Gln Leu Ala Asp His
                565                 570                 575

Tyr Gln Gln Asn Thr Pro Ile Gly Asp Gly Pro Val Leu Leu Pro Asp
            580                 585                 590

Asn His Tyr Leu Ser Thr Gln Ser Ala Leu Ser Lys Asp Pro Asn Glu
        595                 600                 605

Lys Arg Asp His Met Val Leu Leu Glu Phe Val Thr Ala Ala Gly Ile
    610                 615                 620

Thr His Gly Met Asp Glu Leu Tyr Lys Ala
625                 630
```

<210> SEQ ID NO 16
<211> LENGTH: 3026
<212> TYPE: DNA
<213> ORGANISM: Artificial Sequence
<220> FEATURE:
<223> OTHER INFORMATION: Chimaera rGRF3-GFP

<400> SEQUENCE: 16
atggatttgc aactgaaaca atggagaagc cagcagcagc aacaacatca gacagagtca    60

```
gaagaacaac cttctgcagc taagatacca aaacatgtct ttgaccagat tcattctcac    120
actgcaactt ctactgctct tcctctcttt acccctgagc ctacttcttc taaactctcc    180
tctttgtctc ctgattcttc ctccaggttc cccagtgagt cttttcttcc tcttatctta    240
tctttcttga taaagaatta gacttttcat tcatatagtt tgtgtttaat tgattttgat    300 tccttttttgt agagatgggg agcttcttta gctgggcaca gtggcaagaa cttgaactac    360
aagctctgat ctacaggtac atgttggctg gtgctgctgt tcctcaggag ctccttttac    420
caatcaagaa aagccttctc catctatctc cttcctactt tcttcaccat cctcttcaac    480
acctacctca ttaccaacct gcttgtgagt ctcgagaaca gtcttcatct atctattttt    540
taaatataaa tgggttttgt gctactggtg ttggagttgt gttcccaaga tccagacttt    600
caatattagt atattatctc gttttgccaa tcttgaagat ctaaacatgt gtgaatggga    660
ttaagtagga ttagaatctt gttattgatc tgatatgtga tatgaatgtt gaaaacaggg    720
tatttgggaa gggcagcgat ggatcctgag ccaggcagat gcaggagaac ggatggtaag    780
aagtggagat gttcaagaga cgtcttcgct ggccacaagt attgcgagcg ccacatgcac    840
cgtggccgca accgttctag aaaaccagta gagactccaa ccaccgtcaa tgcaactgcc    900
acgtccatgg cttcatcagt agcagccgca gccaccacta caacagcaac aacaacatct    960
acgtttgctt ttggtggtgg tggtggtagt gaggaagtgg ttggtcaagg aggatctttc   1020
ttcttctctg gctcttctaa ctcttcatct gaacttctcc accttagtca aaggtaataa   1080
aaagaaactg ttttttttttc tcttaggtct gtctgttta gctgttgaac tttatggtca   1140
aaacattaaa cttaaacaca ttgacttttt tatttcttta gtgttgagcc aataagattc   1200
atggttgaga tttagacaa ttgttttgaa taataatgaa atcgatttaa agcaatactg   1260
attcttgatt tattagtatg aagtatgaac taatgatata cacaacttgg tttgtatgtt   1320
catagcgatg ttgtgaagag aggggtaatg ttggaaattg agagacacat cctttatcatt   1380 ttagggttgg ttggtttgtt tgtttgttga attatgagtt tgatttcatt gtgaaaatat   1440 cttttctttct ttttcttat tgtgttgaga gataatgata acattggatt tgatagaatc   1500 tataaatttga agctaggtgt gagacttttc aaacagagaa aatagaaaga gagagaaatg   1560
gtaggacctt agtgaaagct gacccatata tgtctcatat cttgcagaaa agttaaagct   1620
tttagattct tctgcaccca cctcccctat ccacacacaa cacatgatat acaaaacact   1680
cactttataa ttctatttct atttactgct taatcaattc ttataaaacc cacattaaaa   1740 ggtacttta aagcctataa actaatataa aggctactac tgtctgcaac tttgttgttg   1800
aagcctaaat gtggtttctc ttttgacaaa ttattgcttt tgtgctttgt tttccaat    1860 gagatgtgga ttctgttaac agttgttcgg agatgaagca agaaagcaac aacatgaaca   1920
acaagaggcc atacgagtcc cacatcggat tcagtaacaa cagatcagat ggaggacaca   1980
tcctgaggcc cttctttgac gattggcctc gttcttcgct ccaagaagct gacaatagtt   2040
caagccccat gagctcagcc acttgtctct ccatctccat gcccgggaac tcttcctcag   2100
acgtctctct gaagctgtcc acaggcaacg aagagggagc ccggagcaac aacaatggga   2160
gagatcagca aaacatgagc tggtggagcg gtggaggttc caaccaccat catcacaaca   2220
tgggcggacc attggccgaa gccctgagat cttcttcctc atcttcccca accagtgttc   2280
tccatcagct tggtgtctcg acacaagcct ttcatgtcga cgatctgact agtaaaggag   2340
aagaactttt cactggagta gatggtgatg ttaatgggca caaattttct gtcagtggag   2400
```

```
agggtgaagg tgatgcaaca tacggaaaac ttacccttaa atttatttgc actactggaa    2460
aactacctgt tccgtggcca acacttgtca ctactttctc ttatggtgtt caatgctttt    2520
caagataccc agatcatatg aagcggcacg acttcttcaa gagcgccatg cctgagggat    2580
acgtgcagga ggaggaccatc ttcttcaagg acgacgggaa ctacaagaca cgtgctgaag    2640
tcaagtttga gggagacacc ctcgtcaaca ggatcgagct taagggaatc gatttcaagg    2700
aggacggaaa catcctcggc cacaagttgg aatacaacta caactcccac aacgtataca    2760
tcatggccga caagcaaaag aacggcatca agccaacttc aagacccgca caacatcg      2820 aagacggcgg cgtgcaactc gctgatcatt atcaacaaaa tactccaatt ggcgatggcc    2880
ctgtcctttt accagacaac cattacctgt ccacacaatc tgcccttcg aaagatccca     2940 acgaaaagag agaccacatg gtccttcttg agtttgtaac agctgctggg attacacatg    3000
gcatggatga actatacaaa gcttga                                         3026
```

<210> SEQ ID NO 17
<211> LENGTH: 14133
<212> TYPE: DNA
<213> ORGANISM: Artificial Sequence
<220> FEATURE:
<223> OTHER INFORMATION: Binary vector pJD105 for expression of chimeric
      protein rGRF3-GPF

<400> SEQUENCE: 17

```
ttgatcccga ggggaaccct gtggttggca tgcacataca aatggacgaa cggataaacc      60
ttttcacgcc cttttaaata tccgttattc taataaacgc tcttttctct taggtttacc     120
cgccaatata tcctgtcaaa cactgatagt ttaaactgaa ggcgggaaac gacaatctga     180
tccaagctca agctgctcta gccaatacgc aaaccgcctc tccccgcgcg ttggccgatt     240
cattaatgca gctggcacga caggttttcc cgactggaaa gcgggcagtga gcgcaacgca    300 attaatgtga gttagctcac tcattaggca ccccaggctt tacactttat gcttccggct    360
cgtatgttgt gtggaattgt gagcggataa caatttcaca caggaaacag ctatgaccat    420
gattacgaat tgaaaacgca ggcccatttta catcctccaa acaaaagaa gcaatagaat    480 ccggaactga attaaaaaca tacaaaccaa gaggtaaaga aaacgcatag ttagctaacc    540
cgtccgcaag acgattgacc tccctataca cgtgagaaat acggactaac cagtcccttg    600
atatgaagcc ataacacaaa cgtagtagga aagatagagg atgagaatcc ggtatccctg    660
tctgtaaaaa cccaaccacg atcttcgaat ccacttccag ctcaaggcgt gttattcctt    720 gctcccgac tatgtgtaac ccatagtaga gtccccacaa ctctgctagt ggcgctgaac     780
agatttcgat attcaaagca aaaccccaa cccagttctc gttcccatca cgcaccgcac     840 ctccccgctgc tgctaaccccg ggattctctc tcgaggctcc atccatgttc aactagcctg    900
atgaatttat taaactcatg tttccatttt ttttcccacc agttatgtta gtttgattaa     960 ttttcagtc aattttggca taacgcttta aaataattat atcaaaataa tattttcagt    1020
ttttctgcaa cagattcatt ccaccaagaa ttcagccgat tctacccgaa ttaatattac   1080
cattttcgga ctagatctat gaacgaaggt acaaaattaa tcagttaaaa aagaaaatag    1140
agtggcaagt actacatcta gtgccgtatg atatgataat ataggaacct aaacgaattt    1200
tatactaatt caaatttaaa agtagttagg tttgtcacaa atgcaaatta caattatat     1260 cgacgtaacg cttactcatt aaataatcta aattacttgg ttaaaagact aattaaatat    1320
tcttaacaag taggctttg ttttcattat aaaacaaatt aaaaagctat actaatataa    1380
```

```
aaatggagat tggtatttcc aaagcagcaa agacagaaaa actgcaggtt attatctctc    1440
catcttcatc ttgcagagtg gttctttctg ggttttctga cttgcttttc attttttat     1500 tgatacaaat gttaaaccaa ttattttaaa tagtctttga gattaatgaa gagagatttg    1560
tgaacacaat taataaagag ttatactata gtagtagtct ttttactgt atagtatttt     1620 ctccccgcat ctgtcttgtc tcactgtctt tttctcgcaa gtctctctat taaaaacctc    1680
tttccctcta ctctgtcctt tctctctctg cagaagaagc tcagatacag aaactgacta    1740
ccaagaacaa agcttttttcc ttcgagcaaa gaaagttctt ttttcttttc ttttgctctt    1800
cgtaacccaa ccaacaagac tttcataagc tattaaatca gaaccctgga agacaaaaaa    1860
ggggaaaaac cattatcctt aaagtaacca acacttctct ctctctttct tcaggtacca    1920
tggatttgca actgaaacaa tggagaagcc agcagcagca acaacatcag acagagtcag    1980
aagaacaacc ttctgcagct aagataccaa acatgtctt tgaccagatt cattctcaca    2040
ctgcaacttc tactgctctt cctctctttta cccctgagcc tacttcttct aaactctcct    2100
ctttgtctcc tgattcttcc tccaggttcc ccagtgagtc ttttcttcct cttatcttat    2160
ctttcttgat aaagaattag acttttcatt catatagttt gtgtttaatt gattttgatt    2220
cctttttgta gagatgggga gcttcttttag ctgggcacag tggcaagaac ttgaactaca    2280
agctctgatc tacaggtaca tgttggctgg tgctgctgtt cctcaggagc tccttttacc    2340
aatcaagaaa agccttctcc atctatctcc ttcctacttt cttcaccatc ctcttcaaca    2400
cctacctcat taccaacctg cttgtgagtc tcgagaacag tcttcatcta tctattttt    2460 aaatataaat gggttttgtg ctactggtgt tggagttgtg ttcccaagat ccagactttc    2520
aatattagta tattatctcg ttttgccaat cttgaagatc taaacatgtg tgaatgggat    2580
taagtaggat tagaatcttg ttattgatct gatatgtgat atgaatgttg aaaacagggt    2640
atttgggaag ggcagcgatg gatcctgagc caggcagatg caggagaacg gatggtaaga    2700
agtggagatg ttcaagagac gtcttcgctg gccacaagta ttgcgagcgc cacatgcacc    2760
gtggccgcaa ccgttctaga aaaccagtag agactccaac caccgtcaat gcaactgcca    2820
cgtccatggc ttcatcagta gcagccgcag ccaccactac aacagcaaca acaacatcta    2880 cgtttgctt tggtggtggt ggtggtagtg aggaagtggt tggtcaagga ggatcttct     2940 tcttctctgg ctcttctaac tcttcatctg aacttctcca ccttagtcaa aggtaataaa    3000
aagaaactgt tttttttttct cttaggtctg tctgttttag ctgttgaact ttatggtcaa    3060
aacattaaac ttaaacacat tgactttttt atttctttag tgttgagcca ataagattca    3120
tggttgagat tttagacaat tgttttgaat aataatgaaa tcgatttaaa gcaatactga    3180
ttcttgattt attagtatga agtatgaact aatgatatac acaacttggt ttgtatgttc    3240
atagcgatgt tgtgaagaga ggggtaatgt tggaaattga gagacacatc cttatcattt    3300
tagggttggt tggtttgttt gtttgttgaa ttatgagttt gatttcattg tgaaaatatc    3360
tttctttctt ttttcttatt gtgttgagag ataatgataa cattggattt gatagaatct    3420
ataatttgaa gctaggtgtg agacttttca aacagagaaa atagaaagag agagaaatgg    3480 taggaccta gtgaaagctg acccatatat gtctcatatc ttgcagaaaa gttaaagctt    3540
ttagattctt ctgcacccac ctcccctatc cacacacaac acatgatata caaaacactc    3600
actttataat tctatttcta tttactgctt aatcaattct tataaaaccc acattaaaag    3660
gtacttttaa agcctataaa ctaatataaa ggctactact gtctgcaact tgttgttga     3720 agcctaaatg tggttttctct tttgacaaat tattgctttt gtgctttgtt ttcaccaatg    3780
```

```
agatgtggat tctgttaaca gttgttcgga gatgaagcaa gaaagcaaca acatgaacaa    3840
caagaggcca tacgagtccc acatcggatt cagtaacaac agatcagatg gaggacacat    3900
cctgaggccc ttctttgacg attggcctcg ttcttcgctc caagaagctg acaatagttc    3960 aagcccatg agctcagcca cttgtctctc catctccatg cccgggaact cttcctcaga     4020
cgtctctctg aagctgtcca caggcaacga agagggagcc cggagcaaca acaatgggag    4080
agatcagcaa acatgagct ggtggagcgg tggaggttcc aaccaccatc atcacaacat     4140
gggcggacca ttggccgaag ccctgagatc ttcttcctca tcttccccaa ccagtgttct    4200
ccatcagctt ggtgtctcga cacaagcctt tcatgtcgac gatctgacta gtaaaggaga    4260
agaacttttc actggagtag atggtgatgt taatgggcac aaatttttctg tcagtggaga   4320 gggtgaaggt gatgcaacat acggaaaact taccccttaaa tttatttgca ctactggaaa   4380
actacctgtt ccgtggccaa cacttgtcac tactttctct tatggtgttc aatgcttttc    4440 aagatacccca gatcatatga agcggcacga cttcttcaag agcgccatgc ctgagggata  4500
cgtgcaggag aggaccatct tcttcaagga cgacgggaac tacaagacac gtgctgaagt   4560
caagtttgag ggagacaccc tcgtcaacag gatcgagctt aagggaatcg atttcaagga   4620
ggacggaaac atcctcggcc acaagttgga atacaactac aactcccaca cgtatacat    4680 catgccgac aagcaaaaga acggcatcaa agccaacttc aagacccgcc acaacatcga    4740
agacggcggc gtgcaactcg ctgatcatta tcaacaaaat actccaattg gcgatggccc   4800 tgtccttttta ccagacaacc attacctgtc cacacaatct gcccttttcga aagatcccaa  4860 cgaaaagaga gaccacatgg tccttcttga gtttgtaaca gctgctggga ttacacatgg   4920
catggatgaa ctatacaaag cttgactgca gagctttcgt tcgtatcatc ggtttcgaca   4980
acgttcgtca agttcaatgc atcagtttca ttgcgcacac accagaatcc tactgagttc   5040
gagtattatg gcattgggaa acatgttttt cttgtaccat ttgttgtgct tgtaatttac    5100
tgtgtttttt attcggtttt cgctatcgaa ctgtgaaatg gaaatggatg gagaagagtt    5160
aatgaatgat atggtccttt tgttcattct caaattaata ttatttgttt tttctcttat    5220
ttgttgtgtg ttgaatttga aaatataaga gatatgcaaa catttttgttt tgagtaaaaa   5280 tgtgtcaaat cgtggcctct aatgaccgaa gttaatatga ggagtaaaac acttgtagtt    5340
gtaccattat gcttattcac taggcaacaa atatattttc agacctagaa aagctgcaaa   5400
tgttactgaa tacaagtatg tcctcttgtg ttttagacat ttatgaactt tcctttatgt    5460
aattttccag aatccttgtc agattctaat cattgcttta taattatagt tatactcatg    5520
gatttgtagt tgagtatgaa aatattttt aatgcatttt atgacttgcc aattgattga     5580
caacatgcat caatcgaagc ttggcactgg ccgtcgtttt acaacgtcgt gactgggaaa    5640
accctggcgt tacccaactt aatcgccttg cagcacatcc ccctttcgcc agctggcgta    5700
atagcgaaga ggcccgcacc gatcgccctt cccaacagtt gcgcagcctg aatggcgaat    5760
gctagagcag cttgccaaca tggtggagca cgacactctc gtctactcca agaatatcaa    5820
agatacagtc tcagaagacc aaagggctat tgagacttttt caacaaaggg taatatcggg   5880
aaacctcctc ggattccatt gcccagctat ctgtcacttc atcaaaagga cagtagaaaa    5940
ggaaggtggc acctacaaat gccatcattg cgataaagga aaggctatcg ttcaagatgc    6000
ctctgccgac agtggtccca agatggacc cccacccacg aggagcatcg tggaaaaaga    6060
agacgttcca accacgtctt caaagcaagt ggattgatgt gataacatgg tggagcacga    6120
```

```
cactctcgtc tactccaaga atatcaaaga tacagtctca gaagaccaaa gggctattga   6180
gacttttcaa caaagggtaa tatcgggaaa cctcctcgga ttccattgcc cagctatctg   6240
tcacttcatc aaaaggacag tagaaaagga aggtggcacc tacaaatgcc atcattgcga   6300
taaaggaaag gctatcgttc aagatgcctc tgccgacagt ggtcccaaag atggaccccc   6360
acccacgagg agcatcgtgg aaaaagaaga cgttccaacc acgtcttcaa agcaagtgga   6420
ttgatgtgat atctccactg acgtaaggga tgacgcacaa tcccactatc cttcgcaaga   6480
cccttcctct atataaggaa gttcatttca tttggagagg acacgctgaa atcaccagtc   6540
tctctctaca aatctatctc tctcgattcg cagatctgtc gatcgaccat ggggattgaa   6600
caagatggat tgcacgcagg ttctccggcc gcttgggtgg agaggctatt cggctatgac   6660
tgggcacaac agacaatcgg ctgctctgat gccgccgtgt tccggctgtc agcgcagggg   6720
cgcccggttc tttttgtcaa gaccgacctg tccggtgccc tgaatgaact ccaggacgag   6780
gcagcgcggc tatcgtggct ggccacgacg ggcgttcctt gcgcagctgt gctcgacgtt   6840
gtcactgaag cgggaaggga ctggctgcta ttgggcgaag tgccggggca ggatctcctg   6900
tcatctcacc ttgctcctgc cgagaaagta tccatcatgg ctgatgcaat gcggcggctg   6960
catacgcttg atccggctac ctgcccattc gaccaccaag cgaaacatcg catcgagcga   7020
gcacgtactc ggatggaagc cggtcttgtc gatcaggatg atctggacga agagcatcag   7080
gggctcgcgc cagccgaact gttcgccagg ctcaaggcgc gcatgcccga cggcgaggat   7140
ctcgtcgtga cacatggcga tgcctgcttg ccgaatatca tggtggaaaa tggccgcttt   7200
tctggattca tcgactgtgg ccggctgggt gtggcggacc gctatcagga catagcgttg   7260
gctacccgtg atattgctga agagcttggc ggcgaatggg ctgaccgctt cctcgtgctt   7320
tacggtatcg ccgctcccga ttcgcagcgc atcgccttct atcgccttct tgacgagttc   7380
ttctgagcgg gactctgggg ttcggatcga tcctctagct agagtcgatc gacatcgagt   7440
ttctccataa taatgtgtga gtagttccca gataagggaa ttagggttct tatagggttt   7500
cgctcacgtg ttgagcatat aagaaaccct tagtatgtat ttgtatttgt aaaatacttc   7560
tatcaataaa atttctaatt cctaaaacca aatccagta ctaaaatcca gatcacctaa   7620
agtccctata gatcccccga attaattcgg cgttaattca gtacattaaa aacgtccgca   7680
atgtgttatt aagttgtcta agcgtcaatt tgtttacacc acaatatatc ctgccaccag   7740
ccagccaaca gctccccgac cggcagctcg gcacaaaatc accactcgat acaggcagcc   7800
catcagtccg ggacggcgtc agcggggagg ccgttgtaag gcggcagact ttgctcatgt   7860
taccgatgct attcggaaga acggcaacta agctgccggg tttgaaacac ggatgatctc   7920
gcggagggta gcatgttgat tgtaacgatg acagagcgtt gctgcctgtg atcaattcgg   7980
gcacgaaccc agtggacata agcctcgttc ggttcgtaag ctgtaatgca agtagcgtaa   8040
ctgccgtcac gcaactggtc cagaaccttg accgaacgca gcggtggtaa cggcgcagtg   8100
gcggttttca tggcttcttg ttatgacatg ttttttggg gtacagtcta tgcctcgggc   8160
atccaagcag caagcgcgtt acgccgtggg tcgatgtttg atgttatgga gcagcaacga   8220
tgttacgcag cagggcagtc gccctaaaac aaagttaaac atcatggggg aagcggtgat   8280
cgccgaagta tcgactcaac tatcagaggt agttggcgtc atcgagcgcc atctcgaacc   8340
gacgttgctg gccgtacatt tgtacggctc cgcagtggat ggcggcctga agccacacag   8400
tgatattgat ttgctggtta cggtgaccgt aaggcttgat gaaacaacgc ggcgagcttt   8460
gatcaacgac cttttggaaa cttcggcttc ccctggagag agcgagattc tccgcgctgt   8520
```

```
agaagtcacc attgttgtgc acgacgacat cattccgtgg cgttatccag ctaagcgcga    8580
actgcaattt ggagaatggc agcgcaatga cattcttgca ggtatcttcg agccagccac    8640
gatcgacatt gatctggcta tcttgctgac aaaagcaaga gaacatagcg ttgccttggt    8700
aggtccagcg gcggaggaac tctttgatcc ggttcctgaa caggatctat ttgaggcgct    8760
aaatgaaacc ttaacgctat ggaactcgcc gcccgactgg gctggcgatg agcgaaatgt    8820
agtgcttacg ttgtcccgca tttggtacag cgcagtaacc ggcaaaatcg cgccgaagga    8880
tgtcgctgcc gactgggcaa tggagcgcct gccggcccag tatcagcccg tcatacttga    8940
agctagacag gcttatcttg gacaagaaga agatcgcttg gcctcgcgcg cagatcagtt    9000
ggaagaattt gtccactacg tgaaaggcga gatcaccaag gtagtcggca ataatgtctt    9060
agctagaaat tcgttcaagc cgacgccgct tcgccggcgt taactcaagc gattagatgc    9120
actaagcaca taattgctca cagccaaact atcaggtcaa gtctgctttt attatttta     9180
agcgtgcata ataagcccta cacaaattgg gagatatatc atgcatgacc aaaatccctt    9240
aacgtgagtt ttcgttccac tgagcgtcag accccgtaga aaagatcaaa ggatcttctt    9300
gagatccttt ttttctgcgc gtaatctgct gcttgcaaac aaaaaaacca ccgctaccag    9360
cggtggtttg tttgccggat caagagctac caactctttt tccgaaggta actggcttca    9420
gcagagcgca gataccaaat actgtccttc tagtgtagcc gtagttaggc caccacttca    9480
agaactctgt agcaccgcct acatacctcg ctctgctaat cctgttacca gtggctgctg    9540
ccagtggcga taagtcgtgt cttaccgggt tggactcaag acgatagtta ccggataagg    9600
cgcagcggtc gggctgaacg gggggttcgt gcacacagcc cagcttggag cgaacgacct    9660
acaccgaact gagatacccta cagcgtgagc tatgagaaag cgccacgctt cccgaaggga    9720
gaaaggcgga caggtatccg gtaagcggca gggtcggaac aggagagcgc acgagggagc    9780
ttccaggggg aaacgcctgg tatctttata gtcctgtcgg gtttcgccac ctctgacttg    9840
agcgtcgatt tttgtgatgc tcgtcagggg ggcggagcct atggaaaaac gccagcaacg    9900
cggccttttt acggttcctg gccttttgct ggccttttgc tcacatgttc tttcctgcgt    9960
tatccctga ttctgtggat aaccgtatta ccgcctttga gtgagctgat accgctcgcc    10020
gcagccgaac gaccgagcgc agcgagtcag tgagcgagga agcggaagag cgcctgatgc    10080
ggtattttct ccttacgcat ctgtgcggta tttcacaccg catatggtgc actctcagta    10140
caatctgctc tgatgccgca tagttaagcc agtatacact ccgctatcgc tacgtgactg    10200
ggtcatggct gcgccccgac acccgccaac cccgctgac gcgccctgac gggcttgtct    10260
gctcccggca tccgcttaca gacaagctgt gaccgtctcc gggagctgca tgtgtcagag    10320
gttttcaccg tcatcaccga aacgcgcgag gcagggtgcc ttgatgtggg cgccggcggt    10380
cgagtggcga cggcgcggct tgtccgcgcc ctggtagatt gcctggccgt aggccagcca    10440
tttttgagcg ccagcggcc gcgataggcc gacgcgaagc ggcggggcgt agggagcgca    10500
gcgaccgaag ggtaggcgct ttttgcagct cttcggctgt gcgctggcca gacagttatg    10560
cacaggccag gcgggtttta agagttttaa taagttttaa agagttttag gcggaaaaat    10620
cgccttttt ctcttttata tcagtcactt acatgtgtga ccggttccca atgtacggct    10680
ttgggttccc aatgtacggg ttccggttcc caatgtacgg ctttgggttc ccaatgtacg    10740
tgctatccac aggaaagaga ccttttcgac cttttttccc tgctagggca atttgcccta    10800
gcatctgctc cgtacattag gaaccggcgg atgcttcgcc ctcgatcagg ttgcggtagc    10860
```

```
gcatgactag gatcgggcca gcctgccccg cctcctcctt caaatcgtac tccggcaggt   10920
catttgaccc gatcagcttg cgcacggtga aacagaactt cttgaactct ccggcgctgc   10980
cactgcgttc gtagatcgtc ttgaacaacc atctggcttc tgccttgcct gcggcgcggc   11040
gtgccaggcg gtagagaaaa cggccgatgc cgggatcgat caaaaagtaa tcggggtgaa   11100
ccgtcagcac gtccgggttc ttgccttctg tgatctcgcg gtacatccaa tcagctagct   11160
cgatctcgat gtactccggc cgcccggttt cgctctttac gatcttgtag cggctaatca   11220
aggcttcacc ctcggatacc gtcaccaggc ggccgttctt ggccttcttc gtacgctgca   11280
tggcaacgtg cgtggtgttt aaccgaatgc aggtttctac caggtcgtct ttctgctttc   11340
cgccatcggc tcgccggcag aacttgagta cgtccgcaac gtgtggacgg aacacgcggc   11400
cgggcttgtc tcccttccct tcccggtatc ggttcatgga ttcggttaga tgggaaaccg   11460
ccatcagtac caggtcgtaa tcccacacac tggccatgcc ggccggccct gcggaaacct   11520
ctacgtgccc gtctggaagc tcgtagcgga tcacctcgcc agctcgtcgg tcacgcttcg   11580
acagacggaa aacggccacg tccatgatgc tgcgactatc gcgggtgccc acgtcataga   11640
gcatcggaac gaaaaaatct ggttgctcgt cgcccttggg cggcttccta atcgacggcg   11700
caccggctgc cggcggttgc cgggattctt tgcggattcg atcagcggcc gcttgccacg   11760
attcaccggg gcgtgcttct gcctcgatgc gttgccgctg gcggcctgc gcggccttca   11820 acttctccac caggtcatca cccagcgcgc cgccgatttg taccgggccg gatggtttgc   11880
gaccgtcacg ccgattcctc gggcttgggg gttccagtgc cattgcaggg ccggcagaca   11940
acccagccgc ttacgcctgg ccaaccgccc gttcctccac acatggggca ttccacggcg   12000
tcggtgcctg gttgttcttg attttccatg ccgcctcctt tagccgctaa aattcatcta   12060
ctcatttatt catttgctca tttactctgg tagctgcgcg atgtattcag atagcagctc   12120
ggtaatggtc ttgccttggc gtaccgcgta catcttcagc ttggtgtgat cctccgccgg   12180
caactgaaag ttgacccgct tcatggctgg cgtgtctgcc aggctggcca acgttgcagc   12240
cttgctgctg cgtgcgctcg gacggccggc acttagcgtg tttgtgcttt tgctcatttt   12300
ctctttacct cattaactca aatgagtttt gatttaattt cagcggccag cgcctggacc   12360
tcgcgggcag cgtcgccctc gggttctgat tcaagaacgg ttgtgccggc ggcggcagtg   12420
cctgggtagc tcacgcgctg cgtgatacgg gactcaagaa tgggcagctc gtacccggcc   12480
agcgcctcgg caacctcacc gccgatgcgc gtgcctttga tcgcccgcga cacgacaaag   12540
gccgcttgta gccttccatc cgtgacctca atgcgctgct taaccagctc caccaggtcg   12600
gcggtggccc atatgtcgta agggcttggc tgcaccggaa tcagcacgaa gtcggctgcc   12660
ttgatcgcgg acacagccaa gtccgccgcc tggggcgctc cgtcgatcac tacgaagtcg   12720
cgccggccga tggccttcac gtcgcggtca atcgtcgggc ggtcgatgcc gacaacggtt   12780
agcggttgat cttcccgcac ggccgcccaa tcgcgggcac tgccctgggg atcggaatcg   12840
actaacagaa catcggcccc ggcgagttgc agggcgcggg ctagatgggt tgcgatggtc   12900
gtcttgcctg accgcctttt ctggttaagt acagcgataa ccttcatgcg ttccccttgc   12960
gtatttgttt atttactcat cgcatcatat acgcagcgac cgcatgacgc aagctgtttt   13020
actcaaatac acatcacctt tttagacggc ggcgctcggt ttcttcagcg ccaagctgg   13080 ccggccaggc cgccagcttg gcatcagaca aacggccag gatttcatgc agccgcacgg   13140
ttgagacgtg cgcgggcggc tcgaacacgt acccggccgc gatcatctcc gcctcgatct   13200
cttcggtaat gaaaaacggt tcgtcctggc cgtcctggtg cggtttcatg cttgttcctc   13260
```

-continued

```
ttggcgttca ttctcggcgg ccgccagggc gtcggcctcg gtcaatgcgt cctcacggaa    13320
ggcaccgcgc cgcctggcct cggtgggcgt cacttcctcg ctgcgctcaa gtgcgcggta    13380
cagggtcgag cgatgcacgc caagcagtgc agccgcctct ttcacggtgc ggccttcctg    13440
gtcgatcagc tcgcgggcgt gcgcgatctg tgccggggtg agggtagggc gggggccaaa    13500
cttcacgcct cgggccttgg cggcctcgcg cccgctccgg gtgcggtcga tgattaggga    13560
acgctcgaac tcggcaatgc cggcgaacac ggtcaacacc atgcggccgg ccggcgtggt    13620
ggtgtcggcc cacggctctg ccaggctacg caggcccgcg ccggcctcct ggatgcgctc    13680
ggcaatgtcc agtaggtcgc gggtgctgcg ggccaggcgg tctagcctgg tcactgtcac    13740
aacgtcgcca gggcgtaggt ggtcaagcat cctggccagc tccgggcggt cgcgcctggt    13800
gccggtgatc ttctcggaaa acagcttggt gcagccggcc gcgtgcagtt cggcccgttg    13860
gttggtcaag tcctggtcgt cggtgctgac gcgggcatag cccagcaggc cagcggcggc    13920
gctcttgttc atggcgtaat gtctccggtt ctagtcgcaa gtattctact ttatgcgact    13980
aaaacacgcg acaagaaaac gccaggaaaa gggcagggcg gcagcctgtc gcgtaactta    14040
ggacttgtgc gacatgtcgt tttcagaaga cggctgcact gaacgtcaga agccgactgc    14100
actatagcag cggaggggtt ggatcaaagt act                                 14133
```

<210> SEQ ID NO 18
<211> LENGTH: 610
<212> TYPE: PRT
<213> ORGANISM: Artificial Sequence
<220> FEATURE:
<223> OTHER INFORMATION: Chimaera GRF3-GIF1

<400> SEQUENCE: 18

```
Met Asp Leu Gln Leu Lys Gln Trp Arg Ser Gln Gln Gln Gln His
1               5                  10                  15

Gln Thr Glu Ser Glu Glu Gln Pro Ser Ala Ala Lys Ile Pro Lys His
            20                  25                  30

Val Phe Asp Gln Ile His Ser His Thr Ala Thr Ser Thr Ala Leu Pro
        35                  40                  45

Leu Phe Thr Pro Glu Pro Thr Ser Ser Lys Leu Ser Ser Leu Ser Pro
    50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Leu Pro Ile Lys Lys Ser
            100                 105                 110

Leu Leu His Leu Ser Pro Ser Tyr Phe Leu His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
                165                 170                 175

Arg Gly Arg Asn Arg Ser Arg Lys Pro Val Glu Thr Pro Thr Thr Val
            180                 185                 190

Asn Ala Thr Ala Thr Ser Met Ala Ser Ser Val Ala Ala Ala Ala Thr
        195                 200                 205
```

```
Thr Thr Thr Ala Thr Thr Thr Ser Thr Phe Ala Phe Gly Gly Gly
    210             215                 220

Gly Ser Glu Glu Val Val Gly Gln Gly Gly Ser Phe Phe Phe Ser Gly
225                 230                 235                 240

Ser Ser Asn Ser Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
        275                 280                 285

Arg Pro Phe Phe Asp Asp Trp Pro Arg Ser Ser Leu Gln Glu Ala Asp
    290                 295                 300

Asn Ser Ser Ser Pro Met Ser Ser Ala Thr Cys Leu Ser Ile Ser Met
305                 310                 315                 320

Pro Gly Asn Ser Ser Asp Val Ser Leu Lys Leu Ser Thr Gly Asn
                325                 330                 335

Glu Glu Gly Ala Arg Ser Asn Asn Gly Arg Asp Gln Gln Asn Met
                340                 345                 350

Ser Trp Trp Ser Gly Gly Ser Asn His His His Asn Met Gly
        355                 360                 365

Gly Pro Leu Ala Glu Ala Leu Arg Ser Ser Ser Ser Ser Pro Thr
370                 375                 380

Ser Val Leu His Gln Leu Gly Val Ser Thr Gln Ala Phe His Val Asp
385                 390                 395                 400

Met Gln Gln His Leu Met Gln Met Gln Pro Met Met Ala Gly Tyr Tyr
            405                 410                 415

Pro Ser Asn Val Thr Ser Asp His Ile Gln Gln Tyr Leu Asp Glu Asn
                420                 425                 430

Lys Ser Leu Ile Leu Lys Ile Val Glu Ser Gln Asn Ser Gly Lys Leu
            435                 440                 445

Ser Glu Cys Ala Glu Asn Gln Ala Arg Leu Gln Arg Asn Leu Met Tyr
450                 455                 460

Leu Ala Ala Ile Ala Asp Ser Gln Pro Gln Pro Pro Ser Val His Ser
465                 470                 475                 480

Gln Tyr Gly Ser Ala Gly Gly Met Ile Gln Gly Glu Gly Gly Ser
                485                 490                 495

His Tyr Leu Gln Gln Gln Ala Thr Gln Gln Gln Met Thr Gln
            500                 505                 510

Gln Ser Leu Met Ala Ala Arg Ser Ser Met Leu Tyr Ala Gln Gln Gln
            515                 520                 525

Gln Gln Gln Gln Pro Tyr Ala Thr Leu Gln His Gln Leu His His
    530                 535                 540

Ser Gln Leu Gly Met Ser Ser Ser Ser Gly Gly Gly Ser Ser Gly
545                 550                 555                 560

Leu His Ile Leu Gln Gly Glu Ala Gly Gly Phe His Asp Phe Gly Arg
                565                 570                 575

Gly Lys Pro Glu Met Gly Ser Gly Gly Gly Glu Gly Arg Gly Gly
            580                 585                 590

Ser Ser Gly Asp Gly Gly Glu Thr Leu Tyr Leu Lys Ser Ser Asp Asp
        595                 600                 605

Gly Asn
    610
```

<210> SEQ ID NO 19
<211> LENGTH: 2954
<212> TYPE: DNA
<213> ORGANISM: Artificial Sequence
<220> FEATURE:
<223> OTHER INFORMATION: Chimaera GRF3-GIF1 DNA

<400> SEQUENCE: 19

| | | | | | |
|---|---|---|---|---|---|
| atggatttgc | aactgaaaca | atggagaagc | cagcagcagc | aacaacatca | gacagagtca | 60 |
| gaagaacaac | cttctgcagc | taagatacca | aaacatgtct | ttgaccagat | tcattctcac | 120 |
| actgcaactt | ctactgctct | tcctctcttt | accoctgagc | ctacttcttc | taaactctcc | 180 |
| tctttgtctc | ctgattcttc | ctccaggttc | cccagtgagt | cttttcttcc | tcttatctta | 240 |
| tctttcttga | taaagaatta | gacttttcat | tcatatagtt | tgtgtttaat | tgattttgat | 300 |
| tccttttgt | agagatgggg | agcttcttta | gctgggcaca | gtggcaagaa | cttgaactac | 360 |
| aagctctgat | ctacaggtac | atgttggctg | gtgctgctgt | tcctcaggag | ctccttttac | 420 |
| caatcaagaa | aagccttctc | catctatctc | cttcctactt | tcttcaccat | cctcttcaac | 480 |
| acctacctca | ttaccaacct | gcttgtgagt | ctcgagaaca | gtcttcatct | atctattttt | 540 |
| taaatataaa | tgggttttgt | gctactggtg | ttggagttgg | gttcccaaga | tccagactttt | 600 |
| caatattagt | atattatctc | gttttgccaa | tcttgaagat | ctaaacatgt | gtgaatggga | 660 |
| ttaagtagga | ttagaatctt | gttattgatc | tgatatgtga | tatgaatgtt | gaaaacaggg | 720 |
| tatttgggaa | gggcagcgat | ggatcctgag | ccaggcagat | gcaggagaac | ggatggtaag | 780 |
| aagtggagat | gttcaagaga | cgtcttcgct | ggccacaagt | attgcgagcg | ccacatgcac | 840 |
| cgtggccgca | accgttcaag | aaagcctgtg | gaaactccaa | ccaccgtcaa | tgcaactgcc | 900 |
| acgtccatgg | cttcatcagt | agcagccgca | gccaccacta | caacagcaac | aacaacatct | 960 |
| acgtttgctt | tggtggtgg | tggtggtagt | gaggaagtgg | ttggtcaagg | aggatctttc | 1020 |
| ttcttctctg | gctcttctaa | ctcttcatct | gaacttctcc | accttagtca | aaggtaataa | 1080 |
| aaagaaactg | tttttttttc | tcttaggtct | gtctgtttta | gctgttgaac | tttatggtca | 1140 |
| aaacattaaa | cttaaacaca | ttgactttt | tatttcttta | gtgttgagcc | aataagattc | 1200 |
| atggttgaga | ttttagacaa | ttgttttgaa | taataatgaa | atcgatttaa | agcaatactg | 1260 |
| attcttgatt | tattagtatg | aagtatgaac | taatgatata | cacaacttgg | tttgtatgtt | 1320 |
| catagcgatg | ttgtgaagag | aggggtaatg | ttggaaattg | agagacacat | ccttatcatt | 1380 |
| ttagggttgg | ttggttttgtt | tgtttgttga | attatgagtt | tgatttcatt | gtgaaaatat | 1440 |
| cttttctttct | tttttcttat | tgtgttgaga | gataatgata | acattggatt | tgatagaatc | 1500 |
| tataatttga | agctaggtgt | gagactttc | aaacagagaa | aatagaaaga | gagagaaatg | 1560 |
| gtaggaccctt | agtgaaagct | gacccatata | tgtctcatat | cttgcagaaa | agttaaagct | 1620 |
| tttagattct | tctgcaccca | cctcccctat | ccacacacaa | cacatgatat | acaaaacact | 1680 |
| cactttataa | ttctatttct | atttactgct | taatcaattc | ttataaaacc | cacattaaaa | 1740 |
| ggtactttta | aagcctataa | actaatataa | aggctactac | tgtctgcaac | tttgttgttg | 1800 |
| aagcctaaat | gtggtttctc | ttttgacaaa | ttattgcttt | tgtgctttgt | tttcaccaat | 1860 |
| gagatgtgga | ttctgttaac | agttgttcgg | agatgaagca | agaaagcaac | aacatgaaca | 1920 |
| acaagaggcc | atacgagtcc | cacatcggat | tcagtaacaa | cagatcagat | ggaggacaca | 1980 |
| tcctgaggcc | cttctttgac | gattggcctc | gttcttcgct | ccaagaagct | gacaatagtt | 2040 |
| caagccccat | gagctcagcc | acttgtctct | ccatctccat | gcccgggaac | tcttcctcag | 2100 |

```
acgtctctct gaagctgtcc acaggcaacg aagagggagc ccggagcaac aacaatggga    2160
gagatcagca aaacatgagc tggtggagcg gtggaggttc caaccaccat catcacaaca    2220
tgggcggacc attggccgaa gccctgagat cttcttcctc atcttcccca accagtgttc    2280
tccatcagct tggtgtctcg acacaagcct ttcatgtcga catgcaacag cacctgatgc    2340
agatgcagcc catgatggct ggttactacc ccagcaatgt tacctctgat catatccaac    2400
agtacttgga cgaaaacaaa tcgttgattc tgaagattgt tgagtctcaa aactctggaa    2460
agcttagcga atgcgccgag aatcaagcaa ggcttcaacg caacctaatg tacctagctg    2520
caatagcaga ttctcagcct cagccaccaa gtgtgcatag ccagtatgga tctgctggtg    2580
gtgggatgat tcaggagaa ggagggtcac actatttgca gcagcaacaa gcgactcaac    2640
agcaacagat gactcagcag tctctaatgg cggctcgatc ttcaatgttg tatgctcagc    2700
aacagcagca gcagcagcct tacgcgacgc ttcagcatca gcaattgcac catagccagc    2760
ttggaatgag ctcgagcagc ggaggaggag gaagcagtgg tctccatatc cttcagggag    2820
aggctggtgg gtttcatgat tttggccgtg ggaagccgga aatgggaagt ggtggtggcg    2880
gtgaaggcag aggaggaagt tcaggggatg gtggagaaac cctttacttg aaatcatcag    2940
atgatgggaa ttga                                                     2954

<210> SEQ ID NO 20
<211> LENGTH: 14072
<212> TYPE: DNA
<213> ORGANISM: Artificial Sequence
<220> FEATURE:
<223> OTHER INFORMATION: Binary vector pJD149 for expression of chimeric
      protein GRF3-GIF1

<400> SEQUENCE: 20
ttgatcccga ggggaaccct gtggttggca tgcacataca aatggacgaa cggataaacc     60
ttttcacgcc cttttaaata tccgttattc taataaacgc tcttttctct taggtttacc    120
cgccaatata tcctgtcaaa cactgatagt ttaaactgaa ggcgggaaac gacaatctga    180
tccaagctca agctgctcta gccaatacgc aaaccgcctc tccccgcgcg ttggccgatt    240
cattaatgca gctggcacga caggtttccc gactggaaag cgggcagtga gcgcaacgca    300
attaatgtga gttagctcac tcattaggca ccccaggctt tacactttat gcttccggct    360
cgtatgttgt gtggaattgt gagcggataa caatttcaca caggaaacag ctatgaccat    420
gattacgaat tgaaaacgca ggcccattta tcctccaa aacaaagaa gcaatagaat    480 ccggaactga attaaaaaca tacaaaccaa gaggtaaaga aaacgcatag ttagctaacc    540
cgtccgcaag acgattgacc tccctataca cgtgagaaat acggactaac cagtcccttg    600
atatgaagcc ataacacaaa cgtagtagga agatagagg atgagaatcc ggtatccctg    660
tctgtaaaaa cccaaccacg atcttcgaat ccacttccag ctcaaggcgt gttattcctt    720
gctcccagac tatgtgtaac ccatagtaga gtccccacaa ctctgctagt ggcgctgaac    780
agatttcgat attcaaagca aaaccccaa cccagttctc gttcccatca cgcaccgcac    840
ctcccgctgc tgctaacccg ggattctctc tcgaggctcc atccatgttc aactagcctg    900
atgaatttat taaactcatg tttccatttt ttttcccacc agttatgtta gtttgattaa    960 ttttcagtc aatttggca taacgcttta aaataattat atcaaaataa tatttcagt    1020 ttttctgcaa cagattcatt ccaccaagaa ttcagccgat tctacccgaa ttaatattac    1080 catttctcgga ctagatctat gaacgaaggt acaaaattaa tcagttaaaa aagaaaatag    1140
```

```
agtggcaagt actacatcta gtgccgtatg atatgataat ataggaacct aaacgaattt   1200
tatactaatt caaatttaaa agtagttagg tttgtcacaa atgcaaatta caaattatat   1260
cgacgtaacg cttactcatt aaataatcta aattacttgg ttaaaagact aattaaatat   1320
tcttaacaag taggcttttg ttttcattat aaaacaaatt aaaaagctat actaatataa   1380
aaatggagat tggtatttcc aaagcagcaa agacagaaaa actgcaggtt attatctctc   1440
catcttcatc ttgcagagtg gttctttctg ggttttctga cttgcttttc atttttttat   1500
tgatacaaat gttaaaccaa ttattttaaa tagtctttga gattaatgaa gagagatttg   1560
tgaacacaat taataaagag ttatactata gtagtagtct tttttactgt atagtatttt   1620
ctccccgcat ctgtcttgtc tcactgtctt tttctcgcaa gtctctctat taaaaacctc   1680
tttccctcta ctctgtcctt tctctctctg cagaagaagc tcagatacag aaactgacta   1740
ccaagaacaa agcttttttcc ttcgagcaaa gaaagttctt ttttcttttc ttttgctctt   1800
cgtaacccaa ccaacaagac tttcataagc tattaaatca gaaccctgga agacaaaaag   1860
gggaaaaacc attatcctta aagtaaccaa cacttctctc tctctttctt caggtaccat   1920
ggatttgcaa ctgaaacaat ggagaagcca gcagcagcaa caacatcaga cagagtcaga   1980
agaacaacct tctgcagcta agataccaaa acatgtcttt gaccagattc attctcacac   2040
tgcaacttct actgctcttc ctctctttac ccctgagcct acttcttcta aactctcctc   2100
tttgtctcct gattcttcct ccaggttccc cagtgagtct tttcttcctc ttatcttatc   2160
tttcttgata aagaattaga cttttcattc atatagtttg tgtttaattg attttgattc   2220
ctttttgtag agatggggag cttctttagc tgggcacagt ggcaagaact tgaactacaa   2280
gctctgatct acaggtacat gttggctggt gctgctgttc ctcaggagct ccttttacca   2340
atcaagaaaa gccttctcca tctatctcct tcctactttc ttcaccatcc tcttcaacac   2400
ctacctcatt accaacctgc ttgtgagtct cgagaacagt cttcatctat ctattttta   2460 aatataaatg ggttttgtgc tactggtgtt ggagttgtgt tcccaagatc cagactttca   2520
atattagtat attatctcgt tttgccaatc ttgaagatct aaacatgtgt gaatgggatt   2580
aagtaggatt agaatcttgt tattgatctg atatgtgata tgaatgttga aaacagggta   2640
tttgggaagg gcagcgatgg atcctgagcc aggcagatgc aggagaacgg atggtaagaa   2700
gtggagatgt tcaagagacg tcttcgctgg ccacaagtat tgcgagcgcc acatgcaccg   2760
tggccgcaac cgttcaagaa agcctgtgga aactccaacc accgtcaatg caactgccac   2820
gtccatggct tcatcagtag cagccgcagc caccactaca acagcaacaa caacatctac   2880
gtttgctttt ggtggtggtg gtggtagtga ggaagtggtt ggtcaaggag gatctttctt   2940
cttctctggc tcttctaact cttcatctga acttctccac cttagtcaaa ggtaataaaa   3000
agaaactgtt tttttttctc ttaggtctgt ctgttttagc tgttgaactt tatggtcaaa   3060
acattaaact taaacacatt gacttttta tttctttagt gttgagccaa taagattcat   3120
ggttgagatt ttagacaatt gttttgaata ataatgaaat cgatttaaag caatactgat   3180
tcttgattta ttagtatgaa gtatgaacta atgatataca caacttggtt tgtatgttca   3240
tagcgatgtt gtgaagagag gggtaatgtt ggaaattgag agacacatcc ttatcatttt   3300
agggttggtt ggtttgtttg tttgttgaat tatgagtttg atttcattgt gaaaatatct   3360
ttctttcttt tttcttattg tgttgagaga taatgataac attggatttg atagaatcta   3420
taatttgaag ctaggtgtga gacttttcaa acagagaaaa tagaaagaga gagaaatggt   3480
```

```
aggaccttag tgaaagctga cccatatatg tctcatatct tgcagaaaag ttaaagcttt    3540
tagattcttc tgcacccacc tcccctatcc acacacaaca catgatatac aaaacactca    3600
ctttataatt ctatttctat ttactgctta atcaattctt ataaaaccca cattaaaagg    3660
tacttttaaa gcctataaac taatataaag gctactactg tctgcaactt tgttgttgaa    3720
gcctaaatgt ggtttctctt ttgacaaatt attgcttttg tgctttgttt tcaccaatga    3780
gatgtggatt ctgttaacag ttgttcggag atgaagcaag aaagcaacaa catgaacaac    3840
aagaggccat acgagtccca catcggattc agtaacaaca gatcagatgg aggacacatc    3900
ctgaggccct tctttgacga ttggcctcgt tcttcgctcc aagaagctga caatagttca    3960
agccccatga gctcagccac ttgtctctcc atctccatgc ccgggaactc ttcctcagac    4020
gtctctctga agctgtccac aggcaacgaa gagggagccc ggagcaacaa caatgggaga    4080
gatcagcaaa acatgagctg gtggagcggt ggaggttcca accaccatca tcacaacatg    4140
ggcggaccat tggccgaagc cctgagatct tcttcctcat cttccccaac cagtgttctc    4200
catcagcttg gtgtctcgac acaagccttt catgtcgaca tgcaacagca cctgatgcag    4260
atgcagccca tgatggctgg ttactacccc agcaatgtta cctctgatca tatccaacag    4320
tacttggacg aaaacaaatc gttgattctg aagattgttg agtctcaaaa ctctggaaag    4380
cttagcgaat gcgccgagaa tcaagcaagg cttcaacgca acctaatgta cctagctgca    4440
atagcagatt ctcagcctca gccaccaagt gtgcatagcc agtatggatc tgctggtggt    4500
gggatgattc agggagaagg agggtcacac tatttgcagc agcaacaagc gactcaacag    4560
caacagatga ctcagcagtc tctaatggcg gctcgatctt caatgttgta tgctcagcaa    4620
cagcagcagc agcagcctta cgcgacgctt cagcatcagc aattgcacca tagccagctt    4680
ggaatgagct cgagcagcgg aggaggagga agcagtggtc tccatatcct tcagggagag    4740
gctggtgggt ttcatgattt tggccgtggg aagccggaaa tgggaagtgg tggtggcggt    4800
gaaggcagag gaggaagttc aggggatggt ggagaaaccc tttacttgaa atcatcagat    4860
gatgggaatt gaaagccatg ggggctgcag agctttcgtt cgtatcatcg gtttcgacaa    4920
cgttcgtcaa gttcaatgca tcagtttcat tgcgcacaca ccagaatcct actgagttcg    4980
agtattatgg cattgggaaa catgtttttc ttgtaccatt tgttgtgctt gtaatttact    5040 gtgttttta ttcggttttc gctatcgaac tgtgaaatgg aaatggatgg agaagagtta    5100
atgaatgata tggtcctttt gttcattctc aaattaatat tatttgtttt ttctcttatt    5160
tgttgtgtgt tgaatttgaa aatataagag atatgcaaac attttgtttt gagtaaaaat    5220
gtgtcaaatc gtggcctcta atgaccgaag ttaatatgag gagtaaaaca cttgtagttg    5280
taccattatg cttattcact aggcaacaaa tatattttca gacctagaaa agctgcaaat    5340
gttactgaat acaagtatgt cctcttgtgt tttagacatt tatgaacttt cctttatgta    5400
attttccaga atccttgtca gattctaatc attgctttat aattatagtt atactcatgg    5460
atttgtagtt gagtatgaaa atattttta atgcatttta tgacttgcca attgattgac    5520
aacatgcatc aatcgaagct tggcactggc cgtcgtttta caacgtcgtg actgggaaaa    5580
ccctggcgtt acccaactta atcgccttgc agcacatccc cctttcgcca gctgcgtaa    5640 tagcgaagag gcccgcaccg atcgcccttc ccaacagttg cgcagcctga atggcgaatg    5700
ctagagcagc ttgccaacat ggtggagcac gacactctcg tctactccaa gaatatcaaa    5760
gatacagtct cagaagacca aagggctatt gagacttttt aacaaagggt aatatcggga    5820
aacctcctcg gattccattg cccagctatc tgtcacttca tcaaaaggac agtagaaaag    5880
```

```
gaaggtggca cctacaaatg ccatcattgc gataaaggaa aggctatcgt tcaagatgcc    5940
tctgccgaca gtggtcccaa agatggaccc ccacccacga ggagcatcgt ggaaaaagaa    6000
gacgttccaa ccacgtcttc aaagcaagtg gattgatgtg ataacatggt ggagcacgac    6060
actctcgtct actccaagaa tatcaaagat acagtctcag aagaccaaag gctattgag     6120 acttttcaac aaagggtaat atcgggaaac ctcctcggat tccattgccc agctatctgt    6180
cacttcatca aaaggacagt agaaaaggaa ggtggcacct acaaatgcca tcattgcgat    6240
aaaggaaagg ctatcgttca agatgcctct gccgacagtg gtcccaaaga tggaccccca    6300
cccacgagga gcatcgtgga aaagaagac gttccaacca cgtcttcaaa gcaagtggat      6360
tgatgtgata tctccactga cgtaagggat gacgcacaat cccactatcc ttcgcaagac    6420
ccttcctcta tataaggaag ttcatttcat ttggagagga cacgctgaaa tcaccagtct    6480
ctctctacaa atctatctct ctcgattcgc agatctgtcg atcgaccatg gggattgaac    6540
aagatggatt gcacgcaggt tctccggccg cttgggtgga gaggctattc ggctatgact    6600
gggcacaaca gacaatcggc tgctctgatg ccgccgtgtt ccggctgtca gcgcaggggc    6660
gcccggttct ttttgtcaag accgacctgt ccggtgccct gaatgaactc caggacgagg    6720
cagcgcggct atcgtggctg gccacgacgg gcgttccttg cgcagctgtg ctcgacgttg    6780
tcactgaagc gggaagggac tggctgctat tgggcgaagt gccggggcag gatctcctgt    6840
catctcacct tgctcctgcc gagaaagtat ccatcatggc tgatgcaatg cggcggctgc    6900
atacgcttga tccggctacc tgcccattcg accaccaagc gaaacatcgc atcgagcgag    6960
cacgtactcg gatggaagcc ggtcttgtcg atcaggatga tctggacgaa gagcatcagg    7020
ggctcgcgcc agccgaactg ttcgccaggc tcaaggcgcg catgcccgac ggcgaggatc    7080
tcgtcgtgac acatggcgat gcctgcttgc cgaatatcat ggtggaaaat ggccgctttt    7140
ctggattcat cgactgtggc cggctgggtg tggcggaccg ctatcaggac atagcgttgg    7200
ctacccgtga tattgctgaa gagcttggcg gcgaatgggc tgaccgcttc ctcgtgcttt    7260
acggtatcgc cgctcccgat tcgcagcgca tcgccttcta tcgccttctt gacgagttct    7320
tctgagcggg actctggggt tcggatcgat cctctagcta gagtcgatcg acatcgagtt    7380
tctccataat aatgtgtgag tagttcccag ataagggaat tagggttctt atagggtttc    7440
gctcacgtgt tgagcatata agaaaccctt agtatgtatt tgtatttgta aaatacttct    7500
atcaataaaa tttctaattc ctaaaaccaa aatccagtac taaaatccag atcacctaaa    7560
gtccctatag atcccccgaa ttaattcggc gttaattcag tacattaaaa acgtccgcaa    7620
tgtgttatta agttgtctaa gcgtcaattt gtttacacca caatatatcc tgccaccagc    7680
cagccaacag ctccccgacc ggcagctcgg cacaaaatca ccactcgata caggcagccc    7740
atcagtccgg gacggcgtca gcgggagagc cgttgtaagg cggcagactt tgctcatgtt    7800
accgatgcta ttcggaagaa cggcaactaa gctgccgggt ttgaaacacg gatgatctcg    7860
cggagggtag catgttgatt gtaacgatga cagagcgttg ctgcctgtga tcaattcggg    7920
cacgaaccca gtggacataa gcctcgttcg gttcgtaagc tgtaatgcaa gtagcgtaac    7980
tgccgtcacg caactggtcc agaaccttga ccgaacgcag cggtggtaac ggcgcagtgg    8040
cggttttcat ggcttcttgt tatgacatgt ttttttgggg tacagtctat gcctcgggca    8100
tccaagcagc aagcgcgtta cgccgtgggt cgatgtttga tgttatggag cagcaacgat    8160
gttacgcagc agggcagtcg ccctaaaaca aagttaaaca tcatggggga agcggtgatc    8220
```

```
gccgaagtat cgactcaact atcagaggta gttggcgtca tcgagcgcca tctcgaaccg    8280
acgttgctgg ccgtacattt gtacggctcc gcagtggatg gcggcctgaa gccacacagt    8340
gatattgatt tgctggttac ggtgaccgta aggcttgatg aaacaacgcg gcgagctttg    8400
atcaacgacc ttttggaaac ttcggcttcc cctggagaga gcgagattct ccgcgctgta    8460
gaagtcacca ttgttgtgca cgacgacatc attccgtggc gttatccagc taagcgcgaa    8520
ctgcaatttg gagaatggca gcgcaatgac attcttgcag gtatcttcga gccagccacg    8580
atcgacattg atctggctat cttgctgaca aaagcaagag aacatagcgt tgccttggta    8640
ggtccagcgg cggaggaact ctttgatccg gttcctgaac aggatctatt tgaggcgcta    8700
aatgaaacct taacgctatg gaactcgccg cccgactggg ctggcgatga gcgaaatgta    8760
gtgcttacgt tgtcccgcat ttggtacagc gcagtaaccg gcaaaatcgc gccgaaggat    8820
gtcgctgccg actgggcaat ggagcgcctg ccggcccagt atcagcccgt catacttgaa    8880
gctagacagg cttatcttgg acaagaagaa gatcgcttgg cctcgcgcgc agatcagttg    8940
gaagaatttg tccactacgt gaaaggcgag atcaccaagg tagtcggcaa ataatgtcta    9000
gctagaaatt cgttcaagcc gacgccgctt cgccggcgtt aactcaagcg attagatgca    9060
ctaagcacat aattgctcac agccaaacta tcaggtcaag tctgcttta ttattttaa      9120 gcgtgcataa taagccctac acaaattggg agatatatca tgcatgacca aaatcccta     9180 acgtgagttt tcgttccact gagcgtcaga ccccgtagaa aagatcaaag gatcttcttg    9240
agatcctttt tttctgcgcg taatctgctg cttgcaaaca aaaaaccac cgctaccagc     9300 ggtggtttgt ttgccggatc aagagctacc aactctttt ccgaaggtaa ctggcttcag     9360
cagagcgcag ataccaaata ctgtccttct agtgtagccg tagttaggcc accacttcaa    9420
gaactctgta gcaccgccta catacctcgc tctgctaatc ctgttaccag tggctgctgc    9480
cagtggcgat aagtcgtgtc ttaccgggtt ggactcaaga cgatagttac cggataaggc    9540
gcagcggtcg ggctgaacgg ggggttcgtg cacacagccc agcttggagc gaacgaccta    9600
caccgaactg agatacctac agcgtgagct atgagaaagc gccacgcttc ccgaagggag    9660
aaaggcggac aggtatccgg taagcggcag ggtcggaaca ggagagcgca cgagggagct    9720
tccaggggga aacgcctggt atctttatag tcctgtcggg tttcgccacc tctgacttga    9780
gcgtcgattt ttgtgatgct cgtcaggggg cggagccta tggaaaaacg ccagcaacgc     9840
ggccttttta cggttcctgg ccttttgctg gccttttgct cacatgttct ttcctgcgtt    9900
atcccctgat tctgtggata accgtattac cgcctttgag tgagctgata ccgctcgccg    9960
cagccgaacg accgagcgca gcgagtcagt gagcgaggaa gcggaagagc gcctgatgcg    10020 gtatttctc cttacgcatc tgtgcggtat ttcacaccgc atatggtgca ctctcagtac     10080
aatctgctct gatgccgcat agttaagcca gtatacactc cgctatcgct acgtgactgg    10140 gtcatgctg cgccccgaca cccgccaaca cccgctgacg cgccctgacg ggcttgtctg     10200
ctcccggcat ccgcttacag acaagctgtg accgtctccg ggagctgcat gtgtcagagg    10260
ttttcaccgt catcaccgaa acgcgcgagg cagggtgcct tgatgtgggc gccggcggtc    10320
gagtggcgac ggcgcggctt gtccgcgccc tggtagattg cctggccgta ggccagccat    10380
ttttgagcgg ccagcggccg cgataggccg acgcgaagcg gcggggcgta gggagcgcag    10440
cgaccgaagg gtaggcgctt tttgcagctc ttcggctgtg cgctggccag acagttatgc    10500
acaggccagg cggttttaa gagttttaat aagttttaaa gagttttagg cggaaaaatc     10560
gccttttttc tcttttatat cagtcactta catgtgtgac cggttcccaa tgtacggctt    10620
```

```
tgggttccca atgtacgggt tccggttccc aatgtacggc tttgggttcc caatgtacgt   10680
gctatccaca ggaaagagac cttttcgacc tttttcccct gctagggcaa tttgccctag   10740
catctgctcc gtacattagg aaccggcgga tgcttcgccc tcgatcaggt tgcggtagcg   10800
catgactagg atcgggccag cctgccccgc ctcctccttc aaatcgtact ccggcaggtc   10860
atttgacccg atcagcttgc gcacggtgaa acagaacttc ttgaactctc cggcgctgcc   10920
actgcgttcg tagatcgtct tgaacaacca tctggcttct gccttgcctg cggcgcggcg   10980
tgccaggcgg tagagaaaac ggccgatgcc gggatcgatc aaaaagtaat cggggtgaac   11040
cgtcagcacg tccgggttct tgccttctgt gatctcgcgg tacatccaat cagctagctc   11100
gatctcgatg tactccggcc gcccggtttc gctctttacg atcttgtagc ggctaatcaa   11160
ggcttcaccc tcggataccg tcaccaggcg gccgttcttg gccttcttcg tacgctgcat   11220
ggcaacgtgc gtggtgttta accgaatgca ggtttctacc aggtcgtctt tctgctttcc   11280
gccatcggct cgccggcaga acttgagtac gtccgcaacg tgtggacgga acacgcggcc   11340
gggcttgtct cccttccctt cccggtatcg gttcatggat tcggttagat gggaaaccgc   11400
catcagtacc aggtcgtaat cccacacact ggccatgccg gccggccctg cggaaacctc   11460
tacgtgcccg tctggaagct cgtagcggat cacctcgcca gctcgtcggt cacgcttcga   11520
cagacggaaa acgccacgt ccatgatgct gcgactatcg cgggtgccca cgtcatagag   11580
```

```
ctcaaataca catcaccttt ttagacggcg gcgctcggtt tcttcagcgg ccaagctggc   13020
cggccaggcc gccagcttgg catcagacaa accggccagg atttcatgca gccgcacggt   13080
tgagacgtgc gcgggcggct cgaacacgta cccggccgcg atcatctccg cctcgatctc   13140
ttcggtaatg aaaaacggtt cgtcctggcc gtcctggtgc ggtttcatgc ttgttcctct   13200
tggcgttcat tctcggcggc cgccagggcg tcggcctcgg tcaatgcgtc ctcacggaag   13260
gcaccgcgcc gcctggcctc ggtgggcgtc acttcctcgc tgcgctcaag tgcgcggtac   13320
agggtcgagc gatgcacgcc aagcagtgca gccgcctctt tcacggtgcg gccttcctgg   13380
tcgatcagct cgcggggcgtg cgcgatctgt gccggggtga gggtagggcg ggggccaaac   13440
ttcacgcctc gggccttggc ggcctcgcgc ccgctccggg tgcggtcgat gattagggaa   13500
cgctcgaact cggcaatgcc ggcgaacacg tcaacacca tgcggccggc cggcgtggtg   13560
gtgtcggccc acggctctgc caggctacgc aggcccgcgc cggcctcctg gatgcgctcg   13620
gcaatgtcca gtaggtcgcg ggtgctgcgg gccaggcggt ctagcctggt cactgtcaca   13680
acgtcgccag ggcgtaggtg gtcaagcatc ctggccagct ccgggcggtc gcgcctggtg   13740
ccggtgatct tctcggaaaa cagcttggtg cagccggccg cgtgcagttc ggcccgttgg   13800
ttggtcaagt cctggtcgtc ggtgctgacg cgggcatagc ccagcaggcc agcggcggcg   13860
ctcttgttca tggcgtaatg tctccggttc tagtcgcaag tattctactt tatgcgacta   13920
aaacacgcga caagaaaacg ccaggaaaag ggcagggcgg cagcctgtcg cgtaacttag   13980
gacttgtgcg acatgtcgtt ttcagaagac ggctgcactg aacgtcagaa gccgactgca   14040
ctatagcagc ggaggggttg gatcaaagta ct                                 14072
```

<210> SEQ ID NO 21
<211> LENGTH: 610
<212> TYPE: PRT
<213> ORGANISM: Artificial Sequence
<220> FEATURE:
<223> OTHER INFORMATION: Chimaera rGRF3-GIF1

<400> SEQUENCE: 21

```
Met Asp Leu Gln Leu Lys Gln Trp Arg Ser Gln Gln Gln Gln His
1               5                   10                  15

Gln Thr Glu Ser Glu Glu Gln Pro Ala Ala Lys Ile Pro Lys His
                20                  25                  30

Val Phe Asp Gln Ile His Ser His Thr Ala Thr Ser Thr Ala Leu Pro
            35                  40                  45

Leu Phe Thr Pro Glu Pro Thr Ser Ser Lys Leu Ser Ser Leu Ser Pro
        50                  55                  60

Asp Ser Ser Ser Arg Phe Pro Lys Met Gly Ser Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Leu Pro Ile Lys Lys Ser
            100                 105                 110

Leu Leu His Leu Ser Pro Ser Tyr Phe Leu His His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
```

-continued

```
                165                 170                 175
Arg Gly Arg Asn Arg Ser Arg Lys Pro Val Glu Thr Pro Thr Thr Val
            180                 185                 190
Asn Ala Thr Ala Thr Ser Met Ala Ser Ser Val Ala Ala Ala Ala Thr
            195                 200                 205
Thr Thr Thr Ala Thr Thr Thr Ser Thr Phe Ala Phe Gly Gly Gly Gly
            210                 215                 220
Gly Ser Glu Glu Val Val Gly Gln Gly Gly Ser Phe Phe Phe Ser Gly
225                 230                 235                 240
Ser Ser Asn Ser Ser Ser Glu Leu Leu His Leu Ser Gln Ser Cys Ser
            245                 250                 255
Glu Met Lys Gln Glu Ser Asn Asn Met Asn Asn Lys Arg Pro Tyr Glu
            260                 265                 270
Ser His Ile Gly Phe Ser Asn Asn Arg Ser Asp Gly His Ile Leu
            275                 280                 285
Arg Pro Phe Phe Asp Asp Trp Pro Arg Ser Ser Leu Gln Glu Ala Asp
            290                 295                 300
Asn Ser Ser Ser Pro Met Ser Ser Ala Thr Cys Leu Ser Ile Ser Met
305                 310                 315                 320
Pro Gly Asn Ser Ser Ser Asp Val Ser Leu Lys Leu Ser Thr Gly Asn
                    325                 330                 335
Glu Glu Gly Ala Arg Ser Asn Asn Asn Gly Arg Asp Gln Gln Asn Met
            340                 345                 350
Ser Trp Trp Ser Gly Gly Gly Ser Asn His His His Asn Met Gly
            355                 360                 365
Gly Pro Leu Ala Glu Ala Leu Arg Ser Ser Ser Ser Ser Pro Thr
            370                 375                 380
Ser Val Leu His Gln Leu Gly Val Ser Thr Gln Ala Phe His Val Asp
385                 390                 395                 400
Met Gln Gln His Leu Met Gln Met Gln Pro Met Met Ala Gly Tyr Tyr
                    405                 410                 415
Pro Ser Asn Val Thr Ser Asp His Ile Gln Gln Tyr Leu Asp Glu Asn
            420                 425                 430
Lys Ser Leu Ile Leu Lys Ile Val Glu Ser Gln Asn Ser Gly Lys Leu
            435                 440                 445
Ser Glu Cys Ala Glu Asn Gln Ala Arg Leu Gln Arg Asn Leu Met Tyr
450                 455                 460
Leu Ala Ala Ile Ala Asp Ser Gln Pro Gln Pro Pro Ser Val His Ser
465                 470                 475                 480
Gln Tyr Gly Ser Ala Gly Gly Met Ile Gln Gly Glu Gly Ser
            485                 490                 495
His Tyr Leu Gln Gln Gln Gln Ala Thr Gln Gln Gln Met Thr Gln
            500                 505                 510
Gln Ser Leu Met Ala Ala Arg Ser Ser Met Leu Tyr Ala Gln Gln
            515                 520                 525
Gln Gln Gln Gln Pro Tyr Ala Thr Leu Gln His Gln Leu His His
            530                 535                 540
Ser Gln Leu Gly Met Ser Ser Ser Gly Gly Gly Ser Ser Gly
545                 550                 555                 560
Leu His Ile Leu Gln Gly Glu Ala Gly Gly Phe His Asp Phe Gly Arg
                    565                 570                 575
Gly Lys Pro Glu Met Gly Ser Gly Gly Gly Glu Gly Arg Gly Gly
            580                 585                 590
```

Ser Ser Gly Asp Gly Gly Glu Thr Leu Tyr Leu Lys Ser Ser Asp Asp
        595                 600                 605

Gly Asn
    610

<210> SEQ ID NO 22
<211> LENGTH: 2954
<212> TYPE: DNA
<213> ORGANISM: Artificial Sequence
<220> FEATURE:
<223> OTHER INFORMATION: Chimaera rGRF3-GIF1

<400> SEQUENCE: 22

| | | | | | |
|---|---|---|---|---|---|
| atggatttgc | aactgaaaca | atggagaagc | cagcagcagc | aacaacatca | gacagagtca | 60 |
| gaagaacaac | cttctgcagc | taagatacca | aaacatgtct | tgaccagat | tcattctcac | 120 |
| actgcaactt | ctactgctct | tcctctcttt | accccctgagc | ctacttcttc | taaactctcc | 180 |
| tctttgtctc | ctgattcttc | ctccaggttc | cccagtgagt | cttttcttcc | tcttatctta | 240 |
| tctttcttga | taaagaatta | gactttcat | tcatatagtt | tgtgtttaat | tgattttgat | 300 |
| tccttttgt | agagatgggg | agcttcttta | gctgggcaca | gtggcaagaa | cttgaactac | 360 |
| aagctctgat | ctacaggtac | atgttggctg | gtgctgctgt | tcctcaggag | ctccttttac | 420 |
| caatcaagaa | aagccttctc | catctatctc | cttcctactt | tcttcaccat | cctcttcaac | 480 |
| acctacctca | ttaccaacct | gcttgtgagt | ctcgagaaca | gtcttcatct | atctattttt | 540 |
| taaatataaa | tgggttttgt | gctactggtg | ttggagttgt | gttcccaaga | tccagacttt | 600 |
| caatattagt | atattatctc | gttttgccaa | tcttgaagat | ctaaacatgt | gtgaatggga | 660 |
| ttaagtagga | ttagaatctt | gttattgatc | tgatatgtga | tatgaatgtt | gaaaacaggg | 720 |
| tatttgggaa | gggcagcgat | ggatcctgag | ccaggcagat | gcaggagaac | ggatggtaag | 780 |
| aagtggagat | gttcaagaga | cgtcttcgct | ggccacaagt | attgcgagcg | ccacatgcac | 840 |
| cgtggccgca | accgttctag | aaaaccagta | gagactccaa | ccaccgtcaa | tgcaactgcc | 900 |
| acgtccatgg | cttcatcagt | agcagccgca | gccaccacta | caacagcaac | aacaacatct | 960 |
| acgtttgctt | ttggtggtgg | tggtggtagt | gaggaagtgg | ttggtcaagg | aggatctttc | 1020 |
| ttcttctctg | gctcttctaa | ctcttcatct | gaacttctcc | accttagtca | aaggtaataa | 1080 |
| aaagaaactg | tttttttttc | tcttaggtct | gtctgtttta | gctgttgaac | tttatggtca | 1140 |
| aaacattaaa | cttaaacaca | ttgactttt | tatttcttta | gtgttgagcc | aataagattc | 1200 |
| atggttgaga | ttttagacaa | ttgttttgaa | taataatgaa | atcgatttaa | agcaatactg | 1260 |
| attcttgatt | tattagtatg | aagtatgaac | taatgatata | cacaacttgg | tttgtatgtt | 1320 |
| catagcgatg | ttgtgaagag | aggggtaatg | ttggaaattg | agacacat | ccttatcatt | 1380 |
| ttagggttgg | ttggtttgtt | tgtttgttga | attatgagtt | tgatttcatt | gtgaaaatat | 1440 |
| ctttctttct | tttttcttat | tgtgttgaga | gataatgata | acattggatt | tgatagaatc | 1500 |
| tataatttga | agctaggtgt | gagacttttc | aaacagagaa | aatagaaaga | gagagaaatg | 1560 |
| gtaggacctt | agtgaaagct | gacccatata | tgtctcatat | cttgcagaaa | agttaaagct | 1620 |
| tttagattct | tctgcaccca | cctccccctat | ccacacacaa | cacatgatat | acaaaacact | 1680 |
| cactttataa | ttctatttct | atttactgct | taatcaattc | ttataaaacc | cacattaaaa | 1740 |
| ggtacttta | aagcctataa | actaatataa | aggctactac | tgtctgcaac | tttgttgttg | 1800 |
| aagcctaaat | gtggtttctc | ttttgacaaa | ttattgcttt | tgtgctttgt | tttcaccaat | 1860 |

```
gagatgtgga ttctgttaac agttgttcgg agatgaagca agaaagcaac aacatgaaca    1920
acaagaggcc atacgagtcc cacatcggat tcagtaacaa cagatcagat ggaggacaca    1980
tcctgaggcc cttctttgac gattggcctc gttcttcgct ccaagaagct gacaatagtt    2040
caagccccat gagctcagcc acttgtctct ccatctccat gcccgggaac tcttcctcag    2100
acgtctctct gaagctgtcc acaggcaacg aagagggagc ccggagcaac aacaatggga    2160
gagatcagca aacatgagc tggtggagcg gtggaggttc caaccaccat catcacaaca    2220
tgggcggacc attggccgaa gccctgagat cttcttcctc atcttcccca accagtgttc    2280
tccatcagct tggtgtctcg acacaagcct tcatgtcga catgcaacag cacctgatgc    2340
agatgcagcc catgatggct ggttactacc ccagcaatgt tacctctgat catatccaac    2400
agtacttgga cgaaaacaaa tcgttgattc tgaagattgt tgagtctcaa aactctggaa    2460
agcttagcga atgcgccgag aatcaagcaa ggcttcaacg caacctaatg tacctagctg    2520
caatagcaga ttctcagcct cagccaccaa gtgtgcatag ccagtatgga tctgctggtg    2580
gtgggatgat tcagggagaa ggagggtcac actatttgca gcagcaacaa gcgactcaac    2640
agcaacagat gactcagcag tctctaatgg cggctcgatc ttcaatgttg tatgctcagc    2700
aacagcagca gcagcagcct tacgcgacgc ttcagcatca gcaattgcac catagccagc    2760
ttggaatgag ctcgagcagc ggaggaggag gaagcagtgg tctccatatc cttcagggag    2820
aggctggtgg gtttcatgat tttggccgtg ggaagccgga aatggaagt ggtggtggcg    2880 gtgaaggcag aggaggaagt tcaggggatg gtggagaaac cctttacttg aaatcatcag    2940
atgatgggaa ttga                                                      2954
```

<210> SEQ ID NO 23
<211> LENGTH: 14072
<212> TYPE: DNA
<213> ORGANISM: Artificial Sequence
<220> FEATURE:
<223> OTHER INFORMATION: Binary vector pJD150 for expression of chimeric
      protein rGRF3-GIF1

<400> SEQUENCE: 23

```
ttgatcccga ggggaacccct gtggttggca tgcacataca aatggacgaa cggataaacc      60
ttttcacgcc cttttaaata tccgttattc taataaacgc tcttttctct taggtttacc     120
cgccaatata tcctgtcaaa cactgatagt ttaaactgaa ggcgggaaac gacaatctga     180
tccaagctca agctgctcta gccaatacgc aaaccgcctc tccccgcgcg ttggccgatt     240
cattaatgca gctggcacga caggtttccc gactggaaag cgggcagtga gcgcaacgca     300
attaatgtga gttagctcac tcattaggca ccccaggctt tacactttat gcttccggct     360
cgtatgttgt gtggaattgt gagcggataa caatttcaca caggaaacag ctatgaccat     420
gattacgaat tgaaaacgca ggcccattta tcctccaa acaaaagaa gcaatagaat     480 ccggaactga attaaaaaca tacaaaccaa gaggtaaaga aaacgcatag ttagctaacc     540
cgtccgcaag acgattgacc tccctataca cgtgagaaat acggactaac cagtcccttg     600
atatgaagcc ataacacaaa cgtagtagga aagatagagg atgagaatcc ggtatccctg     660
tctgtaaaaa cccaaccacg atcttcgaat ccacttccag ctcaaggcgt gttattcctt     720
gctcccagac tatgtgtaac ccatagtaga gtccccacaa ctctgctagt ggcgctgaac     780
agatttcgat attcaaagca aaaccccaa cccagttctc gttcccatca cgcaccgcac     840
ctcccgctgc tgctaacccg ggattctctc tcgaggctcc atccatgttc aactagcctg     900
```

```
atgaatttat taaactcatg tttccatttt ttttcccacc agttatgtta gtttgattaa    960
tttttcagtc aattttggca taacgcttta aaataattat atcaaaataa tattttcagt   1020
ttttctgcaa cagattcatt ccaccaagaa ttcagccgat tctacccgaa ttaatattac   1080
cattttcgga ctagatctat gaacgaaggt acaaaattaa tcagttaaaa aagaaaatag   1140
agtggcaagt actacatcta gtgccgtatg atatgataat ataggaacct aaacgaattt   1200
tatactaatt caaatttaaa agtagttagg tttgtcacaa atgcaaatta caaattatat   1260
cgacgtaacg cttactcatt aaataatcta aattacttgg ttaaaagact aattaaatat   1320
tcttaacaag taggcttttg ttttcattat aaaacaaatt aaaagctat actaatataa    1380
aaatggagat tggtatttcc aaagcagcaa agacagaaaa actgcaggtt attatctctc   1440
catcttcatc ttgcagagtg gttctttctg ggttttctga cttgcttttc atttttttat   1500
tgatacaaat gttaaaccaa ttattttaaa tagtctttga gattaatgaa gagagatttg   1560
tgaacacaat taataaagag ttatactata gtagtagtct ttttactgt atagtatttt    1620
ctccccgcat ctgtcttgtc tcactgtctt tttctgcaa gtctctctat taaaaacctc    1680
tttccctcta ctctgtcctt tctctctctg cagaagaagc tcagatacag aaactgacta   1740
ccaagaacaa agcttttttcc ttcgagcaaa gaaagttctt ttttcttttc ttttgctctt  1800
cgtaacccaa ccaacaagac tttcataagc tattaaatca gaaccctgga agacaaaaag  1860
gggaaaaacc attatcctta aagtaaccaa cacttctctc tctctttctt caggtaccat   1920
ggatttgcaa ctgaaacaat ggagaagcca gcagcagcaa caacatcaga cagagtcaga   1980
agaacaacct tctgcagcta agataccaaa acatgtcttt gaccagattc attctcacac   2040
tgcaacttct actgctcttc ctctctttac ccctgagcct acttcttcta aactctcctc   2100
tttgtctcct gattcttcct ccaggttccc cagtgagtct tttcttcctc ttatcttatc   2160
tttcttgata aagaattaga cttttcattc atatagtttg tgtttaattg attttgattc   2220
cttttttgtag agatggggag cttctttagc tgggcacagt ggcaagaact tgaactacaa   2280
gctctgatct acaggtacat gttggctggt gctgctgttc ctcaggagct ccttttacca   2340
atcaagaaaa gccttctcca tctatctcct tcctactttc ttcaccatcc tcttcaacac   2400
ctacctcatt accaacctgc ttgtgagtct cgagaacagt cttcatctat ctatttttta   2460
aatataaatg ggttttgtgc tactggtgtt ggagttgtgt tcccaagatc cagactttca   2520
atattagtat attatctcgt tttgccaatc ttgaagatct aaacatgtgt gaatgggatt   2580
aagtaggatt agaatcttgt tattgatctg atatgtgata tgaatgttga aaacagggta   2640
tttgggaagg gcagcgatgg atcctgagcc aggcagatgc aggagaacgg atggtaagaa   2700
gtggagatgt tcaagagacg tcttcgctgg ccacaagtat tgcgagcgcc acatgcaccg   2760
tggccgcaac cgttctagaa aaccagtaga gactccaacc accgtcaatg caactgccac   2820
gtccatggct tcatcagtag cagccgcagc caccactaca acagcaacaa caacatctac   2880
gtttgctttt ggtggtggtg gtggtagtga ggaagtggtt ggtcaaggag atctttctt    2940
cttctctggc tcttctaact cttcatctga acttctccac cttagtcaaa ggtaataaaa   3000
agaaactgtt tttttttctc ttaggtctgt ctgttttagc tgttgaactt tatggtcaaa   3060
acattaaact taaacacatt gacttttta tttctttagt gttgagccaa taagattcat     3120
ggttgagatt ttagacaatt gttttgaata ataatgaaat cgatttaaag caatactgat   3180
tcttgattta ttagtatgaa gtatgaacta atgatataca caacttggtt tgtatgttca   3240
tagcgatgtt gtgaagagag gggtaatgtt ggaaattgag agacacatcc ttatcatttt   3300
```

```
agggttggtt ggtttgtttg tttgttgaat tatgagtttg atttcattgt gaaaatatct    3360
ttctttcttt tttcttattg tgttgagaga taatgataac attggatttg atagaatcta    3420
taatttgaag ctaggtgtga acttttcaa acagagaaaa tagaaagaga gagaaatggt     3480
aggaccttag tgaaagctga cccatatatg tctcatatct tgcagaaaag ttaaagcttt    3540
tagattcttc tgcacccacc tccctatcc acacacaaca catgatatac aaaacactca     3600
ctttataatt ctatttctat ttactgctta atcaattctt ataaaaccca cattaaaagg    3660
tacttttaaa gcctataaac taatataaag gctactactg tctgcaactt tgttgttgaa    3720
gcctaaatgt ggtttctctt ttgacaaatt attgcttttg tgctttgttt tcaccaatga    3780
gatgtggatt ctgttaacag ttgttcggag atgaagcaag aaagcaacaa catgaacaac    3840
aagaggccat acgagtccca catcggattc agtaacaaca gatcagatgg aggacacatc    3900
ctgaggccct tctttgacga ttggcctcgt tcttcgctcc aagaagctga caatagttca    3960
agccccatga gctcagccac ttgtctctcc atctccatgc ccgggaactc ttcctcagac    4020
gtctctctga agctgtccac aggcaacgaa gagggagccc ggagcaacaa caatgggaga    4080
gatcagcaaa acatgagctg gtggagcggt ggaggttcca accaccatca tcacaacatg    4140
ggcggaccat tggccgaagc cctgagatct tcttcctcat cttccccaac cagtgttctc    4200
catcagcttg tgtctcgac acaagccttt catgtcgaca tgcaacagca cctgatgcag     4260
atgcagccca tgatggctgg ttactacccc agcaatgtta cctctgatca tatccaacag    4320
tacttggacg aaaacaaatc gttgattctg aagattgttg agtctcaaaa ctctggaaag    4380
cttagcgaat gcgccgagaa tcaagcaagg cttcaacgca acctaatgta cctagctgca    4440
atagcagatt ctcagcctca gccaccaagt gtgcatagcc agtatggatc tgctggtggt    4500
gggatgattc agggagaagg agggtcacac tatttgcagc agcaacaagc gactcaacag    4560
caacagatga ctcagcagtc tctaatggcg gctcgatctt caatgttgta tgctcagcaa    4620
cagcagcagc agcagcctta cgcgacgctt cagcatcagc aattgcacca tagccagctt    4680
ggaatgagct cgagcagcgg aggaggagga agcagtggtc tccatatcct tcagggagag    4740
gctggtgggt ttcatgattt tggccgtggg aagccggaaa tgggaagtgg tggtggcggt    4800
gaaggcagag gaggaagttc aggggatggt ggagaaaccc tttacttgaa atcatcagat    4860
gatgggaatt gaaagccatg ggggctgcag agctttcgtt cgtatcatcg gtttcgacaa    4920
cgttcgtcaa gttcaatgca tcagtttcat tgcgcacaca ccagaatcct actgagttcg    4980
agtattatgg cattgggaaa catgttttc ttgtaccatt tgttgtgctt gtaatttact     5040 gtgttttta ttcggttttc gctatcgaac tgtgaaatgg aaatggatgg agaagagtta     5100
atgaatgata tggtccttt gttcattctc aaattaatat tatttgtttt ttctcttatt     5160
tgttgtgtgt tgaatttgaa aatataagag atatgcaaac attttgtttt gagtaaaaat    5220
gtgtcaaatc gtggcctcta atgaccgaag ttaatgagag gagtaaaaca cttgtagttg    5280
taccattatg cttattcact aggcaacaaa tatattttca gacctagaaa agctgcaaat    5340
gttactgaat acaagtatgt cctcttgtgt tttagacatt tatgaacttt cctttatgta    5400
attttccaga atccttgtca gattctaatc attgctttat aattatagtt atactcatgg    5460
atttgtagtt gagtatgaaa atatttttta atgcatttta tgacttgcca attgattgac    5520
aacatgcatc aatcgaagct tggcactggc cgtcgtttta caacgtcgtg actgggaaaa    5580
ccctggcgtt acccaactta atcgccttgc agcacatccc cctttcgcca gctggcgtaa    5640
```

```
tagcgaagag gcccgcaccg atcgcccttc caacagttg cgcagcctga atggcgaatg    5700
ctagagcagc ttgccaacat ggtggagcac gacactctcg tctactccaa gaatatcaaa    5760
gatacagtct cagaagacca aagggctatt gagactttc aacaaagggt aatatcggga    5820
aacctcctcg gattccattg cccagctatc tgtcacttca tcaaaaggac agtagaaaag    5880
gaaggtggca cctacaaatg ccatcattgc gataaaggaa aggctatcgt tcaagatgcc    5940
tctgccgaca gtggtcccaa agatggaccc ccacccacga ggagcatcgt ggaaaaagaa    6000
gacgttccaa ccacgtcttc aaagcaagtg gattgatgtg ataacatggt ggagcacgac    6060
actctcgtct actccaagaa tatcaaagat acagtctcag aagaccaaag gctattgag    6120 acttttcaac aaagggtaat atcgggaaac ctcctcggat tccattgccc agctatctgt    6180
cacttcatca aaaggacagt agaaaaggaa ggtggcacct acaaatgcca tcattgcgat    6240
aaaggaaagg ctatcgttca agatgcctct gccgacagtg gtcccaaaga tggaccccca    6300
cccacgagga gcatcgtgga aaagaagac gttccaacca cgtcttcaaa gcaagtggat    6360
tgatgtgata tctccactga cgtaagggat gacgcacaat cccactatcc ttcgcaagac    6420
ccttcctcta taaggaag ttcatttcat ttggagagga cacgctgaaa tcaccagtct    6480
ctctctacaa atctatctct ctcgattcgc agatctgtcg atcgaccatg gggattgaac    6540
aagatggatt gcacgcaggt tctccggccg cttgggtgga aggctattc ggctatgact    6600 gggcacaaca gacaatcggc tgctctgatg ccgccgtgtt ccggctgtca gcgcagggc    6660 gcccggttct ttttgtcaag accgacctgt ccggtgccct gaatgaactc caggacgagg    6720
cagcgcggct atcgtggctg gccacgacgg gcgttccttg cgcagctgtg ctcgacgttg    6780
tcactgaagc gggaagggac tggctgctat gggcgaagt gccggggcag gatctcctgt    6840
catctcacct tgctcctgcc gagaaagtat ccatcatggc tgatgcaatg cggcggctgc    6900
atacgcttga tccggctacc tgcccattcg accaccaagc gaaacatcgc atcgagcgag    6960
cacgtactcg gatggaagcc ggtcttgtcg atcaggatga tctggacgaa gagcatcagg    7020
ggctcgcgcc agccgaactg ttcgccaggc tcaaggcgcg catgcccgac ggcgaggatc    7080
tcgtcgtgac acatggcgat gcctgcttgc cgaatatcat ggtggaaaat ggccgctttt    7140
ctggattcat cgactgtggc cggctgggtg tggcggaccg ctatcaggac atagcgttgg    7200
ctacccgtga tattgctgaa gagcttggcg gcgaatggc tgaccgcttc ctcgtgcttt    7260
acggtatcgc cgctcccgat tcgcagcgca tcgccttcta tcgccttctt gacgagttct    7320
tctgagcggg actctggggt tcggatcgat cctctagcta gagtcgatcg acatcgagtt    7380
tctccataat aatgtgtgag tagttcccag ataagggaat tagggttctt atagggtttc    7440
gctcacgtgt tgagcatata agaaacccctt agtatgtatt tgtatttgta aaatacttct    7500
atcaataaaa tttctaattc ctaaaaccaa aatccagtac taaaatccag atcacctaaa    7560
gtccctatag atccccgaa ttaattcggc gttaattcag tacattaaaa acgtccgcaa    7620
tgtgttatta agttgtctaa gcgtcaattt gtttacacca aatatatcc tgccaccagc    7680 cagccaacag ctccccgacc ggcagctcgg cacaaaatca ccactcgata caggcagccc    7740
atcagtccgg gacggcgtca gcgggagagc cgttgtaagg cggcagactt tgctcatgtt    7800
accgatgcta ttcggaagaa cggcaactaa gctgccgggt ttgaaacacg gatgatctcg    7860
cggagggtag catgttgatt gtaacgatga cagagcgttg ctgcctgtga tcaattcggg    7920
cacgaaccca gtggacataa gcctcgttcg gttcgtaagc tgtaatgcaa gtagcgtaac    7980
tgccgtcacg caactggtcc agaaccttga ccgaacgcag cggtggtaac ggcgcagtgg    8040
```

```
cggttttcat ggcttcttgt tatgacatgt ttttttgggg tacagtctat gcctcgggca    8100
tccaagcagc aagcgcgtta cgccgtgggt cgatgtttga tgttatggag cagcaacgat    8160
gttacgcagc agggcagtcg ccctaaaaca aagttaaaca tcatgggGga agcggtgatc    8220
gccgaagtat cgactcaact atcagaggta gttggcgtca tcgagcgcca tctcgaaccg    8280
acgttgctgg ccgtacattt gtacggctcc gcagtggatg gcggcctgaa gccacacagt    8340
gatattgatt tgctggttac ggtgaccgta aggcttgatg aaacaacgcg gcgagctttg    8400
atcaacgacc ttttggaaac ttcggcttcc cctggagaga gcgagattct ccgcgctgta    8460
gaagtcacca ttgttgtgca cgacgacatc attccgtggc gttatccagc taagcgcgaa    8520
ctgcaatttg gagaatggca gcgcaatgac attcttgcag gtatcttcga gccagccacg    8580
atcgacattg atctggctat cttgctgaca aaagcaagag aacatagcgt tgccttggta    8640
ggtccagcgg cggaggaact ctttgatccg gttcctgaac aggatctatt tgaggcgcta    8700
aatgaaacct aacgctatg gaactcgccg cccgactggg ctggcgatga gcgaaatgta    8760
gtgcttacgt tgtcccgcat ttggtacagc gcagtaaccg gcaaaatcgc gccgaaggat    8820
gtcgctgccg actgggcaat ggagcgcctg ccggcccagt atcagcccgt catacttgaa    8880
gctagacagg cttatcttgg acaagaagaa gatcgcttgg cctcgcgcgc agatcagttg    8940
gaagaatttg tccactacgt gaaaggcgag atcaccaagg tagtcggcaa ataatgtcta    9000
gctagaaatt cgttcaagcc gacgccgctt cgccggcgtt aactcaagcg attagatgca    9060
ctaagcacat aattgctcac agccaaacta tcaggtcaag tctgctttta ttattttaa    9120
gcgtgcataa taagccctac acaaattggg agatatatca tgcatgacca aaatccctta    9180
acgtgagttt tcgttccact gagcgtcaga ccccgtagaa aagatcaaag gatcttcttg    9240
agatcctttt tttctgcgcg taatctgctg cttgcaaaca aaaaaccac cgctaccagc    9300
ggtggtttgt ttgccggatc aagagctacc aactcttttt ccgaaggtaa ctggcttcag    9360
cagagcgcag ataccaaata ctgtccttct agtgtagccg tagttaggcc accacttcaa    9420
gaactctgta gcaccgccta catacctcgc tctgctaatc ctgttaccag tggctgctgc    9480
cagtggcgat aagtcgtgtc ttaccgggtt ggactcaaga cgatagttac cggataaggc    9540
gcagcggtcg ggctgaacgg ggggttcgtg cacacagccc agcttggagc gaacgaccta    9600
caccgaactg agatacctac agcgtgagct atgagaaagc gccacgcttc ccgaagggag    9660
aaaggcggac aggtatccgg taagcggcag ggtcggaaca ggagagcgca cgagggagct    9720
tccaggggga aacgcctggt atctttatag tcctgtcggg tttcgccacc tctgacttga    9780
gcgtcgattt ttgtgatgct cgtcaggggg gcggagccta tggaaaaacg ccagcaacgc    9840
ggcctttta cggttcctgg ccttttgctg gccttttgct cacatgttct ttcctgcgtt    9900
atcccctgat tctgtggata accgtattac cgcctttgag tgagctgata ccgctcgccg    9960
cagccgaacg accgagcgca gcgagtcagt gagcgaggaa gcggaagagc gcctgatgcg   10020
gtattttctc cttacgcatc tgtgcggtat ttcacaccgc atatggtgca ctctcagtac   10080
aatctgctct gatgccgcat agttaagcca gtatacactc cgctatcgct acgtgactgg   10140
gtcatgctg cgccccgaca cccgccaaca cccgctgacg cgccctgacg ggcttgtctg   10200
ctcccggcat ccgcttacag acaagctgtg accgtctccg ggagctgcat gtgtcagagg   10260
ttttcaccgt catcaccgaa acgcgcgagg cagggtgcct tgatgtgggc gccggcggtc   10320
gagtggcgac ggcgcggctt gtccgcgccc tggtagattg cctggccgta ggccagccat   10380
```

```
ttttgagcgg ccagcggccg cgataggccg acgcgaagcg gcggggcgta gggagcgcag    10440
cgaccgaagg gtaggcgctt tttgcagctc ttcggctgtg cgctggccag acagttatgc    10500
acaggccagg cgggttttaa gagttttaat aagttttaaa gagttttagg cggaaaaatc    10560
gccttttttc tcttttatat cagtcactta catgtgtgac cggttcccaa tgtacggctt    10620
tgggttccca atgtacgggt tccggttccc aatgtacggc tttgggttcc caatgtacgt    10680
gctatccaca ggaaagagac cttttcgacc tttttcccct gctagggcaa tttgccctag    10740
catctgctcc gtacattagg aaccggcgga tgcttcgccc tcgatcaggt tgcggtagcg    10800
catgactagg atcgggccag cctgccccgc ctcctccttc aaatcgtact ccggcaggtc    10860
atttgacccg atcagcttgc gcacggtgaa acagaacttc ttgaactctc cggcgctgcc    10920
actgcgttcg tagatcgtct tgaacaacca tctggcttct gccttgcctg cggcgcggcg    10980
tgccaggcgg tagagaaaac ggccgatgcc gggatcgatc aaaaagtaat cggggtgaac    11040
cgtcagcacg tccgggttct tgccttctgt gatctcgcgg tacatccaat cagctagctc    11100
gatctcgatg tactccggcc gcccggtttc gctctttacg atcttgtagc ggctaatcaa    11160
ggcttcaccc tcggatatccg tcaccaggcg gccgttcttg gccttcttcg tacgctgcat    11220
ggcaacgtgc gtggtgttta accgaatgca ggtttctacc aggtcgtctt tctgctttcc    11280
gccatcggct cgccggcaga acttgagtac gtccgcaacg tgtggacgga cacgcggcc    11340 gggcttgtct cccttccctt cccggtatcg gttcatggat tcggttagat gggaaaccgc    11400
catcagtacc aggtcgtaat cccacacact ggccatgccg gccggccctg cggaaacctc    11460
tacgtgcccg tctggaagct cgtagcggat cacctcgcca gctcgtcggt cacgcttcga    11520
cagacggaaa acggccacgt ccatgatgct gcgactatcg cgggtgccca cgtcatagag    11580
catcggaacg aaaaaatctg gttgctcgtc gcccttgggc ggcttcctaa tcgacgcgc    11640 accggctgcc ggcggttgcc gggattcttt gcggattcga tcagcggccg cttgccacga    11700
ttcaccgggg cgtgcttctg cctcgatgcg ttgccgctgg gcggcctgcg cggccttcaa    11760
cttctccacc aggtcatcac ccagcgccgc gccgatttgt accgggccgg atggtttgcg    11820
accgtcacgc cgattcctcg ggcttggggg ttccagtgcc attgcagggc ggcagacaa    11880 cccagccgct tacgcctggc caaccgcccg ttcctccaca catggggcat ccacggcgt    11940 cggtgcctgg ttgttcttga ttttccatgc cgcctccttt agccgctaaa attcatctac    12000
tcatttattc atttgctcat ttactctggt agctgcgcga tgtattcaga tagcagctcg    12060
gtaatggtct tgccttggcg taccgcgtac atcttcagct tggtgtgatc ctccgccggc    12120
aactgaaagt tgacccgctt catggctggc gtgtctgcca ggctggccaa cgttgcagcc    12180
ttgctgctgc gtgcgctcgg acggccggca cttagcgtgt ttgtgctttt gctcattttc    12240
tctttacctc attaactcaa atgagttttg atttaatttc agcggccagc gcctggacct    12300
cgcgggcagc gtcgccctcg ggttctgatt caagaacggt tgtgccggcg gcggcagtgc    12360
ctgggtagct cacgcgctgc gtgatacggg actcaagaat gggcagctcg tacccggcca    12420
gcgcctcggc aacctcaccg ccgatgcgcg tgcctttgat cgcccgcgac acgacaaagg    12480
ccgcttgtag ccttccatcc gtgacctcaa tgcgctgctt aaccagctcc accaggtcgg    12540
cggtggccca tatgtcgtaa gggcttggct gcaccggaat cagcacgaag tcggctgcct    12600
tgatcgcgga cacagccaag tccgccgcct ggggcgctcc gtcgatcact acgaagtcgc    12660 gccgccgat ggccttcacg tcgcggtcaa tcgtcgggcg gtcgatgccg acaacgtta    12720 gcggttgatc ttcccgcacg gccgcccaat cgcgggcact gccctgggga tcggaatcga    12780
```

```
ctaacagaac atcggcccg gcgagttgca gggcgcgggc tagatgggtt gcgatggtcg   12840
tcttgcctga cccgcctttc tggttaagta cagcgataac cttcatgcgt tccccttgcg   12900
tatttgttta tttactcatc gcatcatata cgcagcgacc gcatgacgca agctgtttta   12960
ctcaaataca catcaccttt ttagacggcg gcgctcggtt tcttcagcgg ccaagctggc   13020
cggccaggcc gccagcttgg catcagacaa accggccagg atttcatgca gccgcacggt   13080
tgagacgtgc gcgggcggct cgaacacgta cccggccgcg atcatctccg cctcgatctc   13140
ttcggtaatg aaaaacggtt cgtcctggcc gtcctggtgc ggtttcatgc ttgttcctct   13200
tggcgttcat tctcggcggc cgccaggcg tcggcctcgg tcaatgcgtc ctcacggaag   13260
gcaccgcgcc gcctggcctc ggtgggcgtc acttcctcgc tgcgctcaag tgcgcggtac   13320
agggtcgagc gatgcacgcc aagcagtgca gccgcctctt tcacggtgcg gccttcctgg   13380
tcgatcagct cgcgggcgtg cgcgatctgt gccggggtga gggtagggcg ggggccaaac   13440
ttcacgcctc gggccttggc ggcctcgcgc ccgctccggg tgcggtcgat gattagggaa   13500
cgctcgaact cggcaatgcc ggcgaacacg gtcaacacca tgcggccggc cggcgtggtg   13560
gtgtcggccc acggctctgc caggctacgc aggcccgcgc cggcctcctg gatgcgctcg   13620
gcaatgtcca gtaggtcgcg ggtgctgcgg gccaggcggt ctagcctggt cactgtcaca   13680
acgtcgccag ggcgtaggtg gtcaagcatc ctggccagct ccgggcggtc gcgcctggtg   13740
ccggtgatct tctcggaaaa cagcttggtg cagccggccg cgtgcagttc ggcccgttgg   13800
ttggtcaagt cctggtcgtc ggtgctgacg cgggcatagc ccagcaggcc agcggcggcg   13860
ctcttgttca tggcgtaatg tctccggttc tagtcgcaag tattctactt tatgcgacta   13920
aaacacgcga caagaaaacg ccaggaaaag ggcagggcgg cagcctgtcg cgtaacttag   13980
gacttgtgcg acatgtcgtt ttcagaagac ggctgcactg aacgtcagaa gccgactgca   14040
ctatagcagc ggaggggttg gatcaaagta ct                                  14072
```

<210> SEQ ID NO 24
<211> LENGTH: 902
<212> TYPE: PRT
<213> ORGANISM: Artificial Sequence
<220> FEATURE:
<223> OTHER INFORMATION: Chimaera rGRF3-GR-GIF1

<400> SEQUENCE: 24

```
Met Asp Leu Gln Leu Lys Gln Trp Arg Ser Gln Gln Gln Gln His
1               5                   10                  15

Gln Thr Glu Ser Glu Glu Gln Pro Ser Ala Ala Lys Ile Pro Lys His
            20                  25                  30

Val Phe Asp Gln Ile His Ser His Thr Ala Thr Ser Thr Ala Leu Pro
        35                  40                  45

Leu Phe Thr Pro Glu Pro Thr Ser Ser Lys Leu Ser Ser Leu Ser Pro
    50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Leu Pro Ile Lys Lys Ser
            100                 105                 110

Leu Leu His Leu Ser Pro Ser Tyr Phe Leu His Pro Leu Gln His
        115                 120                 125
```

```
Leu Pro His Tyr Gln Pro Ala Trp Tyr Leu Gly Arg Ala Ala Met Asp
            130                 135                 140

Pro Glu Pro Gly Arg Cys Arg Thr Asp Gly Lys Lys Trp Arg Cys
145                 150                 155                 160

Ser Arg Asp Val Phe Ala Gly His Lys Tyr Cys Glu Arg His Met His
                    165                 170                 175

Arg Gly Arg Asn Arg Ser Arg Lys Pro Val Glu Thr Pro Thr Thr Val
                180                 185                 190

Asn Ala Thr Ala Thr Ser Met Ala Ser Ser Val Ala Ala Ala Thr
            195                 200                 205

Thr Thr Thr Ala Thr Thr Thr Ser Thr Phe Ala Phe Gly Gly Gly
210                 215                 220

Gly Ser Glu Glu Val Val Gly Gln Gly Gly Ser Phe Phe Ser Gly
225                 230                 235                 240

Ser Ser Asn Ser Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
            275                 280                 285

Arg Pro Phe Phe Asp Asp Trp Pro Arg Ser Ser Leu Gln Glu Ala Asp
            290                 295                 300

Asn Ser Ser Ser Pro Met Ser Ser Ala Thr Cys Leu Ser Ile Ser Met
305                 310                 315                 320

Pro Gly Asn Ser Ser Ser Asp Val Ser Leu Lys Leu Ser Thr Gly Asn
                325                 330                 335

Glu Glu Gly Ala Arg Ser Asn Asn Asn Gly Arg Asp Gln Gln Asn Met
            340                 345                 350

Ser Trp Trp Ser Gly Gly Ser Asn His His His Asn Met Gly
            355                 360                 365

Gly Pro Leu Ala Glu Ala Leu Arg Ser Ser Ser Ser Ser Pro Thr
370                 375                 380

Ser Val Leu His Gln Leu Gly Val Ser Thr Gln Ala Phe His Val Asp
385                 390                 395                 400

Glu Ala Arg Lys Thr Lys Lys Ile Lys Gly Ile Gln Gln Ala Thr
                405                 410                 415

Ala Gly Val Ser Gln Asp Thr Ser Glu Asn Pro Asn Lys Thr Ile Val
            420                 425                 430

Pro Ala Ala Leu Pro Gln Leu Thr Pro Thr Leu Val Ser Leu Leu Glu
            435                 440                 445

Val Ile Glu Pro Glu Val Leu Tyr Ala Gly Tyr Asp Ser Ser Val Pro
450                 455                 460

Asp Ser Ala Trp Arg Ile Met Thr Thr Leu Asn Met Leu Gly Gly Arg
465                 470                 475                 480

Gln Val Ile Ala Ala Val Lys Trp Ala Lys Ala Ile Pro Gly Leu Arg
                485                 490                 495

Asn Leu His Leu Asp Asp Gln Met Thr Leu Leu Gln Tyr Ser Trp Met
            500                 505                 510

Phe Leu Met Ala Phe Ala Leu Gly Trp Arg Ser Tyr Arg Gln Ser Ser
            515                 520                 525

Gly Asn Leu Leu Cys Phe Ala Pro Asp Leu Ile Ile Asn Glu Gln Arg
            530                 535                 540

Met Ser Leu Pro Cys Met Tyr Asp Gln Cys Lys His Met Leu Phe Val
```

```
                545                 550                 555                 560
Ser Ser Glu Leu Gln Arg Leu Gln Val Ser Tyr Glu Tyr Leu Cys
            565                 570                 575
Met Lys Thr Leu Leu Leu Ser Ser Val Pro Lys Glu Gly Leu Lys
            580                 585                 590
Ser Gln Glu Leu Phe Asp Glu Ile Arg Met Thr Tyr Ile Lys Glu Leu
            595                 600                 605
Gly Lys Ala Ile Val Lys Arg Glu Gly Asn Ser Ser Gln Asn Trp Gln
    610                 615                 620
Arg Phe Tyr Gln Leu Thr Lys Leu Leu Asp Ser Met His Glu Val Val
625                 630                 635                 640
Glu Asn Leu Leu Thr Tyr Cys Phe Gln Thr Phe Leu Asp Lys Thr Met
                645                 650                 655
Ser Ile Glu Phe Pro Glu Met Leu Ala Glu Ile Ile Thr Asn Gln Ile
                660                 665                 670
Pro Lys Tyr Ser Asn Gly Asn Ile Lys Lys Leu Leu Phe His Gln Lys
            675                 680                 685
Gly Ser Val Asp Met Gln Gln His Leu Met Gln Met Gln Pro Met Met
    690                 695                 700
Ala Gly Tyr Tyr Pro Ser Asn Val Thr Ser Asp His Ile Gln Gln Tyr
705                 710                 715                 720
Leu Asp Glu Asn Lys Ser Leu Ile Leu Lys Ile Val Glu Ser Gln Asn
                725                 730                 735
Ser Gly Lys Leu Ser Glu Cys Ala Glu Asn Gln Ala Arg Leu Gln Arg
            740                 745                 750
Asn Leu Met Tyr Leu Ala Ala Ile Ala Asp Ser Gln Pro Gln Pro Pro
            755                 760                 765
Ser Val His Ser Gln Tyr Gly Ser Ala Gly Gly Met Ile Gln Gly
            770                 775                 780
Glu Gly Gly Ser His Tyr Leu Gln Gln Gln Ala Thr Gln Gln
785                 790                 795                 800
Gln Met Thr Gln Gln Ser Leu Met Ala Ala Arg Ser Ser Met Leu Tyr
                805                 810                 815
Ala Gln Gln Gln Gln Gln Pro Tyr Ala Thr Leu Gln His Gln
            820                 825                 830
Gln Leu His His Ser Gln Leu Gly Met Ser Ser Ser Gly Gly Gly
            835                 840                 845
Gly Ser Ser Gly Leu His Ile Leu Gln Gly Glu Ala Gly Gly Phe His
    850                 855                 860
Asp Phe Gly Arg Gly Lys Pro Glu Met Gly Ser Gly Gly Gly Glu
865                 870                 875                 880
Gly Arg Gly Gly Ser Ser Gly Asp Gly Gly Glu Thr Leu Tyr Leu Lys
            885                 890                 895
Ser Ser Asp Asp Gly Asn
            900

<210> SEQ ID NO 25
<211> LENGTH: 3830
<212> TYPE: DNA
<213> ORGANISM: Artificial Sequence
<220> FEATURE:
<223> OTHER INFORMATION: Chimaera rGRF3-GR-GIF1

<400> SEQUENCE: 25
atggatttgc aactgaaaca atggagaagc cagcagcagc aacaacatca gacagagtca      60
```

```
gaagaacaac cttctgcagc taagatacca aaacatgtct ttgaccagat tcattctcac    120
actgcaactt ctactgctct tcctctcttt acccctgagc ctacttcttc taaactctcc    180
tctttgtctc ctgattcttc ctccaggttc cccagtgagt cttttcttcc tcttatctta    240
tctttcttga taaagaatta gacttttcat tcatatagtt tgtgtttaat tgattttgat    300
tcctttttgt agagatgggg agcttcttta gctgggcaca gtggcaagaa cttgaactac    360
aagctctgat ctacaggtac atgttggctg gtgctgctgt tcctcaggag ctccttttac    420
caatcaagaa aagccttctc catctatctc cttcctactt tcttcaccat cctcttcaac    480
acctacctca ttaccaacct gcttgtgagt ctcgagaaca gtcttcatct atctattttt    540
taaatataaa tgggttttgt gctactggtg ttggagttgt gttcccaaga tccagacttt    600
caatattagt atattatctc gttttgccaa tcttgaagat ctaaacatgt gtgaatggga    660
ttaagtagga ttagaatctt gttattgatc tgatatgtga tatgaatgtt gaaaacaggg    720
tatttgggaa gggcagcgat ggatcctgag ccaggcagat gcaggagaac ggatggtaag    780
aagtggagat gttcaagaga cgtcttcgct ggccacaagt attgcgagcg ccacatgcac    840
cgtggccgca accgttctag aaaaccagta gagactccaa ccaccgtcaa tgcaactgcc    900
acgtccatgg cttcatcagt agcagccgca gccaccacta caacagcaac aacaacatct    960
acgtttgctt ttggtggtgg tggtggtagt gaggaagtgg ttggtcaagg aggatctttc   1020
ttcttctctg gctcttctaa ctcttcatct gaacttctcc accttagtca aggtaataa    1080 aaagaaactg ttttttttttc tcttaggtct gtctgtttta gctgttgaac tttatggtca   1140
aaacattaaa cttaaacaca ttgactttt tatttcttta gtgttgagcc aataagattc    1200
atggttgaga tttagacaa ttgttttgaa taataatgaa atcgatttaa agcaatactg    1260
attcttgatt tattagtatg aagtatgaac taatgatata cacaacttgg tttgtatgtt    1320
catagcgatg ttgtgaagag aggggtaatg ttggaaattg agagacacat ccttatcatt   1380
ttagggttgg ttggtttgtt tgtttgttga attatgagtt tgatttcatt gtgaaaatat   1440 cttttctttct tttttcttat tgtgttgaga gataatgata acattggatt tgatagaatc   1500
tataatttga agctaggtgt gagacttttc aaacagagaa aatagaaaga gagagaaatg   1560
gtaggacctt agtgaaagct gacccatata tgtctcatat cttgcagaaa agttaaagct   1620
tttagattct tctgcaccca cctcccctat ccacacacaa cacatgatat acaaaacact   1680
cactttataa ttctatttct atttactgct taatcaattc ttataaaacc cacattaaaa   1740
ggtactttta aagcctataa actaatataa aggctactac tgtctgcaac tttgttgttg   1800
aagcctaaat gtggtttctc ttttgacaaa ttattgcttt tgtgctttgt tttcaccaat   1860
gagatgtgga ttctgttaac agttgttcgg agatgaagca agaaagcaac aacatgaaca   1920
acaagaggcc atacgagtcc cacatcggat tcagtaacaa cagatcagat ggaggacaca   1980
tcctgaggcc cttcttttgac gattggcctc gttcttcgct ccaagaagct gacaatagtt   2040
caagccccat gagctcagcc acttgtctct ccatctccat gcccgggaac tcttcctcag   2100
acgtctctct gaagctgtcc acaggcaacg aagagggagc ccggagcaac aacaatggga   2160
gagatcagca aaacatgagc tggtggagcg gtggaggttc caaccaccat catcacaaca   2220
tgggcggacc attggccgaa gccctgagat cttcttcctc atcttcccca accagtgttc   2280
tccatcagct tggtgtctcg acacaagcct ttcatgtcga cgaagctcga aaacaaaga   2340 aaaaaatcaa agggattcag caagccactg caggagtctc acaagacact tcggaaaatc   2400
```

```
ctaacaaaac aatagttcct gcagcattac cacagctcac ccctaccttg gtgtcactgc   2460
tggaggtgat tgaacccgag gtgttgtatg caggatatga tagctctgtt ccagattcag   2520
catggagaat tatgaccaca ctcaacatgt taggtgggcg tcaagtgatt gcagcagtga   2580
aatgggcaaa ggcgatacca ggcctgagaa acttacacct ggatgaccaa atgaccctgc   2640
tacagtactc atggatgttt ctcatggcat ttgccctggg ttggagatca tacagacaat   2700
caagtggaaa cctgctctgc tttgctcctg atctgattat taatgagcag agaatgtctc   2760
taccctgcat gtatgaccaa tgtaaacaca tgctgtttgt ctcctctgaa ttacaaagat   2820
tgcaggtatc ctatgaagag tatctctgta tgaaaacctt actgcttctc tcctcagttc   2880
ctaaggaagg tctgaagagc caagagttat ttgatgagat tcgaatgact tatatcaaag   2940
agctaggaaa agccatcgtc aaaagggaag ggaactccag tcagaactgg caacggtttt   3000
accaactgac aaagcttctg gactccatgc atgaggtggt tgagaatctc cttacctact   3060
gcttccagac attttttggat aagaccatga gtattgaatt cccagagatg ttagctgaaa   3120
tcatcactaa tcagatacca aaatattcaa atggaaatat caaaaagctt ctgtttcatc   3180
aaaaaggatc cgtcgacatg caacagcacc tgatgcagat gcagcccatg atggctggtt   3240
actaccccag caatgttacc tctgatcata tccaacagta cttggacgaa aacaaatcgt   3300
tgattctgaa gattgttgag tctcaaaact ctggaaagct tagcgaatgc gccgagaatc   3360
aagcaaggct tcaacgcaac ctaatgtacc tagctgcaat agcagattct cagcctcagc   3420
caccaagtgt gcatagccag tatggatctg ctggtggtgg gatgattcag ggagaaggag   3480
ggtcacacta tttgcagcag caacaagcga ctcaacagca acagatgact cagcagtctc   3540
taatggcggc tcgatcttca atgttgtatg ctcagcaaca gcagcagcag cagccttacg   3600
cgacgcttca gcatcagcaa ttgcaccata gccagcttgg aatgagctcg agcagcggag   3660
gaggaggaag cagtggtctc catatccttc agggagaggc tggtgggttt catgattttg   3720
gccgtgggaa gccggaaatg ggaagtggtg gtggcggtga aggcagagga ggaagttcag   3780
gggatggtgg agaaacccctt tacttgaaat catcagatga tgggaattga   3830
```

<210> SEQ ID NO 26  
<211> LENGTH: 14949  
<212> TYPE: DNA  
<213> ORGANISM: Artificial Sequence  
<220> FEATURE:  
<223> OTHER INFORMATION: Binary vector pJD155 for expression of chimeric protein rGRF3-GR-GIF1

<400> SEQUENCE: 26

```
ttgatcccga ggggaaccct gtggttggca tgcacataca aatggacgaa cggataaacc    60
ttttcacgcc cttttaaata tccgttattc aataaacgc tcttttctct taggtttacc    120
cgccaatata tcctgtcaaa cactgatagt ttaaactgaa ggcgggaaac gacaatctga   180
tccaagctca agctgctcta gccaatacgc aaaccgcctc tccccgcgcg ttggccgatt   240
cattaatgca gctggcacga caggtttccc gactggaaag cgggcagtga gcgcaacgca   300
attaatgtga gttagctcac tcattaggca ccccaggctt tacactttat gcttccggct   360
cgtatgttgt gtggaattgt gagcggataa caatttcaca caggaaacag ctatgaccat   420
gattacgaat tgaaaacgca ggcccattta tcctccaa aacaaagaa gcaatagaat   480 ccggaactga attaaaaaca tacaaaccaa gaggtaaaga aaacgcatag ttagctaacc   540
cgtccgcaag acgattgacc tccctataca cgtgagaaat acggactaac cagtcccttg   600
```

```
atatgaagcc ataacacaaa cgtagtagga aagatagagg atgagaatcc ggtatccctg    660
tctgtaaaaa cccaaccacg atcttcgaat ccacttccag ctcaaggcgt gttattcctt    720
gctcccagac tatgtgtaac ccatagtaga gtccccacaa ctctgctagt ggcgctgaac    780
agatttcgat attcaaagca aaaccccaa cccagttctc gttcccatca cgcaccgcac     840
ctcccgctgc tgctaacccg ggattctctc tcgaggctcc atccatgttc aactagcctg    900
atgaatttat taaactcatg tttccatttt ttttcccacc agttatgtta gtttgattaa    960
tttttcagtc aattttggca taacgcttta aaataattat atcaaaataa tattttcagt   1020
ttttctgcaa cagattcatt ccaccaagaa ttcagccgat tctacccgaa ttaatattac   1080
cattttcgga ctagatctat gaacgaaggt acaaaattaa tcagttaaaa aagaaaatag   1140
agtggcaagt actacatcta gtgccgtatg atatgataat ataggaacct aaacgaattt   1200
tatactaatt caaatttaaa agtagttagg tttgtcacaa atgcaaatta caaattatat   1260
cgacgtaacg cttactcatt aaataatcta aattacttgg ttaaaagact aattaaatat   1320
tcttaacaag taggcttttg ttttcattat aaaacaaatt aaaaagctat actaatataa   1380
aaatggagat tggtatttcc aaagcagcaa agacagaaaa actgcaggtt attatctctc   1440
catcttcatc ttgcagagtg gttctttctg ggttttctga cttgcttttc attttttat    1500
tgatacaaat gttaaaccaa ttattttaaa tagtctttga gattaatgaa gagagatttg   1560
tgaacacaat taataaagag ttatactata gtagtagtct tttttactgt atagtatttt   1620
ctccccgcat ctgtcttgtc tcactgtctt tttctcgcaa gtctctctat taaaaacctc   1680
tttccctcta ctctgtcctt tctctctctg cagaagaagc tcagatacag aaactgacta   1740
ccaagaacaa agcttttttcc ttcgagcaaa gaaagttctt tttcttttc ttttgctctt   1800
cgtaacccaa ccaacaagac tttcataagc tattaaatca gaaccctgga agacaaaaaa   1860
ggggaaaaac cattatcctt aaagtaacca acacttctct ctctctttct tcaggtacca   1920
tggatttgca actgaaacaa tggagaagcc agcagcagca acaacatcag acagagtcag   1980
aagaacaacc ttctgcagct aagataccaa acatgtctt tgaccagatt cattctcaca   2040
ctgcaacttc tactgctctt cctctctttta cccctgagcc tacttcttct aaactctcct   2100
ctttgtctcc tgattcttcc tccaggttcc ccagtgagtc ttttcttcct cttatcttat   2160
ctttcttgat aaagaattag acttttcatt catatagttt gtgtttaatt gattttgatt   2220
cctttttgta gagatgggga gcttctttag ctgggcacag tggcaagaac ttgaactaca   2280
agctctgatc tacaggtaca tgttggctgg tgctgctgtt cctcaggagc tccttttacc   2340
aatcaagaaa agccttctcc atctatctcc ttcctacttt cttccaccatc ctcttcaaca   2400
cctacctcat taccaacctg cttgtgagtc tcgagaacag tcttcatcta tctatttttt   2460
aaatataaat gggttttgtg ctactggtgt tggagttgtg ttcccaagat ccagactttc   2520
aatattagta tattatctcg ttttgccaat cttgaagatc taaacatgtg tgaatgggat   2580
taagtaggat tagaatcttg ttattgatct gatatgtgat atgaatgttg aaaacagggt   2640
atttgggaag ggcagcgatg gatcctgagc caggcagatg caggagaacg gatggtaaga   2700
agtggagatg ttcaagagac gtcttcgctg gccacaagta ttgcgagcgc cacatgcacc   2760
gtggccgcaa ccgttctaga aaaccagtag agactccaac caccgtcaat gcaactgcca   2820
cgtccatggc ttcatcagta gcagccgcag ccaccactac aacagcaaca acaacatcta   2880
cgtttgcttt tggtggtggt ggtggtagtg aggaagtggt tggtcaagga ggatctttct   2940
tcttctctgg ctcttctaac tcttcatctg aacttctcca ccttagtcaa aggtaataaa   3000
```

```
aagaaactgt ttttttttct cttaggtctg tctgttttag ctgttgaact ttatggtcaa    3060
aacattaaac ttaaacacat tgactttttt atttctttag tgttgagcca ataagattca    3120
tggttgagat tttagacaat tgttttgaat aataatgaaa tcgatttaaa gcaatactga    3180
ttcttgattt attagtatga agtatgaact aatgatatac acaacttggt ttgtatgttc    3240
atagcgatgt tgtgaagaga ggggtaatgt tggaaattga gagacacatc cttatcattt    3300
tagggttggt tggtttgttt gtttgttgaa ttatgagttt gatttcattg tgaaaatatc    3360
tttctttctt ttttcttatt gtgttgagag ataatgataa cattggATTT gatagaatct    3420
ataatttgaa gctaggtgtg agacttttca aacagagaaa atagaaagag agagaaatgg    3480
taggacctta gtgaaagctg acccatatat gtctcatatc ttgcagaaaa gttaaagctt    3540
ttagattctt ctgcacccac ctcccctatc cacacacaac acatgatata caaaacactc    3600
actttataat tctatttcta tttactgctt aatcaattct tataaaaccc acattaaaag    3660
gtacttttaa agcctataaa ctaatataaa ggctactact gtctgcaact ttgttgttga    3720
agcctaaatg tggtttctct tttgacaaat tattgctttt gtgctttgtt ttcaccaatg    3780
agatgtggat tctgttaaca gttgttcgga gatgaagcaa gaaagcaaca acatgaacaa    3840
caagaggcca tacgagtccc acatcggatt cagtaacaac agatcagatg gaggacacat    3900
cctgaggccc ttcttTgacg attggcctcg ttcttcgctc caagaagctg acaatagttc    3960
aagcccCATG agctcagcca cttgtctctc catctccatg cccgggaact cttcctcaga    4020
cgtctctctg aagctgtcca caggcaacga agagggagcc cggagcaaca acaatgggag    4080
agatcagcaa acatgagct ggtggagcgg tggaggttcc aaccaccatc atcacaacat    4140
gggcggacca ttggccgaag ccctgagatc ttcttcctca tcttcCccaa ccagtgttct    4200
ccatcagctt ggtgtctcga cacaagcctt tcatgtcgac gaagctcgaa aaacaaagaa    4260
aaaaatcaaa gggattcagc aagccactgc aggagtctca caagacactt cggaaaatcc    4320
taacaaaaca atagttcctg cagcattacc acagctcacc cctaccttgg tgtcactgct    4380
ggaggtgatt gaacccgagg tgttgtatgc aggatatgat agctctgttc cagattcagc    4440
atggagaatt atgaccacac tcaacatgtt aggtgggcgt caagtgattg cagcagtgaa    4500
atgggcaaag gcgataccag gcctgagaaa cttacacctg gatgaccaaa tgaccctgct    4560
acagtactca tggatgtttc tcatggcatt tgccctgggt tggagatcat acagacaatc    4620
aagtggaaac ctgctctgct ttgctcctga tctgattatt aatgagcaga gaatgtctct    4680
accctgcatg tatgaccaat gtaaacacat gctgtttgtc tcctctgaat acaaagatt    4740 gcaggtatcc tatgaagagt atctctgtat gaaaaccttA ctgcttctct cctcagttcc    4800
taaggaaggt ctgaagagcc aagagttatt tgatgagatt cgaatgactt atatcaaaga    4860
gctaggaaaa gccatcgtca aaagggaagg gaactccagt cagaactggc aacggtttta    4920
ccaactgaca aagcttctgg actccatgca tgaggtggtt gagaatctcc ttacctactg    4980
cttccagaca tttttggata agaccatgag tattgaattc ccagagatgt tagctgaaat    5040
catcactaat cagataccaa aatattcaaa tggaaatatc aaaaagcttc tgtttcatca    5100
aaaaggatcc gtcgacatgc aacagcacct gatgcagatg cagcccatga tggctggtta    5160
ctaccccagc aatgttacct ctgatcatat ccaacagtac ttggacgaaa acaaatcgtt    5220
gattctgaag attgttgagt ctcaaaactc tggaaagctt agcgaatgcg ccgagaatca    5280
agcaaggctt caacgcaacc taatgtacct agctgcaata gcagattctc agcctcagcc    5340
```

```
accaagtgtg catagccagt atggatctgc tggtggtggg atgattcagg gagaaggagg    5400
gtcacactat ttgcagcagc aacaagcgac tcaacagcaa cagatgactc agcagtctct    5460
aatggcggct cgatcttcaa tgttgtatgc tcagcaacag cagcagcagc agccttacgc    5520
gacgcttcag catcagcaat tgcaccatag ccagcttgga atgagctcga gcagcggagg    5580
aggaggaagc agtggtctcc atatccttca gggagaggct ggtgggtttc atgattttgg    5640
ccgtgggaag ccggaaatgg gaagtggtgg tggcggtgaa ggcagaggag gaagttcagg    5700
ggatggtgga gaaacccttt acttgaaatc atcagatgat gggaattgaa agccatgggg    5760
gctgcagagc tttcgttcgt atcatcggtt tcgacaacgt tcgtcaagtt caatgcatca    5820
gtttcattgc gcacacacca gaatcctact gagttcgagt attatggcat tgggaaacat    5880
gttttttcttg taccatttgt tgtgcttgta atttactgtg ttttttattc ggttttcgct    5940
atcgaactgt gaaatggaaa tggatggaga agagttaatg aatgatatgg tccttttgtt    6000
cattctcaaa ttaatattat ttgttttttc tcttatttgt tgtgtgttga atttgaaaat    6060
ataagagata tgcaaacatt ttgttttgag taaaaatgtg tcaaatcgtg gcctctaatg    6120
accgaagtta atatgaggag taaaacactt gtagttgtac cattatgctt attcactagg    6180
caacaaatat attttcagac ctagaaaagc tgcaaatgtt actgaataca agtatgtcct    6240
cttgtgttttt agacatttat gaactttcct ttatgtaatt ttccagaatc cttgtcagat    6300
tctaatcatt gctttataat tatagttata ctcatggatt tgtagttgag tatgaaaata    6360
tttttttaatg cattttatga cttgccaatt gattgacaac atgcatcaat cgaagcttgg    6420
cactggccgt cgttttacaa cgtcgtgact gggaaaaccc tggcgttacc caacttaatc    6480
gccttgcagc acatccccct ttcgccagct ggcgtaatag cgaagaggcc cgcaccgatc    6540
gcccttccca acagttgcgc agcctgaatg gcgaatgcta gagcagcttg ccaacatggt    6600
ggagcacgac actctcgtct actccaagaa tatcaaagat acagtctcag aagaccaaag    6660
ggctattgag acttttcaac aaagggtaat atcgggaaac ctcctcggat tccattgccc    6720
agctatctgt cacttcatca aaaggacagt agaaaaggaa ggtggcacct acaaatgcca    6780
tcattgcgat aaaggaaagg ctatcgttca agatgcctct gccgacagtg gtcccaaaga    6840
tggaccccca cccacgagga gcatcgtgga aaagaagac gttccaacca cgtcttcaaa    6900
gcaagtggat tgatgtgata acatggtgga gcacgacact ctcgtctact ccaagaatat    6960
caaagataca gtctcagaag accaagggc tattgagact tttcaacaaa gggtaatatc    7020
gggaaacctc ctcggattcc attgcccagc tatctgtcac ttcatcaaaa ggacagtaga    7080
aaaggaaggt ggcacctaca aatgccatca ttgcgataaa ggaaaggcta tcgttcaaga    7140
tgcctctgcc gacagtggtc ccaaagatgg accccaccc acgaggagca tcgtggaaaa    7200
agaagacgtt ccaaccacgt cttcaaagca agtggattga tgtgatatct ccactgacgt    7260
aagggatgac gcacaatccc actatccttc gcaagaccct tcctctatat aaggaagttc    7320
atttcatttg gagaggacac gctgaaatca ccagtctctc tctacaaatc tatctctctc    7380
gattcgcaga tctgtcgatc gaccatgggg attgaacaag atggattgca cgcaggttct    7440
ccggccgctt gggtggagag gctattcggc tatgactggg cacaacagac aatcggctgc    7500
tctgatgccg ccgtgttccg gctgtcagcg caggggcgcc cggttctttt tgtcaagacc    7560
gacctgtccg gtgccctgaa tgaactccag gacgaggcag cgcggctatc gtggctggcc    7620
acgacgggcg ttccttgcgc agctgtgctc gacgttgtca ctgaagcggg aagggactgg    7680
ctgctattgg gcgaagtgcc ggggcaggat ctcctgtcat ctcaccttgc tcctgccgag    7740
```

```
aaagtatcca tcatggctga tgcaatgcgg cggctgcata cgcttgatcc ggctacctgc    7800
ccattcgacc accaagcgaa acatcgcatc gagcgagcac gtactcggat ggaagccggt    7860
cttgtcgatc aggatgatct ggacgaagag catcaggggc tcgcgccagc cgaactgttc    7920
gccaggctca aggcgcgcat gcccgacggc gaggatctcg tcgtgacaca tggcgatgcc    7980
tgcttgccga atatcatggt ggaaaatggc cgcttttctg gattcatcga ctgtggccgg    8040
ctgggtgtgg cggaccgcta tcaggacata gcgttggcta cccgtgatat tgctgaagag    8100
cttggcggcg aatgggctga ccgcttcctc gtgctttacg gtatcgccgc tcccgattcg    8160
cagcgcatcg ccttctatcg ccttcttgac gagttcttct gagcgggact ctggggttcg    8220
gatcgatcct ctagctagag tcgatcgaca tcgagtttct ccataataat gtgtgagtag    8280
ttcccagata agggaattag ggttcttata gggtttcgct cacgtgttga gcatataaga    8340
aacccttagt atgtatttgt atttgtaaaa tacttctatc aataaaattt ctaattccta    8400
aaaccaaaat ccagtactaa aatccagatc acctaaagtc cctatagatc ccccgaatta    8460
attcggcgtt aattcagtac attaaaaacg tccgcaatgt gttattaagt tgtctaagcg    8520
tcaatttgtt tacaccacaa tatatcctgc caccagccag ccaacagctc cccgaccggc    8580
agctcggcac aaaatcacca ctcgatacag gcagcccatc agtccgggac ggcgtcagcg    8640
ggagagccgt tgtaaggcgg cagactttgc tcatgttacc gatgctattc ggaagaacgg    8700
caactaagct gccgggtttg aaacacggat gatctcgcgg agggtagcat gttgattgta    8760
acgatgacag agcgttgctg cctgtgatca attcgggcac gaacccagtg gacataagcc    8820
tcgttcggtt cgtaagctgt aatgcaagta gcgtaactgc cgtcacgcaa ctggtccaga    8880
accttgaccg aacgcagcgg tggtaacggc gcagtggcgg ttttcatggc ttcttgttat    8940
gacatgtttt tttggggtac agtctatgcc tcgggcatcc aagcagcaag cgcgttacgc    9000
cgtgggtcga tgtttgatgt tatggagcag caacgatgtt acgcagcagg gcagtcgccc    9060
taaaacaaag ttaaacatca tgggggaagc ggtgatcgcc gaagtatcga ctcaactatc    9120
agaggtagtt ggcgtcatcg agcgccatct cgaaccgacg ttgctggccg tacatttgta    9180
cggctccgca gtggatggcg gcctgaagcc acacagtgat attgatttgc tggttacggt    9240
gaccgtaagg cttgatgaaa caacgcggcg agctttgatc aacgaccttt tggaaacttc    9300
ggcttcccct ggagagagcg agattctccg cgctgtagaa gtcaccattg ttgtgcacga    9360
cgacatcatt ccgtggcgtt atccagctaa gcgcgaactg caatttggag aatggcagcg    9420
caatgacatt cttgcaggta tcttcgagcc agccacgatc gacattgatc tggctatctt    9480
gctgacaaaa gcaagagaac atagcgttgc cttggtaggt ccagcggcgg aggaactctt    9540
tgatccggtt cctgaacagg atctatttga ggcgctaaat gaaaccttaa cgctatggaa    9600
ctcgccgccc gactgggctg gcgatgagcg aaatgtagtg cttacgttgt cccgcatttg    9660
gtacagcgca gtaaccggca aaatcgcgcc gaaggatgtc gctgccgact gggcaatgga    9720
gcgcctgccg gcccagtatc agcccgtcat acttgaagct agacaggctt atcttggaca    9780
agaagaagat cgcttggcct cgcgcgcaga tcagttggaa gaatttgtcc actacgtgaa    9840
aggcgagatc accaaggtag tcggcaaata atgtctagct agaaattcgt tcaagccgac    9900
gccgcttcgc cggcgttaac tcaagcgatt agatgcacta agcacataat tgctcacagc    9960
caaactatca ggtcaagtct gcttttatta tttttaagcg tgcataataa gccctacaca   10020
aattgggaga tatatcatgc atgaccaaaa tcccttaacg tgagttttcg ttccactgag   10080
```

-continued

```
cgtcagaccc cgtagaaaag atcaaaggat cttcttgaga tccttttttt ctgcgcgtaa    10140
tctgctgctt gcaaacaaaa aaaccaccgc taccagcggt ggtttgtttg ccggatcaag    10200
agctaccaac tcttttccg aaggtaactg gcttcagcag agcgcagata ccaaatactg    10260
tccttctagt gtagccgtag ttaggccacc acttcaagaa ctctgtagca ccgcctacat    10320
acctcgctct gctaatcctg ttaccagtgg ctgctgccag tggcgataag tcgtgtctta    10380
ccgggttgga ctcaagacga tagttaccgg ataaggcgca gcggtcgggc tgaacggggg    10440
gttcgtgcac acagcccagc ttggagcgaa cgacctacac cgaactgaga tacctacagc    10500
gtgagctatg agaaagcgcc acgcttcccg aagggagaaa ggcggacagg tatccggtaa    10560
gcggcagggt cggaacagga gagcgcacga gggagcttcc agggggaaac gcctggtatc    10620
tttatagtcc tgtcgggttt cgccacctct gacttgagcg tcgatttttg tgatgctcgt    10680
caggggggcg gagcctatgg aaaaacgcca gcaacgcggc cttttacgg ttcctggcct     10740
tttgctggcc ttttgctcac atgttctttc ctgcgttatc ccctgattct gtggataacc    10800
gtattaccgc ctttgagtga gctgataccg ctcgccgcag ccgaacgacc gagcgcagcg    10860
agtcagtgag cgaggaagcg gaagagcgcc tgatgcggta ttttctcctt acgcatctgt    10920
gcggtatttc acaccgcata tggtgcactc tcagtacaat ctgctctgat gccgcatagt    10980
taagccagta tacactccgc tatcgctacg tgactgggtc atggctgcgc ccgacaccc     11040
gccaacaccc gctgacgcgc cctgacgggc ttgtctgctc ccggcatccg cttacagaca    11100
agctgtgacc gtctccggga gctgcatgtg tcagaggttt tcaccgtcat caccgaaacg    11160
cgcgaggcag ggtgccttga tgtgggcgcc ggcggtcgag tggcgacggc gcggcttgtc    11220
cgcgccctgg tagattgcct ggccgtaggc cagccatttt tgagcggcca gcggccgcga    11280
taggccgacg cgaagcggcg gggcgtaggg agcgcagcga ccgaagggta ggcgcttttt    11340
gcagctcttc ggctgtgcgc tggccagaca gttatgcaca ggccaggcgg gttttaagag    11400
ttttaataag ttttaaagag ttttaggcgg aaaaatcgcc ttttttctct tttatatcag    11460
tcacttacat gtgtgaccgg ttcccaatgt acggctttgg gttcccaatg tacgggttcc    11520
ggttcccaat gtacggcttt gggttcccaa tgtacgtgct atccacagga aagagacctt    11580
ttcgaccttt ttccctgct agggcaattt gccctagcat ctgctccgta cattaggaac     11640
cggcggatgc ttcgccctcg atcaggttgc ggtagcgcat gactaggatc gggccagcct    11700
gccccgcctc ctccttcaaa tcgtactccg gcaggtcatt tgacccgatc agcttgcgca    11760
cggtgaaaca gaacttcttg aactctccgg cgctgccact gcgttcgtag atcgtcttga    11820
acaaccatct ggcttctgcc ttgcctgcgg cgcggcgtgc caggcggtag agaaaacggc    11880
cgatgccggg atcgatcaaa aagtaatcgg ggtgaaccgt cagcacgtcc gggttcttgc    11940
cttctgtgat ctcgcggtac atccaatcag ctagctcgat ctcgatgtac tccggccgcc    12000
cggtttcgct ctttacgatc ttgtagcggc taatcaaggc ttcaccctcg gataccgtca    12060
ccaggcggcc gttcttggcc ttcttcgtac gctgcatggc aacgtgcgtg gtgtttaacc    12120
gaatgcaggt ttctaccagg tcgtcttct gctttccgcc atcggctcgc cggcagaact    12180
tgagtacgtc cgcaacgtgt ggacggaaca cgcggccggg cttgtctccc ttcccttccc    12240
ggtatcggtt catggattcg gttagatggg aaaccgccat cagtaccagg tcgtaatccc    12300
acacactggc catgccggcc ggccctgcgg aaacctctac gtgcccgtct ggaagctcgt    12360
agcggatcac ctcgccagct cgtcggtcac gcttcgacag acggaaaacg gccacgtcca    12420
tgatgctgcg actatcgcgg gtgcccacgt catagagcat cggaacgaaa aaatctggtt    12480
```

```
gctcgtcgcc cttgggcggc ttcctaatcg acggcgcacc ggctgccggc ggttgccggg    12540
attctttgcg gattcgatca gcggccgctt gccacgattc accggggcgt gcttctgcct    12600
cgatgcgttg ccgctgggcg gcctgcgcgg ccttcaactt ctccaccagg tcatcaccca    12660
gcgccgcgcc gatttgtacc gggccggatg gtttgcgacc gtcacgccga ttcctcgggc    12720
ttgggggttc cagtgccatt gcagggccgg cagacaaccc agccgcttac gcctggccaa    12780
ccgcccgttc ctccacacat gggcattcc acggcgtcgg tgcctggttg ttcttgattt    12840
tccatgccgc ctcctttagc cgctaaaatt catctactca tttattcatt tgctcattta    12900
ctctggtagc tgcgcgatgt attcagatag cagctcggta atggtcttgc cttggcgtac    12960
cgcgtacatc ttcagcttgg tgtgatcctc cgccggcaac tgaaagttga cccgcttcat    13020
ggctggcgtg tctgccaggc tggccaacgt tgcagccttg ctgctgcgtg cgctcggacg    13080
gccggcactt agcgtgtttg tgcttttgct cattttctct ttacctcatt aactcaaatg    13140
agttttgatt taatttcagc ggccagcgcc tggacctcgc gggcagcgtc gccctcgggt    13200
tctgattcaa gaacggttgt gccggcggcg gcagtgcctg ggtagctcac gcgctgcgtg    13260
atacgggact caagaatggg cagctcgtac ccggccagcg cctcggcaac ctcaccgccg    13320
atgcgcgtgc ctttgatcgc ccgcgacacg acaaaggccg cttgtagcct tccatccgtg    13380
acctcaatgc gctgcttaac cagctccacc aggtcggcgg tggcccatat gtcgtaaggg    13440
cttggctgca ccggaatcag cacgaagtcg gctgccttga tcgcggacac agccaagtcc    13500
gccgcctggg gcgctccgtc gatcactacg aagtcgcgcc ggcgatggc cttcacgtcg    13560 cggtcaatcg tcgggcggtc gatgccgaca acggttagcg gttgatcttc ccgcacggcc    13620
gcccaatcgc gggcactgcc ctggggatcg gaatcgacta acagaacatc ggccccggcg    13680
agttgcaggg cgcgggctag atgggttgcg atggtcgtct tgcctgaccc gccttctgg    13740 ttaagtacag cgataacctt catgcgttcc ccttgcgtat ttgtttattt actcatcgca    13800
tcatatacgc agcgaccgca tgacgcaagc tgttttactc aaatacacat cacctttta    13860 gacggcggcg ctcggtttct tcagcggcca agctggccgg ccaggccgcc agcttggcat    13920
cagacaaacc ggccaggatt tcatgcagcc gcacggttga cacgtgcgcg ggcggctcga    13980
acacgtaccc ggccgcgatc atctccgcct cgatctcttc ggtaatgaaa aacggttcgt    14040
cctggccgtc ctggtgcggt ttcatgcttg ttcctcttgg cgttcattct cggcggccgc    14100
cagggcgtcg gcctcggtca atgcgtcctc acggaaggca ccgcgccgcc tggcctcggt    14160
gggcgtcact tcctcgctgc gctcaagtgc gcggtacagg gtcgagcgat gcacgccaag    14220
cagtgcagcc gcctctttca cggtgcggcc ttcctggtcg atcagctcgc gggcgtgcgc    14280
gatctgtgcc ggggtgaggg tagggcgggg gccaaacttc acgcctcggg ccttggcggc    14340
ctcgcgcccg ctccgggtgc ggtcgatgat tagggaacgc tcgaactcgg caatgccggc    14400
gaacacggtc aacaccatgc ggccggccgg cgtggtggtg tcggcccacg gctctgccag    14460
gctacgcagg cccgcgccgg cctcctggat gcgctcggca atgtccagta ggtcgcgggt    14520
gctgcgggcc aggcggtcta gcctggtcac tgtcacaacg tcgccagggc gtaggtggtc    14580
aagcatcctg gccagctccg ggcggtcgcg cctggtgccg tgatcttct cggaaaacag    14640 cttggtgcag ccggccgcgt gcagttcggc ccgttggttg gtcaagtcct ggtcgtcggt    14700
gctgacgcgg gcatagccca gcaggccagc ggcggcgctc ttgttcatgg cgtaatgtct    14760
ccggttctag tcgcaagtat tctactttat gcgactaaaa cacgcgacaa gaaacgcca    14820
```

```
ggaaaagggc agggcggcag cctgtcgcgt aacttaggac ttgtgcgaca tgtcgttttc    14880
agaagacggc tgcactgaac gtcagaagcc gactgcacta tagcagcgga ggggttggat    14940
caaagtact                                                            14949
```

<210> SEQ ID NO 27
<211> LENGTH: 618
<212> TYPE: PRT
<213> ORGANISM: Artificial Sequence
<220> FEATURE:
<223> OTHER INFORMATION: Chimaera STM-GFP

<400> SEQUENCE: 27

```
Met Glu Ser Gly Ser Asn Ser Thr Ser Cys Pro Met Ala Phe Ala Gly
1               5                   10                  15

Asp Asn Ser Asp Gly Pro Met Cys Pro Met Met Met Met Met Pro Pro
            20                  25                  30

Ile Met Thr Ser His Gln His His Gly His Asp His Gln His Gln Gln
        35                  40                  45

Gln Glu His Asp Gly Tyr Ala Tyr Gln Ser His His Gln Gln Ser Ser
    50                  55                  60

Ser Leu Phe Leu Gln Ser Leu Ala Pro Pro Gln Gly Thr Lys Asn Lys
65                  70                  75                  80

Val Ala Ser Ser Ser Pro Ser Ser Cys Ala Pro Ala Tyr Ser Leu
                85                  90                  95

Met Glu Ile His His Asn Glu Ile Val Ala Gly Gly Ile Asn Pro Cys
            100                 105                 110

Ser Ser Ser Ser Ser Ala Ser Val Lys Ala Lys Ile Met Ala His
            115                 120                 125

Pro His Tyr His Arg Leu Leu Ala Ala Tyr Val Asn Cys Gln Lys Val
130                 135                 140

Gly Ala Pro Pro Glu Val Val Ala Arg Leu Glu Glu Ala Cys Ser Ser
145                 150                 155                 160

Ala Ala Ala Ala Ala Ser Met Gly Pro Thr Gly Cys Leu Gly Glu
                165                 170                 175

Asp Pro Gly Leu Asp Gln Phe Met Glu Ala Tyr Cys Glu Met Leu Val
            180                 185                 190

Lys Tyr Glu Gln Glu Leu Ser Lys Pro Phe Lys Glu Ala Met Val Phe
        195                 200                 205

Leu Gln Arg Val Glu Cys Gln Phe Lys Ser Leu Ser Leu Ser Ser Pro
    210                 215                 220

Ser Ser Phe Ser Gly Tyr Gly Glu Thr Ala Ile Asp Arg Asn Asn Asn
225                 230                 235                 240

Gly Ser Ser Glu Glu Val Asp Met Asn Asn Glu Phe Val Asp Pro
                245                 250                 255

Gln Ala Glu Asp Arg Glu Leu Lys Gly Gln Leu Leu Arg Lys Tyr Ser
            260                 265                 270

Gly Tyr Leu Gly Ser Leu Lys Gln Glu Phe Met Lys Lys Arg Lys Lys
        275                 280                 285

Gly Lys Leu Pro Lys Glu Ala Arg Gln Gln Leu Leu Asp Trp Trp Ser
    290                 295                 300

Arg His Tyr Lys Trp Pro Tyr Pro Ser Glu Gln Gln Lys Leu Ala Leu
305                 310                 315                 320

Ala Glu Ser Thr Gly Leu Asp Gln Lys Gln Ile Asn Asn Trp Phe Ile
                325                 330                 335
```

Asn Gln Arg Lys Arg His Trp Lys Pro Ser Glu Asp Met Gln Phe Val
                340                 345                 350

Val Met Asp Ala Thr His Pro His His Tyr Phe Met Asp Asn Val Leu
                355                 360                 365

Gly Asn Pro Phe Pro Met Asp His Ile Ser Ser Thr Met Leu Val Asp
                370                 375                 380

Asp Leu Thr Ser Lys Gly Glu Glu Leu Phe Thr Gly Val Asp Gly Asp
385                 390                 395                 400

Val Asn Gly His Lys Phe Ser Val Ser Gly Glu Gly Glu Gly Asp Ala
                405                 410                 415

Thr Tyr Gly Lys Leu Thr Leu Lys Phe Ile Cys Thr Thr Gly Lys Leu
                420                 425                 430

Pro Val Pro Trp Pro Thr Leu Val Thr Thr Phe Ser Tyr Gly Val Gln
                435                 440                 445

Cys Phe Ser Arg Tyr Pro Asp His Met Lys Arg His Asp Phe Phe Lys
                450                 455                 460

Ser Ala Met Pro Glu Gly Tyr Val Gln Glu Arg Thr Ile Phe Phe Lys
465                 470                 475                 480

Asp Asp Gly Asn Tyr Lys Thr Arg Ala Glu Val Lys Phe Glu Gly Asp
                485                 490                 495

Thr Leu Val Asn Arg Ile Glu Leu Lys Gly Ile Asp Phe Lys Glu Asp
                500                 505                 510

Gly Asn Ile Leu Gly His Lys Leu Glu Tyr Asn Tyr Asn Ser His Asn
                515                 520                 525

Val Tyr Ile Met Ala Asp Lys Gln Lys Asn Gly Ile Lys Ala Asn Phe
                530                 535                 540

Lys Thr Arg His Asn Ile Glu Asp Gly Gly Val Gln Leu Ala Asp His
545                 550                 555                 560

Tyr Gln Gln Asn Thr Pro Ile Gly Asp Gly Pro Val Leu Leu Pro Asp
                565                 570                 575

Asn His Tyr Leu Ser Thr Gln Ser Ala Leu Ser Lys Asp Pro Asn Glu
                580                 585                 590

Lys Arg Asp His Met Val Leu Leu Glu Phe Val Thr Ala Ala Gly Ile
                595                 600                 605

Thr His Gly Met Asp Glu Leu Tyr Lys Ala
                610                 615

<210> SEQ ID NO 28
<211> LENGTH: 1857
<212> TYPE: DNA
<213> ORGANISM: Artificial Sequence
<220> FEATURE:
<223> OTHER INFORMATION: Chimaera STM-GFP

<400> SEQUENCE: 28
atggagagtg gttccaacag cacttcttgt ccaatggctt ttgccgggga taatagtgat      60
ggtccgatgt gtcctatgat gatgatgatg ccgcccatca tgacatcaca tcaacatcat     120
ggtcatgatc atcaacatca acaacaagaa catgatggtt atgcatatca gtcacaccac     180
caacaaagta gttccctttt tcttcaatca ctagctcctc cccaaggaac taagaacaaa     240
gttgcttctt cttcttctcc ttcctcttgt gctcctgcct attctctaat ggagatccat     300
cataacgaaa tcgttgcagg aggaatcaac ccttgctcct cttcctcttc ttcagcctct     360
gtcaaggcca agatcatggc tcatcctcac taccaccgcc tcttggccgc ttatgtcaat     420
tgtcagaagg ttggagcacc accggaggtt gtggcgaggc tggaggaggc atgctcgtct     480

```
gccgcagccg cagccgcatc tatggggcca cagggtgtc ttggtgaaga tccagggctt    540
gatcaattca tggaagctta ctgtgaaatg ctcgttaagt atgagcaaga gctctccaaa    600
cctttcaagg aagctatggt cttccttcaa cgtgtcgagt gtcaattcaa atccctctct    660
ctatcctcac cttcctcttt ctccggttat ggagagacag caattgatag gaacaataat    720
gggtcatccg aggaagaagt cgatatgaac aatgaatttg tagatccaca agctgaggat    780
agagagctta aggacagct cttgcgcaag tacagtggtt acttagggag cctcaagcaa    840
gagttcatga agaagaggaa gaaaggaaag ctccctaaag aagctcgtca caactgctt    900 gattggtgga gccgccacta caaatggcct taccccttcgg agcaacaaaa gctcgccctt    960
gcggaatcaa cggggctgga ccagaaacag ataaacaatt ggttcataaa ccagaggaaa   1020
cggcattgga agccgtcgga ggacatgcag tttgtagtaa tggacgcaac acatcctcac   1080
cattacttca tggataatgt cttgggcaat cctttcccaa tggatcacat ctcctccacc   1140
atgcttgtcg acgatctgac tagtaaagga gaagaacttt tcactggagt agatggtgat   1200
gttaatgggc acaaattttc tgtcagtgga gagggtgaag tgatgcaac atacggaaaa   1260 cttacccctta aatttatttg cactactgga aaactacctg ttccgtggcc aacacttgtc   1320
actactttct cttatggtgt tcaatgcttt tcaagatacc cagatcatat gaagcggcac   1380
gacttcttca agagcgccat gcctgaggga tacgtgcagg agaggaccat cttcttcaag   1440
gacgacggga actacaagac acgtgctgaa gtcaagtttg agggagacac cctcgtcaac   1500
aggatcgagc ttaagggaat cgatttcaag gaggacggaa acatcctcgg ccacaagttg   1560
gaatacaact acaactccca caacgtatac atcatggccg acaagcaaaa gaacggcatc   1620
aaagccaact tcaagacccg ccacaacatc gaagacggcg gcgtgcaact cgctgatcat   1680
tatcaacaaa atactccaat tggcgatggc cctgtcccttt taccagacaa ccattacctg   1740
tccacacaat ctgcccttc gaaagatccc aacgaaaaga gagaccacat ggtccttctt   1800
gagtttgtaa cagctgctgg gattacacat ggcatggatg aactatacaa agcttga      1857
```

<210> SEQ ID NO 29
<211> LENGTH: 12346
<212> TYPE: DNA
<213> ORGANISM: Artificial Sequence
<220> FEATURE:
<223> OTHER INFORMATION: Binary vector pJD220 for expression of chimeric protein STM-GPF

<400> SEQUENCE: 29

```
ttgatcccga ggggaaccct gtggttggca tgcacataca aatggacgaa cggataaacc     60
ttttcacgcc cttttaaata tccgttattc aataaacgc tcttttctct taggtttacc    120
cgccaatata tcctgtcaaa cactgatagt ttaaactgaa ggcgggaaac gacaatctga    180
tccaagctca agctgctcta gccaatacgc aaaccgcctc tccccgcgcg ttggccgatt    240
cattaatgca gctggcacga caggtttccc gactggaaag cgggcagtga gcgcaacgca    300
attaatgtga gttagctcac tcattaggca ccccaggctt tacactttat gcttccggct    360
cgtatgttgt gtggaattgt gagcggataa caatttcaca caggaaacag ctatgaccat    420
gattacgaat tcggtcccca gattagcctt ttcaatttca gaaagaatgc taacccacag    480
atggttagag aggcttacgc agcaggtctc atcaagacga tctacccgag caataatctc    540
caggaaatca aatccttcc caagaaggtt aaagatgcag tcaaaagatt caggactaac    600
tgcatcaaga acacagagaa agatatattt ctcaagatca gaagtactat tccagtatgg    660
```

```
acgattcaag gcttgcttca caaaccaagg caagtaatag agattggagt ctctaaaaag    720
gtagttccca ctgaatcaaa ggccatggag tcaaagattc aaatagagga cctaacagaa    780
ctcgccgtaa agactggcga acagttcata cagagtctct tacgactcaa tgacaagaag    840
aaaatcttcg tcaacatggt ggagcacgac acacttgtct actccaaaaa tatcaaagat    900
acagtctcag aagaccaaag gcaattgag acttttcaac aaagggtaat atccggaaac     960
ctcctcggat tccattgccc agctatctgt cactttattg tgaagatagt ggaaaaggaa   1020
ggtggctcct acaaatgcca tcattgcgat aaaggaaagg ccatcgttga agatgcctct   1080
gccgacagtg gtcccaaaga tggaccccca cccacgagga gcatcgtgga aaaagaagac   1140
gttccaacca cgtcttcaaa gcaagtggat tgatgtgata tctccactga cgtaagggat   1200
gacgcacaat cccactatcc ttcgcaagac ccttcctcta tataaggaag ttcatttcat   1260
ttggagagaa cacgggggac gagctcggta cccggggatc catggagagt ggttccaaca   1320
gcacttcttg tccaatggct tttgccgggg ataatagtga tggtccgatg tgtcctatga   1380
tgatgatgat gccgcccatc atgacatcac atcaacatca tggtcatgat catcaacatc   1440
aacaacaaga acatgatggt tatgcatatc agtcacacca ccaacaaagt agttcccttt   1500
ttcttcaatc actagctcct ccccaaggaa ctaagaacaa agttgcttct tcttcttctc   1560
cttcctcttg tgctcctgcc tattctctaa tggagatcca tcataacgaa atcgttgcag   1620
gaggaatcaa cccttgctcc tcttcctctt cttcagcctc tgtcaaggcc aagatcatgg   1680
ctcatcctca ctaccaccgc ctcttggccg cttatgtcaa ttgtcagaag gttggagcac   1740
caccggaggt tgtggcgagg ctggaggagg catgctcgtc tgccgcagcc gcagccgcat   1800
ctatggggcc aacagggtgt cttggtgaag atccagggct tgatcaattc atggaagctt   1860
actgtgaaat gctcgttaag tatgagcaag agctctccaa acctttcaag gaagctatgg   1920
tcttccttca acgtgtcgag tgtcaattca aatccctctc tctatcctca ccttcctctt   1980
tctccggtta tggagagaca gcaattgata ggaacaataa tgggtcatcc gaggaagaag   2040
tcgatatgaa caatgaattt gtagatccac aagctgagga tagagagctt aaaggacagc   2100
tcttgcgcaa gtacagtggt tacttaggga gcctcaagca agagttcatg aagaagagga   2160
agaaaggaaa gctccctaaa gaagctcgtc aacaactgct tgattggtgg agccgccact   2220
acaaatggcc ttacccttcg gagcaacaaa agctcgccct tgcggaatca acggggctgg   2280
accagaaaca gataaacaat tggttcataa accagaggaa acggcattgg aagccgtcgg   2340
aggacatgca gtttgtagta atggacgcaa cacatcctca ccattacttc atggataatg   2400
tcttgggcaa tccttttccca atggatcaca tctcctccac catgcttgtc gacgatctga   2460
ctagtaaagg agaagaactt ttcactggag tagatggtga tgttaatggg cacaaatttt   2520
ctgtcagtgg agagggtgaa ggtgatgcaa catacggaaa acttaccctt aaatttattt   2580
gcactactgg aaaactacct gttccgtggc caacacttgt cactactttc tcttatggtg   2640
ttcaatgctt ttcaagatac ccagatcata tgaagcggca cgacttcttc aagagcgcca   2700
tgcctgaggg atacgtgcag gagaggacca tcttcttcaa ggacgacggg aactacaaga   2760
cacgtgctga agtcaagttt gagggagaca cccctcgtca caggatcgag cttaagggaa   2820
tcgatttcaa ggaggacgga aacatcctcg gccacaagtt ggaatacaac tacaactccc   2880
acaacgtata catcatggcc gacaagcaaa agaacggcat caaagccaac ttcaagaccc   2940
gccacaacat cgaagacggc ggcgtgcaac tcgctgatca ttatcaacaa aatactccaa   3000
```

```
ttggcgatgg ccctgtcctt ttaccagaca accattacct gtccacacaa tctgcccttt    3060
cgaaagatcc caacgaaaag agagaccaca tggtccttct tgagtttgta acagctgctg    3120
ggattacaca tggcatggat gaactataca aagcttgact gcagagcttt cgttcgtatc    3180
atcggtttcg acaacgttcg tcaagttcaa tgcatcagtt tcattgcgca cacaccagaa    3240
tcctactgag ttcgagtatt atggcattgg gaaacatgtt tttcttgtac catttgttgt    3300
gcttgtaatt tactgtgttt tttattcggt tttcgctatc gaactgtgaa atggaaatgg    3360
atggagaaga gttaatgaat gatatggtcc ttttgttcat tctcaaatta atattatttg    3420
ttttttctct tatttgttgt gtgttgaatt tgaaaatata agagatatgc aaacattttg    3480
ttttgagtaa aaatgtgtca atcgtggcc tctaatgacc gaagttaata tgaggagtaa    3540
aacacttgta gttgtaccat tatgcttatt cactaggcaa caaatatatt ttcagaccta    3600
gaaaagctgc aaatgttact gaatacaagt atgtcctctt gtgttttaga catttatgaa    3660
cttttcctta tgtaattttc cagaatcctt gtcagattct aatcattgct ttataattat    3720
agttatactc atggatttgt agttgagtat gaaaatattt tttaatgcat tttatgactt    3780
gccaattgat tgacaacatg catcaatcga agcttggcac tggccgtcgt tttacaacgt    3840
cgtgactggg aaaaccctgg cgttacccaa cttaatcgcc ttgcagcaca tcccccttc    3900
gccagctggc gtaatagcga agaggcccgc accgatcgcc cttcccaaca gttgcgcagc    3960
ctgaatggcg aatgctagag cagcttgcca acatggtgga gcacgacact ctcgtctact    4020
ccaagaatat caaagataca gtctcagaag accaagggc tattgagact tttcaacaaa    4080
gggtaatatc gggaaaacct ctcggattcc attgcccagc tatctgtcac ttcatcaaaa    4140
ggacagtaga aaaggaaggt ggcacctaca aatgccatca ttgcgataaa ggaaaggcta    4200
tcgttcaaga tgcctctgcc gacagtggtc ccaaagatgg accccacc acgaggagca    4260
tcgtggaaaa agaagacgtt ccaaccacgt cttcaaagca agtggattga tgtgataaca    4320
tggtggagca cgacactctc gtctactcca agaatatcaa agatacagtc tcagaagacc    4380
aaagggctat tgagactttt caacaaaggg taatatcggg aaacctcctc ggattccatt    4440
gcccagctat ctgtcacttc atcaaaagga cagtagaaaa ggaaggtggc acctacaaat    4500
gccatcattg cgataaagga aggctatcg ttcaagatgc ctctgccgac agtggtccca    4560
aagatggacc cccaccacg aggagcatcg tggaaaaaga acgttcca ccacgtctt    4620
caaagcaagt ggattgatgt gatatctcca ctgacgtaag ggatgacgca caatcccact    4680
atccttcgca agacccttcc tctatataag gaagttcatt tcatttggag aggacacgct    4740
gaaatcacca gtctctctct acaaatctat ctctctcgat tcgcagatct gtcgatcgac    4800
catgggattt gaacaagatg gattgcacgc aggttctccg gccgcttggg tggagaggct    4860
attcggctat gactgggcac aacagacaat cggctgctct gatgccgccg tgttccggct    4920
gtcagcgcag gggcgcccgg ttcttttgt caagaccgac ctgtccggtg ccctgaatga    4980
actccaggac gaggcagcgc ggctatcgtg gctggccacg acgggcgttc cttgcgcagc    5040
tgtgctcgac gttgtcactg aagcgggaag ggactggctg ctattgggcg aagtgccggg    5100
gcaggatctc ctgtcatctc accttgctcc tgccgagaaa gtatccatca tggctgatgc    5160
aatgcggcgg ctgcatacgc ttgatccggc tacctgccca ttcgaccacc aagcgaaaca    5220
tcgcatcgag cgagcacgta ctcggatgga agccggtctt gtcgatcagg atgatctgga    5280
cgaagagcat caggggctcg cgccagccga actgttcgcc aggctcaagg cgcgcatgcc    5340
cgacggcgag gatctcgtcg tgacacatgg cgatgcctgc ttgccgaata tcatggtgga    5400
```

```
aaatggccgc ttttctggat tcatcgactg tggccggctg ggtgtggcgg accgctatca    5460
ggacatagcg ttggctaccc gtgatattgc tgaagagctt ggcggcgaat gggctgaccg    5520
cttcctcgtg ctttacggta tcgccgctcc cgattcgcag cgcatcgcct tctatcgcct    5580
tcttgacgag ttcttctgag cgggactctg gggttcggat cgatcctcta gctagagtcg    5640
atcgacatcg agtttctcca taataatgtg tgagtagttc ccagataagg gaattagggt    5700
tcttataggg tttcgctcac gtgttgagca tataagaaac ccttagtatg tatttgtatt    5760
tgtaaaatac ttctatcaat aaaatttcta attcctaaaa ccaaaatcca gtactaaaat    5820
ccagatcacc taaagtccct atagatcccc gaattaatt cggcgttaat tcagtacatt    5880
aaaaacgtcc gcaatgtgtt attaagttgt ctaagcgtca atttgtttac accacaatat    5940
atcctgccac cagccagcca acagctcccc gaccggcagc tcggcacaaa atcaccactc    6000
gatacaggca gcccatcagt ccgggacggc gtcagcggga gagccgttgt aaggcggcag    6060
actttgctca tgttaccgat gctattcgga agaacggcaa ctaagctgcc gggtttgaaa    6120
cacggatgat ctcgcggagg gtagcatgtt gattgtaacg atgacagagc gttgctgcct    6180
gtgatcaatt cgggcacgaa cccagtggac ataagcctcg ttcggttcgt aagctgtaat    6240
gcaagtagcg taactgccgt cacgcaactg gtccagaacc ttgaccgaac gcagcggtgg    6300
taacggcgca gtgcggttt tcatggcttc ttgttatgac atgtttttt ggggtacagt    6360 ctatgcctcg ggcatccaag cagcaagcgc gttacgccgt gggtcgatgt ttgatgttat    6420
ggagcagcaa cgatgttacg cagcagggca gtcgccctaa aacaaagtta acatcatgg    6480 gggaagcggt gatcgccgaa gtatcgactc aactatcaga ggtagttggc gtcatcgagc    6540
gccatctcga accgacgttg ctggccgtac atttgtacgg ctccgcagtg gatggcggcc    6600
tgaagccaca cagtgatatt gatttgctgg ttacggtgac cgtaaggctt gatgaaacaa    6660
cgcggcgagc tttgatcaac gaccttttgg aaacttcggc ttcccctgga gagagcgaga    6720
ttctccgcgc tgtagaagtc accattgttg tgcacgacga catcattccg tggcgttatc    6780
cagctaagcg cgaactgcaa tttggagaat ggcagcgcaa tgacattctt gcaggtatct    6840
tcgagccagc cacgatcgac attgatctgg ctatcttgct gacaaaagca agagaacata    6900
gcgttgcctt ggtaggtcca gcggcggagg aactctttga tccggttcct gaacaggatc    6960
tatttgaggc gctaaatgaa accttaacgc tatggaactc gccgcccgac tgggctggcg    7020
atgagcgaaa tgtagtgctt acgttgtccc gcatttggta cagcgcagta accggcaaaa    7080
tcgcgccgaa ggatgtcgct gccgactggg caatggagcg cctgccggcc cagtatcagc    7140
ccgtcatact tgaagctaga caggcttatc ttggacaaga agaagatcgc ttggcctcgc    7200
gcgcagatca gttggaagaa tttgtccact acgtgaaagg cgagatcacc aaggtagtcg    7260
gcaaataatg tctagctaga aattcgttca agccgacgcc gcttcgccgg cgttaactca    7320
agcgattaga tgcactaagc acataattgc tcacagccaa actatcaggt caagtctgct    7380
tttattattt ttaagcgtgc ataataagcc ctacacaaat tgggagatat atcatgcatg    7440
accaaaatcc cttaacgtga gttttcgttc cactgagcgt cagacccgt agaaaagatc    7500 aaaggatctc ttgagatcc ttttttctg cgcgtaatct gctgcttgca acaaaaaaa    7560 ccaccgctac cagcggtggt ttgtttgccg gatcaagagc taccaactct ttttccgaag    7620
gtaactggct tcagcagagc gcagatacca aatactgtcc ttctagtgta gccgtagtta    7680
ggccaccact tcaagaactc tgtagcaccg cctacatacc tcgctctgct aatcctgtta    7740
```

```
ccagtggctg ctgccagtgg cgataagtcg tgtcttaccg ggttggactc aagacgatag    7800
ttaccggata aggcgcagcg gtcgggctga acgggggtt cgtgcacaca gcccagcttg     7860
gagcgaacga cctacaccga actgagatac ctacagcgtg agctatgaga aagcgccacg    7920
cttcccgaag ggagaaaggc ggacaggtat ccggtaagcg gcagggtcgg aacaggagag    7980
cgcacgaggg agcttccagg gggaaacgcc tggtatcttt atagtcctgt cgggtttcgc    8040
cacctctgac ttgagcgtcg attttttgtga tgctcgtcag gggggcggag cctatggaaa   8100
aacgccagca acgcggcctt tttacggttc ctggccttttt gctggccttt tgctcacatg   8160
ttctttcctg cgttatcccc tgattctgtg gataaccgta ttaccgcctt tgagtgagct    8220
gataccgctc gccgcagccg aacgaccgag cgcagcgagt cagtgagcga ggaagcggaa    8280
gagcgcctga tgcggtattt tctccttacg catctgtgcg gtatttcaca ccgcatatgg    8340
tgcactctca gtacaatctg ctctgatgcc gcatagttaa gccagtatac actccgctat    8400
cgctacgtga ctgggtcatg gctgcgcccc gacacccgcc aacacccgct gacgcgccct    8460
gacgggcttg tctgctcccg gcatccgctt acagacaagc tgtgaccgtc tccgggagct    8520
gcatgtgtca gaggttttca ccgtcatcac cgaaacgcgc gaggcagggt gccttgatgt    8580
gggcgccggc ggtcgagtgg cgacggcgcg gcttgtccgc gccctggtag attgcctggc    8640
cgtaggccag ccattttga gcggccagcg gccgcgatag gccgacgcga agcggcgggg    8700
cgtagggagc gcagcgaccg aagggtaggc gcttttttgca gctcttcggc tgtgcgctgg    8760
ccagacagtt atgcacaggc caggcgggtt ttaagagttt taataagttt taaagagttt    8820
taggcggaaa aatcgccttt tttctctttt atatcagtca cttacatgtg tgaccggttc    8880
ccaatgtacg gctttgggtt cccaatgtac gggttccggt tcccaatgta cggctttggg    8940
ttcccaatgt acgtgctatc cacaggaaag agaccttttc gacctttttc ccctgctagg    9000
gcaatttgcc ctagcatctg ctccgtacat taggaaccgg cggatgcttc gccctcgatc    9060
aggttgcggt agcgcatgac taggatcggg ccagcctgcc ccgcctcctc cttcaaatcg    9120
tactccggca ggtcatttga cccgatcagc ttgcgcacgg tgaaacagaa cttcttgaac    9180
tctccggcgc tgccactgcg ttcgtagatc gtcttgaaca accatctggc ttctgccttg    9240
cctgcggcgc ggcgtgccag gcggtagaga aaacggccga tgccgggatc gatcaaaaag    9300
taatcggggt gaaccgtcag cacgtccggg ttcttgcctt ctgtgatctc gcggtacatc    9360
caatcagcta gctcgatctc gatgtactcc ggccgcccgg tttcgctctt tacgatcttg    9420
tagcggctaa tcaaggcttc accctcggat accgtcacca ggcggccgtt cttggccttc    9480
ttcgtacgct gcatggcaac gtgcgtggtg tttaaccgaa tgcaggtttc taccaggtcg    9540
tctttctgct ttccgccatc ggctcgccgg cagaacttga gtacgtccgc aacgtgtgga    9600
cggaacacgc ggccgggctt gtctcccttc ccttcccggt atcggttcat ggattcggtt    9660
agatgggaaa ccgccatcag taccaggtcg taatcccaca cactggccat gccggccggc    9720
cctgcggaaa cctctacgtg cccgtctgga agctcgtagc ggatcacctc gccagctcgt    9780
cggtcacgct tcgacagacg gaaaacggcc acgtccatga tgctgcgact atcgcgggtg    9840
cccacgtcat agagcatcgg aacgaaaaaa tctggttgct cgtcgccctt gggcggcttc    9900
ctaatcgacg gcgcaccggc tgccggcggt tgccgggatt ctttgcggat tcgatcagcg    9960
gccgcttgcc acgattcacc ggggcgtgct tctgcctcga tgcgttgccg ctgggcggcc   10020
tgcgcggcct tcaacttctc caccaggtca tcacccagcg ccgcgccgat ttgtaccggg   10080
ccggatggtt tgcgaccgtc acgccgattc ctcgggcttg ggggttccag tgccattgca   10140
```

```
gggccggcag acaacccagc cgcttacgcc tggccaaccg cccgttcctc cacacatggg    10200
gcattccacg gcgtcggtgc ctggttgttc ttgattttcc atgccgcctc ctttagccgc    10260
taaaattcat ctactcattt attcatttgc tcatttactc tggtagctgc gcgatgtatt    10320
cagatagcag ctcggtaatg gtcttgcctt ggcgtaccgc gtacatcttc agcttggtgt    10380
gatcctccgc cggcaactga aagttgaccc gcttcatggc tggcgtgtct gccaggctgg    10440
ccaacgttgc agccttgctg ctgcgtgcgc tcggacggcc ggcacttagc gtgtttgtgc    10500
ttttgctcat tttctcttta cctcattaac tcaaatgagt tttgatttaa tttcagcggc    10560
cagcgcctgg acctcgcggg cagcgtcgcc ctcgggttct gattcaagaa cggttgtgcc    10620
ggcggcggca gtgcctgggt agctcacgcg ctgcgtgata cgggactcaa gaatgggcag    10680
ctcgtacccg gccagcgcct cggcaacctc accgccgatg cgcgtgcctt tgatcgcccg    10740
cgacacgaca aaggccgctt gtagccttcc atccgtgacc tcaatgcgct gcttaaccag    10800
ctccaccagg tcggcggtgg cccatatgtc gtaagggctt ggctgcaccg gaatcagcac    10860
gaagtcggct gccttgatcg cggacacagc caagtccgcc gcctggggcg ctccgtcgat    10920
cactacgaag tcgcgccggc cgatggcctt cacgtcgcgg tcaatcgtcg ggcggtcgat    10980
gccgacaacg gttagcggtt gatcttcccg cacggccgcc caatcgcggg cactgccctg    11040
gggatcggaa tcgactaaca gaacatcggc cccggcgagt gcagggcgc gggctagatg     11100
ggttgcgatg gtcgtcttgc ctgacccgcc tttctggtta agtacagcga taaccttcat    11160
gcgttcccct tgcgtatttg tttatttact catcgcatca tatacgcagc gaccgcatga    11220
cgcaagctgt tttactcaaa tacacatcac cttttttagac ggcggcgctc ggtttcttca   11280
gcggccaagc tggccggcca ggccgccagc ttggcatcag acaaaccggc caggatttca    11340
tgcagccgca cggttgagac gtgcgcgggc ggctcgaaca cgtacccggc cgcgatcatc    11400
tccgcctcga tctcttcggt aatgaaaaac ggttcgtcct ggccgtcctg gtgcggtttc    11460
atgcttgttc ctcttggcgt tcattctcgg cggccgccag ggcgtcggcc tcggtcaatg    11520
cgtcctcacg gaaggcaccg cgccgcctgg cctcggtggg cgtcacttcc tcgctgcgct    11580
caagtgcgcg gtacagggtc gagcgatgca cgccaagcag tgcagccgcc tctttcacgg    11640
tgcggccttc ctggtcgatc agctcgcggg cgtgcgcgat ctgtgccggg gtgagggtag    11700
ggcggggggcc aaacttcacg cctcgggcct tggcggcctc gcgcccgctc cgggtgcggt    11760
cgatgattag ggaacgctcg aactcggcaa tgccggcgaa cacggtcaac accatgcggc    11820
cggccggcgt ggtggtgtcg gcccacggct ctgccaggct acgcaggccc gcgccggcct    11880
cctggatgcg ctcggcaatg tccagtaggt cgcgggtgct gcgggccagg cggtctagcc    11940
tggtcactgt cacaacgtcg ccagggcgta ggtggtcaag catcctggcc agctccggc     12000
ggtcgcgcct ggtgccggtg atcttctcgg aaaacagctt ggtgcagccg ccgcgtgca     12060
gttcggcccg ttggttggtc aagtcctggt cgtcggtgct gacgcgggca tagcccagca    12120
ggccagcggc ggcgctcttg ttcatggcgt aatgtctccg gttctagtcg caagtattct    12180
actttatgcg actaaaacac gcgacaagaa aacgccagga aaagggcagg gcggcagcct    12240
gtcgcgtaac ttaggacttg tgcgacatgt cgttttcaga agacggctgc actgaacgtc    12300
agaagccgac tgcactatag cagcggaggg gttggatcaa agtact         12346
```

<210> SEQ ID NO 30
<211> LENGTH: 594
<212> TYPE: PRT

<213> ORGANISM: Artificial Sequence
<220> FEATURE:
<223> OTHER INFORMATION: Chimaera STM-GIF1

<400> SEQUENCE: 30

```
Met Glu Ser Gly Ser Asn Ser Thr Ser Cys Pro Met Ala Phe Ala Gly
1               5                   10                  15

Asp Asn Ser Asp Gly Pro Met Cys Pro Met Met Met Met Met Pro Pro
                20                  25                  30

Ile Met Thr Ser His Gln His Gly His Asp His Gln His Gln Gln
            35                  40                  45

Gln Glu His Asp Gly Tyr Ala Tyr Gln Ser His Gln Gln Ser Ser
    50                  55                  60

Ser Leu Phe Leu Gln Ser Leu Ala Pro Pro Gln Gly Thr Lys Asn Lys
65              70                  75                  80

Val Ala Ser Ser Ser Pro Ser Ser Cys Ala Pro Ala Tyr Ser Leu
                85                  90                  95

Met Glu Ile His His Asn Glu Ile Val Ala Gly Gly Ile Asn Pro Cys
                100                 105                 110

Ser Ser Ser Ser Ser Ala Ser Val Lys Ala Lys Ile Met Ala His
            115                 120                 125

Pro His Tyr His Arg Leu Leu Ala Ala Tyr Val Asn Cys Gln Lys Val
                130                 135                 140

Gly Ala Pro Pro Glu Val Val Ala Arg Leu Glu Ala Cys Ser Ser
145                 150                 155                 160

Ala Ala Ala Ala Ala Ser Met Gly Pro Thr Gly Cys Leu Gly Glu
                165                 170                 175

Asp Pro Gly Leu Asp Gln Phe Met Glu Ala Tyr Cys Glu Met Leu Val
                180                 185                 190

Lys Tyr Glu Gln Glu Leu Ser Lys Pro Phe Lys Glu Ala Met Val Phe
            195                 200                 205

Leu Gln Arg Val Glu Cys Gln Phe Lys Ser Leu Ser Leu Ser Ser Pro
    210                 215                 220

Ser Ser Phe Ser Gly Tyr Gly Glu Thr Ala Ile Asp Arg Asn Asn Asn
225                 230                 235                 240

Gly Ser Ser Glu Glu Glu Val Asp Met Asn Asn Glu Phe Val Asp Pro
                245                 250                 255

Gln Ala Glu Asp Arg Glu Leu Lys Gly Gln Leu Leu Arg Lys Tyr Ser
                260                 265                 270

Gly Tyr Leu Gly Ser Leu Lys Gln Glu Phe Met Lys Lys Arg Lys Lys
            275                 280                 285

Gly Lys Leu Pro Lys Glu Ala Arg Gln Gln Leu Leu Asp Trp Trp Ser
290                 295                 300

Arg His Tyr Lys Trp Pro Tyr Pro Ser Glu Gln Gln Lys Leu Ala Leu
305                 310                 315                 320

Ala Glu Ser Thr Gly Leu Asp Gln Lys Gln Ile Asn Asn Trp Phe Ile
                325                 330                 335

Asn Gln Arg Lys Arg His Trp Lys Pro Ser Glu Asp Met Gln Phe Val
                340                 345                 350

Val Met Asp Ala Thr His Pro His Tyr Phe Met Asp Asn Val Leu
                355                 360                 365

Gly Asn Pro Phe Pro Met Asp His Ile Ser Ser Thr Met Leu Val Asp
            370                 375                 380

Met Gln Gln His Leu Met Gln Met Gln Pro Met Met Ala Gly Tyr Tyr
```

```
                385                 390                 395                 400
        Pro Ser Asn Val Thr Ser Asp His Ile Gln Gln Tyr Leu Asp Glu Asn
                        405                 410                 415
        Lys Ser Leu Ile Leu Lys Ile Val Glu Ser Gln Asn Ser Gly Lys Leu
                    420                 425                 430
        Ser Glu Cys Ala Glu Asn Gln Ala Arg Leu Gln Arg Asn Leu Met Tyr
                435                 440                 445
        Leu Ala Ala Ile Ala Asp Ser Gln Pro Gln Pro Pro Ser Val His Ser
            450                 455                 460
        Gln Tyr Gly Ser Ala Gly Gly Met Ile Gln Gly Glu Gly Ser
        465                 470                 475                 480
        His Tyr Leu Gln Gln Gln Ala Thr Gln Gln Gln Met Thr Gln
                        485                 490                 495
        Gln Ser Leu Met Ala Ala Arg Ser Ser Met Leu Tyr Ala Gln Gln Gln
                    500                 505                 510
        Gln Gln Gln Gln Pro Tyr Ala Thr Leu Gln His Gln Gln Leu His His
                515                 520                 525
        Ser Gln Leu Gly Met Ser Ser Ser Gly Gly Gly Ser Ser Gly
            530                 535                 540
        Leu His Ile Leu Gln Gly Glu Ala Gly Gly Phe His Asp Phe Gly Arg
        545                 550                 555                 560
        Gly Lys Pro Glu Met Gly Ser Gly Gly Gly Glu Gly Arg Gly Gly
                        565                 570                 575
        Ser Ser Gly Asp Gly Gly Glu Thr Leu Tyr Leu Lys Ser Ser Asp Asp
                    580                 585                 590
        Gly Asn

<210> SEQ ID NO 31
<211> LENGTH: 1785
<212> TYPE: DNA
<213> ORGANISM: Artificial Sequence
<220> FEATURE:
<223> OTHER INFORMATION: Chimera STM-GIF1

<400> SEQUENCE: 31
atggagagtg gttccaacag cacttcttgt ccaatggctt ttgccgggga taatagtgat      60
ggtccgatgt gtcctatgat gatgatgatg ccgcccatca tgacatcaca tcaacatcat     120
ggtcatgatc atcaacatca acaacaagaa catgatggtt atgcatatca gtcacaccac     180
caacaaagta gttcccttt tcttcaatca ctagctcctc cccaaggaac taagaacaaa      240
gttgcttctt cttcttctcc ttcctcttgt gctcctgcct attctctaat ggagatccat     300
cataacgaaa tcgttgcagg aggaatcaac ccttgctcct cttcctcttc ttcagcctct     360
gtcaaggcca agatcatggc tcatcctcac taccaccgcc tcttggccgc ttatgtcaat     420
tgtcagaagg ttggagcacc accggaggtt gtggcgaggc tggaggaggc atgctcgtct     480
gccgcagccg cagccgcatc tatggggcca acagggtgtc ttggtgaaga tccagggctt     540
gatcaattca tggaagctta ctgtgaaatg ctcgttaagt atgagcaaga gctctccaaa     600
cctttcaagg aagctatggt cttccttcaa cgtgtcgagt gtcaattcaa atccctctct     660
ctatcctcac cttcctcttt ctccggttat ggagagacag caattgatag gaacaataat     720
gggtcatccg aggaagaagt cgatatgaac aatgaatttg tagatccaca agctgaggat     780
agagagctta aggacagctc ttgcgcaag tacagtggtt acttagggag cctcaagcaa      840
gagttcatga agaagaggaa gaaaggaaag ctccctaaag aagctcgtca acaactgctt     900
```

```
gattggtgga gccgccacta caaatggcct taccctttcgg agcaacaaaa gctcgcccctt    960 gcggaatcaa cggggctgga ccagaaacag ataaacaatt ggttcataaa ccagaggaaa   1020
cggcattgga agccgtcgga ggacatgcag tttgtagtaa tggacgcaac acatcctcac   1080
cattacttca tggataatgt cttgggcaat ccttttcccaa tggatcacat ctcctccacc   1140
atgcttgtcg acatgcaaca gcacctgatg cagatgcagc ccatgatggc tggttactac   1200
cccagcaatg ttacctctga tcatatccaa cagtacttgg acgaaaacaa atcgttgatt   1260
ctgaagattg ttgagtctca aaactctgga aagcttagcg aatgcgccga gaatcaagca   1320
aggcttcaac gcaacctaat gtacctagct gcaatagcag attctcagcc tcagccacca   1380
agtgtgcata gccagtatgg atctgctggt ggtgggatga ttcagggaga aggagggtca   1440
cactatttgc agcagcaaca agcgactcaa cagcaacaga tgactcagca gtctctaatg   1500
gcggctcgat cttcaatgtt gtatgctcag caacagcagc agcagcagcc ttacgcgacg   1560
cttcagcatc agcaattgca ccatagccag cttggaatga gctcgagcag cggaggagga   1620
ggaagcagtg gtctccatat ccttcaggga gaggctggtg ggtttcatga ttttggccgt   1680
gggaagccgg aaatgggaag tggtggtggc ggtgaaggca gaggaggaag ttcagggggat   1740 ggtggagaaa ccctttactt gaaatcatca gatgatggga attga               1785

<210> SEQ ID NO 32
<211> LENGTH: 12286
<212> TYPE: DNA
<213> ORGANISM: Artificial Sequence
<220> FEATURE:
<223> OTHER INFORMATION: Binary vector pJD221 for expression of chimeric
      protein STM-GIF1

<400> SEQUENCE: 32
ttgatcccga ggggaaccct gtggttggca tgcacataca aatggacgaa cggataaacc     60
ttttcacgcc cttttaaata tccgttattc taataaacgc tcttttctct taggtttacc    120
cgccaatata tcctgtcaaa cactgatagt ttaaactgaa ggcgggaaac gacaatctga    180
tccaagctca agctgctcta gccaatacgc aaaccgcctc tccccgcgcg ttggccgatt    240
cattaatgca gctggcacga caggtttccc gactggaaag cgggcagtga gcgcaacgca    300
attaatgtga gttagctcac tcattaggca ccccaggctt tacactttat gcttccggct    360
cgtatgttgt gtggaattgt gagcggataa caatttcaca caggaaacag ctatgaccat    420
gattacgaat tcggtcccca gattagcctt ttcaatttca gaaagaatgc taacccacag    480
atggttagag aggcttacgc agcaggtctc atcaagacga tctacccgag caataatctc    540
caggaaatca ataccttcc  caagaaggtt aaagatgcag tcaaaagatt caggactaac    600
tgcatcaaga acacagagaa agatatattt ctcaagatca gaagtactat tccagtatgg    660
acgattcaag gcttgcttca caaaccaagg caagtaatag agattggagt ctctaaaaag    720
gtagttccca ctgaatcaaa ggccatggag tcaaagattc aaatagagga cctaacagaa    780
ctcgccgtaa agactggcga acagttcata cagagtctct tacgactcaa tgacaagaag    840
aaaatcttcg tcaacatggt ggagcacgac acacttgtct actccaaaaa tatcaaagat    900
acagtctcag aagaccaaag ggcaattgag acttttcaac aaagggtaat atccggaaac    960
ctcctcggat tccattgccc agctatctgt cactttattg tgaagatagt ggaaaaggaa   1020
ggtggctcct acaaatgcca tcattgcgat aaaggaaagg ccatcgttga agatgcctct   1080
gccgacagtg gtcccaaaga tggacccccca cccacgagga gcatcgtgga aaaagaagac   1140
```

```
gttccaacca cgtcttcaaa gcaagtggat tgatgtgata tctccactga cgtaagggat    1200
gacgcacaat cccactatcc ttcgcaagac ccttcctcta tataaggaag ttcatttcat    1260
ttggagagaa cacggggggac gagctcggta cccggggatc catggagagt ggttccaaca    1320
gcacttcttg tccaatggct tttgccgggg ataatagtga tggtccgatg tgtcctatga    1380
tgatgatgat gccgcccatc atgacatcac atcaacatca tggtcatgat catcaacatc    1440
aacaacaaga acatgatggt tatgcatatc agtcacacca ccaacaaagt agttcccttt    1500
ttcttcaatc actagctcct ccccaaggaa ctaagaacaa agttgcttct tcttcttctc    1560
cttcctcttg tgctcctgcc tattctctaa tggagatcca tcataacgaa atcgttgcag    1620
gaggaatcaa cccttgctcc tcttcctctt cttcagcctc tgtcaaggcc aagatcatgg    1680
ctcatcctca ctaccaccgc ctcttggccg cttatgtcaa ttgtcagaag gttggagcac    1740
caccggaggt tgtggcgagg ctggaggagg catgctcgtc tgccgcagcc gcagccgcat    1800
ctatggggcc aacagggtgt cttggtgaag atccagggct tgatcaattc atggaagctt    1860
actgtgaaat gctcgttaag tatgagcaag agctctccaa accttcaag gaagctatgg     1920 tcttccttca acgtgtcgag tgtcaattca aatccctctc tctatcctca ccttcctctt    1980
tctccggtta tggagagaca gcaattgata ggaacaataa tgggtcatcc gaggaagaag    2040
tcgatatgaa caatgaattt gtagatccac aagctgagga tagagagctt aaaggacagc    2100
tcttgcgcaa gtacagtggt tacttaggga gcctcaagca agagttcatg aagaagagga    2160
agaaaggaaa gctccctaaa gaagctcgtc aacaactgct tgattggtgg agccgccact    2220
acaaatggcc ttacccttcg gagcaacaaa agctcgccct tgcggaatca acggggctgg    2280
accagaaaca gataaacaat tggttcataa accagaggaa acggcattgg aagccgtcgg    2340
aggacatgca gtttgtagta atggacgcaa cacatcctca ccattacttc atggataatg    2400
tcttgggcaa tccttttccca atggatcaca tctcctccac catgcttgtc gacatgcaac    2460
agcacctgat gcagatgcag cccatgatgg ctggttacta ccccagcaat gttacctctg    2520
atcatatcca acagtacttg gacgaaaaca aatcgttgat tctgaagatt gttgagtctc    2580
aaaactctgg aaagcttagc gaatgcgccg agaatcaagc aaggcttcaa cgcaacctaa    2640
tgtacctagc tgcaatagca gattctcagc ctcagccacc aagtgtgcat agccagtatg    2700
gatctgctgg tggtgggatg attcaggag aaggagggtc acactatttg cagcagcaac     2760
aagcgactca acagcaacag atgactcagc agtctctaat ggcggctcga tcttcaatgt    2820
tgtatgctca gcaacagcag cagcagcagc cttacgcgac gcttcagcat cagcaattgc    2880
accatagcca gcttggaatg agctcgagca gcggaggagg aggaagcagt ggtctccata    2940
tccttcaggg agaggctggt gggtttcatg attttggccg tggaagccg gaaatgggaa      3000 gtggtggtgg cggtgaaggc agaggaggaa gttcagggga tggtggagaa acccttact     3060 tgaaatcatc agatgatggg aattgaaagc catgggggct gcagagcttt cgttcgtatc    3120
atcggtttcg acaacgttcg tcaagttcaa tgcatcagtt tcattgcgca cacaccagaa    3180
tcctactgag ttcgagtatt atggcattgg gaaacatgtt tttcttgtac catttgttgt    3240
gcttgtaatt tactgtgttt tttattcggt ttcgctatc gaactgtgaa atggaaatgg     3300
atggagaaga gttaatgaat gatatggtcc ttttgttcat tctcaaatta atattatttg    3360
ttttttctct tatttgttgt gtgttgaatt tgaaaatata agagatatgc aaacatttttg   3420 ttttgagtaa aaatgtgtca aatcgtggcc tctaatgacc gaagttaata tgaggagtaa    3480
```

-continued

```
aacacttgta gttgtaccat tatgcttatt cactaggcaa caaatatatt ttcagaccta    3540
gaaaagctgc aaatgttact gaatacaagt atgtcctctt gtgttttaga catttatgaa    3600
ctttccttta tgtaattttc cagaatcctt gtcagattct aatcattgct ttataattat    3660
agttatactc atggatttgt agttgagtat gaaatatttt ttaatgcat tttatgactt     3720
gccaattgat tgacaacatg catcaatcga agcttggcac tggccgtcgt tttacaacgt    3780
cgtgactggg aaaaccctgg cgttacccaa cttaatcgcc ttgcagcaca tccccctttc    3840
gccagctggc gtaatagcga agaggcccgc accgatcgcc cttcccaaca gttgcgcagc    3900
ctgaatggcg aatgctagag cagcttgcca acatggtgga gcacgacact ctcgtctact    3960
ccaagaatat caaagataca gtctcagaag accaagggc tattgagact tttcaacaaa     4020
gggtaatatc gggaaacctc ctcggattcc attgcccagc tatctgtcac ttcatcaaaa    4080
ggacagtaga aaaggaaggt ggcacctaca aatgccatca ttgcgataaa ggaaaggcta    4140
tcgttcaaga tgcctctgcc gacagtggtc ccaaagatgg accccacccc acgaggagca    4200
tcgtggaaaa agaagacgtt ccaaccacgt cttcaaagca gtggattga tgtgataaca     4260
tggtggagca cgacactctc gtctactcca agaatatcaa agatacagtc tcagaagacc    4320
aaagggctat tgagactttt caacaaaggg taatatcggg aaacctcctc ggattccatt    4380
gcccagctat ctgtcacttc atcaaagga cagtagaaaa ggaaggtggc acctacaaat     4440
gccatcattg cgataaagga aaggctatcg ttcaagatgc ctctgccgac agtggtccca    4500
aagatggacc cccacccacg aggagcatcg tggaaaaaga acgttcca accacgtctt      4560
caaagcaagt ggattgatgt gatatctcca ctgacgtaag gatgacgca caatcccact     4620
atccttcgca agaccctccc tctatataag gaagttcatt tcatttggag aggacacgct    4680
gaaatcacca gtctctctct acaaatctat ctctctcgat tcgcagatct gtcgatcgac    4740
catgggatt gaacaagatg gattgcacgc aggttctccg gccgcttggg tggagaggct     4800
attcggctat gactgggcac aacagacaat cggctgctct gatgccgccg tgttccggct    4860
gtcagcgcag gggcgcccgg ttcttttttgt caagaccgac ctgtccggtg ccctgaatga   4920
actccaggac gaggcagcgc ggctatcgtg gctggccacg acgggcgttc cttgcgcagc    4980
tgtgctcgac gttgtcactg aagcgggaag ggactggctg ctattgggcg aagtgccggg    5040
gcaggatctc ctgtcatctc accttgctcc tgccgagaaa gtatccatca tggctgatgc    5100
aatgcggcgg ctgcatacgc ttgatccggc tacctgccca ttcgaccacc aagcgaaaca    5160
tcgcatcgag cgagcacgta ctcggatgga agccggtctt gtcgatcagg atgatctgga    5220
cgaagagcat caggggctcg cgccagccga actgttcgcc aggctcaagg cgcgcatgcc    5280
cgacggcgag gatctcgtcg tgacacatgg cgatgcctgc ttgccgaata tcatggtgga    5340
aaatggccgc ttttctggat tcatcgactg tggccggctg ggtgtggcgg accgctatca    5400
ggacatagcg ttggctaccc gtgatattgc tgaagagctt ggcggcgaat gggctgaccg    5460
cttcctcgtg ctttacggta tcgccgctcc cgattcgcag cgcatcgcct tctatcgcct    5520
tcttgacgag ttcttctgag cgggactctg gggttcggat cgatcctcta gctagagtcg    5580
atcgacatcg agtttctcca taataatgtg tgagtagttc ccagataagg gaattagggt    5640
tcttataggg tttcgctcac gtgttgagca tataagaaac ccttagtatg tatttgtatt    5700
tgtaaaatac ttctatcaat aaaatttcta attcctaaaa ccaaaatcca gtactaaaat    5760
ccagatcacc taaagtccct atagatcccc cgaattaatt cggcgttaat tcagtacatt    5820
aaaaacgtcc gcaatgtgtt attaagttgt ctaagcgtca atttgtttac accacaatat    5880
```

```
atcctgccac cagccagcca acagctcccc gaccggcagc tcggcacaaa atcaccactc   5940
gatacaggca gcccatcagt ccgggacggc gtcagcggga gagccgttgt aaggcggcag   6000
actttgctca tgttaccgat gctattcgga agaacggcaa ctaagctgcc gggtttgaaa   6060 cacgcgatgat ctcgcggagg gtagcatgtt gattgtaacg atgacagagc gttgctgcct   6120
gtgatcaatt cgggcacgaa cccagtggac ataagcctcg ttcggttcgt aagctgtaat   6180
gcaagtagcg taactgccgt cacgcaactg gtccagaacc ttgaccgaac gcagcggtgg   6240
taacggcgca gtggcggttt tcatggcttc ttgttatgac atgttttttt ggggtacagt   6300
ctatgcctcg ggcatccaag cagcaagcgc gttacgccgt gggtcgatgt ttgatgttat   6360
ggagcagcaa cgatgttacg cagcagggca gtcgccctaa acaaagtta aacatcatgg   6420 gggaagcggt gatcgccgaa gtatcgactc aactatcaga ggtagttggc gtcatcgagc   6480
gccatctcga accgacgttg ctggccgtac atttgtacgg ctccgcagtg gatggcggcc   6540
tgaagccaca cagtgatatt gatttgctgg ttacggtgac cgtaaggctt gatgaaacaa   6600
cgcggcgagc tttgatcaac gaccttttgg aaacttcggc ttccctgga gagagcgaga   6660 ttctccgcgc tgtagaagtc accattgttg tgcacgacga catcattccg tggcgttatc   6720
cagctaagcg cgaactgcaa tttggagaat ggcagcgcaa tgacattctt gcaggtatct   6780
tcgagccagc cacgatcgac attgatctgg ctatcttgct gacaaaagca agagaacata   6840
gcgttgcctt ggtaggtcca gcggcggagg aactctttga tccggttcct gaacaggatc   6900
tatttgaggc gctaaatgaa accttaacgc tatggaactc gccgcccgac tgggctggcg   6960
atgagcgaaa tgtagtgctt acgttgtccc gcatttggta cagcgcagta accggcaaaa   7020
tcgcgccgaa ggatgtcgct gccgactggg caatggagcg cctgccggcc cagtatcagc   7080
ccgtcatact tgaagctaga caggcttatc ttggacaaga agaagatcgc ttggcctcgc   7140
gcgcagatca gttggaagaa tttgtccact acgtgaaagg cgagatcacc aaggtagtcg   7200
gcaaataatg tctagctaga aattcgttca agccgacgcc gcttcgccgg cgttaactca   7260
agcgattaga tgcactaagc acataattgc tcacagccaa actatcaggt caagtctgct   7320
tttattattt ttaagcgtgc ataataagcc ctacacaaat tgggagatat atcatgcatg   7380
accaaaatcc cttaacgtga gttttcgttc cactgagcgt cagacccgt agaaaagatc   7440 aaaggatctt cttgagatcc ttttttttctg cgcgtaatct gctgcttgca acaaaaaaa   7500 ccaccgctac cagcggtggt ttgtttgccg gatcaagagc taccaactct ttttccgaag   7560
gtaactggct tcagcagagc gcagatacca aatactgtcc ttctagtgta gccgtagtta   7620
ggccaccact tcaagaactc tgtagcaccg cctacatacc tcgctctgct aatcctgtta   7680
ccagtggctg ctgccagtgg cgataagtcg tgtcttaccg ggttggactc aagacgatag   7740
ttaccggata aggcgcagcg gtcgggctga acggggggtt cgtgcacaca gcccagcttg   7800
gagcgaacga cctacaccga actgagatac ctacagcgtg agctatgaga aagcgccacg   7860
cttcccgaag ggagaaaggc ggacaggtat ccggtaagcg gcagggtcgg aacaggagag   7920
cgcacgaggg agcttccagg gggaaacgcc tggtatcttt atagtcctgt cgggtttcgc   7980
cacctctgac ttgagcgtcg attttttgtga tgctcgtcag ggggcggag cctatggaaa   8040 aacgccagca acgcggcctt tttacggttc ctggccttt gctggccttt tgctcacatg   8100
ttctttcctg cgttatcccc tgattctgtg ataaccgta ttaccgcctt tgagtgagct   8160
gataccgctc gccgcagccg aacgaccgag cgcagcgagt cagtgagcga ggaagcggaa   8220
```

```
gagcgcctga tgcggtattt tctccttacg catctgtgcg gtatttcaca ccgcatatgg    8280
tgcactctca gtacaatctg ctctgatgcc gcatagttaa gccagtatac actccgctat    8340
cgctacgtga ctgggtcatg gctgcgcccc gacacccgcc aacacccgct gacgcgccct    8400
gacgggcttg tctgctcccg gcatccgctt acagacaagc tgtgaccgtc tccgggagct    8460
gcatgtgtca gaggttttca ccgtcatcac cgaaacgcgc gaggcagggt gccttgatgt    8520
gggcgccggc ggtcgagtgg cgacggcgcg gcttgtccgc gccctggtag attgcctggc    8580
cgtaggccag ccattttttga gcggccagcg gccgcgatag gccgacgcga agcggcgggg    8640
cgtagggagc gcagcgaccg aagggtaggc gcttttttgca gctcttcggc tgtgcgctgg    8700
ccagacagtt atgcacaggc caggcgggtt ttaagagttt taataagttt taaagagttt    8760
taggcggaaa aatcgccttt tttctctttt atatcagtca cttacatgtg tgaccggttc    8820
ccaatgtacg gctttgggtt cccaatgtac gggttccggt tcccaatgta cggctttggg    8880
ttcccaatgt acgtgctatc cacaggaaag agccttttc gacctttttc ccctgctagg    8940
gcaatttgcc ctagcatctg ctccgtacat taggaaccgg cggatgcttc gccctcgatc    9000
aggttgcggt agcgcatgac taggatcggg ccagcctgcc ccgcctcctc cttcaaatcg    9060
tactccggca ggtcatttga cccgatcagc ttgcgcacgg tgaaacagaa cttcttgaac    9120
tctccggcgc tgccactgcg ttcgtagatc gtcttgaaca accatctggc ttctgccttg    9180
cctgcgcgcg ggcgtgccag gcggtagaga aacggccga tgccgggatc gatcaaaaag    9240
taatcggggt gaaccgtcag cacgtccggg ttcttgcctt ctgtgatctc gcggtacatc    9300
caatcagcta gctcgatctc gatgtactcc ggccgcccgg tttcgctctt tacgatcttg    9360
tagcggctaa tcaaggcttc accctcggat accgtcacca ggcggccgtt cttggccttc    9420
ttcgtacgct gcatggcaac gtgcgtggtg tttaaccgaa tgcaggtttc taccaggtcg    9480
tctttctgct ttccgccatc ggctcgccgg cagaacttga gtacgtccgc aacgtgtgga    9540
cggaacacgc ggccgggctt gtctcccttc ccttcccgt atcggttcat ggattcggtt    9600
agatgggaaa ccgccatcag taccaggtcg taatcccaca cactggccat gccggccggc    9660
cctgcggaaa cctctacgtg cccgtctgga agctcgtagc ggatcacctc gccagctcgt    9720
cggtcacgct tcgacagacg gaaaacggcc acgtccatga tgctgcgact atcgcgggtg    9780
cccacgtcat agagcatcgg aacgaaaaaa tctggttgct cgtcgccctt gggcggcttc    9840
ctaatcgacg gcgcaccggc tgccggcggt tgccgggatt ctttgcggat tcgatcagcg    9900
gccgcttgcc acgattcacc ggggcgtgct tctgcctcga tgcgttgccg ctgggcggcc    9960
tgcgcggcct tcaacttctc caccaggtca tcacccagcg ccgcgccgat ttgtaccggg    10020
ccggatggtt tgcgaccgtc acgccgattc tcgggcttg ggggttccag tgccattgca    10080
gggccggcag acaacccagc cgcttacgcc tggccaaccg cccgttcctc cacacatggg    10140
gcattccacg gcgtcggtgc ctggttgttc ttgatttcc atgccgcctc ctttagccgc    10200
taaaattcat ctactcattt attcatttgc tcatttactc tggtagctgc gcgatgtatt    10260
cagatagcag ctcggtaatg gtcttgcctt ggcgtaccgc gtacatcttc agcttggtgt    10320
gatcctccgc cggcaactga agttgaccc gcttcatggc tggcgtgtct gccaggctgg    10380
ccaacgttgc agccttgctg ctgcgtgcgc tcggacggcc ggcacttagc gtgtttgtgc    10440
ttttgctcat tttctcttta cctcattaac tcaaatgagt tttgatttaa tttcagcggc    10500
cagcgcctgg acctcgcggg cagcgtcgcc ctcgggttct gattcaagaa cggttgtgcc    10560
ggcggcggca gtgcctgggt agctcacgcg ctgcgtgata cgggactcaa gaatgggcag    10620
```

```
ctcgtacccg gccagcgcct cggcaacctc accgccgatg cgcgtgcctt tgatcgcccg   10680
cgacacgaca aaggccgctt gtagccttcc atccgtgacc tcaatgcgct gcttaaccag   10740
ctccaccagg tcggcggtgg cccatatgtc gtaagggctt ggctgcaccg gaatcagcac   10800
gaagtcggct gccttgatcg cggacacagc caagtccgcc gctgggggcg ctccgtcgat   10860
cactacgaag tcgcgccggc cgatggcctt cacgtcgcgg tcaatcgtcg ggcggtcgat   10920
gccgacaacg gttagcggtt gatcttcccg cacggccgcc caatcgcggg cactgccctg   10980
gggatcggaa tcgactaaca gaacatcggc cccggcgagt gcagggcgc gggctagatg    11040
ggttgcgatg gtcgtcttgc ctgacccgcc tttctggtta agtacagcga taaccttcat   11100
gcgttcccct tgcgtatttg tttatttact catcgcatca tatacgcagc gaccgcatga   11160
cgcaagctgt tttactcaaa tacacatcac ctttttagac ggcggcgctc ggtttcttca   11220
gcggccaagc tggccggcca ggccgccagc ttggcatcag acaaaccggc caggatttca   11280
tgcagccgca cggttgagac gtgcgcgggc ggctcgaaca cgtacccggc cgcgatcatc   11340
tccgcctcga tctcttcggt aatgaaaaac ggttcgtcct ggccgtcctg gtgcggtttc   11400
atgcttgttc ctcttggcgt tcattctcgg cggccgccag ggcgtcggcc tcggtcaatg   11460
cgtcctcacg gaaggcaccg cgccgcctgg cctcggtggg cgtcacttcc tcgctgcgct   11520
caagtgcgcg gtacagggtc gagcgatgca cgccaagcag tgcagccgcc tctttcacgg   11580
tgcggccttc ctggtcgatc agctcgcggg cgtgcgcgat ctgtgccggg gtgagggtag   11640
ggcggggggcc aaacttcacg cctcgggcct tggcggcctc gcgcccgctc cgggtgcggt   11700
cgatgattag ggaacgctcg aactcggcaa tgccggcgaa cacggtcaac accatgcggc   11760
cggccggcgt ggtggtgtcg gcccacggct ctgccaggct acgcaggccc gcgccggcct   11820
cctggatgcg ctcggcaatg tccagtaggt cgcgggtgct gcgggccagg cggtctagcc   11880
tggtcactgt cacaacgtcg ccagggcgta ggtggtcaag catcctggcc agctccgggc   11940
ggtcgcgcct ggtgccggtg atcttctcgg aaaacagctt ggtgcagccg gccgcgtgca   12000
gttcggcccg ttggttggtc aagtcctggt cgtcggtgct gacgcgggca tagcccagca   12060
ggccagcggc ggcgctcttg ttcatggcgt aatgtctccg gttctagtcg caagtattct   12120
actttatgcg actaaaacac gcgacaagaa aacgccagga aaagggcagg gcggcagcct   12180
gtcgcgtaac ttaggacttg tgcgacatgt cgttttcaga agacggctgc actgaacgtc   12240
agaagccgac tgcactatag cagcggaggg gttggatcaa agtact         12286
```

<210> SEQ ID NO 33
<211> LENGTH: 580
<212> TYPE: PRT
<213> ORGANISM: Artificial Sequence
<220> FEATURE:
<223> OTHER INFORMATION: Chimera TCP2-GIF1

<400> SEQUENCE: 33

Met Ile Gly Asp Leu Met Lys Asn Asn Asn Gly Asp Val Val Asp
1               5                   10                  15

Asn Glu Val Asn Asn Arg Leu Ser Arg Trp His His Asn Ser Ser Arg
            20                  25                  30

Ile Ile Arg Val Ser Arg Ala Ser Gly Gly Lys Asp Arg His Ser Lys
        35                  40                  45

Val Leu Thr Ser Lys Gly Pro Arg Asp Arg Arg Val Arg Leu Ser Val
    50                  55                  60

Ser Thr Ala Leu Gln Phe Tyr Asp Leu Gln Asp Arg Leu Gly Tyr Asp
 65                  70                  75                  80

Gln Pro Ser Lys Ala Val Glu Trp Leu Ile Lys Ala Ala Glu Asp Ser
             85                  90                  95

Ile Ser Glu Leu Pro Ser Leu Asn Asn Thr His Phe Pro Thr Asp Asp
            100                 105                 110

Glu Asn His Gln Asn Gln Thr Leu Thr Thr Val Ala Ala Asn Ser Leu
            115                 120                 125

Ser Lys Ser Ala Cys Ser Ser Asn Ser Asp Thr Ser Lys Asn Ser Ser
130                 135                 140

Gly Leu Ser Leu Ser Arg Ser Glu Leu Arg Asp Lys Ala Arg Glu Arg
145                 150                 155                 160

Ala Arg Glu Arg Thr Ala Lys Glu Thr Lys Glu Arg Asp His Asn His
            165                 170                 175

Thr Ser Phe Thr Asp Leu Leu Asn Ser Gly Ser Asp Pro Val Asn Ser
            180                 185                 190

Asn Arg Gln Trp Met Ala Ser Ala Pro Ser Ser Pro Met Glu Tyr
            195                 200                 205

Phe Ser Ser Gly Leu Ile Leu Gly Ser Gly Gln Gln Thr His Phe Pro
210                 215                 220

Ile Ser Thr Asn Ser His Pro Phe Ser Ser Ile Ser Asp His His His
225                 230                 235                 240

His His Pro His His Gln His Gln Glu Phe Ser Val Pro Asp His
            245                 250                 255

Leu Ile Ser Pro Ala Glu Ser Asn Gly Gly Ala Phe Asn Leu Asp Phe
            260                 265                 270

Asn Met Ser Thr Pro Ser Gly Ala Gly Ala Ala Val Ser Ala Ala Ser
            275                 280                 285

Gly Gly Gly Phe Ser Gly Phe Asn Arg Gly Thr Leu Gln Ser Asn Ser
            290                 295                 300

Thr Asn Gln His Gln Ser Phe Leu Ala Asn Leu Gln Arg Phe Pro Thr
305                 310                 315                 320

Ser Glu Ser Gly Gly Gly Pro Gln Phe Leu Phe Gly Ala Leu Pro Ala
            325                 330                 335

Glu Asn His His His Asn His Gln Phe Gln Leu Tyr Tyr Glu Asn Gly
            340                 345                 350

Cys Arg Asn Ser Ser Glu His Lys Gly Lys Gly Lys Asn Lys Gly Pro
            355                 360                 365

Val Asp Met Gln Gln His Leu Met Gln Met Gln Pro Met Met Ala Gly
            370                 375                 380

Tyr Tyr Pro Ser Asn Val Thr Ser Asp His Ile Gln Gln Tyr Leu Asp
385                 390                 395                 400

Glu Asn Lys Ser Leu Ile Leu Lys Ile Val Glu Ser Gln Asn Ser Gly
            405                 410                 415

Lys Leu Ser Glu Cys Ala Glu Asn Gln Ala Arg Leu Gln Arg Asn Leu
            420                 425                 430

Met Tyr Leu Ala Ala Ile Ala Asp Ser Gln Pro Gln Pro Pro Ser Val
            435                 440                 445

His Ser Gln Tyr Gly Ser Ala Gly Gly Gly Met Ile Gln Gly Glu Gly
            450                 455                 460

Gly Ser His Tyr Leu Gln Gln Gln Gln Ala Thr Gln Gln Gln Gln Met
465                 470                 475                 480

Thr Gln Gln Ser Leu Met Ala Ala Arg Ser Ser Met Leu Tyr Ala Gln

```
                485                 490                 495
Gln Gln Gln Gln Gln Gln Pro Tyr Ala Thr Leu Gln His Gln Gln Leu
            500                 505                 510

His His Ser Gln Leu Gly Met Ser Ser Ser Gly Gly Gly Gly Ser
        515                 520                 525

Ser Gly Leu His Ile Leu Gln Gly Glu Ala Gly Phe His Asp Phe
    530                 535                 540

Gly Arg Gly Lys Pro Glu Met Gly Ser Gly Gly Gly Glu Gly Arg
545                 550                 555                 560

Gly Gly Ser Ser Gly Asp Gly Gly Glu Thr Leu Tyr Leu Lys Ser Ser
                565                 570                 575

Asp Asp Gly Asn
        580

<210> SEQ ID NO 34
<211> LENGTH: 1743
<212> TYPE: DNA
<213> ORGANISM: Artificial Sequence
<220> FEATURE:
<223> OTHER INFORMATION: Chimera TCP2-GIF1

<400> SEQUENCE: 34
atgattggag atctaatgaa gaataacaac aatggcgacg ttgtggataa cgaagtgaac      60
aaccggttaa gccggtggca tcacaattct tcccggataa ttagggtttc acgagcttcc    120
ggtggtaaag atcgacacag caaagtcttg acttctaaag gaccacgtga ccgtcgtgtc    180
cggttatcag tctccaccgc tcttcaattc tatgatcttc aagatcggtt aggttatgat    240
caacctagca aagctgttga atggttaatc aaagctgctg aagattcaat ctctgagctt    300
ccttcactca caacactca ttttccgacc gatgacgaga tcaccagaa tcagacatta    360
acaacagttg ctgctaattc cttgtctaaa tctgcttgta gtagcaattc agacacgagc    420
aagaactctt ctggtttgtc tttatcaaga tcggagctta gagataaagc tagagagagg    480
gctagagaga gaacagctaa agagaccaag gaaagagatc ataaccacac ttcgtttacg    540
gatttgttaa attccggttc agatccggtt aactcaaacc ggcaatggat ggcttcagct    600
ccttcttcat ctccaatgga gtatttcagt tcgggtttaa ttctcgggtc gggtcaacaa    660
acccatttcc ctatttcaac aaattctcat cctttctcat caatctccga tcatcatcat    720
catcatcctc atcatcagca tcaagagttt tcattcgttc ccgaccattt gatatcaccg    780
gcagaatcca acggcggagc attcaatctt gattttaata tgtcaacacc ctccggcgcc    840
ggagctgccg tctccgccgc atcaggtggt ggcttcagtg gtttcaacag ggggacccctt    900
cagtccaatt caacaaatca gcatcagtca ttcctcgcta atctacagag gtttccaaca    960
tcagaaagtg gaggaggtcc acagttctta ttcggtgcac tgcctgcaga gaatcaccac   1020
cacaatcacc agtttcagct ttactatgaa aatggatgca gaaactcatc agaacataag   1080
ggtaaaggca gaacaaagg ccctgtcgac atgaacagc acctgatgca gatgcagccc   1140
atgatggctg gttactaccc cagcaatgtt acctctgatc atatccaaca gtacttggac   1200
gaaaacaaat cgttgattct gaagattgtt gagtctcaaa actctggaaa gcttagcgaa   1260
tgcgccgaga tcaagcaag gcttcaacgc aacctaatgt acctagctgc aatagcagat   1320
tctcagcctc agccaccaag tgtgcatagc cagtatggat ctgctggtgg tgggatgatt   1380
cagggagaag gagggtcaca ctatttgcag cagcaacaag cgactcaaca gcaacagatg   1440
actcagcagt ctctaatggc ggctcgatct tcaatgttgt atgctcagca acagcagcag   1500
```

```
cagcagcctt acgcgacgct tcagcatcag caattgcacc atagccagct tggaatgagc    1560
tcgagcagcg gaggaggagg aagcagtggt ctccatatcc ttcagggaga ggctggtggg    1620
tttcatgatt ttggccgtgg gaagccggaa atgggaagtg gtggtggcgg tgaaggcaga    1680
ggaggaagtt caggggatgg tggagaaacc ctttacttga aatcatcaga tgatgggaat    1740
tga                                                                 1743
```

<210> SEQ ID NO 35
<211> LENGTH: 12244
<212> TYPE: DNA
<213> ORGANISM: Artificial Sequence
<220> FEATURE:
<223> OTHER INFORMATION: Binary vector pJD222 for expression of chimeric
      protein TCP2-GIF1

<400> SEQUENCE: 35

```
ttgatcccga ggggaaccct gtggttggca tgcacataca aatggacgaa cggataaacc     60
ttttcacgcc cttttaaata tccgttattc taataaacgc tcttttctct taggtttacc    120
cgccaatata tcctgtcaaa cactgatagt ttaaactgaa ggcgggaaac gacaatctga    180
tccaagctca agctgctcta gccaatacgc aaaccgcctc tccccgcgcg ttggccgatt    240
cattaatgca gctggcacga caggtttccc gactggaaag cgggcagtga gcgcaacgca    300
attaatgtga gttagctcac tcattaggca ccccaggctt tacactttat gcttccggct    360
cgtatgttgt gtggaattgt gagcggataa caatttcaca caggaaacag ctatgaccat    420
gattacgaat tcgtccccca gattagcctt ttcaatttca gaaagaatgc taacccacag    480
atggttagag aggcttacgc agcaggtctc atcaagacga tctacccgag caataatctc    540
caggaaatca aataccttcc caagaaggtt aaagatgcag tcaaaagatt caggactaac    600
tgcatcaaga acacagagaa agatatattt ctcaagatca gaagtactat tccagtatgg    660
acgattcaag gcttgcttca caaaccaagg caagtaatag agattggagt ctctaaaaag    720
gtagttccca ctgaatcaaa ggccatggag tcaaagattc aaatagagga cctaacagaa    780
ctcgccgtaa agactggcga acagttcata cagagtctct tacgactcaa tgacaagaag    840
aaaatcttcg tcaacatggt ggagcacgac acacttgtct actccaaaaa tatcaaagat    900
acagtctcag aagaccaaag ggcaattgag acttttcaac aaagggtaat atccggaaac    960
ctcctcggat tccattgccc agctatctgt cactttattg tgaagatagt ggaaaaggaa   1020
ggtggctcct acaaatgcca tcattgcgat aaaggaaagg ccatcgttga agatgcctct   1080
gccgacagtg gtcccaaaga tggaccccca cccacgagga gcatcgtgga aaaagaagac   1140
gttccaacca cgtcttcaaa gcaagtggat tgatgtgata tctccactga cgtaagggat   1200
gacgcacaat cccactatcc ttcgcaagac ccttcctcta tataaggaag ttcatttcat   1260
ttggagagaa cacggggac gagctcggta cccggggatc catgattgga gatctaatga   1320
agaataacaa caatggcgac gttgtggata acgaagtgaa caaccggtta agccggtggc   1380
atcacaattc ttcccggata attagggttt cacgagcttc cggtggtaaa gatcgacaca   1440
gcaaagtctt gacttctaaa ggaccacgtg accgtcgtgt ccggttatca gtctccaccg   1500
ctcttcaatt ctatgatctt caagatcggt taggttatga tcaacctagc aaagctgttg   1560
aatggttaat caaagctgct gaagattcaa tctctgagct tccttcactc aacaacactc   1620
attttccgac cgatgacgag aatcaccaga atcagacatt aacaacagtt gctgctaatt   1680
ccttgtctaa atctgcttgt agtagcaatt cagacacgag caagaactct tctggtttgt   1740
```

```
ctttatcaag atcggagctt agagataaag ctagagagag ggctagagag agaacagcta    1800
aagagaccaa ggaaagagat cataaccaca cttcgtttac ggatttgtta aattccggtt    1860
cagatccggt taactcaaac cggcaatgga tggcttcagc tccttcttca tctccaatgg    1920
agtatttcag ttcgggttta attctcgggt cgggtcaaca aacccatttc cctatttcaa    1980
caaattctca tcctttctca tcaatctccg atcatcatca tcatcatcct catcatcagc    2040
atcaagagtt ttcattcgtt cccgaccatt tgatatcacc ggcagaatcc aacggcggag    2100
cattcaatct tgattttaat atgtcaacac cctccggcgc cggagctgcc gtctccgccg    2160
catcaggtgg tggcttcagt ggtttcaaca gggggaccct tcagtccaat tcaacaaatc    2220
agcatcagtc attcctcgct aatctacaga ggtttccaac atcagaaagt ggaggaggtc    2280
cacagttctt attcggtgca ctgcctgcag agaatcacca ccacaatcac cagtttcagc    2340
tttactatga aaatggatgc agaaactcat cagaacataa gggtaaaggc aagaacaaag    2400
gccctgtcga catgcaacag cacctgatgc agatgcagcc catgatggct ggttactacc    2460
ccagcaatgt tacctctgat catatccaac agtacttgga cgaaaacaaa tcgttgattc    2520
tgaagattgt tgagtctcaa aactctggaa agcttagcga atgcgccgag aatcaagcaa    2580
ggcttcaacg caacctaatg tacctagctg caatagcaga ttctcagcct cagccaccaa    2640
gtgtgcatag ccagtatgga tctgctggtg gtgggatgat tcaggagaa ggagggtcac    2700
actatttgca gcagcaacaa gcgactcaac agcaacagat gactcagcag tctctaatgg    2760
cggctcgatc ttcaatgttg tatgctcagc aacagcagca gcagcagcct tacgcgacgc    2820
ttcagcatca gcaattgcac catagccagc ttggaatgag ctcgagcagc ggaggaggag    2880
gaagcagtgg tctccatatc cttcagggag aggctggtgg gtttcatgat tttggccgtg    2940
ggaagccgga aatgggaagt ggtggtggcg gtgaaggcag aggaggaagt tcaggggatg    3000
gtggagaaac cctttacttg aaatcatcag atgatgggaa ttgaaagcca tgggggctgc    3060
agagctttcg ttcgtatcat cggtttcgac aacgttcgtc aagttcaatg catcagtttc    3120
attgcgcaca caccagaatc ctactgagtt cgagtattat ggcattggga acatgttttt    3180
tcttgtacca tttgttgtgc ttgtaattta ctgtgttttt tattcggttt tcgctatcga    3240
actgtgaaat ggaaatggat ggagaagagt taatgaatga tatggtcctt ttgttcattc    3300
tcaaattaat attatttgtt ttttctctta tttgttgtgt gttgaatttg aaaatataag    3360
agatatgcaa acattttgtt ttgagtaaaa atgtgtcaaa tcgtggcctc taatgaccga    3420
agttaatatg aggagtaaaa cacttgtagt tgtaccatta tgcttattca ctaggcaaca    3480
aatatatttt cagacctaga aaagctgcaa atgttactga atacaagtat gtcctcttgt    3540
gttttagaca tttatgaact ttcctttatg taattttcca gaatccttgt cagattctaa    3600
tcattgcttt ataattatag ttatactcat ggatttgtag ttgagtatga aaatatttt     3660
taatgcattt tatgacttgc caattgattg acaacatgca tcaatcgaag cttggcactg    3720
gccgtcgttt tacaacgtcg tgactgggaa acccctggcg ttacccaact taatcgcctt    3780
gcagcacatc ccccttttcgc cagctggcgt aatagcgaag aggcccgcac cgatcgccct    3840
tcccaacagt tgcgcagcct gaatggcgaa tgctagagca gcttgccaac atggtggagc    3900
acgacactct cgtctactcc aagaatatca aagatacagt ctcagaagac caaagggcta    3960
ttgagacttt caacaaaagg gtaatatcgg gaaacctcct cggattccat gcccagcta    4020
tctgtcactt catcaaaagg acagtagaaa aggaaggtgg cacctacaaa tgccatcatt    4080
```

```
gcgataaagg aaaggctatc gttcaagatg cctctgccga cagtggtccc aaagatggac    4140
ccccacccac gaggagcatc gtggaaaaag aagacgttcc aaccacgtct tcaaagcaag    4200
tggattgatg tgataacatg gtggagcacg acactctcgt ctactccaag aatatcaaag    4260
atacagtctc agaagaccaa agggctattg agacttttca acaaagggta atatcgggaa    4320
acctcctcgg attccattgc ccagctatct gtcacttcat caaaaggaca gtagaaaagg    4380
aaggtggcac ctacaaatgc catcattgcg ataaaggaaa ggctatcgtt caagatgcct    4440
ctgccgacag tggtcccaaa gatggacccc cacccacgag gagcatcgtg gaaaagaag     4500 acgttccaac cacgtcttca aagcaagtgg attgatgtga tatctccact gacgtaaggg    4560
atgacgcaca atcccactat ccttcgcaag acccttcctc tatataagga agttcatttc    4620
atttggagag gacacgctga atcaccagt ctctctctac aaatctatct ctctcgattc      4680
gcagatctgt cgatcgacca tggggattga acaagatgga ttgcacgcag gttctccggc    4740
cgcttgggtg gagaggctat tcggctatga ctgggcacaa cagacaatcg gctgctctga    4800
tgccgccgtg ttccggctgt cagcgcaggg gcgcccggtt cttttttgtca agaccgacct    4860 gtccggtgcc ctgaatgaac tccaggacga ggcagcgcgg ctatcgtggc tggccacgac    4920
gggcgttcct tgcgcagctg tgctcgacgt tgtcactgaa gcgggaaggg actggctgct    4980
attgggcgaa gtgccggggc aggatctcct gtcatctcac cttgctcctg ccgagaaagt    5040
atccatcatg gctgatgcaa tgcggcggct gcatacgctt gatccggcta cctgcccatt    5100
cgaccaccaa gcgaaacatc gcatcgagcg agcacgtact cggatggaag ccggtcttgt    5160
cgatcaggat gatctggacg aagagcatca ggggctcgcg ccagccgaac tgttcgccag    5220
gctcaaggcg cgcatgcccg acggcgagga tctcgtcgtg acacatggcg atgcctgctt    5280
gccgaatatc atggtggaaa atggccgctt ttctggattc atcgactgtg gccggctggg    5340
tgtggcggac cgctatcagg acatagcgtt ggctacccgt gatattgctg aagagcttgg    5400
cggcgaatgg gctgaccgct tcctcgtgct ttacggtatc gccgctcccg attcgcagcg    5460
catcgccttc tatcgccttc ttgacgagtt cttctgagcg ggactctggg gttcggatcg    5520
atcctctagc tagagtcgat cgacatcgag tttctccata ataatgtgtg agtagttccc    5580
agataaggga attagggttc ttatagggtt tcgctcacgt gttgagcata taagaaaccc    5640
ttagtatgta tttgtatttg taaaatactt ctatcaataa aatttctaat tcctaaaacc    5700
aaaatccagt actaaaatcc agatcaccta aagtccctat agatccccccg aattaattcg    5760 gcgttaattc agtacattaa aaacgtccgc aatgtgttat taagttgtct aagcgtcaat    5820
ttgtttacac cacaatatat cctgccacca gccagccaac agctccccga ccggcagctc    5880
ggcacaaaat caccactcga tacaggcagc ccatcagtcc gggacggcgt cagcgggaga    5940
gccgttgtaa ggcggcagac tttgctcatg ttaccgatgc tattcggaag aacggcaact    6000
aagctgccgg gtttgaaaca cggatgatct cgcggagggt agcatgttga ttgtaacgat    6060
gacagagcgt tgctgcctgt gatcaattcg ggcacgaacc cagtggacat aagcctcgtt    6120
cggttcgtaa gctgtaatgc aagtagcgta actgccgtca cgcaactggt ccagaaccct    6180
gaccgaacgc agcggtggta acggcgcagt ggcggttttc atggcttctt gttatgacat    6240
gtttttttgg ggtacagtct atgcctcggg catccaagca gcaagcgcgt tacgccgtgg    6300
gtcgatgttt gatgttatgg agcagcaacg atgttacgca gcagggcagt cgccctaaaa    6360
caaagttaaa catcatgggg gaagcggtga tcgccgaagt atcgactcaa ctatcagagg    6420
tagttggcgt catcgagcgc catctcgaac cgacgttgct ggccgtacat ttgtacggct    6480
```

```
ccgcagtgga tggcggcctg aagccacaca gtgatattga tttgctggtt acggtgaccg   6540
taaggcttga tgaaacaacg cggcgagctt tgatcaacga ccttttggaa acttcggctt   6600
cccctggaga gagcgagatt ctccgcgctg tagaagtcac cattgttgtg cacgacgaca   6660
tcattccgtg gcgttatcca gctaagcgcg aactgcaatt tggagaatgg cagcgcaatg   6720
acattcttgc aggtatcttc gagccagcca cgatcgacat tgatctggct atcttgctga   6780
caaaagcaag agaacatagc gttgccttgg taggtccagc ggcggaggaa ctctttgatc   6840
cggttcctga acaggatcta tttgaggcgc taaatgaaac cttaacgcta tggaactcgc   6900
cgcccgactg ggctggcgat gagcgaaatg tagtgcttac gttgtcccgc atttggtaca   6960
gcgcagtaac cggcaaaatc gcgccgaagg atgtcgctgc cgactgggca atggagcgcc   7020
tgccggccca gtatcagccc gtcatacttg aagctagaca ggcttatctt ggacaagaag   7080
aagatcgctt ggcctcgcgc gcagatcagt tggaagaatt tgtccactac gtgaaaggcg   7140
agatcaccaa ggtagtcggc aaataatgtc tagctagaaa ttcgttcaag ccgacgccgc   7200
ttcgccggcg ttaactcaag cgattagatg cactaagcac ataattgctc acagccaaac   7260
tatcaggtca agtctgcttt tattattttt aagcgtgcat aataagccct acacaaattg   7320
ggagatatat catgcatgac caaaatccct taacgtgagt tttcgttcca ctgagcgtca   7380 gacccgtag aaaagatcaa aggatcttct tgagatcctt ttttctgcg cgtaatctgc   7440
```
```
tgcttgcaaa caaaaaaacc accgctacca gcggtggttt gtttgccgga tcaagagcta   7500
ccaactcttt ttccgaaggt aactggcttc agcagagcgc agataccaaa tactgtcctt   7560
ctagtgtagc cgtagttagg ccaccacttc aagaactctg tagcaccgcc tacataccte   7620 gctctgctaa tcctgttacc agtggctgct gccagtggcg ataagtcgtg tcttaccggg   7680
ttggactcaa gacgatagtt accggataag gcgcagcggt cgggctgaac ggggggttcg   7740
tgcacacagc ccagcttgga gcgaacgacc tacaccgaac tgagatacct acagcgtgag   7800
ctatgagaaa gcgccacgct tcccgaaggg agaaaggcgg acaggtatcc ggtaagcggc   7860
agggtcggaa caggagagcg cacgagggag cttccagggg gaaacgcctg gtatctttat   7920
agtcctgtcg ggtttcgcca cctctgactt gagcgtcgat ttttgtgatg ctcgtcaggg   7980
gggcggagcc tatggaaaaa cgccagcaac gcggccttt tacggttcct ggccttttgc   8040
tggccttttg ctcacatgtt ctttcctgcg ttatccctg attctgtgga taaccgtatt   8100
accgcctttg agtgagctga taccgctcgc cgcagccgaa cgaccgagcg cagcgagtca   8160
gtgagcgagg aagcggaaga gcgcctgatg cggtattttc tccttacgca tctgtgcggt   8220
atttcacacc gcatatggtg cactctcagt acaatctgct ctgatgccgc atagttaagc   8280
cagtatacac tccgctatcg ctacgtgact gggtcatggc tgcgcccga cacccgccaa   8340 cacccgctga cgcgccctga cgggcttgtc tgctcccggc atccgcttac agacaagctg   8400
tgaccgtctc cgggagctgc atgtgtcaga ggttttcacc gtcatcaccg aaacgcgcga   8460
ggcagggtgc cttgatgtgg gcgccggcgg tcgagtggcg acggcgcggc ttgtccgcgc   8520
cctggtagat tgcctggccg taggccagcc attttttgagc ggccagcggc cgcgataggc   8580
cgacgcgaag cggcggggcg tagggagcgc agcgaccgaa gggtaggcgc ttttttgcagc   8640 tcttcggctg tgcgctggcc agacagttat gcacaggcca ggcgggtttt aagagtttta   8700
ataagtttta aagagtttta ggcggaaaaa tcgcctttt tctctttat atcagtcact   8760 tacatgtgtg accggttccc aatgtacggc tttgggttcc caatgtacgg gttccggttc   8820
```

-continued

```
ccaatgtacg gctttgggtt cccaatgtac gtgctatcca caggaaagag acctttctga      8880
cctttttccc ctgctagggc aatttgccct agcatctgct ccgtacatta ggaaccggcg      8940
gatgcttcgc cctcgatcag gttgcggtag cgcatgacta ggatcgggcc agcctgcccc      9000
gcctcctcct tcaaatcgta ctccggcagg tcatttgacc cgatcagctt gcgcacggtg      9060
aaacagaact tcttgaactc tccggcgctg ccactgcgtt cgtagatcgt cttgaacaac      9120
catctggctt ctgccttgcc tgcggcgcgg cgtgccaggc ggtagagaaa acggccgatg      9180
ccgggatcga tcaaaaagta atcggggtga accgtcagca cgtccgggtt cttgccttct      9240
gtgatctcgc ggtacatcca atcagctagc tcgatctcga tgtactccgg ccgcccggtt      9300
tcgctcttta cgatcttgta gcggctaatc aaggcttcac cctcggatac cgtcaccagg      9360
cggccgttct tggccttctt cgtacgctgc atggcaacgt gcgtggtgtt taaccgaatg      9420
caggtttcta ccaggtcgtc tttctgcttt ccgccatcgg ctcgccggca gaacttgagt      9480
acgtccgcaa cgtgtggacg gaacacgcgg ccgggcttgt ctcccttccc ttccggtat       9540
cggttcatgg attcggttag atgggaaacc gccatcagta ccaggtcgta atcccacaca     9600
ctggccatgc cggccggccc tgcggaaacc tctacgtgcc cgtctggaag ctcgtagcgg      9660
atcacctcgc cagctcgtcg gtcacgcttc gacagacgga aaacggccac gtccatgatg      9720
ctgcgactat cgcgggtgcc cacgtcatag agcatcggaa cgaaaaaatc tggttgctcg      9780
tcgcccttgg gcggcttcct aatcgacggc gcaccggctg ccggcggttg ccgggattct      9840
ttgcggattc gatcagcggc cgcttgccac gattcaccgg ggcgtgcttc tgcctcgatg      9900
cgttgccgct gggcggcctg cgcggccttc aacttctcca ccaggtcatc acccagcgcc      9960
gcgccgattt gtaccgggcc ggatggtttg cgaccgtcac gccgattcct cgggcttggg     10020
ggttccagtg ccattgcagg gccggcagac aacccagccg cttacgcctg ccaaccgcc      10080
cgttcctcca cacatgggg attccacggc gtcggtgcct ggttgttctt gattttccat     10140
gccgcctcct ttagccgcta aaattcatct actcatttat tcatttgctc atttactctg     10200
gtagctgcgc gatgtattca gatagcagct cggtaatggt cttgccttgg cgtaccgcgt     10260
acatcttcag cttggtgtga tcctccgccg gcaactgaaa gttgacccgc ttcatggctg     10320
gcgtgtctgc caggctggcc aacgttgcag ccttgctgct gcgtgcgctc ggacggccgg     10380
cacttagcgt gtttgtgctt ttgctcattt tctctttacc tcattaactc aaatgagttt     10440
tgatttaatt tcagcggcca gcgcctggac ctcgcgggca gcgtcgccct cgggttctga     10500
ttcaagaacg gttgtgccgg cggcggcagt gcctgggtag ctcacgcgct gcgtgatacg     10560
ggactcaaga atgggcagct cgtacccggc cagcgcctcg gcaacctcac cgccgatgcg     10620
cgtgcctttg atcgcccgcg acacgacaaa ggccgcttgt agccttccat ccgtgacctc     10680
aatgcgctgc ttaaccagct ccaccaggtc ggcggtggcc catatgtcgt aagggcttgg     10740
ctgcaccgga atcagcacga agtcggctgc cttgatcgcg gacacagcca agtccgccgc     10800
ctggggcgct ccgtcgatca ctacgaagtc gcgccggccg atggccttca cgtcgcggtc     10860
aatcgtcggg cggtcgatgc cgacaacggt tagcggttga tcttcccgca cggccgccca     10920
atcgcgggca ctgccctggg gatcggaatc gactaacaga acatcggccc ggcgagttg      10980
cagggcgcgg gctagatggg ttgcgatggt cgtcttgcct gacccgcctt tctggttaag     11040
tacagcgata accttcatgc gttcccctttg cgtatttgtt tatttactca tcgcatcata    11100
tacgcagcga ccgcatgacg caagctgttt tactcaaata cacatcacct ttttagacgg     11160
cggcgctcgg tttcttcagc ggccaagctg gccggccagg ccgccagctt ggcatcagac     11220
```

```
aaaccggcca ggatttcatg cagccgcacg gttgagacgt gcgcgggcgg ctcgaacacg    11280
tacccggccg cgatcatctc cgcctcgatc tcttcggtaa tgaaaaacgg ttcgtcctgg    11340
ccgtcctggt gcggtttcat gcttgttcct cttggcgttc attctcggcg ccgccaggg    11400 cgtcggcctc ggtcaatgcg tcctcacgga aggcaccgcg ccgcctggcc tcggtgggcg    11460
tcacttcctc gctgcgctca agtgcgcggt acagggtcga gcgatgcacg ccaagcagtg    11520
cagccgcctc tttcacggtg cggccttcct ggtcgatcag ctcgcgggcg tgcgcgatct    11580
gtgccggggt gagggtaggg cggggccaa acttcacgcc tcgggccttg gcggcctcgc    11640
gcccgctccg ggtgcggtcg atgattaggg aacgctcgaa ctcggcaatg ccggcgaaca    11700
cggtcaacac catgcggccg gccggcgtgg tggtgtcggc ccacggctct gccaggctac    11760
gcaggcccgc gccggcctcc tggatgcgct cggcaatgtc cagtaggtcg cgggtgctgc    11820
gggccaggcg gtctagcctg gtcactgtca caacgtcgcc agggcgtagg tggtcaagca    11880
tcctggccag ctccgggcgg tcgcgcctgg tgccggtgat cttctcggaa aacagcttgg    11940
tgcagccggc cgcgtgcagt tcggcccgtt ggttggtcaa gtcctggtcg tcggtgctga    12000
cgcgggcata gcccagcagg ccagcggcgg cgctcttgtt catggcgtaa tgtctccggt    12060
tctagtcgca agtattctac tttatgcgac taaaacacgc gacaagaaaa cgccaggaaa    12120
agggcagggc ggcagcctgt cgcgtaactt aggacttgtg cgacatgtcg ttttcagaag    12180
acggctgcac tgaacgtcag aagccgactg cactatagca gcggaggggt tggatcaaag    12240
tact                                                                12244
```

<210> SEQ ID NO 36
<211> LENGTH: 604
<212> TYPE: PRT
<213> ORGANISM: Artificial Sequence
<220> FEATURE:
<223> OTHER INFORMATION: Chimaera TCP2-GFP

<400> SEQUENCE: 36

Met Ile Gly Asp Leu Met Lys Asn Asn Asn Gly Asp Val Val Asp
1               5                   10                  15

Asn Glu Val Asn Asn Arg Leu Ser Arg Trp His His Asn Ser Ser Arg
            20                  25                  30

Ile Ile Arg Val Ser Arg Ala Ser Gly Gly Lys Asp Arg His Ser Lys
        35                  40                  45

Val Leu Thr Ser Lys Gly Pro Arg Asp Arg Val Arg Leu Ser Val
    50                  55                  60

Ser Thr Ala Leu Gln Phe Tyr Asp Leu Gln Asp Arg Leu Gly Tyr Asp
65                  70                  75                  80

Gln Pro Ser Lys Ala Val Glu Trp Leu Ile Lys Ala Ala Glu Asp Ser
                85                  90                  95

Ile Ser Glu Leu Pro Ser Leu Asn Asn Thr His Phe Pro Thr Asp Asp
            100                 105                 110

Glu Asn His Gln Asn Gln Thr Leu Thr Thr Val Ala Ala Asn Ser Leu
        115                 120                 125

Ser Lys Ser Ala Cys Ser Ser Asn Ser Asp Thr Ser Lys Asn Ser Ser
    130                 135                 140

Gly Leu Ser Leu Ser Arg Ser Glu Leu Arg Asp Lys Ala Arg Glu Arg
145                 150                 155                 160

Ala Arg Glu Arg Thr Ala Lys Glu Thr Lys Glu Arg Asp His Asn His
                165                 170                 175

-continued

```
Thr Ser Phe Thr Asp Leu Leu Asn Ser Gly Ser Asp Pro Val Asn Ser
            180                 185                 190

Asn Arg Gln Trp Met Ala Ser Ala Pro Ser Ser Ser Pro Met Glu Tyr
        195                 200                 205

Phe Ser Ser Gly Leu Ile Leu Gly Ser Gly Gln Thr His Phe Pro
    210                 215                 220

Ile Ser Thr Asn Ser His Pro Phe Ser Ser Ile Ser Asp His His His
225                 230                 235                 240

His His Pro His His Gln His Gln Glu Phe Ser Phe Val Pro Asp His
                245                 250                 255

Leu Ile Ser Pro Ala Glu Ser Asn Gly Gly Ala Phe Asn Leu Asp Phe
            260                 265                 270

Asn Met Ser Thr Pro Ser Gly Ala Gly Ala Ala Val Ser Ala Ala Ser
        275                 280                 285

Gly Gly Gly Phe Ser Gly Phe Asn Arg Gly Thr Leu Gln Ser Asn Ser
    290                 295                 300

Thr Asn Gln His Gln Ser Phe Leu Ala Asn Leu Gln Arg Phe Pro Thr
305                 310                 315                 320

Ser Glu Ser Gly Gly Pro Gln Phe Leu Phe Gly Ala Leu Pro Ala
                325                 330                 335

Glu Asn His His His Asn His Gln Phe Gln Leu Tyr Tyr Glu Asn Gly
            340                 345                 350

Cys Arg Asn Ser Ser Glu His Lys Gly Lys Gly Lys Asn Lys Gly Pro
        355                 360                 365

Val Asp Asp Leu Thr Ser Lys Gly Glu Glu Leu Phe Thr Gly Val Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Phe Ile Cys Thr Thr Gly
                405                 410                 415

Lys Leu Pro Val Pro Trp Pro Thr Leu Val Thr Thr Phe Ser Tyr Gly
            420                 425                 430

Val Gln Cys Phe Ser Arg Tyr Pro Asp His Met Lys Arg His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Asp Phe Lys
                485                 490                 495

Glu Asp Gly Asn Ile Leu Gly His Lys Leu Glu Tyr Asn Tyr Asn Ser
            500                 505                 510

His Asn Val Tyr Ile Met Ala Asp Lys Gln Lys Asn Gly Ile Lys Ala
        515                 520                 525

Asn Phe Lys Thr Arg His Asn Ile Glu Asp Gly Gly Val Gln Leu Ala
    530                 535                 540

Asp His Tyr Gln Gln Asn Thr Pro Ile Gly Asp Gly Pro Val Leu Leu
545                 550                 555                 560

Pro Asp Asn His Tyr Leu Ser Thr Gln Ser Ala Leu Ser Lys Asp Pro
                565                 570                 575

Asn Glu Lys Arg Asp His Met Val Leu Leu Glu Phe Val Thr Ala Ala
            580                 585                 590
```

Gly Ile Thr His Gly Met Asp Glu Leu Tyr Lys Ala
        595                 600

<210> SEQ ID NO 37
<211> LENGTH: 1815
<212> TYPE: DNA
<213> ORGANISM: Artificial Sequence
<220> FEATURE:
<223> OTHER INFORMATION: Chimaera TCP2-GFP

<400> SEQUENCE: 37

```
atgattggag atctaatgaa gaataacaac aatggcgacg ttgtggataa cgaagtgaac      60
aaccggttaa gccggtggca tcacaattct tcccggataa ttagggtttc acgagcttcc     120
ggtggtaaag atcgacacag caaagtcttg acttctaaag gaccacgtga ccgtcgtgtc     180
cggttatcag tctccaccgc tcttcaattc tatgatcttc aagatcggtt aggttatgat     240
caacctagca aagctgttga atggttaatc aaagctgctg aagattcaat ctctgagctt     300
ccttcactca acaacactca ttttccgacc gatgacgaga tcaccagaa tcagacatta     360
acaacagttg ctgctaattc cttgtctaaa tctgcttgta gtagcaattc agacacgagc     420
aagaactctt ctggtttgtc tttatcaaga tcggagctta gagataaagc tagagagagg     480
gctagagaga gaacagctaa agagaccaag gaaagagatc ataaccacac ttcgtttacg     540
gatttgttaa attccggttc agatccggtt aactcaaacc ggcaatggat ggcttcagct     600
ccttcttcat ctccaatgga gtatttcagt tcgggtttaa ttctcgggtc gggtcaacaa     660
acccatttcc ctatttcaac aaattctcat cctttctcat caatctccga tcatcatcat     720
catcatcctc atcatcagca tcaagagttt tcattcgttc ccgaccattt gatatcaccg     780
gcagaatcca acggcggagc attcaatctt gattttaata tgtcaacacc ctccggcgcc     840
ggagctgccg tctccgccgc atcaggtggt ggcttcagtg gtttcaacag ggggacccct    900
cagtccaatt caacaaatca gcatcagtca ttcctcgcta atctacagag gtttccaaca     960
tcagaaagtg gaggaggtcc acagttctta ttcggtgcac tgcctgcaga gaatcaccac    1020
cacaatcacc agtttcagct ttactatgaa aatggatgca gaaactcatc agaacataag    1080
ggtaaaggca agaacaaagg ccctgtcgac gatctgacta gtaaaggaga gaacttttc    1140
actggagtag atggtgatgt taatgggcac aaattttctg tcagtggaga gggtgaaggt    1200
gatgcaacat acggaaaact tacccttaaa tttatttgca ctactggaaa actacctgtt    1260
ccgtggccaa cacttgtcac tactttctct tatggtgttc aatgcttttc aagatcccca    1320
gatcatatga gcggcacga cttcttcaag agcgccatgc ctgagggata cgtgcaggag    1380
aggaccatct tcttcaagga cgacgggaac tacaagacac gtgctgaagt caagtttgag    1440
ggagacaccc tcgtcaacag gatcgagctt aagggaatcg atttcaagga ggacggaaac    1500
atcctcggcc acaagttgga atacaactac aactcccaca cgtatacat catggccgac    1560
aagcaaaaga acggcatcaa agccaacttc aagacccgcc acaacatcga agacggcggc    1620
gtgcaactcg ctgatcatta tcaacaaaat actccaattg gcgatggccc tgtccttta    1680
ccagacaacc attacctgtc cacacaatct gccctttcga agatcccaa cgaaaagaga    1740
gaccacatgg tccttcttga gtttgtaaca gctgctggga ttacacatgg catggatgaa    1800
ctatacaaag cttga                                                     1815
```

<210> SEQ ID NO 38
<211> LENGTH: 12304
<212> TYPE: DNA

<213> ORGANISM: Artificial Sequence
<220> FEATURE:
<223> OTHER INFORMATION: Binary vector pCS55 for expression of chimeric protein TCP2-GPF

<400> SEQUENCE: 38

```
ttgatcccga ggggaacccct gtggttggca tgcacataca aatggacgaa cggataaacc    60
ttttcacgcc cttttaaata tccgttattc taataaacgc tcttttctct taggtttacc   120
cgccaatata tcctgtcaaa cactgatagt ttaaactgaa ggcgggaaac gacaatctga   180
tccaagctca agctgctcta gccaatacgc aaaccgcctc tccccgcgcg ttggccgatt   240
cattaatgca gctggcacga caggtttccc gactggaaag cgggcagtga gcgcaacgca   300
attaatgtga gttagctcac tcattaggca ccccaggctt tacactttat gcttccggct   360
cgtatgttgt gtggaattgt gagcggataa caatttcaca caggaaacag ctatgaccat   420
gattacgaat tcggtcccca gattagcctt ttcaatttca gaaagaatgc taacccacag   480
atggttagag aggcttacgc agcaggtctc atcaagacga tctacccgag caataatctc   540
caggaaatca ataccttcc caagaaggtt aaagatgcag tcaaaagatt caggactaac   600
tgcatcaaga acacagagaa agatatattt ctcaagatca gaagtactat tccagtatgg   660
acgattcaag gcttgcttca caaaccaagg caagtaatag agattggagt ctctaaaaag   720
gtagttccca ctgaatcaaa ggccatggag tcaaagattc aaatagagga cctaacagaa   780
ctcgccgtaa agactggcga acagttcata cagagtctct tacgactcaa tgacaagaag   840
aaaatcttcg tcaacatggt ggagcacgac acacttgtct actccaaaaa tatcaaagat   900
acagtctcag aagaccaaag ggcaattgag acttttcaac aaagggtaat atccggaaac   960
ctcctcggat tccattgccc agctatctgt cactttattg tgaagatagt ggaaaaggaa  1020
ggtggctcct acaaatgcca tcattgcgat aaaggaaagg ccatcgttga agatgcctct  1080
gccgacagtg gtcccaaaga tggaccccca cccacgagga gcatcgtgga aaaagaagac  1140
gttccaacca cgtcttcaaa gcaagtggat tgatgtgata tctccactga cgtaagggat  1200
gacgcacaat cccactatcc ttcgcaagac ccttcctcta taaggaag ttcatttcat  1260
ttggagagaa cacgggggac gagctcggta cccggggatc catgattgga gatctaatga  1320
agaataacaa caatggcgac gttgtggata acgaagtgaa caaccggtta gccggtggc   1380
atcacaattc ttcccggata attagggttt cacgagcttc cggtggtaaa gatcgacaca  1440
gcaaagtctt gacttctaaa ggaccacgtg accgtcgtgt ccggttatca gtctccaccg  1500
ctcttcaatt ctatgatctt caagatcggt taggttatga tcaacctagc aaagctgttg  1560
aatggttaat caaagctgct gaagattcaa tctctgagct tccttcactc aacaacactc  1620
attttccgac cgatgacgag aatcaccaga atcagacatt aacaacagtt gctgctaatt  1680
ccttgtctaa atctgcttgt agtagcaatt cagacacgag caagaactct tctggtttgt  1740
ctttatcaag atcggagctt agagataaag ctagagagag gctagagag agaacagcta  1800
aagagaccaa ggaaagagat cataaccaca cttcgtttac ggatttgtta aattccggtt  1860
cagatccggt taactcaaac cggcaatgga tggcttcagc tccttcttca tctccaatgg  1920
agtatttcag ttcgggttta attctcgggt cgggtcaaca aacccatttc cctatttcaa  1980
caaattctca tcctttctca tcaatctccg atcatcatca tcatcatcct catcatcagc  2040
atcaagagtt ttcattcgtt cccgaccatt tgatatcacc ggcagaatcc aacggcggag  2100
cattcaatct tgattttaat atgtcaacac cctccggcgc cggagctgcc gtctccgccg  2160
```

```
catcaggtgg tggcttcagt ggtttcaaca gggggaccct tcagtccaat tcaacaaatc  2220
agcatcagtc attcctcgct aatctacaga ggtttccaac atcagaaagt ggaggaggtc  2280
cacagttctt attcggtgca ctgcctgcag agaatcacca ccacaatcac cagtttcagc  2340
tttactatga aaatggatgc agaaactcat cagaacataa gggtaaaggc aagaacaaag  2400
gccctgtcga cgatctgact agtaaaggag aagaactttt cactggagta gatggtgatg  2460
ttaatgggca caattttcct gtcagtggag agggtgaagg tgatgcaaca tacggaaaac  2520
ttacccttaa atttatttgc actactggaa aactacctgt tccgtggcca acacttgtca  2580
ctactttctc ttatggtgtt caatgctttt caagataccc agatcatatg aagcggcacg  2640
acttcttcaa gagcgccatg cctgagggat acgtgcagga gaggaccatc ttcttcaagg  2700
acgacgggaa ctacaagaca cgtgctgaag tcaagtttga gggagacacc ctcgtcaaca  2760
ggatcgagct taagggaatc gatttcaagg aggacggaaa catcctcggc cacaagttgg  2820
aatacaacta caactcccac aacgtataca tcatggccga caagcaaaag aacggcatca  2880
aagccaactt caagacccgc cacaacatcg aagacggcgg cgtgcaactc gctgatcatt  2940
atcaacaaaa tactccaatt ggcgatggcc ctgtcctttt accagacaac cattacctgt  3000
ccacacaatc tgccctttcg aaagatccca acgaaaagag agaccacatg gtccttcttg  3060
agtttgtaac agctgctggg attacacatg gcatggatga actatacaaa gcttgactgc  3120
agagctttcg ttcgtatcat cggtttcgac aacgttcgtc aagttcaatg catcagtttc  3180
attgcgcaca caccagaatc ctactgagtt cgagtattat ggcattggga aacatgtttt  3240
tcttgtacca tttgttgtgc ttgtaattta ctgtgttttt tattcggttt tcgctatcga  3300
actgtgaaat ggaaatggat ggagaagagt taatgaatga tatggtcctt ttgttcattc  3360
tcaaattaat attatttgtt ttttctctta tttgttgtgt gttgaatttg aaaatataag  3420
agatatgcaa acattttgtt ttgagtaaaa atgtgtcaaa tcgtggcctc taatgaccga  3480
agttaatatg aggagtaaaa cacttgtagt tgtaccatta tgcttattca ctaggcaaca  3540
aatatatttt cagacctaga aaagctgcaa atgttactga atacaagtat gtcctcttgt  3600
gttttagaca tttatgaact ttcctttatg taattttcca gaatccttgt cagattctaa  3660
tcattgcttt ataattatag ttatactcat ggatttgtag ttgagtatga aaatattttt  3720
taatgcattt tatgacttgc caattgattg acaacatgca tcaatcgaag cttggcactg  3780
gccgtcgttt tacaacgtcg tgactgggaa acccctggcg ttacccaact taatcgcctt  3840
gcagcacatc cccctttcgc cagctggcgt aatagcgaag aggcccgcac cgatcgccct  3900
tcccaacagt tgcgcagcct gaatggcgaa tgctagagca gcttgccaac atggtggagc  3960 acgcacactct cgtctactcc aagaatatca aagatacagt ctcagaagac caaagggcta  4020
ttgagacttt tcaacaaagg gtaatatcgg gaaacctcct cggattccat tgcccagcta  4080
tctgtcactt catcaaaagg acagtagaaa aggaaggtgg cacctacaaa tgccatcatt  4140
gcgataaagg aaaggctatc gttcaagatg cctctgccga cagtggtccc aaagatggac  4200
ccccacccac gaggagcatc gtggaaaaag aagacgttcc aaccacgtct tcaaagcaag  4260
tggattgatg tgataacatg gtggagcacg acactctcgt ctactccaag aatatcaaag  4320
atacagtctc agaagaccaa agggctattg agacttttca acaaagggta atatcgggaa  4380
acctcctcgg attccattgc ccagctatct gtcacttcat caaaaggaca gtagaaaagg  4440
aaggtggcac ctacaaatgc catcattgcg ataaaggaaa ggctatcgtt caagatgcct  4500
ctgccgacag tggtcccaaa gatggacccc cacccacgag gagcatcgtg gaaaagaag  4560
```

```
acgttccaac cacgtcttca aagcaagtgg attgatgtga tatctccact gacgtaaggg    4620
atgacgcaca atcccactat ccttcgcaag acccttcctc tatataagga agttcatttc    4680
atttggagag acacgctga aatcaccagt ctctctctac aaatctatct ctctcgattc     4740
gcagatctgt cgatcgacca tggggattga acaagatgga ttgcacgcag gttctccggc    4800
cgcttgggtg gagaggctat tcggctatga ctgggcacaa cagacaatcg gctgctctga    4860
tgccgccgtg ttccggctgt cagcgcaggg gcgcccggtt cttttgtca agaccgacct     4920
gtccggtgcc ctgaatgaac tccaggacga ggcagcgcgg ctatcgtggc tggccacgac    4980
gggcgttcct tgcgcagctg tgctcgacgt tgtcactgaa gcgggaaggg actggctgct    5040
attgggcgaa gtgccggggc aggatctcct gtcatctcac cttgctcctg ccgagaaagt    5100
atccatcatg gctgatgcaa tgcggcggct gcatacgctt gatccggcta cctgcccatt    5160
cgaccaccaa gcgaaacatc gcatcgagcg agcacgtact cggatggaag ccggtcttgt    5220
cgatcaggat gatctggacg aagagcatca ggggctcgcg ccagccgaac tgttcgccag    5280
gctcaaggcg cgcatgcccg acggcgagga tctcgtcgtg acacatggcg atgcctgctt    5340
gccgaatatc atggtggaaa atggccgctt ttctggattc atcgactgtg gccggctggg    5400
tgtggcggac cgctatcagg acatagcgtt ggctacccgt gatattgctg aagagcttgg    5460
cggcgaatgg gctgaccgct tcctcgtgct ttacggtatc gccgctcccg attcgcagcg    5520
catcgccttc tatcgccttc ttgacgagtt cttctgagcg ggactctggg gttcggatcg    5580
atcctctagc tagagtcgat cgacatcgag tttctccata ataatgtgtg agtagttccc    5640
agataaggga attagggttc ttatagggtt tcgctcacgt gttgagcata taagaaaccc    5700
ttagtatgta tttgtatttg taaaatactt ctatcaataa aatttctaat tcctaaaacc    5760
aaaatccagt actaaaatcc agatcaccta aagtccctat agatccccg aattaattcg     5820
gcgttaattc agtacattaa aaacgtccgc aatgtgttat taagttgtct aagcgtcaat    5880
ttgtttacac cacaatatat cctgccacca gccagccaac agctccccga ccggcagctc    5940
ggcacaaaat caccactcga tacaggcagc ccatcagtcc gggacggcgt cagcgggaga    6000
gccgttgtaa ggcggcagac tttgctcatg ttaccgatgc tattcggaag aacggcaact    6060
aagctgccgg gtttgaaaca cggatgatct cgcggagggt agcatgttga ttgtaacgat    6120
gacagagcgt tgctgcctgt gatcaattcg ggcacgaacc cagtggacat aagcctcgtt    6180
cggttcgtaa gctgtaatgc aagtagcgta actgccgtca cgcaactggt ccagaacctt    6240
gaccgaacgc agcggtggta acggcgcagt ggcggttttc atggcttctt gttatgacat    6300
gtttttttgg ggtacagtct atgcctcggg catccaagca gcaagcgcgt tacgccgtgg    6360
gtcgatgttt gatgttatgg agcagcaacg atgttacgca gcagggcagt cgccctaaaa    6420
caaagttaaa catcatgggg gaagcggtga tcgccgaagt atcgactcaa ctatcagagg    6480
tagttggcgt catcgagcgc catctcgaac cgacgttgct ggccgtacat ttgtacggct    6540
ccgcagtgga tggcggcctg aagccacaca gtgatattga tttgctggtt acggtgaccg    6600
taaggcttga tgaaacaacg cggcgagctt tgatcaacga ccttttggaa acttcggctt    6660
cccctggaga gagcgagatt ctccgcgctg tagaagtcac cattgttgtg cacgacgaca    6720
tcattccgtg gcgttatcca gctaagcgcg aactgcaatt tggagaatgg cagcgcaatg    6780
acattcttgc aggtatcttc gagccagcca cgatcgacat tgatctggct atcttgctga    6840
caaaagcaag agaacatagc gttgccttgg taggtccagc ggcggaggaa ctctttgatc    6900
```

```
cggttcctga acaggatcta tttgaggcgc taaatgaaac cttaacgcta tggaactcgc    6960
cgcccgactg ggctggcgat gagcgaaatg tagtgcttac gttgtcccgc atttggtaca    7020
gcgcagtaac cggcaaaatc gcgccgaagg atgtcgctgc cgactgggca atggagcgcc    7080
tgccggccca gtatcagccc gtcatacttg aagctagaca ggcttatctt ggacaagaag    7140
aagatcgctt ggcctcgcgc gcagatcagt tggaagaatt tgtccactac gtgaaggcg     7200
agatcaccaa ggtagtcggc aaataatgtc tagctagaaa ttcgttcaag ccgacgccgc    7260
ttcgccggcg ttaactcaag cgattagatg cactaagcac ataattgctc acagccaaac    7320
tatcaggtca agtctgcttt tattattttt aagcgtgcat aataagccct acacaaattg    7380
ggagatatat catgcatgac caaaatccct taacgtgagt tttcgttcca ctgagcgtca    7440
gaccccgtag aaaagatcaa aggatcttct tgagatcctt ttttctgcg cgtaatctgc     7500
tgcttgcaaa caaaaaaacc accgctacca gcggtggttt gtttgccgga tcaagagcta    7560
ccaactcttt ttccgaaggt aactggcttc agcagagcgc agataccaaa tactgtcctt    7620
ctagtgtagc cgtagttagg ccaccacttc aagaactctg tagcaccgcc tacataccctc   7680
gctctgctaa tcctgttacc agtgctgct gccagtggcg ataagtcgtg tcttaccggg     7740
ttggactcaa gacgatagtt accggataag gcgcagcggt cgggctgaac ggggggttcg    7800
tgcacacagc ccagcttgga gcgaacgacc tacaccgaac tgagatacct acagcgtgag    7860
ctatgagaaa gcgccacgct tcccgaaggg agaaaggcgg acaggtatcc ggtaagcggc    7920
agggtcggaa caggagagcg cacgagggag cttccagggg gaaacgcctg gtatctttat    7980
agtcctgtcg ggtttcgcca cctctgactt gagcgtcgat ttttgtgatg ctcgtcaggg    8040
gggcggagcc tatggaaaaa cgccagcaac gcggcctttt tacggttcct ggccttttgc    8100
tggccttttg ctcacatgtt ctttcctgcg ttatccctg attctgtgga taaccgtatt     8160
accgcctttg agtgagctga taccgctcgc cgcagccgaa cgaccgagcg cagcgagtca    8220
gtgagcgagg aagcggaaga gcgcctgatg cggtattttc tccttacgca tctgtgcggt    8280
atttcacacc gcatatggtg cactctcagt acaatctgct ctgatgccgc atagttaagc    8340
cagtatacac tccgctatcg ctacgtgact gggtcatggc tgcgcccga cacccgccaa     8400
cacccgctga cgcgccctga cgggcttgtc tgctcccggc atccgcttac agacaagctg    8460
tgaccgtctc cgggagctgc atgtgtcaga ggttttcacc gtcatcaccg aaacgcgcga    8520
ggcagggtgc cttgatgtgg gcgccggcgg tcgagtggcg acggcgcggc ttgtccgcgc    8580
cctggtagat tgcctggccg taggccagcc attttttgagc ggccagcggc cgcgataggc   8640
cgacgcgaag cggcggggcg tagggagcgc agcgaccgaa gggtaggcgc ttttttgcagc   8700
tcttcggctg tgcgctggcc agacagttat gcacaggcca ggcgggtttt aagagttta    8760
ataagtttta aagagtttta ggcggaaaaa tcgccttttt tctcttttat atcagtcact    8820
tacatgtgtg accggttccc aatgtacggc tttgggttcc caatgtacgg gttccgttc    8880
ccaatgtacg gctttgggtt cccaatgtac gtgctatcca caggaaagag acctttcga    8940
ccttttttccc ctgctagggc aatttgccct agcatctgct ccgtacatta ggaaccggcg    9000
gatgcttcgc cctcgatcag gttgcggtag cgcatgacta ggatcgggcc agcctgcccc    9060
gcctcctcct tcaaatcgta ctccggcagg tcatttgacc cgatcagctt gcgcacggtg    9120
aaacagaact tcttgaactc tccggcgctg ccactgcgtt cgtagatcgt cttgaacaac    9180
catctggctt ctgccttgcc tgcggcgcgg cgtgccaggc ggtagagaaa acggccgatg    9240
ccgggatcga tcaaaaagta atcggggtga accgtcagca cgtccgggtt cttgccttct    9300
```

-continued

```
gtgatctcgc ggtacatcca atcagctagc tcgatctcga tgtactccgg ccgcccggtt    9360
tcgctcttta cgatcttgta gcggctaatc aaggcttcac cctcggatac cgtcaccagg    9420
cggccgttct tggccttctt cgtacgctgc atggcaacgt gcgtggtgtt taaccgaatg    9480
caggtttcta ccaggtcgtc tttctgcttt ccgccatcgg ctcgccggca gaacttgagt    9540
acgtccgcaa cgtgtggacg gaacacgcgg ccgggcttgt ctcccttccc ttcccggtat    9600
cggttcatgg attcggttag atgggaaacc gccatcagta ccaggtcgta atcccacaca    9660
ctggccatgc cggccggccc tgcggaaacc tctacgtgcc cgtctggaag ctcgtagcgg    9720
atcacctcgc cagctcgtcg gtcacgcttc gacagacgaa aaacggccac gtccatgatg    9780
ctgcgactat cgcgggtgcc cacgtcatag agcatcggaa cgaaaaaatc tggttgctcg    9840
tcgcccttgg gcggcttcct aatcgacggc gcaccggctg ccggcggttg ccgggattct    9900
ttgcggattc gatcagcggc cgcttgccac gattcaccgg ggcgtgcttc tgcctcgatg    9960
cgttgccgct gggcggcctg cgcggccttc aacttctcca ccaggtcatc acccagcgcc   10020
gcgccgattt gtaccgggcc ggatggtttg cgaccgtcac gccgattcct cgggcttggg   10080
ggttccagtg ccattgcagg gccggcagac aacccagccg cttacgcctg ccaaccgcc    10140
cgttcctcca cacatggggc attccacggc gtcggtgcct ggttgttctt gattttccat   10200
gccgcctcct ttagccgcta aaattcatct actcatttat tcatttgctc atttactctg   10260
gtagctgcgc gatgtattca gatagcagct cggtaatggt cttgccttgg cgtaccgcgt   10320
acatcttcag cttggtgtga tcctccgccg gcaactgaaa gttgacccgc ttcatggctg   10380
gcgtgtctgc caggctggcc aacgttgcag ccttgctgct gcgtgcgctc ggacggccgg   10440
cacttagcgt gtttgtgctt ttgctcattt tctctttacc tcattaactc aaatgagttt   10500
tgatttaatt tcagcggcca cgcctggac ctcgcgggca gcgtcgccct cgggttctga    10560
ttcaagaacg gttgtgccgg cggcggcagt gcctgggtag ctcacgcgct gcgtgatacg   10620
ggactcaaga atgggcagct cgtacccggc cagcgcctcg gcaacctcac cgccgatgcg   10680
cgtgcctttg atcgcccgcg acacgacaaa ggccgcttgt agccttccat ccgtgacctc   10740
aatgcgctgc ttaaccagct ccaccaggtc ggcggtggcc catatgtcgt aagggcttgg   10800
ctgcaccgga atcagcacga agtcggctgc cttgatcgcg gacacagcca gtccgccgc    10860
ctggggcgct ccgtcgatca ctacgaagtc gcgccggccg atggccttca cgtcgcggtc   10920
aatcgtcggg cggtcgatgc cgacaacggt tagcggttga tcttcccgca cggccgccca   10980
atcgcgggca ctgccctggg gatcggaatc gactaacaga acatcggccc cggcgagttg   11040
cagggcgcgg gctagatggg ttgcgatggt cgtcttgcct gacccgcctt tctggttaag   11100
tacagcgata accttcatgc gttcccctttg cgtatttgtt tatttactca tcgcatcata   11160
tacgcagcga ccgcatgacg caagctgttt tactcaaata cacatcacct ttttagacgg   11220
cggcgctcgg tttcttcagc ggccaagctg gccggcagg ccgccagctt ggcatcagac    11280
aaaccggcca ggatttcatg cagccgcacg gttgagacgt gcgcgggcgg ctcgaacacg   11340
tacccggccg cgatcatctc cgcctcgatc tcttcggtaa tgaaaaacgg ttcgtcctgg   11400
ccgtcctggt gcggtttcat gcttgttcct cttggcgttc attctcggcg gccgccaggg   11460
cgtcggcctc ggtcaatgcg tcctcacgga aggcaccgcg ccgcctggcc tcggtgggcg   11520
tcacttcctc gctgcgctca agtgcgcggt acagggtcga gcgatgcacg ccaagcagtg   11580
cagccgcctc tttcacggtg cggccttcct ggtcgatcag ctcgcgggcg tgcgcgatct   11640
```

-continued

```
gtgccggggt gagggtaggg cgggggccaa acttcacgcc tcgggccttg gcggcctcgc    11700
gcccgctccg ggtgcggtcg atgattaggg aacgctcgaa ctcggcaatg ccggcgaaca    11760
cggtcaacac catgcggccg ccggcgtgg tggtgtcggc ccacggctct gccaggctac     11820
gcaggcccgc gccggcctcc tggatgcgct cggcaatgtc cagtaggtcg cgggtgctgc    11880
gggccaggcg gtctagcctg gtcactgtca caacgtcgcc agggcgtagg tggtcaagca    11940
tcctggccag ctccgggcgg tcgcgcctgg tgccggtgat cttctcggaa aacagcttgg    12000
tgcagccggc cgcgtgcagt tcggcccgtt ggttggtcaa gtcctggtcg tcggtgctga    12060
cgcgggcata gcccagcagg ccagcggcgg cgctcttgtt catggcgtaa tgtctccggt    12120
tctagtcgca agtattctac tttatgcgac taaaacacgc gacaagaaaa cgccaggaaa    12180
agggcagggc ggcagcctgt cgcgtaactt aggacttgtg cgacatgtcg ttttcagaag    12240
acggctgcac tgaacgtcag aagccgactg cactatagca gcggaggggt tggatcaaag    12300
tact                                                                 12304
```

<210> SEQ ID NO 39
<211> LENGTH: 195
<212> TYPE: PRT
<213> ORGANISM: Arabidopsis thaliana

<400> SEQUENCE: 39

```
Met Gln Gln Gln Ser Pro Gln Met Phe Pro Met Val Pro Ser Ile
1               5                   10                  15

Pro Pro Ala Asn Asn Ile Thr Thr Glu Gln Ile Gln Lys Tyr Leu Asp
            20                  25                  30

Glu Asn Lys Lys Leu Ile Met Ala Ile Met Glu Asn Gln Asn Leu Gly
        35                  40                  45

Lys Leu Ala Glu Cys Ala Gln Tyr Gln Ala Leu Leu Gln Lys Asn Leu
    50                  55                  60

Met Tyr Leu Ala Ala Ile Ala Asp Ala Gln Pro Pro Pro Thr Pro
65                  70                  75                  80

Gly Pro Ser Pro Ser Thr Ala Val Ala Ala Gln Met Ala Thr Pro His
                85                  90                  95

Ser Gly Met Gln Pro Pro Ser Tyr Phe Met Gln His Pro Gln Ala Ser
            100                 105                 110

Pro Ala Gly Ile Phe Ala Pro Arg Gly Pro Leu Gln Phe Gly Ser Pro
        115                 120                 125

Leu Gln Phe Gln Asp Pro Gln Gln Gln Gln Ile His Gln Gln Ala
    130                 135                 140

Met Gly His Met Gly Ile Arg Pro Met Gly Met Thr Asn Asn Gly
145                 150                 155                 160

Met Gln His Ala Met Gln Gln Pro Glu Thr Gly Leu Gly Gly Asn Val
                165                 170                 175

Gly Leu Arg Gly Gly Lys Gln Asp Gly Ala Asp Gly Gln Gly Lys Asp
            180                 185                 190

Asp Gly Lys
        195
```

<210> SEQ ID NO 40
<211> LENGTH: 223
<212> TYPE: PRT
<213> ORGANISM: Arabidopsis thaliana

<400> SEQUENCE: 40

```
Met Gln Gln Ser Pro Gln Met Ile Pro Met Val Leu Pro Ser Phe Pro
1               5                   10                  15

Pro Thr Asn Asn Ile Thr Thr Glu Gln Ile Gln Lys Tyr Leu Asp Glu
            20                  25                  30

Asn Lys Lys Leu Ile Met Ala Ile Leu Glu Asn Gln Asn Leu Gly Lys
            35                  40                  45

Leu Ala Glu Cys Ala Gln Tyr Gln Ala Leu Leu Gln Lys Asn Leu Met
50                  55                  60

Tyr Leu Ala Ala Ile Ala Asp Ala Gln Pro Gln Pro Ala Ala Thr
65                  70                  75                  80

Leu Thr Ser Gly Ala Met Thr Pro Gln Ala Met Ala Pro Asn Pro Ser
                85                  90                  95

Ser Met Gln Pro Pro Ser Tyr Phe Met Gln Gln His Gln Ala Val
            100                 105                 110

Gly Met Ala Gln Gln Ile Pro Pro Gly Ile Phe Pro Pro Arg Gly Pro
            115                 120                 125

Leu Gln Phe Gly Ser Pro His Gln Phe Leu Asp Pro Gln Gln Gln Leu
        130                 135                 140

His Gln Gln Ala Met Gln Gly His Met Gly Ile Arg Pro Met Gly Leu
145                 150                 155                 160

Asn Asn Asn Asn Gly Leu Gln His Gln Met His His Glu Thr Ala
            165                 170                 175

Leu Ala Ala Asn Asn Ala Gly Pro Asn Asp Ala Ser Gly Gly Gly Lys
                180                 185                 190

Pro Asp Gly Thr Asn Met Ser Gln Ser Gly Ala Asp Gly Gln Gly Gly
            195                 200                 205

Ser Ala Ala Arg His Gly Gly Gly Asp Ala Lys Thr Glu Gly Lys
        210                 215                 220

<210> SEQ ID NO 41
<211> LENGTH: 210
<212> TYPE: PRT
<213> ORGANISM: Glycine max

<400> SEQUENCE: 41

Met Gln Gln His Leu Met Gln Met Gln Pro Met Met Ala Ala Tyr Tyr
1               5                   10                  15

Pro Asn Asn Val Thr Thr Asp His Ile Gln Gln Tyr Leu Asp Glu Asn
            20                  25                  30

Lys Ser Leu Ile Leu Lys Ile Val Glu Ser Gln Asn Ser Gly Lys Leu
            35                  40                  45

Ser Glu Cys Ala Glu Asn Gln Ala Arg Leu Gln Arg Asn Leu Met Tyr
50                  55                  60

Leu Ala Ala Ile Ala Asp Ser Gln Pro Gln Pro Thr Met Ser Gly
65                  70                  75                  80

Gln Tyr Pro Pro Ser Gly Met Met Gln Gln Gly Ala Gln Tyr Met Gln
                85                  90                  95

Ala Gln Gln Gln Ala Gln Gln Met Thr Pro Gln Gln Leu Met Ala Ala
            100                 105                 110

Arg Ser Ser Leu Leu Tyr Ala Gln Gln Pro Tyr Ser Ala Leu Gln Gln
            115                 120                 125

Gln Gln Ala Met His Ser Ala Leu Gly Ser Ser Ser Gly Leu His Met
        130                 135                 140

Leu Gln Ser Glu Gly Ser Asn Val Asn Val Gly Gly Gly Phe Pro Asp
145                 150                 155                 160
```

Phe Val Arg Gly Gly Ser Ser Thr Gly Glu Gly Leu His Ser Gly Gly
                165                 170                 175

Arg Gly Ile Ile Gly Ser Ser Lys Gln Glu Met Gly Gly Ser Ser Glu
            180                 185                 190

Gly Arg Gly Glu Gly Gly Glu Asn Leu Tyr Leu Lys Val Ala Asp Asp
        195                 200                 205

Gly Asn
    210

<210> SEQ ID NO 42
<211> LENGTH: 212
<212> TYPE: PRT
<213> ORGANISM: Glycine max

<400> SEQUENCE: 42

Met Gln Gln His Leu Met Gln Met Gln Pro Ile Met Ala Ala Tyr Tyr
1               5                   10                  15

Pro Asn Asn Val Thr Thr Asp His Ile Gln Gln Tyr Leu Asp Glu Asn
            20                  25                  30

Lys Ser Leu Ile Leu Lys Ile Val Glu Ser Gln Asn Ser Gly Lys Leu
        35                  40                  45

Ser Glu Cys Ala Glu Asn Gln Ser Arg Leu Gln Arg Asn Leu Met Tyr
50                  55                  60

Leu Ala Ala Ile Ala Asp Ser Gln Pro Gln Pro Ser Pro Met Pro Gly
65                  70                  75                  80

Gln Tyr Pro Ser Ser Gly Leu Met Gln Gln Gly Ala His Tyr Met Gln
                85                  90                  95

Ala Gln Gln Ala Gln Gln Met Ser Gln Gln Leu Met Ala Ser Arg
            100                 105                 110

Ser Ser Leu Leu Tyr Ser Gln Gln Pro Phe Ser Val Leu Gln Gln Gln
        115                 120                 125

Gln Gly Met His Ser Gln Leu Gly Met Ser Ser Asn Gly Ser Gln Gly
    130                 135                 140

Leu His Met Leu Gln Thr Glu Ala Thr Asn Val Gly Gly Asn Ala Thr
145                 150                 155                 160

Ile Gly Thr Gly Gly Arg Phe Pro Asp Phe Val Arg Ile Ala Ser Gly
                165                 170                 175

Lys Gln Asp Ile Gly Ser Ser Gly Glu Gly Arg Gly Gly Ser Ser Ser
            180                 185                 190

Gly His Ser Gly Asp Gly Gly Glu Thr Leu Asn Tyr Leu Lys Ala Ala
        195                 200                 205

Gly Asp Gly Asn
    210

<210> SEQ ID NO 43
<211> LENGTH: 213
<212> TYPE: PRT
<213> ORGANISM: Glycine max

<400> SEQUENCE: 43

Met Gln Gln Thr Pro Pro Met Ile Pro Met Met Pro Ser Phe Pro Pro
1               5                   10                  15

Thr Asn Ile Thr Thr Glu Gln Ile Gln Lys Tyr Leu Asp Glu Asn Lys
            20                  25                  30

Lys Leu Ile Leu Ala Ile Leu Asp Asn Gln Asn Leu Gly Lys Leu Ala
        35                  40                  45

```
Glu Cys Ala Gln Tyr Gln Ala Gln Leu Gln Lys Asn Leu Met Tyr Leu
 50                  55                  60

Ala Ala Ile Ala Asp Ala Gln Pro Gln Thr Pro Ala Met Pro Pro Gln
 65                  70                  75                  80

Met Ala Pro His Pro Ala Met Gln Pro Gly Phe Tyr Met Gln His Pro
                 85                  90                  95

Gln Ala Ala Ala Ala Met Ala Gln Gln Gln Gly Met Phe Pro
                100                 105                 110

Gln Lys Met Pro Leu Gln Phe Gly Asn Pro His Gln Met Gln Glu Gln
                115                 120                 125

Gln Gln Gln Leu His Gln Ala Ile Gln Gly Gln Met Gly Leu Arg
    130                 135                 140

Pro Gly Asp Ile Asn Asn Gly Met His Pro Met His Ser Glu Ala Ala
145                 150                 155                 160

Leu Gly Gly Gly Asn Ser Gly Gly Pro Pro Ser Ala Thr Gly Pro Asn
                165                 170                 175

Asp Ala Arg Gly Gly Ser Lys Gln Asp Ala Ser Glu Ala Gly Thr Ala
                180                 185                 190

Gly Gly Asp Gly Gln Gly Ser Ser Ala Ala Ala His Asn Ser Gly Asp
                195                 200                 205

Gly Glu Glu Ala Lys
            210

<210> SEQ ID NO 44
<211> LENGTH: 204
<212> TYPE: PRT
<213> ORGANISM: Oryza sativa

<400> SEQUENCE: 44

Met Gln Gln Gln Met Ala Met Pro Ala Gly Ala Ala Ala Ala Ala Val
  1               5                  10                  15

Pro Pro Ala Ala Gly Ile Thr Thr Glu Gln Ile Gln Lys Tyr Leu Asp
                 20                  25                  30

Glu Asn Lys Gln Leu Ile Leu Ala Ile Leu Glu Asn Gln Asn Leu Gly
             35                  40                  45

Lys Leu Ala Glu Cys Ala Gln Tyr Gln Ala Gln Leu Gln Lys Asn Leu
 50                  55                  60

Leu Tyr Leu Ala Ala Ile Ala Asp Ala Gln Pro Pro Gln Asn Pro Gly
 65                  70                  75                  80

Ser Arg Pro Gln Met Met Gln Pro Gly Ala Thr Pro Gly Ala Gly His
                 85                  90                  95

Tyr Met Ser Gln Val Pro Met Phe Pro Pro Arg Thr Pro Leu Pro Gln
                100                 105                 110

Gln Met Gln Glu Gln Gln Gln Gln Leu Gln Gln Gln Gln Ala Gln
            115                 120                 125

Ala Leu Ala Phe Pro Gly Gln Met Leu Met Arg Pro Gly Thr Val Asn
    130                 135                 140

Gly Met Gln Ser Ile Pro Val Ala Asp Pro Ala Arg Ala Ala Asp Leu
145                 150                 155                 160

Gln Thr Ala Ala Pro Gly Ser Val Asp Gly Arg Gly Asn Lys Gln Asp
                165                 170                 175

Ala Thr Ser Glu Pro Ser Gly Thr Glu Ser His Lys Ser Ala Gly Ala
                180                 185                 190

Asp Asn Asp Ala Gly Gly Asp Ile Ala Glu Lys Ser
```

```
                 195                 200

<210> SEQ ID NO 45
<211> LENGTH: 184
<212> TYPE: PRT
<213> ORGANISM: Oryza sativa

<400> SEQUENCE: 45

Met Gln Gln Gln Pro Met Pro Met Pro Ala Gln Ala Pro Pro Thr Ala
1               5                   10                  15

Gly Ile Thr Thr Glu Gln Ile Gln Lys Tyr Leu Asp Glu Asn Lys Gln
                20                  25                  30

Leu Ile Leu Ala Ile Leu Glu Asn Gln Asn Leu Gly Lys Leu Ala Glu
            35                  40                  45

Cys Ala Gln Tyr Gln Ala Gln Leu Gln Lys Asn Leu Leu Tyr Leu Ala
        50                  55                  60

Ala Ile Ala Asp Thr Gln Pro Gln Thr Thr Ile Ser Arg Pro Gln Met
65                  70                  75                  80

Val Pro His Gly Ala Ser Pro Gly Leu Gly Gly Gln Tyr Met Ser Gln
                85                  90                  95

Val Pro Met Phe Pro Pro Arg Thr Pro Leu Thr Pro Gln Gln Met Gln
            100                 105                 110

Glu Gln Gln Leu Gln Gln Gln Ala Gln Leu Leu Ser Phe Gly Gly
        115                 120                 125

Gln Met Val Met Arg Pro Gly Trp Asn Gly Ile Pro Gln Leu Leu Gln
130                 135                 140

Gly Glu Met His Arg Gly Ala Asp His Gln Asn Ala Gly Gly Ala Thr
145                 150                 155                 160

Ser Glu Pro Ser Glu Ser His Arg Ser Thr Gly Thr Glu Asn Asp Gly
                165                 170                 175

Gly Ser Asp Phe Gly Asp Gln Ser
            180

<210> SEQ ID NO 46
<211> LENGTH: 227
<212> TYPE: PRT
<213> ORGANISM: Oryza sativa

<400> SEQUENCE: 46

Met Gln Gln Gln His Leu Met Gln Met Asn Gln Gly Met Met Gly Gly
1               5                   10                  15

Tyr Ala Ser Pro Thr Thr Val Thr Thr Asp Leu Ile Gln Gln Tyr Leu
                20                  25                  30

Asp Glu Asn Lys Gln Leu Ile Leu Ala Ile Leu Asp Asn Gln Asn Asn
            35                  40                  45

Gly Lys Val Glu Glu Cys Ala Arg Asn Gln Ala Lys Leu Gln His Asn
        50                  55                  60

Leu Met Tyr Leu Ala Ala Ile Ala Asp Ser Gln Pro Pro Gln Thr Ala
65                  70                  75                  80

Ala Met Ser Gln Tyr Pro Ser Asn Leu Met Met Gln Ser Gly Ala Arg
                85                  90                  95

Tyr Met Pro Gln Gln Ser Ala Gln Met Met Ala Pro Gln Ser Leu Met
            100                 105                 110

Ala Ala Arg Ser Ser Met Met Tyr Ala Gln Pro Ala Leu Ser Pro Leu
        115                 120                 125

Gln Gln Gln Gln Gln Gln Gln Ala Ala Ala Ala His Gly Gln Leu Gly
```

-continued

```
            130                 135                 140
Met Gly Ser Gly Gly Thr Thr Ser Gly Phe Ser Ile Leu His Gly Glu
145                 150                 155                 160

Ala Ser Met Gly Gly Gly Gly Gly Gly Ala Gly Asn Ser Met
                165                 170                 175

Met Asn Ala Gly Val Phe Ser Asp Phe Gly Arg Gly Gly Gly Gly
                180                 185                 190

Gly Lys Glu Gly Ser Thr Ser Leu Ser Val Asp Val Arg Gly Ala Asn
                195                 200                 205

Ser Gly Ala Gln Ser Gly Asp Gly Glu Tyr Leu Lys Gly Thr Glu Glu
                210                 215                 220

Glu Gly Ser
225

<210> SEQ ID NO 47
<211> LENGTH: 227
<212> TYPE: PRT
<213> ORGANISM: Zea mays

<400> SEQUENCE: 47

Met Gln Gln Gln His Leu Met Gln Met Asn Gln Asn Met Met Gly Gly
1               5                   10                  15

Tyr Thr Ser Pro Ala Ala Val Thr Thr Asp Leu Ile Gln Gln Tyr Leu
                20                  25                  30

Asp Glu Asn Lys Gln Leu Ile Leu Ala Ile Leu Asp Asn Gln Asn Asn
                35                  40                  45

Gly Lys Ala Glu Glu Cys Glu Arg His Gln Ala Lys Leu Gln His Asn
50                  55                  60

Leu Met Tyr Leu Ala Ala Ile Ala Asp Ser Gln Pro Pro Gln Thr Ala
65                  70                  75                  80

Pro Leu Ser Gln Tyr Pro Ser Asn Leu Met Met Gln Pro Gly Pro Arg
                85                  90                  95

Tyr Met Pro Pro Gln Ser Gly Gln Met Met Asn Pro Gln Ser Leu Met
                100                 105                 110

Ala Ala Arg Ser Ser Met Met Tyr Ala His Pro Ser Leu Ser Pro Leu
                115                 120                 125

Gln Gln Gln Gln Ala Ala His Gly Gln Leu Gly Met Ala Pro Gly Gly
130                 135                 140

Gly Gly Gly Gly Thr Thr Ser Gly Phe Ser Ile Leu His Gly Glu Ala
145                 150                 155                 160

Ser Met Gly Gly Gly Gly Ala Gly Ala Gly Ala Gly Asn Asn Met Met
                165                 170                 175

Asn Ala Gly Met Phe Ser Gly Phe Gly Arg Ser Gly Ser Gly Ala Lys
                180                 185                 190

Glu Gly Ser Thr Ser Leu Ser Val Asp Val Arg Gly Thr Ser Ser
                195                 200                 205

Gly Ala Gln Ser Gly Asp Gly Glu Tyr Leu Lys Val Gly Thr Glu Glu
                210                 215                 220

Glu Gly Ser
225

<210> SEQ ID NO 48
<211> LENGTH: 220
<212> TYPE: PRT
<213> ORGANISM: Zea mays
```

```
<400> SEQUENCE: 48

Met Gln Gln Gln Met Pro Met Pro Pro Ala Pro Ala Ala Ala Ala Ala
1               5                   10                  15

Ala Ala Pro Pro Ala Ala Gly Ile Thr Thr Glu Gln Ile Gln Lys Tyr
            20                  25                  30

Leu Asp Glu Asn Lys Gln Leu Ile Leu Ala Ile Leu Glu Asn Gln Asn
        35                  40                  45

Leu Gly Lys Leu Ala Glu Cys Ala Gln Tyr Gln Ala Gln Leu Gln Lys
    50                  55                  60

Asn Leu Leu Tyr Leu Ala Ala Ile Ala Asp Ala Gln Pro Gln Pro Pro
65                  70                  75                  80

Gln Asn Pro Ala Gly Arg Pro Gln Met Met Gln Pro Gly Ile Val Pro
                85                  90                  95

Gly Ala Gly His Tyr Met Ser Gln Val Pro Met Phe Pro Pro Arg Thr
            100                 105                 110

Pro Leu Thr Pro Gln Gln Met Gln Glu Gln Gln Gln Gln Gln Gln Phe
        115                 120                 125

Gln Gln Gln Gln Gln Gln Val Gln Ala Leu Thr Phe Pro Gly Gln Met
    130                 135                 140

Val Met Arg Pro Gly Thr Ile Asn Gly Met Gln Gln Gln Gln Pro Met
145                 150                 155                 160

Gln Ala Asp Pro Ala Arg Ala Ala Ala Glu Leu Gln Gln Ala Ala Pro
                165                 170                 175

Ile Pro Ala Asp Gly Arg Gly Ser Lys Gln Asp Thr Ala Gly Gly Ala
            180                 185                 190

Ser Ser Glu Pro Ser Ala Asn Glu Ser His Lys Ser Ala Thr Gly Ala
        195                 200                 205

Asp Thr Glu Ala Gly Gly Asp Val Ala Glu Lys Ser
    210                 215                 220

<210> SEQ ID NO 49
<211> LENGTH: 183
<212> TYPE: PRT
<213> ORGANISM: Zea mays

<400> SEQUENCE: 49

Met Pro Met Gln Pro Gln Ala Pro Ser Met Thr Pro Ala Ala Gly Ile
1               5                   10                  15

Thr Thr Glu Gln Ile Gln Lys Tyr Leu Asp Glu Asn Lys Gln Leu Ile
            20                  25                  30

Leu Ala Ile Leu Glu Asn Gln Asn Leu Gly Lys Leu Ala Glu Cys Ala
        35                  40                  45

Gln Tyr Gln Ser Gln Leu Gln Lys Asn Leu Leu Tyr Leu Ala Ala Ile
    50                  55                  60

Ala Asp Ala Gln Pro Glu Thr Ala Val Ser Arg Pro Gln Met Ala Pro
65                  70                  75                  80

Pro Gly Ala Ser Pro Gly Val Gly Gln Tyr Met Ser Gln Val Pro Met
                85                  90                  95

Phe Pro Pro Arg Thr Pro Leu Thr Pro Gln Gln Met Leu Glu Gln Gln
            100                 105                 110

Leu Gln Gln Gln Ala Gln Leu Leu Asn Phe Ser Gly Gln Met Val
        115                 120                 125

Ala Arg Pro Gly Met Val Asn Gly Met Leu Gln Ala Met Gln Val Gln
    130                 135                 140
```

Gln Ala Gln Pro Ser Pro Val Met Asn Arg Pro Asp Ala Gly Gly Ile
145                 150                 155                 160

Ala Ser Glu Pro Ser Gly Thr Glu Ser His Arg Thr Ser Thr Gly Gly
            165                 170                 175

Asp Asn Gly Gly Gly Ser Asp
            180

<210> SEQ ID NO 50
<211> LENGTH: 228
<212> TYPE: DNA
<213> ORGANISM: Arabidopsis thaliana

<400> SEQUENCE: 50
atgcaacagc acctgatgca gatgcagccc atgatggctg ttactaccc cagcaatgtt      60 acctctgatc atatccaaca gtacttggac gaaaacaaat cgttgattct gaagattgtt    120
gagtctcaaa actctggaaa gcttagcgaa tgcgccgaga tcaagcaag cttcaacgc      180 aacctaatgt acctagctgc aatagcagat tctcagcctc agccatga                 228

<210> SEQ ID NO 51
<211> LENGTH: 336
<212> TYPE: DNA
<213> ORGANISM: Arabidopsis thaliana

<400> SEQUENCE: 51
atgcaacagc acctgatgca gatgcagccc atgatggctg ttactaccc cagcaatgtt      60 acctctgatc atatccaaca gtacttggac gaaaacaaat cgttgattct gaagattgtt    120
gagtctcaaa actctggaaa gcttagcgaa tgcgccgaga tcaagcaag cttcaacgc      180 aacctaatgt acctagctgc aatagcagat tctcagcctc agccaccaag tgtgcatagc    240
cagtatggat ctgctggtgg tgggatgatt cagggagaag gagggtcaca ctatttgcag    300
cagcaacaag cgactcaaca gcaacagatg acttga                              336

<210> SEQ ID NO 52
<211> LENGTH: 180
<212> TYPE: DNA
<213> ORGANISM: Arabidopsis thaliana

<400> SEQUENCE: 52
cccagcaatg ttacctctga tcatatccaa cagtacttgg acgaaaacaa atcgttgatt     60
ctgaagattg ttgagtctca aaactctgga aagcttagcg aatgcgccga gatcaagca    120 aggcttcaac gcaacctaat gtacctagct gcaatagcag attctcagcc tcagccatga   180

<210> SEQ ID NO 53
<211> LENGTH: 288
<212> TYPE: DNA
<213> ORGANISM: Arabidopsis thaliana

<400> SEQUENCE: 53
cccagcaatg ttacctctga tcatatccaa cagtacttgg acgaaaacaa atcgttgatt     60
ctgaagattg ttgagtctca aaactctgga aagcttagcg aatgcgccga gatcaagca    120 aggcttcaac gcaacctaat gtacctagct gcaatagcag attctcagcc tcagccacca   180
agtgtgcata gccagtatgg atctgctggt ggtgggatga ttcagggaga aggagggtca    240
cactatttgc agcagcaaca agcgactcaa cagcaacaga tgacttga                 288

<210> SEQ ID NO 54

<211> LENGTH: 585
<212> TYPE: DNA
<213> ORGANISM: Arabidopsis thaliana

<400> SEQUENCE: 54

```
cccagcaatg ttacctctga tcatatccaa cagtacttgg acgaaaacaa atcgttgatt    60
ctgaagattg ttgagtctca aaactctgga aagcttagcg aatgcgccga gaatcaagca   120
aggcttcaac gcaacctaat gtacctagct gcaatagcag attctcagcc tcagccacca   180
agtgtgcata gccagtatgg atctgctggt ggtgggatga ttcagggaga aggagggtca   240
cactatttgc agcagcaaca agcgactcaa cagcaacaga tgactcagca gtctctaatg   300
gcggctcgat cttcaatgtt gtatgctcag caacagcagc agcagcagcc ttacgcgacg   360
cttcagcatc agcaattgca ccatagccag cttggaatga gctcgagcag cggaggagga   420
ggaagcagtg gtctccatat ccttcaggga gaggctggtg ggtttcatga ttttggccgt   480
gggaagccgg aaatgggaag tggtggtggc ggtgaaggca gaggaggaag ttcaggggat   540
ggtggagaaa ccctttactt gaaatcatca gatgatggga attga              585
```

<210> SEQ ID NO 55
<211> LENGTH: 417
<212> TYPE: DNA
<213> ORGANISM: Arabidopsis thaliana

<400> SEQUENCE: 55

```
cctcagccac caagtgtgca tagccagtat ggatctgctg gtggtgggat gattcaggga    60
gaaggagggt cacactattt gcagcagcaa caagcgactc aacagcaaca gatgactcag   120
cagtctctaa tggcggctcg atcttcaatg ttgtatgctc agcaacagca gcagcagcag   180
ccttacgcga cgcttcagca tcagcaattg caccatagcc agcttggaat gagctcgagc   240
agcggaggag gaggaagcag tggtctccat atccttcagg gagaggctgg tgggtttcat   300
gattttggcc gtgggaagcc ggaaatggga agtggtggtg gcggtgaagg cagaggagga   360
agttcagggg atggtggaga aacccttac ttgaaatcat cagatgatgg gaattga      417
```

<210> SEQ ID NO 56
<211> LENGTH: 309
<212> TYPE: DNA
<213> ORGANISM: Arabidopsis thaliana

<400> SEQUENCE: 56

```
cagatgactc agcagtctct aatggcggct cgatcttcaa tgttgtatgc tcagcaacag    60
cagcagcagc agccttacgc gacgcttcag catcagcaat tgcaccatag ccagcttgga   120
atgagctcga gcagcggagg aggaggaagc agtggtctcc atatccttca gggagaggct   180
ggtgggtttc atgattttgg ccgtgggaag ccggaaatgg gaagtggtgg tggcggtgaa   240
ggcagaggag gaagttcagg ggatggtgga gaaacccttt acttgaaatc atcagatgat   300
gggaattga                                                           309
```

<210> SEQ ID NO 57
<211> LENGTH: 588
<212> TYPE: DNA
<213> ORGANISM: Arabidopsis thaliana

<400> SEQUENCE: 57

```
atgcagcagc agcagtctcc gcaaatgttt ccgatggttc cgtcgattcc ccctgctaac    60
aacatcacta ccgaacagat ccaaaagtac cttgatgaga caagaagct gattatggcc   120
```

```
atcatggaaa accagaatct cggtaaactt gctgagtgcg cccagtacca agctcttctc      180
cagaagaact tgatgtatct tgctgcaatt gctgatgctc aaccccccacc acctacgcca      240 ggaccttcac catctacagc tgtcgctgcc cagatggcaa caccgcattc tgggatgcaa      300
ccacctagct acttcatgca acacccacaa gcatccctg cagggatttt cgctccaagg       360
ggtcctttac agtttggtag cccactccag tttcaggatc cgcaacagca gcagcagata      420
catcagcaag ctatgcaagg acacatgggg attagaccaa tgggtatgac caacaacggg      480
atgcagcatg cgatgcaaca accagaaacc ggtcttggag gaaacgtggg gcttagagga      540
ggaaagcaag atggagcaga tggacaagga aagatgatg gcaagtga                    588
```

<210> SEQ ID NO 58
<211> LENGTH: 672
<212> TYPE: DNA
<213> ORGANISM: Arabidopsis thaliana

<400> SEQUENCE: 58

```
atgcagcaat ctccacagat gattccgatg gttcttcctt catttccgcc caccaataat      60
atcaccaccg aacagatcca aaagtatctt gatgagaaca agaagctgat aatggcgatc     120
ttggaaaatc agaacctcgg taaacttgca gaatgtgctc agtatcaagc tcttctccag     180
aagaatttga tgtatctcgc tgcaattgcg gatgctcaac ctcagccacc agcagctaca     240
ctaacatcag gagccatgac tccccaagca atggctccta atccgtcatc aatgcagcca     300
ccaccaagct acttcatgca gcaacatcaa gctgtgggaa tggctcaaca atacctcct     360 gggattttcc ctcctagagg tccattgcaa tttggtagcc cgcatcagtt tctggatccg     420
cagcaacagt tacatcaaca agctatgcaa gggcacatgg ggattagacc aatgggtttg     480
aataataaca acggactgca acatcaaatg caccaccatg aaactgctct tgccgcaaac     540
aatgcgggtc ctaacgatgc tagtggagga ggtaaaccgg atgggaccaa tatgagccag     600
agtggagctg atgggcaagg tggctcagcc gctagacatg gcggtggtga tgcaaaaact     660
gaaggaaaat ga                                                         672
```

<210> SEQ ID NO 59
<211> LENGTH: 398
<212> TYPE: PRT
<213> ORGANISM: Artificial Sequence
<220> FEATURE:
<223> OTHER INFORMATION: GRF3 mutant decoupled from the control by
    miR396

<400> SEQUENCE: 59

```
Met Asp Leu Gln Leu Lys Gln Trp Arg Ser Gln Gln Gln Gln His
1               5                   10                  15

Gln Thr Glu Ser Glu Glu Gln Pro Ser Ala Ala Lys Ile Pro Lys His
                20                  25                  30

Val Phe Asp Gln Ile His Ser His Thr Ala Thr Ser Thr Ala Leu Pro
            35                  40                  45

Leu Phe Thr Pro Glu Pro Thr Ser Ser Lys Leu Ser Ser Leu Ser Pro
        50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Leu Pro Ile Lys Lys Ser
```

-continued

```
                       100                 105                 110
Leu Leu His Leu Ser Pro Ser Tyr Phe Leu His His Pro Leu Gln His
            115                 120                 125
Leu Pro His Tyr Gln Pro Ala Trp Tyr Leu Gly Arg Ala Ala Met Asp
        130                 135                 140
Pro Glu Pro Gly Arg Cys Arg Arg Thr Asp Gly Lys Lys Trp Arg Cys
145                 150                 155                 160
Ser Arg Asp Val Phe Ala Gly His Lys Tyr Cys Glu Arg His Met His
                165                 170                 175
Arg Gly Arg Asn Arg Ser Arg Lys Pro Val Glu Thr Pro Thr Thr Val
            180                 185                 190
Asn Ala Thr Ala Thr Ser Met Ala Ser Ser Val Ala Ala Ala Ala Thr
        195                 200                 205
Thr Thr Thr Ala Thr Thr Thr Ser Thr Phe Ala Phe Gly Gly Gly Gly
210                 215                 220
Gly Ser Glu Glu Val Val Gly Gln Gly Gly Ser Phe Phe Ser Gly
225                 230                 235                 240
Ser Ser Asn Ser Ser Ser Glu Leu Leu His Leu Ser Gln Ser Cys Ser
                245                 250                 255
Glu Met Lys Gln Glu Ser Asn Asn Met Asn Asn Lys Arg Pro Tyr Glu
            260                 265                 270
Ser His Ile Gly Phe Ser Asn Asn Arg Ser Asp Gly Gly His Ile Leu
        275                 280                 285
Arg Pro Phe Phe Asp Asp Trp Pro Arg Ser Ser Leu Gln Glu Ala Asp
290                 295                 300
Asn Ser Ser Ser Pro Met Ser Ser Ala Thr Cys Leu Ser Ile Ser Met
305                 310                 315                 320
Pro Gly Asn Ser Ser Ser Asp Val Ser Leu Lys Leu Ser Thr Gly Asn
                325                 330                 335
Glu Glu Gly Ala Arg Ser Asn Asn Asn Gly Arg Asp Gln Gln Asn Met
            340                 345                 350
Ser Trp Trp Ser Gly Gly Gly Ser Asn His His His Asn Met Gly
        355                 360                 365
Gly Pro Leu Ala Glu Ala Leu Arg Ser Ser Ser Ser Ser Pro Thr
    370                 375                 380
Ser Val Leu His Gln Leu Gly Val Ser Thr Gln Ala Phe His
385                 390                 395
```

<210> SEQ ID NO 60
<211> LENGTH: 2318
<212> TYPE: DNA
<213> ORGANISM: Artificial Sequence
<220> FEATURE:
<223> OTHER INFORMATION: GRF3 mutant decoupled from control by miR396

<400> SEQUENCE: 60

| | | |
|---|---|---|
| atggatttgc aactgaaaca atggagaagc cagcagcagc aacaacatca gacagagtca | 60 |
| gaagaacaac cttctgcagc taagatacca aaacatgtct ttgaccagat tcattctcac | 120 |
| actgcaactt ctactgctct tcctctcttt accctgagc ctacttcttc taaactctcc | 180 |
| tctttgtctc ctgattcttc ctccaggttc cccagtgagt cttttcttcc tcttatctta | 240 |
| tctttcttga taaagaatta gacttttcat tcatatagtt tgtgtttaat tgattttgat | 300 |
| tcctttttgt agagatgggg agcttcttta gctgggcaca gtggcaagaa cttgaactac | 360 |
| aagctctgat ctacaggtac atgttggctg gtgctgctgt tcctcaggag ctccttttac | 420 |

-continued

```
caatcaagaa aagccttctc catctatctc cttcctactt tcttcaccat cctcttcaac      480
acctacctca ttaccaacct gcttgtgagt ctcgagaaca gtcttcatct atctattttt      540
taaatataaa tgggttttgt gctactggtg ttggagttgt gttcccaaga tccagacttt      600
caatattagt atattatctc gttttgccaa tcttgaagat ctaaacatgt gtgaatggga      660
ttaagtagga ttagaatctt gttattgatc tgatatgtga tatgaatgtt gaaaacaggg      720
tatttgggaa gggcagcgat ggatcctgag ccaggcagat gcaggagaac ggatggtaag      780
aagtggagat gttcaagaga cgtcttcgct ggccacaagt attgcgagcg ccacatgcac      840
cgtggccgca accgttctag aaaaccagta gagactccaa ccaccgtcaa tgcaactgcc      900
acgtccatgg cttcatcagt agcagccgca gccaccacta aacagcaac aacaacatct      960 acgtttgctt tggtggtgg tggtggtagt gaggaagtgg ttggtcaagg aggatctttc     1020
ttcttctctg gctcttctaa ctcttcatct gaacttctcc accttagtca aggtaataa      1080 aaagaaactg ttttttttc tcttaggtct gtctgtttta gctgttgaac tttatggtca     1140
aaacattaaa cttaaacaca ttgactttt tatttcttta gtgttgagcc aataagattc      1200
atggttgaga ttttagacaa ttgttttgaa taataatgaa atcgatttaa agcaatactg     1260
attcttgatt tattagtatg aagtatgaac taatgatata cacaacttgg tttgtatgtt     1320
catagcgatg ttgtgaagag aggggtaatg ttggaaattg agagacacat ccttatcatt     1380
ttagggttgg ttggtttgtt tgtttgttga attatgagtt tgatttcatt gtgaaaatat     1440
ctttctttct tttttcttat tgtgttgaga gataatgata acattggatt tgatagaatc     1500
tataatttga agctaggtgt gagacttttc aaacagagaa aatagaaaga gagagaaatg     1560
gtaggacctt agtgaaagct gacccatata tgtctcatat cttgcagaaa agttaaagct     1620
tttagattct tctgcaccca cctcccctat ccacacacaa cacatgatat acaaaacact     1680
cactttataa ttctatttct atttactgct taatcaattc ttataaaacc cacattaaaa     1740
ggtactttta aagcctataa actaatataa aggctactac tgtctgcaac tttgttgttg     1800
aagcctaaat gtggttctc ttttgacaaa ttattgcttt tgtgctttgt tttcaccaat      1860
gagatgtgga ttctgttaac agttgttcgg agatgaagca agaaagcaac aacatgaaca     1920
acaagaggcc atacgagtcc cacatcggat tcagtaacaa cagatcagat ggaggacaca     1980
tcctgaggcc cttctttgac gattggcctc gttcttcgct ccaagaagct gacaatagtt     2040
caagccccat gagctcagcc acttgtctct ccatctccat gcccgggaac tcttcctcag     2100
acgtctctct gaagctgtcc acaggcaacg aagagggagc ccggagcaac aacaatggga     2160
gagatcagca aaacatgagc tggtggagcg gtggaggttc caaccaccat catcacaaca     2220
tgggcggacc attggccgaa gccctgagat cttcttcctc atcttcccca accagtgttc     2280
tccatcagct tggtgtctcg acacaagcct ttcattga                             2318
```

```
<210> SEQ ID NO 61
<211> LENGTH: 39
<212> TYPE: PRT
<213> ORGANISM: Arabidopsis thaliana

<400> SEQUENCE: 61

Pro Gln Pro Pro Ser Val His Ser Gln Tyr Gly Ser Ala Gly Gly Gly
1               5                   10                  15

Met Ile Gln Gly Glu Gly Gly Ser His Tyr Leu Gln Gln Gln Gln Ala
            20                  25                  30

Thr Gln Gln Gln Gln Met Thr
        35
```

CHIMERIC PROTEINS WHICH ENHANCE THE ACTIVITY OF DNA BINDING DOMAINS (DBD) AND TRANSCRIPTION FACTORS IN PLANTS

FIELD OF THE INVENTION

The present invention relates to enhancement of the activity of transcription factors in plants. More specifically, the invention relates to a method of enhancing the activity of a transcription factor in a plant which comprises expressing in said plant a chimeric protein comprising a GIF moiety comprising a GIF domain or fragment thereof, and a DNA binding domain (DBD) moiety. The invention also relates to polynucleotides and polypeptides useful in the method of the invention.

BACKGROUND OF THE INVENTION

Transcription factors are proteins which regulate the expression of genes by specifically binding to DNA sequences (enhancers or promoters) and affecting the transcription of the genes they regulate. Such specific binding is rendered possible because transcription factors comprise a DNA binding domain (DBD) that is specific for the DNA sequences to which they attach. By up-regulating or down-regulating the expression of their target genes, transcription factors control many vital processes in living organisms, ranging from body pattern formation to resistance to pathogens and response to environmental stress.

The transcriptional activation ability of the transcription factors depends on a region of the transcription factors called transcriptional activation domain (TAD). These transcriptional activation domains can be classified according to their amino acid compositions: proline-, glutamine- or acidic-rich domains. These trans-activation domains retain their activity when fused to any domain that is able to bind DNA. Therefore, a transactivation domain can activate the transcription of any suitable gene whose promoter or adjacent DNA regions can be bound by a DNA-binding domain. These properties of the trans-activation domain make them useful for targeted induction of genes in yeast, animals, plants, and other systems. They are also useful to study DNA-protein and protein-protein interactions. Transactivation domains derived from the herpes simplex virus VP16 domain and the yeast GAL4 are commonly used in research in different systems, including plants. Given the importance of the transactivation domains in research and technology, it is important to find new and different ways to activate and modify transcription factors.

An example of transcription factors known to affect agronomical traits of plants are GROWTH-REGULATING FACTORs (GRFs), a family of transcription factors with an important role in the control of leaf and flower organ development. Expression of GRFs is high at early stages of leaf development, when intense cell proliferation is taking place (Rodriguez, Mecchia et al. 2010; Debernardi, Rodriguez et al. 2012). It has been observed that GRFs upregulate cell proliferation, and overexpression of GRF1, 2, or 5 produces an increase of the leaf size due to an increase in cell division (Kim, Choi et al. 2003; Horiguchi, Kim et al. 2005; Gonzalez, De Bodt et al. 2010).

Also important in regulating different stages of leaf development, including leaf size and shape, organ polarity and senescence are small RNAs in general, and microRNAs (miRNAs) in particular (Pulido and Laufs 2010; Rubio-Somoza and Weigel 2011). In *Arabidopsis thaliana*, seven out of the nine GRFs encoded in its genome are downregulated by miR396 (Rodriguez, Mecchia et al. 2010), a miRNA that accumulates with the age of the leaf reducing the levels of GRFs in later stages of leaf development (Rodriguez, Mecchia et al. 2010; Debernardi, Rodriguez et al. 2012). Mutations in different GRFs (Kim, Choi et al. 2003; Kim and Kende 2004; Horiguchi, Kim et al. 2005; Kim and Lee 2006) or overexpression of miR396 (Liu, Song et al. 2009; Rodriguez, Mecchia et al. 2010; Wang, Gu et al. 2011) reduce the size of the leaf. In contrast, mutating the miR396-binding box of GRF2 generates slightly bigger leaves, similar to what was observed with overexpression of GRFs from the constitutive and strong 35S promoter (Kim, Choi et al. 2003; Horiguchi, Kim et al. 2005; Gonzalez, De Bodt et al. 2010; Rodriguez, Mecchia et al. 2010).

Other examples of transcription factors whose activities have an impact on the agronomic properties of plants have been described (Van Camp 2005; Century, Reuber et al. 2008; Gonzalez, Beemster et al. 2009; Ikeda, Miura et al. 2013), including for instance those whose increased activity results in increased biomass (such as ANT, HB33, GRF3, GRF5, ATAF2, HRC1 and NAC1), increased stress resistance (such as CBF, HAHB4), increased drought tolerance (such as GRF3, HAHB4, ABF3, WIN1/SHN1, HARDY and AtNF-YB1), increased drought and cold tolerance (such as DREB1A/CBF3), delayed leaf senescence (such as GRF3), increased seed production (such as OsSPL14), increased seed size (such as ANT, OsPGL1), increased root growth, increased root elongation speed, increased growth speed (such as rSPL), modified plant architecture (such as TCPs and SPLs), increased chloroplast number and photosynthetic capacity (such as HB17 and GOLDEN2-like transcription factors GLK1 and GLK2), more efficient carbon partitioning, increased resistance to pathogens (such as AtERF1 and TDR1/ERF98), more efficient nutrient use, increased salt tolerance (such as ERF98 and HARDY), and increased production of a target compound (Jirschitzka, Mattern et al. 2013).

In regulating the expression of their target genes, some transcription factors act in combination with transcription co-regulators, which in turn help to recruit and/or activate the RNA polymerase or interact with the chromatin remodeling complex in making DNA more or less accessible for transcription. In the case of GRF proteins discussed above, for instance, they physically interact with GRF-interacting factors (GIF), a family composed by three members in *Arabidopsis* (GIF1, GIF2, and GIF3). GIF proteins lack a DNA-binding motif but share homology and a 24 to 28% of amino acid identity with the human coactivator SYT (Kim and Kende 2004; Horiguchi, Kim et al. 2005). Similar to SYT, GIF proteins have a SNH domain near the N-terminus, and a Gln/Gly-rich region near the C-terminus, denominated QPGY in SYT and QG in GIF. GIF proteins however lack the Met-rich region that is present between the SNH and QPGY domains in SYT (Kim and Kende 2004; Horiguchi, Kim et al. 2005). GIF1 has been shown to interact with chromatin remodeling complexes (Debernardi, Mecchia et al. 2014; Vercruyssen, Verkest et al. 2014). Considering the full protein, while GIF2 and GIF3 share 61% of amino acid identity GIF1 shows 31% of amino acid identity with GIF2 and GIF3 mostly due to a divergent C-terminus (Kim and Kende 2004; Horiguchi, Kim et al. 2005).

A Mutation in GIF1, also known as ANGUSTIFOLIA3 (AN3), causes smaller, narrower leaves and petals, with a reduced number of cells, similar to the phenotypes seen in grf mutants (Kim and Kende 2004; Horiguchi, Kim et al. 2005). The phenotype of double mutants gif1,2 or gif1,3 and of triple mutant gif1,2,3 is more severe, indicating that GIF genes have redundant functions (Lee, Ko et al. 2009). However, single mutants gif2 and gif3 are similar to wild type plants, suggesting that GIF1 has a larger impact on leaf development than other members of the GIF family (Lee, Ko et al. 2009). Combining gif1 mutants with GRF deficient plants has a synergistic effect in leaf area reduction and can also affect the integrity of the apical meristem (Kim and Kende 2004; Horiguchi, Kim et al. 2005; Rodriguez, Mecchia et al. 2010). Ectopic overexpression of all three GIFs can rescue a mutation in GIF1 (Lee, Ko et al. 2009).

Therefore, it becomes evident that there are many transcription factors whose manipulation for an increased activity allows to obtain plants with enhanced agronomical properties, such as increased biomass, delayed leaf senescence, drought resistance, cold resistance, increased photosynthetic capacity, etc.

BRIEF DESCRIPTION OF THE INVENTION

Surprisingly, the inventors have found now that, when expressed as part of a fusion protein, GIF domains or fragments thereof (or even the complete GIF protein) can modify and/or enhance the activity of any plant DNA binding domain (DBD). That is, similar to TAD domains of transcription factors, SNH and QG domains of GIF proteins or fragments thereof can modify and/or enhance the activity of not just their natural partners, but of any plant transcription factor, of which the DBD is a constitutive part.

Therefore, according to a first aspect, the present invention comprises a method of enhancing the activity of a DNA binding domain (DBD) or transcription factor in a plant, the method comprising expressing in said plant a chimeric protein comprising:
a GIF moiety comprising
  a GIF domain or fragment thereof, or
  a polypeptide with an amino acid sequence having at least 85%, preferably at least 90%, even more preferably at least 95% sequence identity to the amino acid sequence of a GIF domain or fragment thereof;
and
a DBD moiety comprising
  the DBD or plant transcription factor whose activity enhancement is intended, or
  a binding protein which is capable of forming a tertiary complex with the DBD or transcription factor whose activity modification and/or enhancement is intended.

In one particular embodiment of the method of the invention, the GIF domain is the SNH domain. In another particular embodiment of the invention, the GIF domain is the QG domain. According to the method of the invention, the GIF domain is preferably a GIF1 domain, such as a GIF1 domain from *Arabidopsis thaliana*. In one particular embodiment of the invention, the GIF moiety comprises or consists of a polypeptide selected from GIF1Δ1 (SEQ ID NO.: 3), GIF1Δ2 (SEQ ID NO.: 4), GIF1Δ3 (SEQ ID NO.: 5), GIF1Δ4 (SEQ ID NO.: 6), GIF1Δ5 (SEQ ID NO.: 7), GIF1Δ6 (SEQ ID NO.: 8), GIF1Δ7 (SEQ ID NO.: 9), and GIF1Δ10 (SEQ ID NO.: 61)

According to another embodiment of the method of the invention, alone or in combination with any of the above or below embodiments, the GIF moiety consists or substantially consists of a complete GIF protein or a protein with an amino acid sequence having at least 85%, preferably at least 90%, even more preferably at least 95% sequence identity to a GIF protein, such as a GIF1 protein, for example GIF1 from *Arabidopsis thaliana*, preferably having the amino acid SEQ ID NO.: 1 or a sequence having at least 85%, preferably at least 90%, even more preferably at least 95% sequence identity to SEQ ID NO.: 1.

According to another embodiment of the method of the invention, alone or in combination with any of the above or below embodiments, the plant DNA-binding domain or transcription factor in the DBD moiety results in increased plant productivity when its function is enhanced. According to this embodiment, the plant transcription factor is for example selected from the group consisting of transcription factors whose enhanced function increases plant productivity by means of one or more of increased yield, increased biomass (such as ANT, HB33, GRF3, GRF5, ATAF2, HRC1 and NAC1), increased stress resistance (such as HAHB4 and CBF), increased drought tolerance (such as GRF3, HAHB4, ABF3, WIN1/SHN1, HARDY and AtNF-YB1), increased drought and cold tolerance (such as DREB1A/CBF3), delayed leaf senescence (such as GRF3), increased seed production (such as OsSPL14), increased seed size (such as ANT, OsPGL1), increased root growth, increased root elongation speed, increased growth speed (such as rSPL), modified plant architecture (such as TCPs and SPLs), increased chloroplast number and photosynthetic capacity (such as HB17 and GOLDEN2-like transcription factors GLK1 and GLK2), more efficient carbon partitioning, increased resistance to pathogens (such as AtERF1 and TDR1/ERF98), more efficient nutrient use, increased salt tolerance (such as ERF98 and HARDY), increased target compound production, and combinations thereof. In one embodiment of the invention, the transcription factor is a GRF, such as GRF3.

According to another embodiment of the method of the invention, alone or in combination with any of the above or below embodiments, the GIF moiety and the DBD moiety are connected directly to each other. According to this embodiment, the chimeric protein has for example an amino acid sequence selected from the group comprising SEQ ID NO.: 18, SEQ ID NO.: 21, SEQ ID NO.: 30, and SEQ ID NO.: 33, ora sequence having at least 85%, preferably at least 90%, even more preferably at least 95% sequence identity to SEQ ID NO.: 18, SEQ ID NO.: 21, SEQ ID NO.: 30, or SEQ ID NO.: 33. In an alternative embodiment, the GIF moiety and the DBD moiety are connected through a peptide linker, such as a GR (Glucocorticoid Receptor) peptide. According to this alternative embodiment, the chimeric protein has for example the amino acid sequence SEQ ID NO.: 24.

According to a second aspect, the present invention provides a chimeric protein comprising
a GIF moiety comprising
  a GIF domain or fragment thereof, or
  a polypeptide with an amino acid sequence having at least 85%, preferably at least 90%, even more preferably at least 95% sequence identity to the amino acid sequence of a GIF domain or fragment thereof;
and
a DBD moiety comprising
  the DBD or plant transcription factor whose activity enhancement is intended, or
  a binding protein which is capable of forming a tertiary complex with the DBD or transcription factor whose activity modification and/or enhancement is intended.

In one particular embodiment of the chimeric protein of the invention, the GIF domain is the SNH domain. In another particular embodiment of the chimeric protein of the invention, the GIF domain is the QG domain. According to the invention, the GIF domain is preferably a GIF1 domain, such as a GIF1 domain from *Arabidopsis thaliana*. In one particular embodiment of the invention, the GIF moiety comprises or consists of a polypeptide selected from GIF1Δ1 (SEQ ID NO.: 3), GIF1Δ2 (SEQ ID NO.: 4), GIF1Δ3 (SEQ ID NO.: 5), GIF1Δ4 (SEQ ID NO.: 6), GIF1Δ5 (SEQ ID NO.: 7), GIF1Δ6 (SEQ ID NO.: 8), GIF1Δ7 (SEQ ID NO.: 9), and GIF1Δ10 (SEQ ID NO.: 61).

According to another embodiment of the chimeric protein of the invention, alone or in combination with any of the above or below embodiments, the GIF moiety consists or substantially consists of a complete GIF protein or a protein with an amino acid sequence having at least 85%, preferably at least 90%, even more preferably at least 95% sequence identity to a GIF protein, such as a GIF1 protein, for example GIF1 from *Arabidopsis thaliana*, preferably having the amino acid SEQ ID NO.: 1 or a sequence having at least 85%, preferably at least 90%, even more preferably at least 95% sequence identity to SEQ ID NO.: 1.

According to another embodiment of the chimeric protein of the invention, alone or in combination with any of the above or below embodiments, the plant DNA-binding domain or transcription factor in the DBD moiety results in increased plant productivity when its function is enhanced. According to this embodiment, the plant transcription factor is for example selected from the group consisting of transcription factors whose enhanced function increases plant productivity by means of one or more of increased yield, increased biomass (such as ANT, HB33, GRF3, GRF5, ATAF2, HRC1 and NAC1), increased stress resistance (such as HAHB4 and CBF), increased drought tolerance (such as GRF3, HAHB4, ABF3, WIN1/SHN1, HARDY and AtNF-YB1), increased drought and cold tolerance (such as DREB1A/CBF3), delayed leaf senescence (such as GRF3), increased seed production (such as OsSPL14), increased seed size (such as ANT, OsPGL1), increased root growth, increased root elongation speed, increased growth speed (such as rSPL), modified plant architecture (such as TCPs and SPLs), increased chloroplast number and photosynthetic capacity (such as HB17 and GOLDEN2-like transcription factors GLK1 and GLK2), more efficient carbon partitioning, increased resistance to pathogens (such as AtERF1 and TDR1/ERF98), more efficient nutrient use, increased salt tolerance (such as ERF98 and HARDY), increased target compound production, and combinations thereof. In one embodiment of the invention, the transcription factor is a GRF, such as GRF3.

According to another embodiment of the chimeric protein of the invention, alone or in combination with any of the above or below embodiments, the GIF moiety and the DBD moiety are connected directly to each other. According to this embodiment, the chimeric protein has for example an amino acid sequence selected from the group comprising SEQ ID NO.: 18, SEQ ID NO.: 21, SEQ ID NO.: 30, and SEQ ID NO.: 33, ora sequence having at least 85%, preferably at least 90%, even more preferably at least 95% sequence identity to SEQ ID NO.: 18, SEQ ID NO.: 21, SEQ ID NO.: 30, or SEQ ID NO.: 33. In an alternative embodiment, the GIF moiety and the DBD moiety are connected through a peptide linker, such as a GR (Glucocorticoid Receptor) peptide. According to this alternative embodiment, the chimeric protein has for example the amino acid sequence SEQ ID NO.: 24.

According to yet another aspect, the invention provides a nucleic acid encoding for the chimeric protein of the invention, for example a nucleic acid encoding for a chimeric protein comprising an amino acid sequence selected from the group comprising SEQ ID NO.: 18, SEQ ID NO.: 21, SEQ ID NO.: 24, SEQ ID NO.: 30, and SEQ ID NO.: 33, or a sequence having at least 85% sequence identity to SEQ ID NO.: 18, SEQ ID NO.: 21, SEQ ID NO.: 24, SEQ ID NO.: 30, or SEQ ID NO.: 33, such as a nucleic acid having a nucleotide sequence selected from the group comprising SEQ ID NO.: 19, SEQ ID NO.: 22, SEQ ID NO.: 25, SEQ ID NO.: 31, and SEQ ID NO.:34, ora sequence having at least 85%, preferably at least 90%, even more preferably at least 95% sequence identity to SEQ ID NO.: 19, SEQ ID NO.: 22, SEQ ID NO.: 25, SEQ ID NO.: 31, or SEQ ID NO.:34.

According to a further aspect, the invention provides a vector comprising a nucleic acid encoding for the chimeric protein of the invention, for example a vector comprising a nucleic acid encoding for a chimeric protein comprising the amino acid sequence SEQ ID NO.: 18, SEQ ID NO.: 21, SEQ ID NO.: 24, SEQ ID NO.: 30, and SEQ ID NO.: 33, or a sequence having at least 85% sequence identity to SEQ ID NO.: 18, SEQ ID NO.: 21, SEQ ID NO.: 24, SEQ ID NO.: 30, or SEQ ID NO.: 33, such as a nucleic acid having a nucleotide sequence selected from the group comprising SEQ ID NO.: 19, SEQ ID NO.: 22, SEQ ID NO.: 25, SEQ ID NO.: 31, and SEQ ID NO.:34, ora sequence having at least 85%, preferably at least 90%, even more preferably at least 95% sequence identity to SEQ ID NO.: 19, SEQ ID NO.: 22, SEQ ID NO.: 25, SEQ ID NO.: 31, or SEQ ID NO.:34, such as vectors pJD104 (SEQ ID NO.:14), pJD105 (SEQ ID NO.:17), pJD149 (SEQ ID NO.:20), pJD150 (SEQ ID NO.:23), pJD155 (SEQ ID NO.:26), pJD220 (SEQ ID NO.:29), pJD221 (SEQ ID NO.:32), pJD222 (SEQ ID NO.:35), and pCS55 (SEQ ID NO.:38).

According to another aspect, the invention provides a transgenic plant comprising a nucleic acid or a vector of the invention. In one embodiment, the transgenic plant of the invention comprises a nucleic acid encoding for a chimeric protein of the invention comprising an amino acid sequence selected from the group comprising SEQ ID NO.: 18, SEQ ID NO.: 21, SEQ ID NO.: 24, SEQ ID NO.: 30, and SEQ ID NO.: 33, or a sequence having at least 85% sequence identity to SEQ ID NO.: 18, SEQ ID NO.: 21, SEQ ID NO.: 24, SEQ ID NO.: 30, or SEQ ID NO.: 33, such as a nucleic acid having a nucleotide sequence selected from the group comprising SEQ ID NO.: 19, SEQ ID NO.: 22, SEQ ID NO.: 25, SEQ ID NO.: 31, and SEQ ID NO.:34, or a sequence having at least 85%, preferably at least 90%, even more preferably at least 95% sequence identity to SEQ ID NO.: 19, SEQ ID NO.: 22, SEQ ID NO.: 25, SEQ ID NO.: 31, or SEQ ID NO.:34, such as a plant comprising a vector comprising a nucleic acid having a nucleotide sequence selected from the group comprising SEQ ID NO.: 19, SEQ ID NO.: 22, SEQ ID NO.: 25, SEQ ID NO.: 31, and SEQ ID NO.:34, or a sequence having at least 85%, preferably at least 90%, even more preferably at least 95% sequence identity to SEQ ID NO.: 19, SEQ ID NO.: 22, SEQ ID NO.: 25, SEQ ID NO.: 31, or SEQ ID NO.:34.

According to yet a further aspect, the invention provides a method for obtaining a transgenic plant, the method comprising transforming a plant cell with the nucleic acid of the invention, for example a nucleic acid encoding for a chimeric protein comprising the amino acid sequence selected from the group comprising SEQ ID NO.: 18, SEQ ID NO.: 21, SEQ ID NO.: 24, SEQ ID NO.: 30, and SEQ ID NO.: 33, or a sequence having at least 85% sequence identity to SEQ ID NO.: 18, SEQ ID NO.: 21, SEQ ID NO.: 24, SEQ ID NO.: 30, or SEQ ID NO.: 33, such as a nucleic acid having a nucleotide sequence selected from the group comprising SEQ ID NO.: 19, SEQ ID NO.: 22, SEQ ID NO.: 25, SEQ ID NO.: 31, and SEQ ID NO.:34 or a sequence having at least 85%, preferably at least 90%, even more preferably at least 95% sequence identity to SEQ ID NO.: 19, SEQ ID NO.: 22, SEQ ID NO.: 25, SEQ ID NO.: 31, or SEQ ID NO.:34, and generating a transgenic plant from the transformed plant cell. In a preferred embodiment, the plant cell is transformed with a vector of the invention, such as a vector comprising a nucleic acid having a nucleotide sequence selected from the group comprising SEQ ID NO.: 19, SEQ ID NO.: 22, SEQ ID NO.: 25, SEQ ID NO.: 31, and SEQ ID NO.:34, or a sequence having at least 85%, preferably at least 90%, even more preferably at least 95% sequence identity to SEQ ID NO.: 19, SEQ ID NO.: 22, SEQ ID NO.: 25, SEQ ID NO.: 31, or SEQ ID NO.:34.

DETAILED DESCRIPTION OF THE INVENTION

Figure 1:
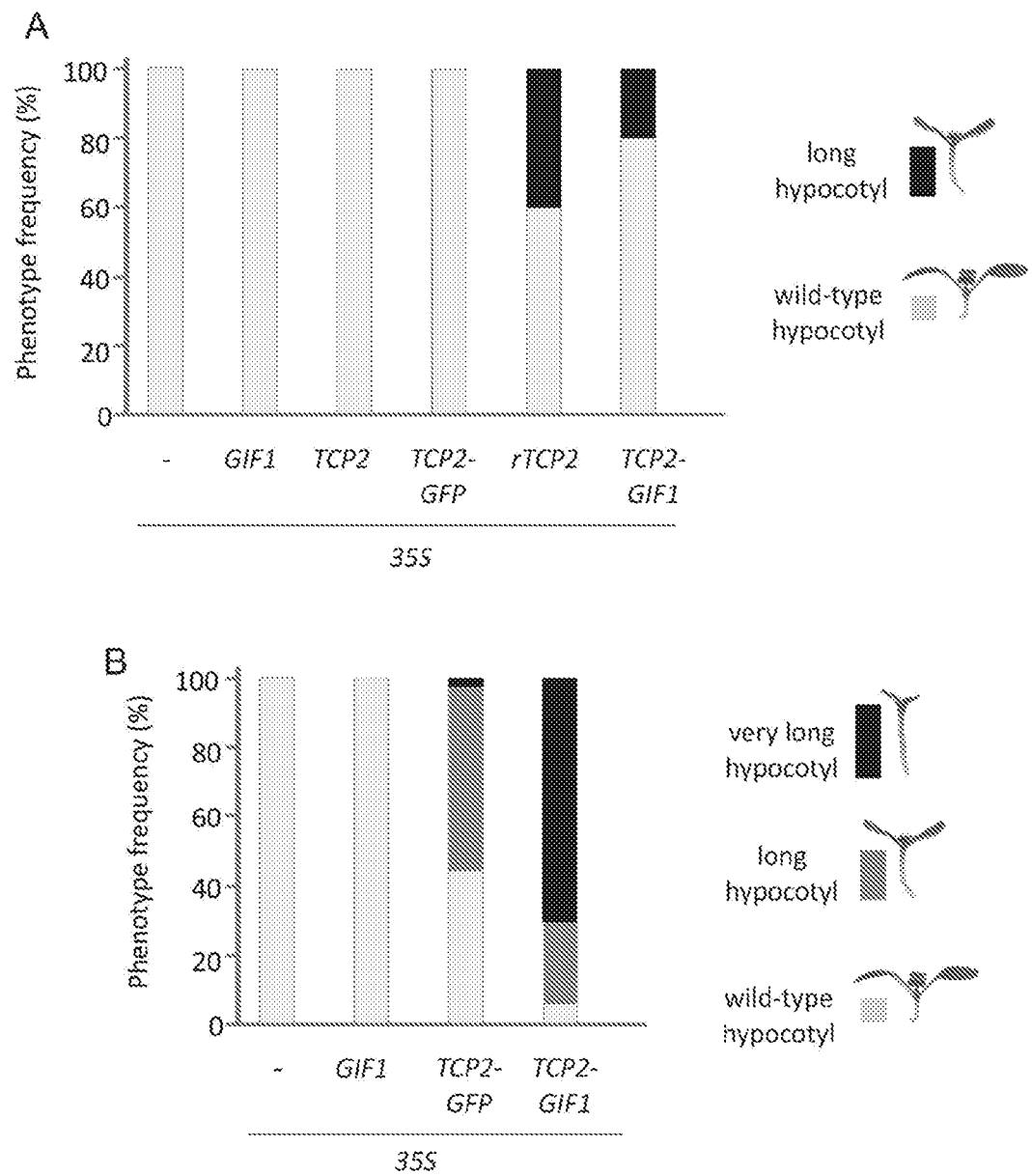
FIG. 1. Chimeric TCP-GIF proteins have an increased activity. A) Phenotype frequency of primary transgenic plants harboring the different vectors as described in Example 1. On the right, pictures of 10 days-old seedlings representing phenotypes observed among the transgenic plants. B) Phenotype frequency for each vector observed in an rdr6 mutant background. On the right, pictures of 10 days-old seedlings representing phenotypes observed among the transgenic plants.

In the context of the present invention, the expressions "chimeric protein" and "fusion protein" mean artificial proteins (i.e., proteins that do not occur in nature) in which at least two different polypeptides which normally are not part of the same polypeptidic chain are fused into a single protein.

The term "moiety" refers to each portion of the chimeric protein originating from a single naturally occurring protein or synthetic homologous thereof, including mutants and variants.

The expressions "GIF" and "GIF protein" designate any of the GRF-interacting factors present in plants, such as GIF1, GIF2, and GIF3 of *Arabidopsis thaliana* (SEQ ID NO.: 1, 39, and 40, respectively) and its homologous proteins in other plant species, such as Glyma19g43580.1 (SEQ ID NO.: 41), Glyma20g36960.1 (SEQ ID NO.: 42), Glyma07g05720.7 (SEQ ID NO.: 43) of soybean, and Os11g40100.3 (SEQ ID NO.:44), Os12g31350.1 (SEQ ID NO.:45) and Os03g52320.1 (SEQ ID NO.:46) of rice, and GRMZM2G180246_T01 (SEQ ID NO.:47), GRMZM2G154169_T01 (SEQ ID NO.:48), and GRMZM2G004988_T01 (SEQ ID NO.:49) of *Zea mays*. In *Arabidopsis thaliana* there is a 61% amino acid identity between GIF2 and GIF3 but only 31% between GIF1 and the other two GIF proteins mainly because of the divergent C-terminal regions, meaning that GIF function is preserved even in peptides with an amino acid identity of about 30%.

The expression "GIF domain" designates any of the two domains of GIF proteins (i.e. a SNH domain or a QG domain, amino acid residue positions 20 to 72 and amino acid residue positions 73 to 210 of SEQ ID NO.: 1, respectively). The expressions "comprise" and "comprising", when applied to a polypeptide, protein, nucleic acid, vector and the like, is used with an inclusive rather than a limiting purpose. For instance, a polypeptide comprising a GIF domain must be interpreted as any polypeptide that contains at least one complete SNH or QG domain, and includes fragments of GIF proteins that are larger than a complete SNH or QG domain, including fragments of GIF proteins containing more than one complete GIF domain, and even complete or substantially complete GIF proteins, such as a complete GIF1 protein.

The expression "GIF motif" designates a polypeptide comprising at least part of a GIF domain and which preserves at least part of the enhancing activity of the GIF protein, including polypeptides comprising a complete GIF domain and polypeptides comprising or consisting of a complete or substantially complete GIF protein.

GRF-interacting factors (GIFs), are proposed to encode transcriptional co-activators (Kim and Kende 2004; Horiguchi, Kim et al. 2005). In *Arabidopsis thaliana* there are three GIF genes, GIF1, GIF2 and GIF3, and loss of function of these genes cause a reduction in the number of cells (Kim and Kende 2004; Lee, Ko et al. 2009). In the inventor's experience, overexpression of GIF1 alone caused no obvious phenotype (see below; (Debernardi, Mecchia et al. 2014); Patent Publication No. WO/2013/102762 A1), although it has been also reported that high levels of GIF1 might cause a slight increase of leaf area (Kim and Kende 2004; Horiguchi, Kim et al. 2005).

GIFs interact with transcription factors belonging to the GRF (GROWTH-REGULATING FACTORS) class which are known to control leaf size (Kim, Choi et al. 2003; Kim and Kende 2004; Horiguchi, Kim et al. 2005; Rodriguez, Mecchia et al. 2010). High activity of GRFs increases the number of cells in plants (Kim, Choi et al. 2003; Rodriguez, Mecchia et al. 2010). The GRF transcription factors contain a WRC domain which binds to DNA (van der Knaap, Kim et al. 2000; Kim, Choi et al. 2003; Kim, Mizoi et al. 2012). In contrast, GIFs lack a DBD, but contain an N-terminal region with homology to the SNH domain, which has been proposed to mediate interactions with chromatin remodeling complexes of the SWI/SNF family (Kim and Kende 2004; Horiguchi, Kim et al. 2005).

Herein, new chimeric proteins are disclosed, in which at least a GIF domain is fused to a plant transcription factor. Unexpectedly, expressing the chimeric proteins of the invention in plants results in an enhanced activity of the DNA-binding domain or transcription factor which is fused to the GIF domain. Thus, expression of the chimeric proteins of the invention is useful for modifying phenotypes of plants, particularly those associated with increased abiotic stress tolerance, increased biotic stress tolerance and increased yield with respect to a control plant (for example, a wild-type plant, a non-transformed plant, or a plant transformed with an "empty" nucleic acid construct lacking a polynucleotide of interest comprised within a nucleic acid construct introduced into an experimental plant).

A vast array of problems could arise when two or more peptides with specific biological functions are fused into a single chimeric polypeptide. Many of these problems would usually result in the loss of biological activity of the moieties fused into the chimera. For instance, the kinetics of folding of each moiety could be very different, and thus the folding of the fusion protein could be trapped in an intermediate state which is not compatible with the original biological function of the peptides forming the chimera. Importantly, even if correct folding is achieved by the individual moieties, association behavior of the members of the chimera could lead to a folding of the protein as a whole in which access to the binding site is blocked, preventing one or more of the moieties to accomplish its function.

Additional problems arise when peptides that work by forming a functional complex among them are fused into a chimera. In this case, even if folding is adequate and binding properties are not affected, it would be expected that the structural constrains imposed to the moieties by the covalent link on the chimera would prevent the formation of the functional complex between the two moieties of a same molecule of the chimera. In turn, this situation will favor cross-linking and aggregation of molecules of the chimeric protein, eventually resulting in loss of solubility and precipitation. Besides being stripped of its intended function, precipitation of the fusion protein could create additional disruption of biologic processes on its own.

Against all expectations, when a GIF domain or fragment thereof and a GRF transcription factor are fused into a single, chimeric protein, both moieties keep their functional properties intact and the activity of the transcription factor is enhanced. While expression of GRF3-GFP did not generate an effect on biomass, even when it could interact with the endogenous GIFs proteins, the chimera GRF3-GIF1 significantly increased leaf area. The interaction between GIFs and GRFs might be subjected to regulation in vivo and formation of the GRF/GIF complex will depend on the concentration of each protein. These issues seem to be avoided in the chimera, which surprisingly keeps the biologic function of the complex formed between GRF and GIF when these are expressed as separate proteins, free to interact without the constrains posed by their incorporation into a fusion protein. Plants have a variable number of GRF and GIF genes (e.g. there are 9 GRFs and 3 GIF genes in *Arabidopsis thaliana* potentially forming 27 different complexes). Although most or all GRFs, GIFs or their complexes are to some extent potential targets to increase plant productivity, not all of them would have the same activity in vivo. The chimera can thus be used to lock the one complex of interest, such as GRF3-GIF1, and specifically increase that single complex.

Even more surprising and with further implications, the transcription factor activity enhancement occurs also when the GIF domain or fragment thereof is fused to a transcription factor that is not its natural partner. Without attaching to any particular explanation, the inventors believe that this is a result of the GIF domain acting as a transcriptional co-regulator of the transcription factors to which it is fused. According to this interpretation, while the transcription factor moiety would attach to the specific DNA sequence determined by its DBD, the GIF domain would enhance the transcription factor activity through the recruitment of chromatin remodeling complexes.

Since polypeptides comprising a GIF domain or a fragment thereof increase the activity of transcription factors belonging to different families when fused as an additional domain in a chimeric protein, including the activity of transcription factors that normally do not interact with GIF proteins, the construction of chimeric proteins with polypeptides comprising GIF domains or fragments thereof can be used to increase or modify the activity of other transcription factors in general. For example, the construction of chimeric proteins with polypeptides comprising GIF domains or fragments thereof can be used to increase the activity and performance of transcription factor with already known functions in plant productivity, like HAHB4, NAC1, ANT, ATAF2, HB33. Moreover, as transcription factors and GIF proteins are conserved in plants, the system can be used to modify transcription factor activity in any plant species, including crops and other species of economic importance, such as soybean, maize, sugar cane, rice, and cotton. The polypeptide comprising a GIF domain or fragment thereof from these crops or from other plant species can be fused with transcription factors isolated from the same species, or other plant species, and can be used for enhanced induction of any target genes in those crop varieties. This approach affords enhanced activation of TF targets while avoiding contamination of the crop genome with expressed genetic materials derived from outside of the plant kingdom.

In particular, the inventors expect that the GIF motif might be used to optimize transcription factors when used in combination with inducible or tissue-specific promoters, such as RD29A which is responsive to drought or cold or ANT which is active in proliferative tissue. For example, rGRF3 increases plant biomass when constitutively overexpressed, but it also causes a delay in plant senescence and flowering time. These latter effects can be avoided if rGRF3 is expressed from the ANT promoter (Debernardi, Mecchia et al. 2014). Therefore, expression of chimeras of GRF3 or any transcription factor with a GIF motif combined with a tissue specific or inducible promoter provides a means of obtaining an enhanced crop without substantial negative phenotypes.

The transcription activation domain and the transcription regulatory protein within the chimeric polypeptide do not occur in nature in the same polypeptide, or do not occur in nature with the same order or orientation or with the same spacing within the same peptide, that is, they are mutually heterologous. The transcription activation domain and the transcription regulatory protein in the chimeric polypeptide also do not occur in the same copy number or configuration in nature.

It is well known to those skilled in the art that certain variation in the amino acid sequence of naturally occurring proteins is allowed without a complete loss of biologic activity. Generally speaking, it can be conservatively expected that proteins with a sequence having at least 85% sequence identity to the amino acid sequence of naturally occurring proteins would retain their biological activity at least to some extent. In the case of GIF genes, these function redundantly as positive regulators of cell proliferation, thereby determining plant organ size. Of course, higher sequence identity values, such as at least 90% or at least 95% will have more chances of retaining most or all the biologic activity of the naturally occurring sequence.

The percent identity can be determined by aligning the secuences whose percent identity is being calculated and comparing sequence information. A suitable alignment method is described by Needleman and Wunsch (J. Mol. Biol. 48:443, 1970) and revised by Smith and Waterman (Adv. Appl. Math 2:482, 1981). This method is implemented in the software program GAP software package, version 6.0 from the University of Wisconsin Genetics Computer Group (UWGCG) (see Devereux et al. 1984. Nucl. Acids Res. 12:387). Preferred default alignment parameters for this software are: (1) a unary comparison matrix (1 for identities and 0 for non-identities) for nucleotides, and the weighted comparison matrix of Gribskov and Burgess (Nucl. Acids Res. 14:6745, 1986), as described in Schwartz and Dayhoff (eds.) (*Atlas of Protein Sequence and Structure, National Biomedical Research Foundation*, pp. 353-358, 1979); (2) a gap penalty of 3.0 and an additional 0.10 penalty for each symbol in each gap; and (3) no penalty for end gaps.

The invention will be now described in relation to the following examples, which are given with the sole purpose of illustrating particular embodiments of the invention, but are not intended to limit in any way the scope of the invention. It will become obvious to the skilled in the art that other particular embodiments of the invention are possible, such as those in which alternative transcription factors, GIFs, or plant species are used, all of which are within the scope of the present invention.

Example 1

"Chimeric Transcription Factors containing a GIF sequences have enhanced activity"
i) TCP Transcription Factors The TCP family of transcription factors is specific of plants, was defined from the names of first genes discovered that encode proteins of this family: TEOSINTE BRANCHED1 from *Zea mays* (Doebley, Stec et al. 1997); CYCLOIDEA from *Antirrhinum majus* (Luo, Carpenter et al. 1996); and PCF 1 y 2 from *Oryza sativa* (Kosugi and Ohashi 1997). The transcription factors of this family share a 59 amino acid domain similar to the bHLH domain (basic Helix-Loop-Helix) that is involved in DNA binding and in protein-protein interactions. The TCP family comprises 24 members in *Arabidopsis* and TCP2 (At4g18390) was chosen for further experiments. Overexpression of TCP2 from the 35S viral promoter causes no obvious effect in seedling development (FIG. 1A) (Palatnik, Allen et al. 2003), and the inventors did not see any effect for the chimeric protein TCP2-GFP (FIG. 1A). It is known that TCP2 is negatively regulated by miRNA miR319, and silent mutations in the miR319-binding site (named rTCP2 because TCP2 becomes resistant to the miRNA repression) avoid this regulation increasing the activity of the transcription factor (Palatnik, Allen et al. 2003). Plants expressing 35S:rTCP2 have longer hypocotyls.

Figure 13:
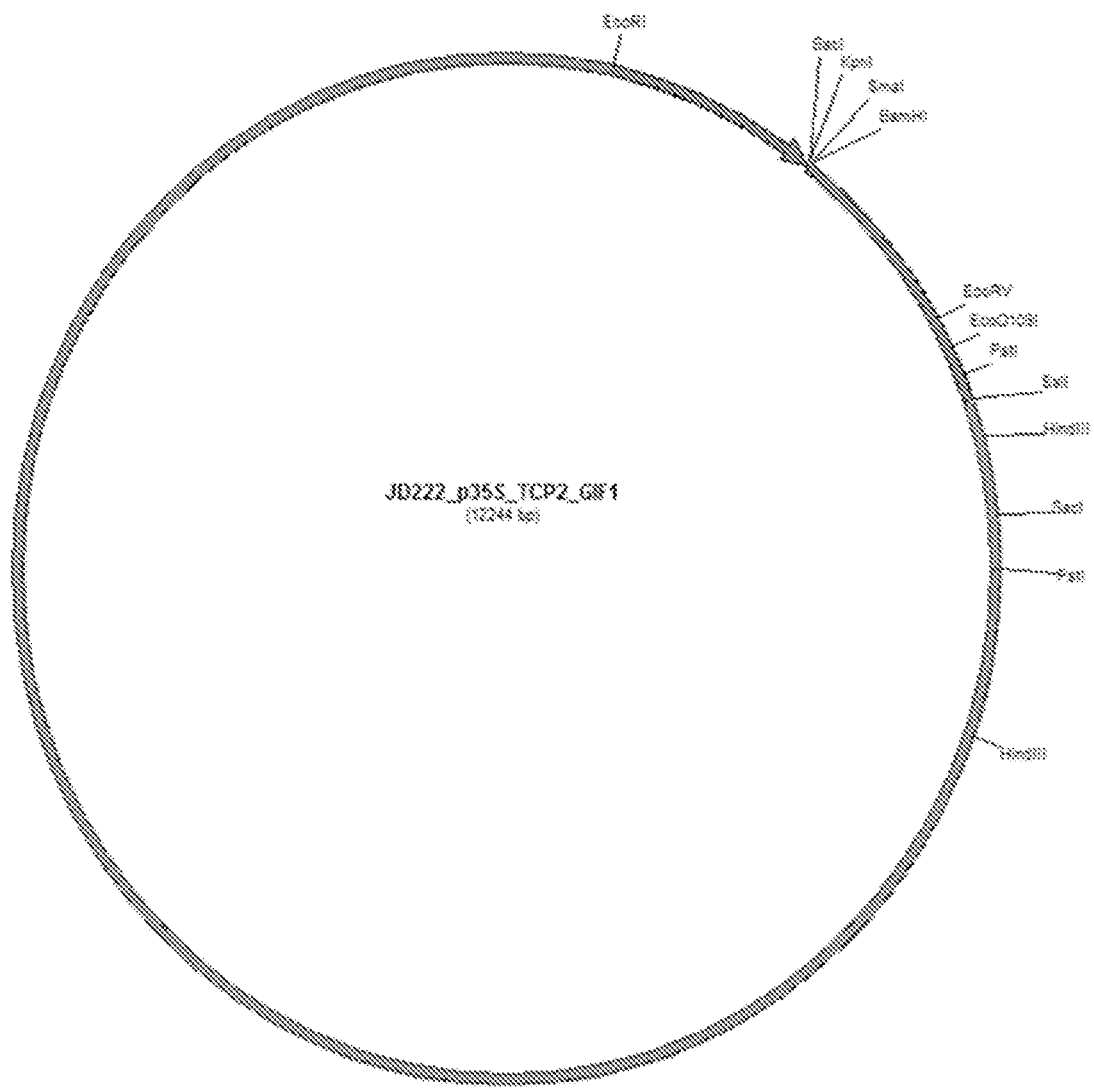
FIG. 13. Map of the binary vector pJD222 (SEQ ID NO.:35) for expression of chimeric protein TCP2-GIF1.
Figure 14:
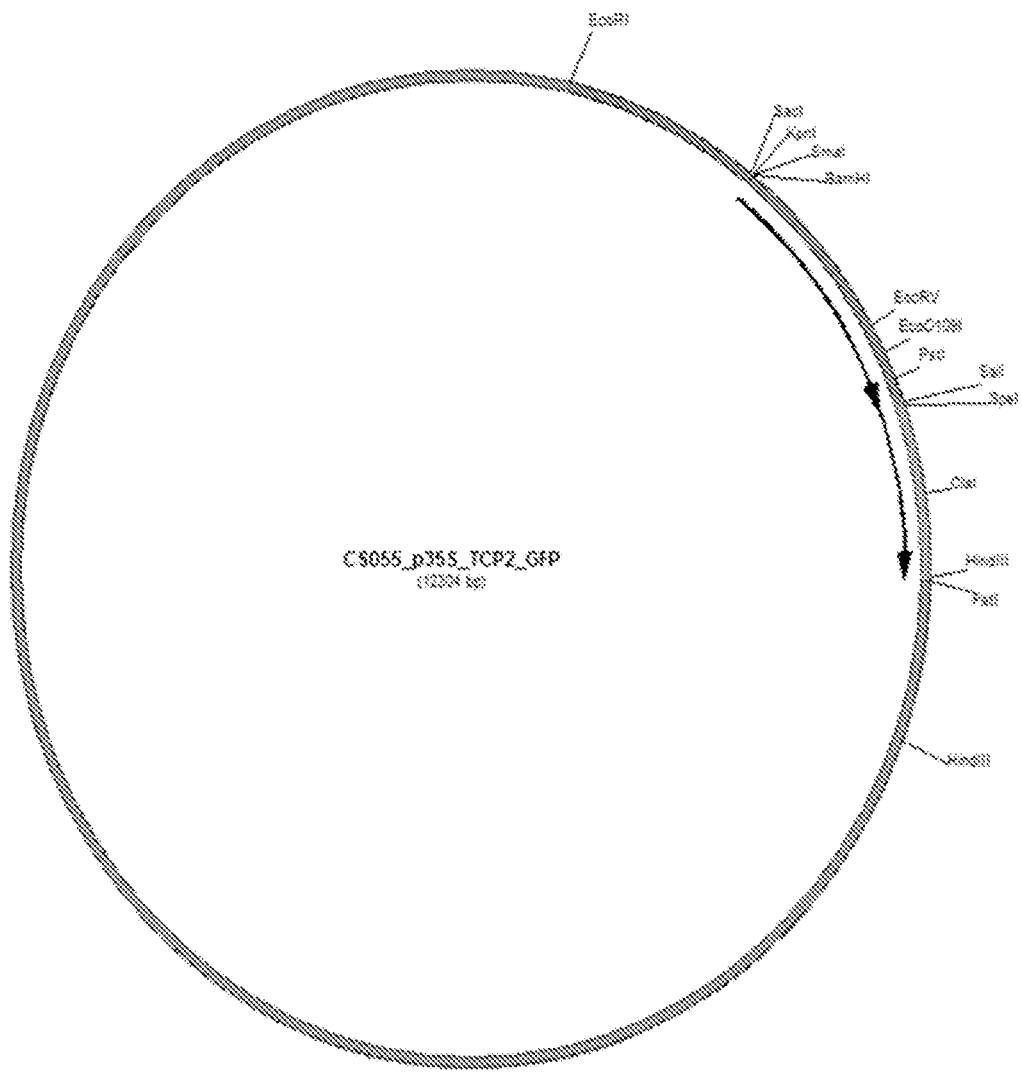
FIG. 14. Map of the binary vector pCS55 (SEQ ID NO.:38) for expression of chimeric protein TCP2-GPF.

To analyze the effect of GIF1 on TCP2 activity a chimeric protein TCP2-GIF1 was generated with the wild-type allele of TCP2 (FIG. 1A). The full sequence of the binary vector used can be found in SEQ ID NO.: 35 and 38, while a map of the binary vector used is illustrated in FIGS. 13 and 14. *Arabidopsis* wild-type plants were then transformed with these vectors and phenotypes of the primary transgenic plants analyzed. It was observed that the TCP2-GIF1 chimeric protein displayed phenotypes typical of plants with high TCP2 activity, similar to those observed in transgenic plants 35S:rTCP2 (FIG. 1A). In contrast the chimeric vector TCP2-GFP and 35S:GIF1 did not have any effect. A TCP2 gain of function can be therefore observed after de-regulation of its post-transcriptional control, or alternatively, by the addition of an extra domain with GIF1 sequences that enhances the activity of the wild-type protein.

It is known that a mutation in the RDR6 gene of *Arabidopsis* allows the higher expression of transgenes. Therefore, rdr6 mutant plants were transformed with vectors expressing the chimeric proteins TCP2-GFP and TCP2-GIF1. In this mutant background, it was observed that TCP2-GFP can cause longer hypocotyls in some of the primary transgenic plants (FIG. 1B). However, the frequency of plants with longer hypocotyls was significantly higher in plants expressing the TCP2-GIF1 chimeric proteins (FIG. 1B). For example, we observed that more than 60% of the 35S:TCP2-GIF1 primary transgenic plants had a very long hypocotyl, while less than 6% had the wild type phenotype (FIG. 1B). Altogether these results show that the addition of a domain containing sequences of GIF1 to TCP2 increases the transcription factor activity.

ii) Homeodomain Transcription Factors

Figure 2:
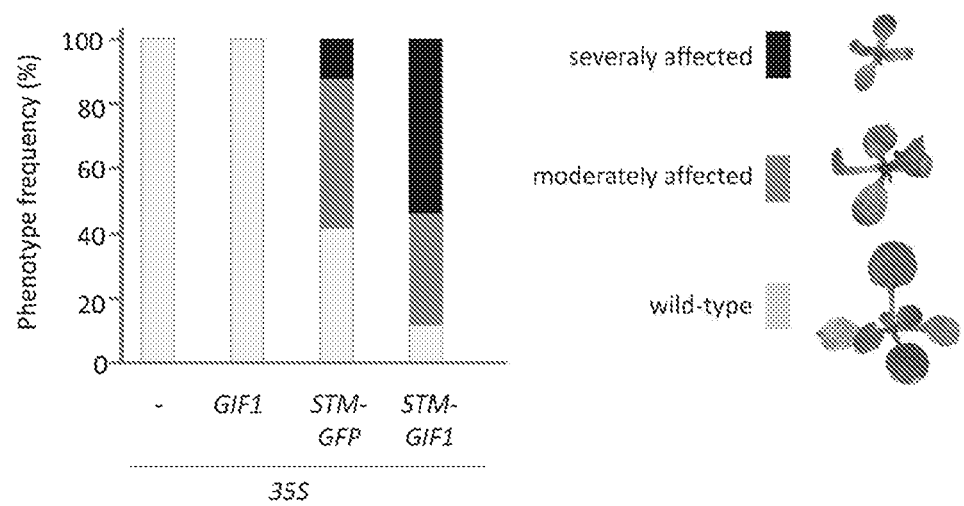
FIG. 2. GIF1 increases the activity of homeodomain transcription factors. Phenotype frequency of primary transgenic plants harboring the different vectors as described in Example 1. On the right, pictures of 15 days-old plants representing phenotypes observed among the transgenic plants.
Figure 11:
FIG. 11. Map of the binary vector pJD220 (SEQ ID NO.:29) for expression of chimeric protein STM-GPF.
Figure 12:
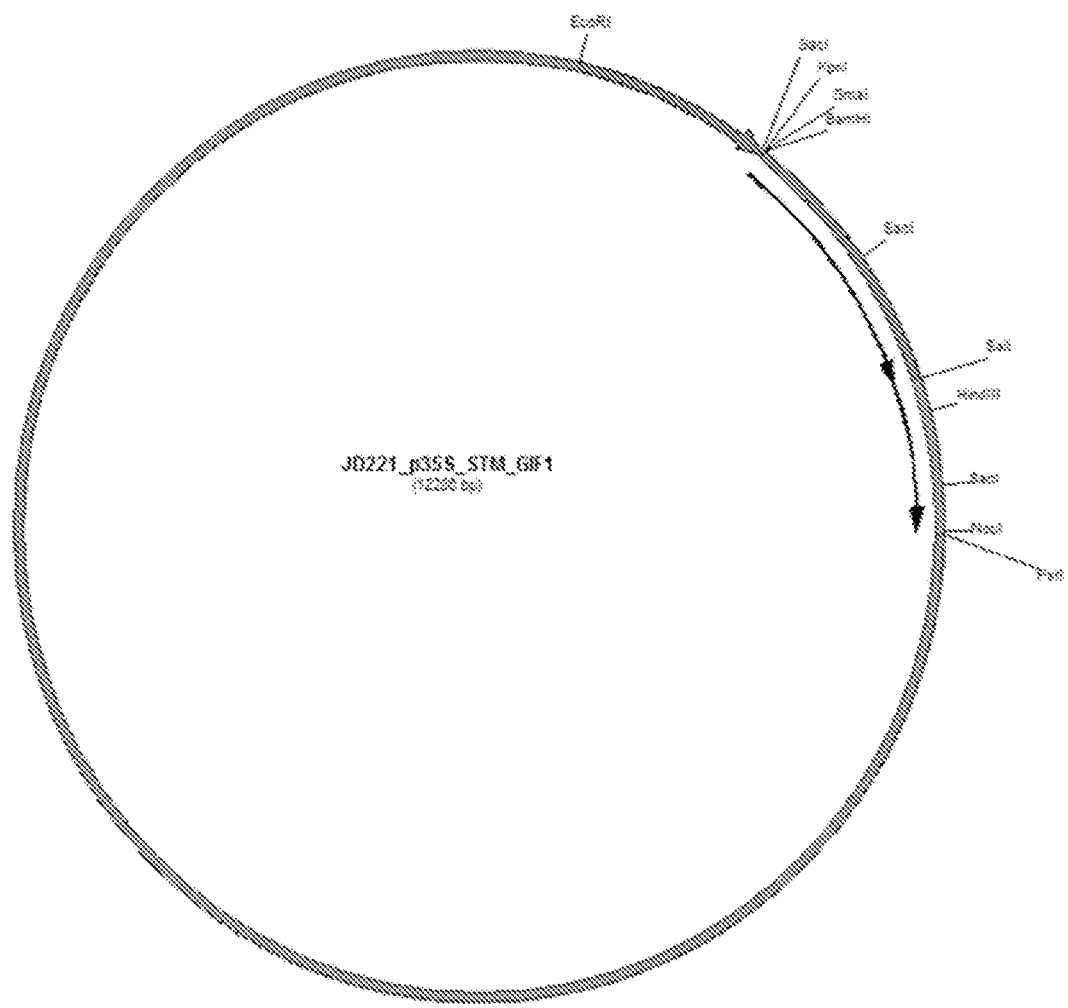
FIG. 12. Map of the binary vector pJD221 (SEQ ID NO.:32) for expression of chimeric protein STM-GIF1.

SHOOT MERISTEMLESS (STM) belongs to class I of KNOX (TALE) homeodomain transcription factors, which are widely distributed in plants and animals. They regulate diverse developmental processes throughout the *Arabidopsis* life cycle (Tsiantis and Hay 2003; Hake, Smith et al. 2004). The effect of GIF1 as an additional domain of STM was analyzed through the generation of a chimeric protein STM-GIF1 and the control STM-GFP (FIG. 2). The full sequence of the binary vector used can be found in SEQ ID NO.: 29 and 32, while a map of the binary vector used is illustrated in FIGS. 11 and 12. *Arabidopsis* Col-0 wild-type plants were then transformed with these constructions and the phenotypes of primary transgenic plants were analyzed. Among the primary transgenic plants expressing STM-GFP or STM-GIF1, plants with distorted organs and growth arrest of leaves and cotyledons were observed (FIG. 2, right panel). However the frequency of these phenotypes was significantly higher in plants harboring 35S:STM-GIF1 transgene than in plants expressing 35S:STM-GFP. We did not observe any significant difference in pools of primary transgenic plants expressing 35S:GIF1 with respect to wild-type plants. These results show that the STM-GIF1 chimera is more active than the STM-GFP chimera.

Materials and Methods:

Plant Material

The *Arabidopsis thaliana* Col-0 accession was used as wild-type control. Transgenic plants are in the Col-0 wild-type or rdr6 mutant background. The rdr6-11 (CS24285) was obtained from the *Arabidopsis* stock center. Plants were grown in long photoperiods (16 hr light/8 hr dark) at 23° C. The plants were grown in MS medium (Murashige and Skoog, 1962) supplemented with 50 µg/ml kanamycin to select the primary transformants.

Bacterial Strains:

All constructs were cloned in the binary vector pCHF3 (Jarvis, Chen et al, 1998). Plant transformations were carried out using the *Agrobacterium tumefaciens* strain ASE harboring the appropriate binary pCHF3 plasmids containing the neomycin phosphotransferase (nptII) selectable marker gene driven by the 35S promoter and the gene(s) of interest, namely GIF1, STM-GFP, STM-GIF1, TCP2-GFP, TCP2-GIF1 and TCP2, driven by the 35S promoter.

The cloning procedure used to make the transformation vectors is described below.

In a first step binary vectors containing the GIF1 or the GFP coding sequences were generated with a SalI restriction site in their 5"end to introduce the corresponding transcription factors to generate the STM-GFP, STM-GIF1, TCP2-GPF and TCP2-GIF1 fusions.

The GIF1 and GFP coding sequences were amplified by PCR using high fidelity Pfx50™ polymerase (Invitrogen). The PCR product was gel purified using a kit (Promega) and ligated to SmaI digested pBluescript plasmid. To 50 µl of DH5α competent *E. coli* cells 2 µl of the ligation reaction was added and transformation by electroporation. The cells were grown in 900 µl of LB medium for 1 hour at 37° C. and shaken at 200 rpm. The cells were centrifuged at 4000 g for 3 minutes at R.T., and the cell pellet was spread onto plates of solid LB medium (Sambrook and Russell, 2001) containing appropriate selection and incubated overnight at 37° C.

*E. coli* colonies were screened by direct colony PCR to ensure that they contained pBluescript with the insert. Twelve PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs known as pBluescript-GIF1 or pBluescript-GFP was confirmed by enzyme digestion and sequencing of the insertion sites.

Digestion of ~1.5 µg pBluescript-GIF1 or pBluescript-GFP in a 50 µl total volume reaction with SalI and PstI (Promega) in the appropriate buffer was performed at 37° C. for 4 hours in a water bath.

Approximately 1 µg of pCHF3 was digested with restriction enzymes SalI and PstI (Promega) in the appropriate buffer for 4 hours at 37° C. The linearised vector was dephosphorylated by incubation at 37° C. for a further hour with shrimp alkaline phosphatase (SAP, Promega). The linearised vector was purified with a PCR product purification kit (Promega).

An overnight ligation reaction was performed at 16° C. and contained the GIF1 or the GFP fragment and the linear pCHF3 at a 3:1 ratio respectively. One unit of T4 ligase (Fermentas) was used in the 10 µl ligation. To 50 µl of DH5α competent *E. coli* cells 2 µl of the ligation reaction was added and transformation by electroporation. The cells were grown in 900 µl of LB medium for 1 hour at 37° C. and shaken at 200 rpm. The cells were centrifuged at 4000 g for 3 minutes, and the cell pellet was spread onto plates of solid LB medium (Sambrook and Russell, 2001) containing appropriate selection and incubated overnight at 37° C.

*E. coli* colonies were screened by direct colony PCR to ensure that they contained pCHF3-GIF1 or pCHF3-GFP. Twelve PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs pCHF3-GIF1 or pCHF3-GFP was confirmed by enzyme digestion and sequencing of the insertion sites.

Phase two of the cloning process involves the steps to create pCHF3-STM-GIF1, pCHF3-STM-GFP, pCHF3-TCP2-GIF1 and pCHF3-TCP2-GFP vectors. The coding regions of STM and TCP2 were amplified by PCR using high fidelity Pfx50™ polymerase (Invitrogen). The PCR product was gel purified using a kit (Promega) and ligated to SmaI digested pBluescript plasmid. To 50 µl of DH5α competent *E. coli* cells 2 µl of the ligation reaction was added and transformation was carried out by electroporation. The cells were grown in 900 µl of LB medium for 1 hour at 37° C. and shaken at 200 rpm. The cells were centrifuged at 4000 g for 3 minutes, and the cell pellet was spread onto plates of solid LB medium (Sambrook and Russell, 2001) containing appropriate selection and incubated overnight at 37° C.

*E. coli* colonies were screened by direct colony PCR to ensure that they contained pBluescript with the insert. Twelve PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs known as pBluescript-GIF1 or pBluescript-GFP was confirmed by enzyme digestion and sequencing of the insertion sites.

Digestion of ~1.5 µg pBluescript-STM or pBluescript-TCP2 in a 50 µl total volume reaction with BamHI and SalI (Promega) in the appropriate buffer was performed at 37° C. for 4 hours in a water bath.

Approximately 1 µg of pCHF3-GIF1 or pCHF3-GPF were digested with restriction enzyme SalI and BamHI (Promega) in the appropriate buffer for 4 hour at 37° C. The linearised vector was dephosphorylated by incubation at 37° C. for a further hour with shrimp alkaline phosphatase (SAP, Promega). The linearised vectors were purified with a PCR product purification kit (Promega).

An overnight ligation reaction was performed at 16° C. and contained the STM or the TCP2 fragment and the linear pCHF3-GIF1 or pCHF3-GFP vectors at a 3:1 ratio respectively. One unit of T4 ligase (Fermentas) was used in the 10 µl ligation. To 50 µl of DH5α competent *E. coli* cells 2 µl of the ligation reaction was added and transformation by electroporation. The cells were grown in 900 µl of LB medium for 1 hour at 37° C. and shaken at 200 rpm. The cells were centrifuged at 4000 g for 3 minutes, and the cell pellet was spread onto plates of solid LB medium (Sambrook and Russell, 2001) containing appropriate selection and incubated overnight at 37° C.

*E. coli* colonies were screened by direct colony PCR to ensure that they contained pCHF3-STM-GIF1, pCHF3-STM-GFP, pCHF3-TCP2-GIF1 or pCHF3-TCP2-GFP. Two PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs pCHF3-STM-GIF1, pCHF3-

STM-GFP, pCHF3-TCP2-GIF1 and pCHF3-TCP2-GFP was confirmed by enzyme digestion and sequencing of the insertion sites.

The plasmids pCHF3-STM-GIF1, pCHF3-STM-GFP, pCHF3-TCP2-GIF1, pCHF3-TCP2-GFP, pCHF3-GIF1 were transformed into *Agrobacterium tumefaciens* strain ASE by electroporation. Briefly, 100 ng of plasmid DNA was added to 40 µl of electro-competent *A. tumefaciens* cells in a pre-chilled electroporation cuvette with 2 mm electrode separation. The cells were electroporated in a GenePulser (Biorad) with the following settings 2.50 kV, 25 µFD and 400 Ohms. Immediately 900 µl of liquid LB medium was added to recover the cells, these were grown at 28° C., shaken at 180 rpm for 2 hours. The *A. tumefaciens* cultures were spread onto solid LB medium (Sambrook and Russell, 2001) containing appropriate selection and incubated at 28° C. for 48 hours. Single colonies were selected and used to inoculate 10 ml of liquid LB media containing the appropriate antibiotics and incubated at 28° C., shaken at 200 rpm for 48 hours. Glycerol stocks and standard inoculums were prepared and stored at −80° C. The plasmids were checked once again, by enzyme digestion, prior to embarking on the *Arabidopsis* transformation experiments.

Plant Transformation:

*Arabidopsis* transgenic plants were obtained by floral-dip. The *A. tumefaciens* transformed with the pCHF3-STM-GIF1, pCHF3-STM-GFP, pCHF3-TCP2-GIF1, pCHF3-TCP2-GFP or pCHF3-GIF1 vectors were streaked onto solid LB medium (Sambrook and Russell, 2001) containing appropriate selection and incubated at 28° C. for 48 hours. A single colony was transferred to 10 ml of liquid LB media containing the appropriate selection and transferred to a 28° C. shaker for 48 hours. A 1 ml aliquot of the resulting bacterial suspension was transferred to 100 ml of LB liquid medium with selection and grown over night in a 28° C. shaker. Overnight cultures were spun down at 3,000 g for 5 minutes at RT before being resuspended in 100 ml transformation medium (5% sucrose, 0.02% Silwett). Inflorescences from 35 days old plants were dipped into the suspension of *Agrobacterium* and plants were maintained overnight in darkness. Then plants were maintained in growth rooms at 23° C. with 16 hour day length. Plants were threshed when dry, and seed stored.

Transgenic Selection and Phenotypic Analysis:

Seeds were surface sterilized in 70% ethanol plus 0.05% Tween-20 for 15 minutes and rinsed once in 96% ethanol. Seeds were sown in MS medium (Murashige and Skoog, 1962) supplemented with 50 µg/ml kanamycin to select the primary transformants. Plants were grown in long photoperiods (16 hr light/8 hr dark) at 23° C. The phenotype analysis of the primary transgenic plants was performed using a dissecting microscope. For each vector at least 100 primary independent transgenic plants were examined.

Conclusion:

The GIF domain can enhance the activity of any transcription regulatory polypeptide unrelated to the sequence of natural interactors (GRF) of the GIF domain when fused in a chimeric protein.

Example 2

"GIF sequences can increase the performance of a natural partner when used as a chimera"

Figure 3:
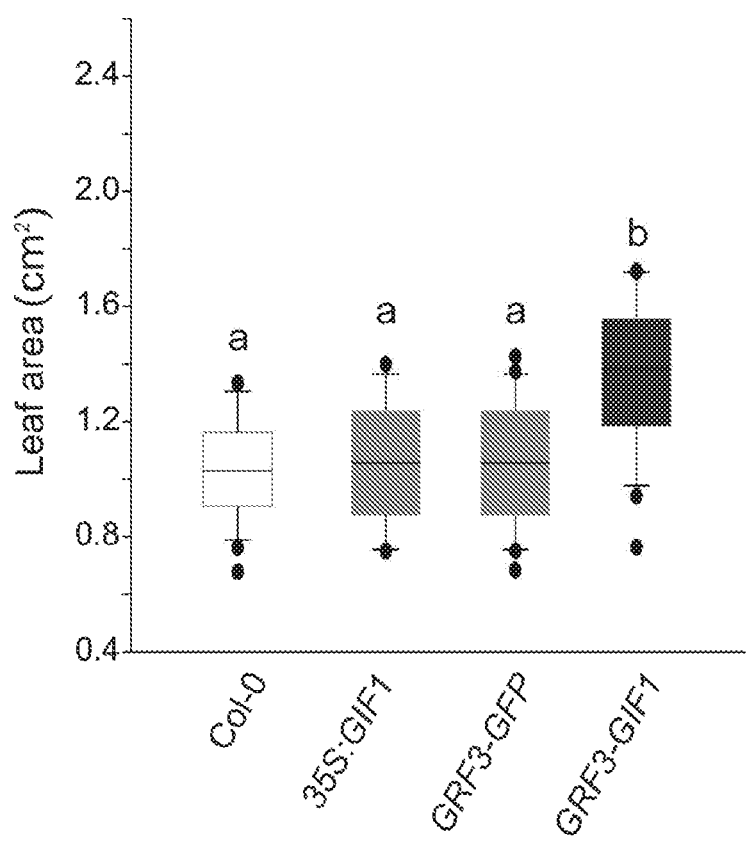
FIG. 3. Increase of GRF activity and leaf area using GRF-GIF chimeric proteins as described in Example 2. Average leaf size corresponding to pools of primary transgenic plants harboring different transgenes. Different letters mean statistically significant differences (p<0.05). At least 50 primary transgenic plants were analyzed in each case.

Chimeric proteins GRF3-GFP (as controls) and GRF3-GIF1 were expressed (FIG. 3). No significant difference was observed in pools of primary transgenic plants expressing 35S:GIF1 or GRF3-GFP and wild-type plants transformed with an empty vector. However, plants expressing the chimera GRF-GIF1 had leaves significantly larger than wild type (FIG. 3). These results show that the chimera GRF-GIF is more efficient in promoting leaf growth than either of the individual components.

Materials and Methods:

Plant Material:

The *Arabidopsis thaliana* Col-0 accession was used as wild-type control. Plants were grown in long photoperiods (16 hr light/8 hr dark) at 23° C. The plants were grown in MS medium (Murashige and Skoog, 1962) supplemented with 50 µg/ml kanamycin and selected primary transformants were transferred to soil.

Bacterial Strains:

All constructs were cloned in the binary vector pCHF3 (Jarvis, Chen et al. 1998). Plant transformations were carried out using the *Agrobacterium tumefaciens* strain ASE harboring the appropriate binary pCHF3 plasmids containing the neomycin phosphotransferase (nptII) selectable marker gene driven by the 35S promoter and the gene(s) of interest, namely GRF3-GFP and GRF3-GIF1 driven by GRF3 native promoter and GIF1 driven by the 35S promoter.

The cloning procedure used to make the transformation vectors is described below.

The binary vectors containing the GIF1 or the GFP coding sequences with a SalI restriction site in their 5"end previously described were used to introduce GRF3 and its promoter to generate the pGRF3:GRF3-GPF and pGRF3:GRF3-GIF1 fusions.

The coding region and the introns of GRF3 and the promoter (1.5 kb upstream the translation initiation site) of GRF3 were amplified by PCR using high fidelity Pfx50™ polymerase (Invitrogen). The PCR products were gel purified using a kit (Promega) and ligated to pGEM-T vector (Promega). To 50 µl of DH5α competent *E. coli* cells 2 µl of the ligation reaction was added and transformation carried out by electroporation. The cells were grown in 900 µl of LB medium for 1 hour at 37° C. and shaken at 200 rpm. The cells were centrifuged at 4000 g for 3 minutes, and the cell pellet was spread onto plates of solid LB medium (Sambrook and Russell, 2001) containing appropriate selection and incubated overnight at 37° C.

*E. coli* colonies were screened by direct colony PCR to ensure that they contained pBluescript with the insert. Twelve PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs known as pGEM-T-GRF3 or pGEM-T-pGRF3 was confirmed by enzyme digestion and sequencing of the insertion sites.

Digestion of ~1.5 µg pGEM-T-GRF3 in a 50 µl total volume reaction with KpnI and SalI (Promega) in the appropriate buffer was performed at 37° C. for 4 hour in a water bath.

Digestion of ~1.5 µg pGEM-T-pGRF3 in a 50 µl total volume reaction with MunI (Fermentas) and KpnI (Promega) in the appropriate buffer was performed at 37° C. for 4 hours in a water bath.

Approximately 1 µg of pCHF3-GIF1 or pCHF3-GPF were digested with restriction enzymes EcoRI and SalI (Promega) in the appropriate buffer for 4 hours at 37° C. The linearised vector was dephosphorylated by incubation at 37° C. for a further hour with shrimp alkaline phosphatase (SAP, Promega). The linearised vectors were purified with a PCR product purification kit (Promega).

An overnight ligation reaction was performed at 16° C. and contained the GRF3 and the pGRF3 fragments and the linear pCHF3-GIF1 or pCHF3-GFP vectors at a 3:3:1 ratio respectively. One unit of T4 ligase (Fermentas) was used in the 10 µl ligation. To 50 µl of DH5α competent E. coli cells 2 µl of the ligation reaction was added and transformation was carried out by electroporation. The cells were grown in 900 µl of LB medium for 1 hour at 37° C. and shaken at 200 rpm. The cells were centrifuged at 4000 g for 3 minutes, and the cell pellet was spread onto plates of solid LB medium (Sambrook and Russell, 2001) containing appropriate selection and incubated overnight at 37° C.

E. coli colonies were screened by direct colony PCR to ensure that they contained pCHF3-pGRF3:GRF3-GIF1 or pCHF3-pGRF3:GRF3-GFP. Two PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs pCHF3-pGRF3:GRF3-GIF1 and pCHF3-pGRF3:GRF3-GFP was confirmed by enzyme digestion and sequencing of the insertion sites.

The plasmids pCHF3-pGRF3:GRF3-GIF1 or pCHF3-pGRF3:GRF3-GFP were transformed into *Agrobacterium tumefaciens* strain ASE by electroporation. Briefly, 100 ng of plasmid DNA was added to 40 µl of electro-competent *A. tumefaciens* cells in a pre-chilled electroporation cuvette with 2 mm electrode separation. The cells were electroporated in a GenePulser (Biorad) with the following settings 2.50 kV, 25 µFD and 400 Ohms. Immediately 900 µl of liquid LB medium was added to recover the cells, these were grown at 28° C., shaken at 180 rpm for 2 hours. The *A. tumefaciens* cultures were spread onto solid LB medium (Sambrook and Russell, 2001) containing appropriate selection and incubated at 28° C. for 48 hours. Single colonies were selected and used to inoculate 10 ml of liquid LB media containing the appropriate antibiotics and incubated at 28° C., shaken at 200 rpm for 48 hours. Glycerol stocks and standard inoculums were prepared and stored at −80° C. The plasmids were checked once again, by enzyme digestion, prior to embarking on the *Arabidopsis* transformation experiments.

Plant Transformation:

*Arabidopsis* transgenic plants were obtained by floral-dip. The *A. tumefaciens* transformed with the pCHF3-pGRF3:GRF3-GIF1, pCHF3-pGRF3:GRF3-GFP or pCHF3-GIF1 vectors were streaked onto solid LB medium (Sambrook and Russell, 2001) containing appropriate selection and incubated at 28° C. for 48 hours. A single colony was transferred to 10 ml of liquid LB media containing the appropriate selection and transferred to a 28° C. shaker for 48 hours. A 1 ml aliquot of the resulting bacterial suspension was transferred to 100 ml of LB liquid medium with selection and grown over night in a 28° C. shaker. Overnight cultures were spun down at 3,000 g for 5 minutes at RT. before being re suspended in 100 ml transformation medium (5% sucrose, 0.02% Silwett). Inflorescences from 35 days old plants were dipped into the suspension of *Agrobacterium* and plants were maintained overnight in darkness. Then plants were maintained in growth rooms at 23° C. with 16 hour day length. Plants were threshed when dry, and seed stored.

Transgenic Selection and Phenotypic Analysis:

Seeds were surface sterilized in 70% ethanol plus 0.05% Tween-20 for 15 minutes and rinsed once in 96% ethanol. Seeds were sown in MS medium (Murashige and Skoog, 1962) supplemented with 50 µg/ml kanamycin to select the primary transformants. Plants were grown in long photoperiods (16 hr light/8 hr dark) at 23° C. for 6 days, after that selected primary transgenics were transferred to soil and maintained under the same conditions of light and temperature. Leaf area was measured by first taking a photograph of detached fully expanded third leaves from 35 days old plants, and then measuring the foliar area with the NIH software ImageJ. For this analysis leaves from at least 50 independent primary transgenic plants were collected for each vector.

Conclusion:

The expression of a single transgene produces a chimeric protein containing both GRF GIF activities.

The chimeric protein GRF3-GIF1 is more active than the GRF3-GFP chimera and induces an increase in plant biomass production.

The chimeric protein GRF3-GIF1 can greatly enhance the performance of GRF3 in plant productivity.

Example 3

"GIF Sequences can Increase the Performance of rGRF3"

A previous report has shown that GRF3 transgenes insensitive to the regulation by microRNA miR396 (rGRF3) caused an increased biomass accumulation and tolerance to drought (Debernardi, Mecchia et al. 2014); Patent Publication No. WO/2013/102762 A1). For that reason, it was evaluated whether a chimeric rGRF-GIF transgene would have an enhanced activity in comparison to rGRF per se.

To test this possibility vectors expressing a miR396-resistant version of GRF3 fused to the N-terminal of GIF1 were generated. Control vectors where an rGRF3 version was fused to the green fluorescent protein (GFP) were generated. The full sequence of the binary vectors used can be found in SEQ ID NO.:14, 17, 20, and 23, while a map of the binary vectors used is illustrated in FIGS. 6 to 9.

Figure 4:
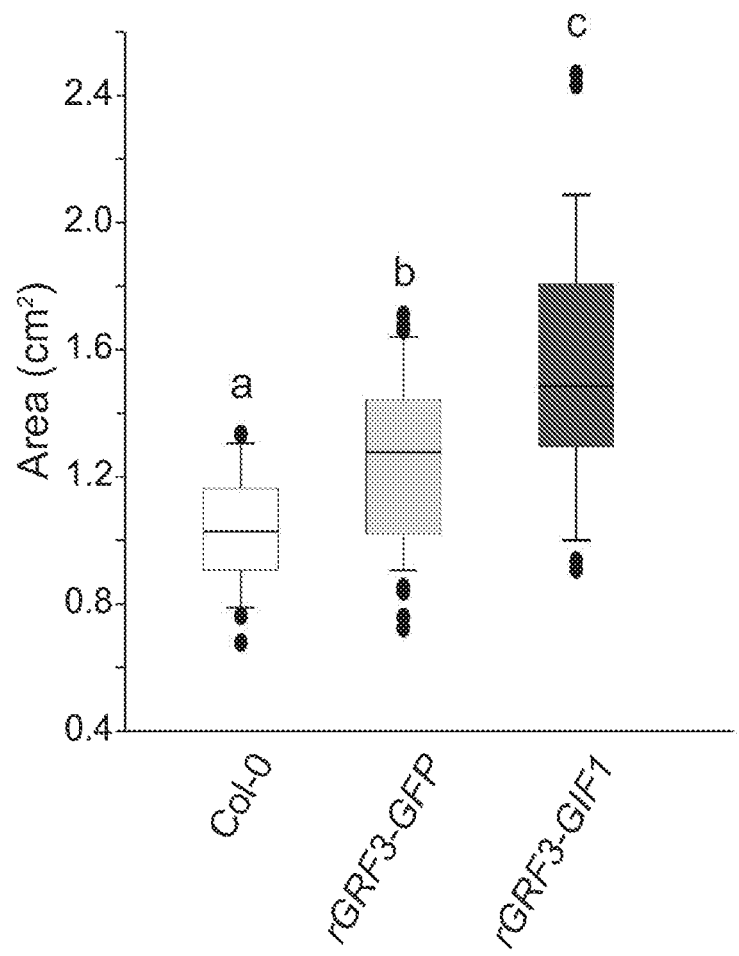
FIG. 4. Increase of rGRF3 activity and leaf area using rGRF3-GIF1 chimera, as described in Example 3. Average leaf size corresponding to pools of primary transgenic plants harboring different transgenes. Different letters mean statistically significant differences (p<0.05). At least 50 primary transgenic plants were analyzed in each case.
Figure 5:
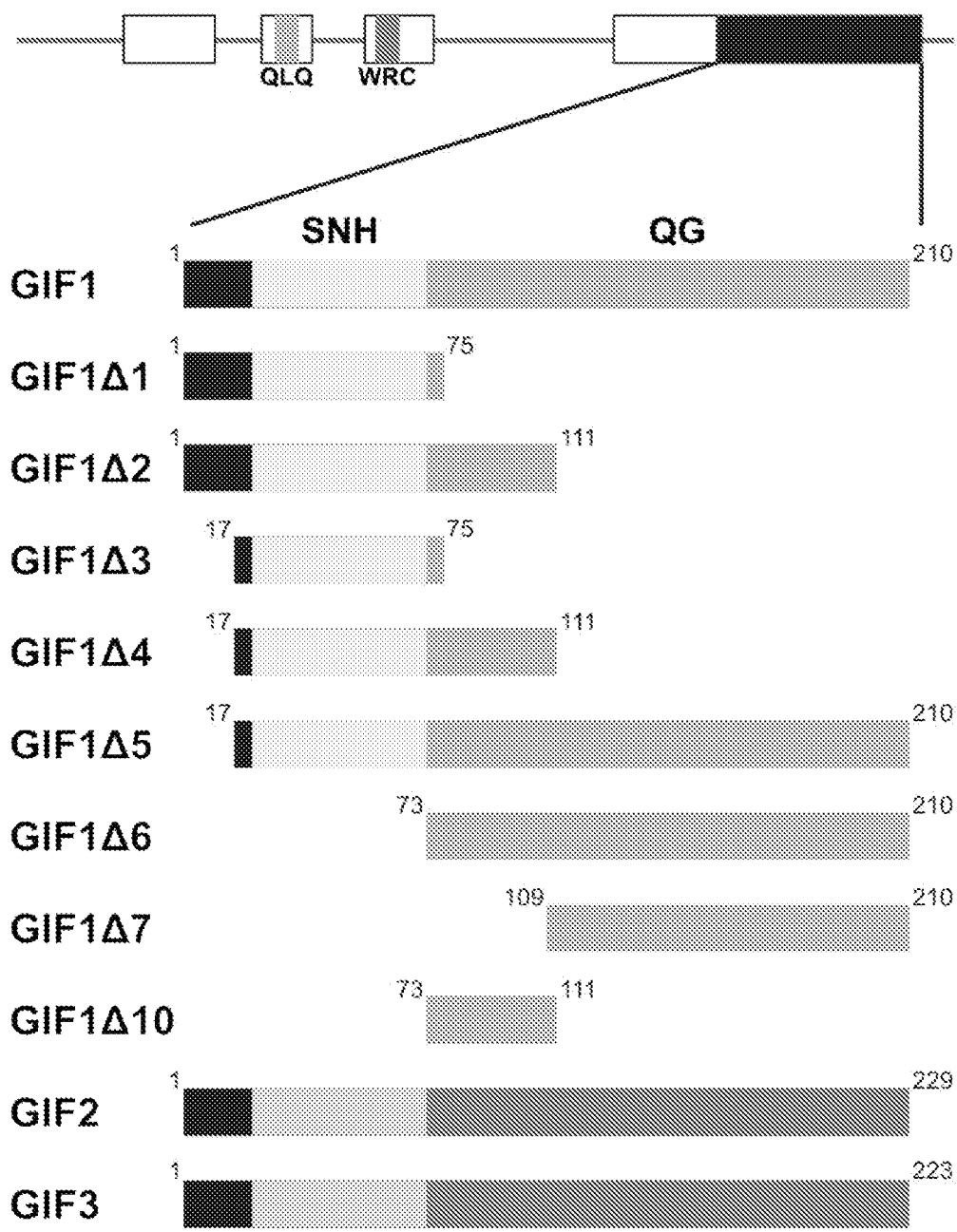
FIG. 5. Schematic representation GIF1 (with fragments GIF1Δ1-GIF1Δ7, and GIF1Δ10), GIF2 and GIF3. GIF1Δ1 corresponds to amino acid residue positions 1 to 75 of GIF1, GIF1Δ2 corresponds to amino acid residue positions 1 to 111 of GIF1, GIF1Δ3 corresponds to amino acid residue positions 17 to 75 of GIF1, GIF1Δ4 corresponds to amino acid residue positions 17 to 111 of GIF1, GIF1Δ5 corresponds to amino acid residue positions 17 to 210 of GIF1, GIF1Δ6 corresponds to amino acid residue positions 73 to 210 of GIF1, GIF1Δ7 corresponds to amino acid residue positions 109 to 210 of GIF1, and GIF1Δ10 corresponds to amino acid residue positions 73 to 111 of GIF1.
Figure 6:
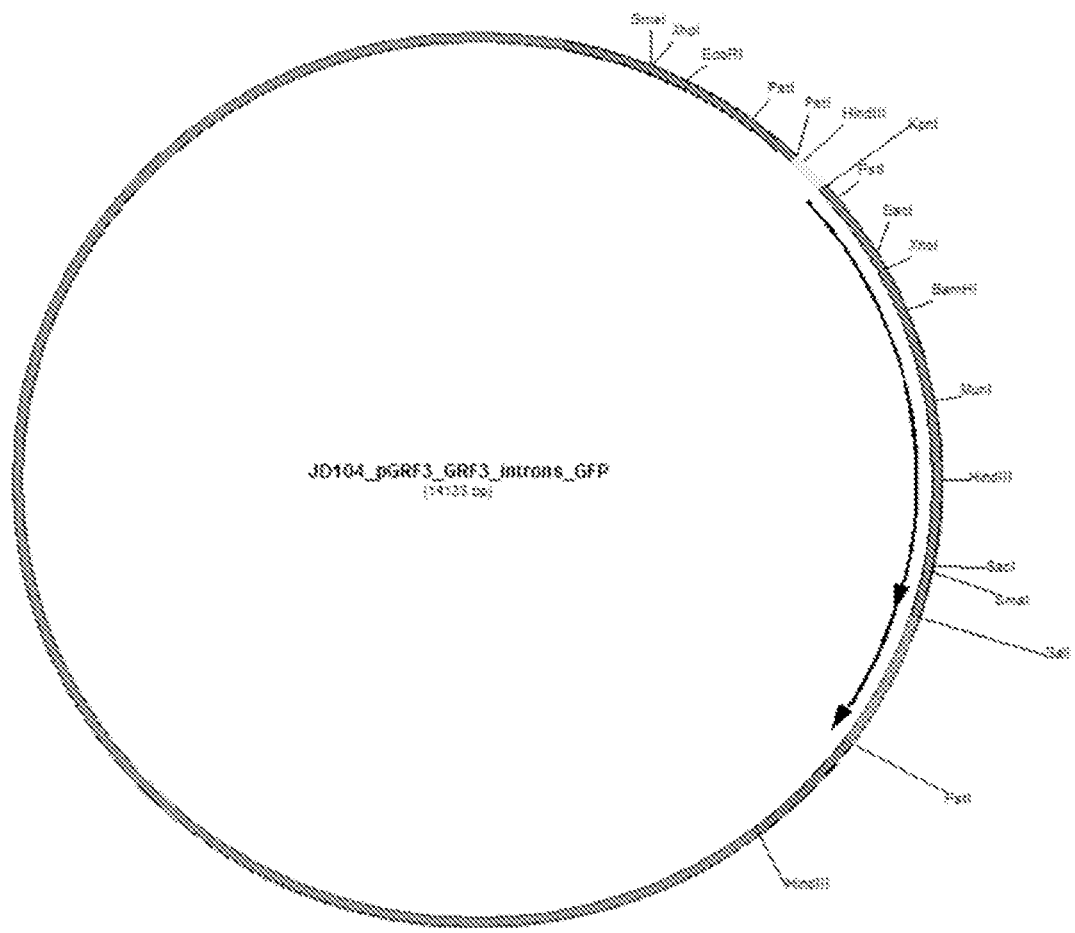
FIG. 6. Map of the binary vector pJD104 (SEQ ID NO.:14) for expression of chimeric protein GRF3-GPF.
Figure 7:
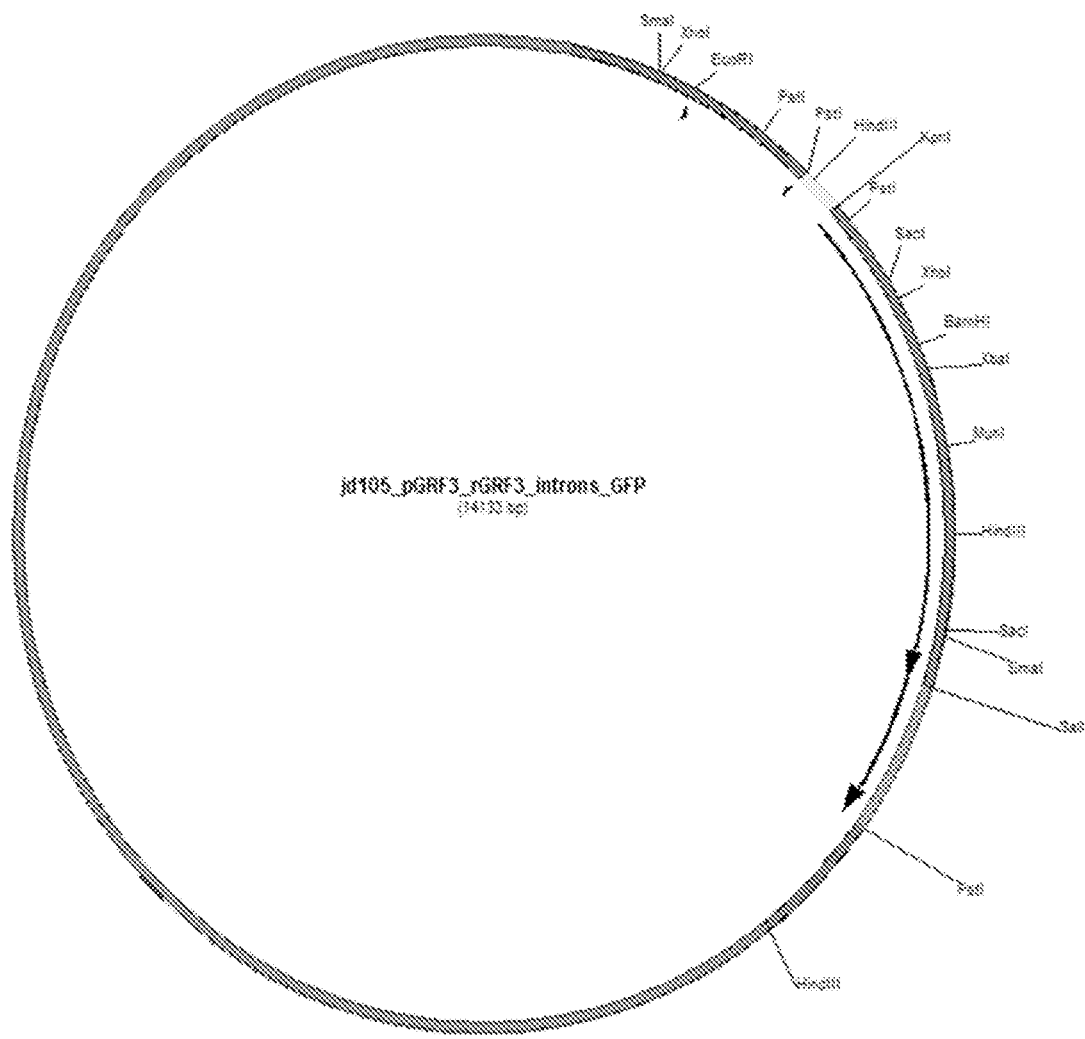
FIG. 7. Map of the binary vector pJD105 (SEQ ID NO.:17) for expression of chimeric protein rGRF3-GPF.
Figure 8:
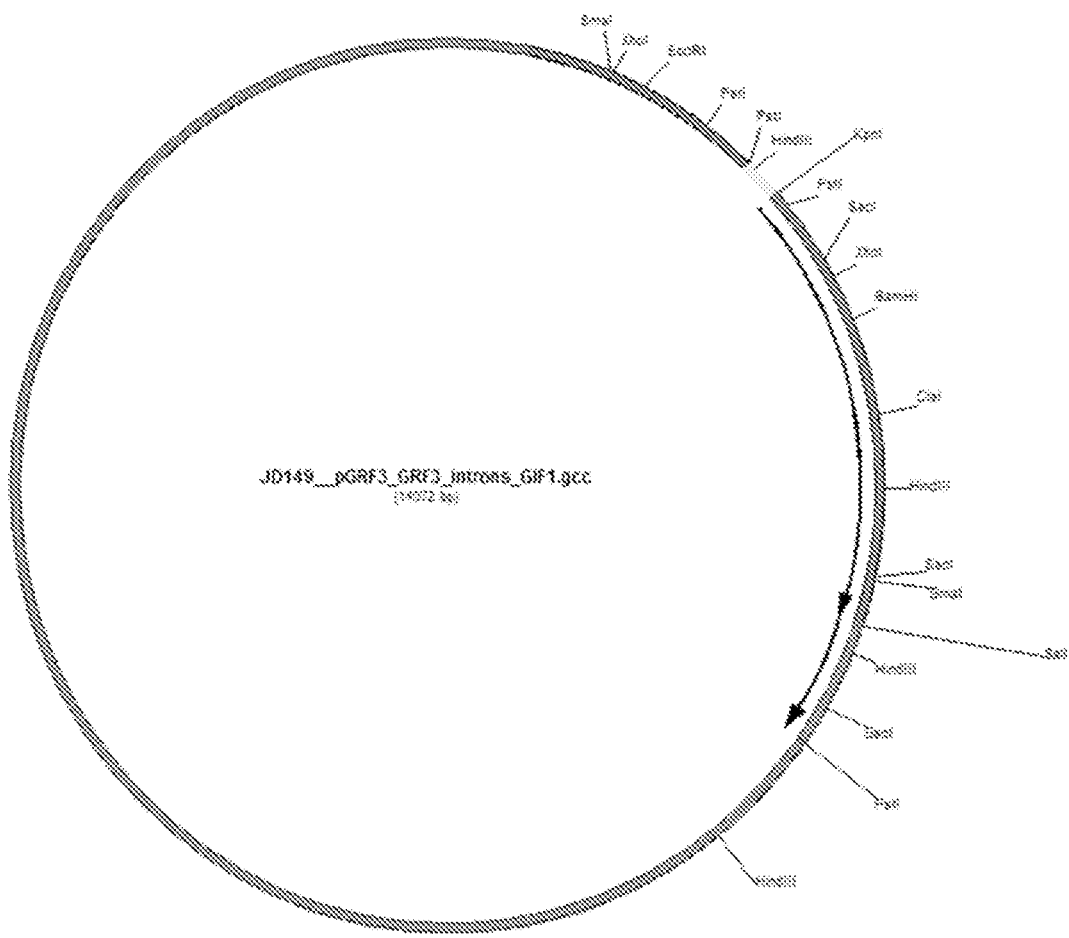
FIG. 8. Map of the binary vector pJD149 (SEQ ID NO.:20) for expression of chimeric protein GRF3-GIF1.
Figure 9:
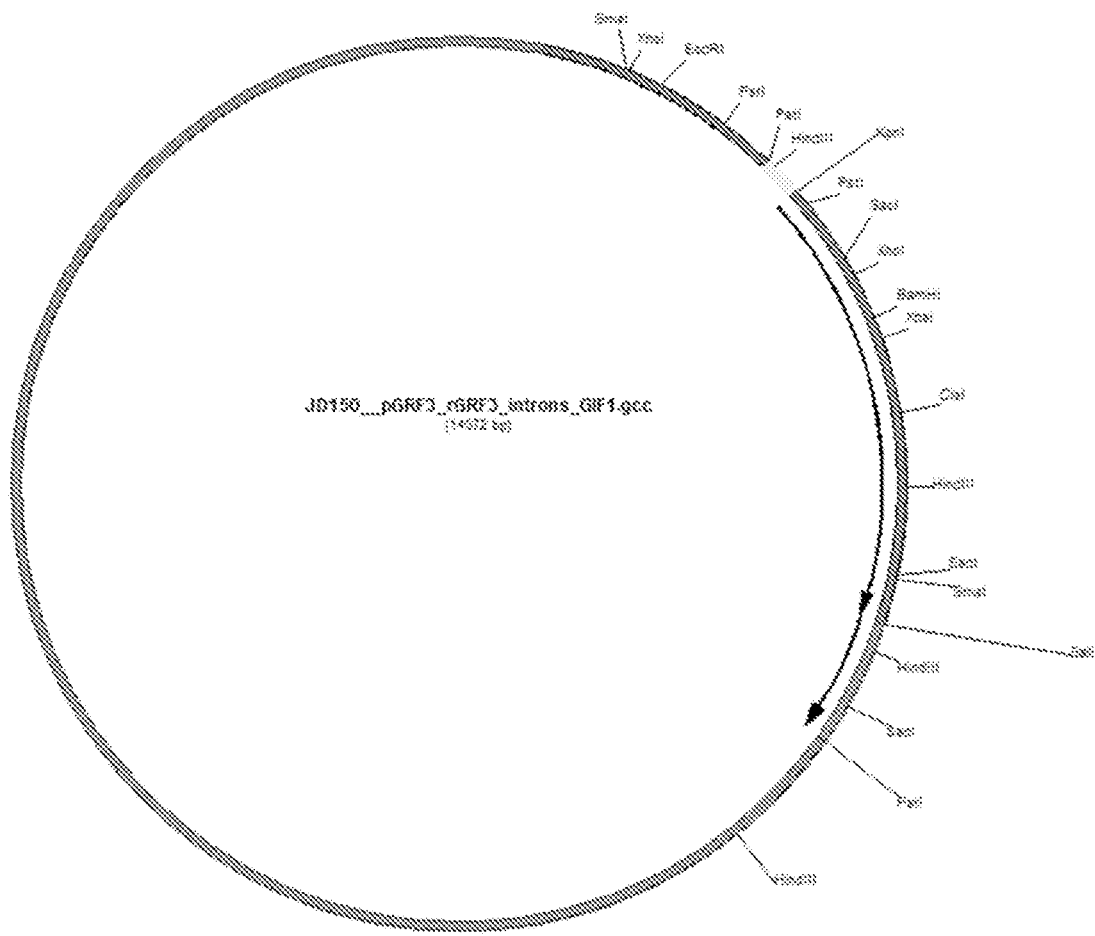
FIG. 9. Map of the binary vector pJD150 (SEQ ID NO.:23) for expression of chimeric protein rGRF3-GIF1.
Figure 10:
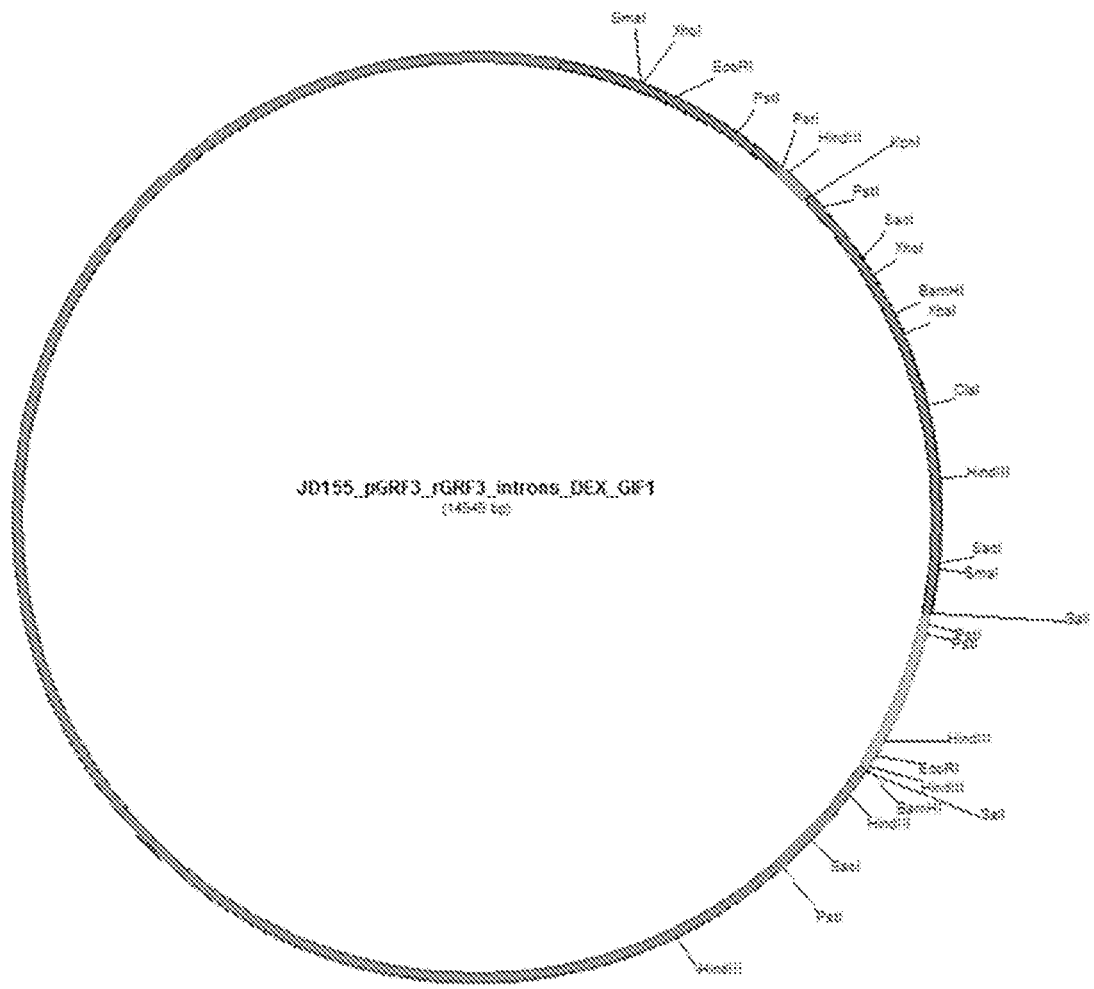
FIG. 10. Map of the binary vector pJD155 (SEQ ID NO.:26) for expression of chimeric protein rGRF3-GR-GIF1.

It was observed that the rGRF3-GFP transgene can increase the leaf area with respect to control plants (FIG. 4), in agreement with previous results (Patent Publication No. WO/2013/102762 A1). However, plants harboring the chimera rGRF3-GIF1 have even larger leaves than rGRF3-GFP (FIG. 4), showing that the chimera can add extra value to an already useful tool to increase plant biomass.

Materials and Methods:

Plant Material:

The *Arabidopsis thaliana* Col-0 accession was used as wild-type control. Plants were grown in long photoperiods (16 hr light/8 hr dark) at 23° C. The plants were grown in MS medium (Murashige and Skoog, 1962) supplemented with 50 µg/ml kanamycin and selected primary transformants were transferred to soil.

Bacterial Strains:

All constructs were cloned in the binary vector pCHF3 (Jarvis, Chen et al. 1998). Plant transformations were carried out using the *Agrobacterium tumefaciens* strain ASE harboring the appropriate binary pCHF3 plasmids containing the neomycin phosphotransferase (nptII) selectable marker gene driven by the 35S promoter and the gene(s) of interest, namely rGRF3-GFP and rGRF3-GIF1 driven by GRF3 native promoter and GIF1 driven by the 35S promoter.

The cloning procedure used to make the transformation vectors is described below. The binary vectors containing the GIF1 or the GFP coding sequences with a SalI restriction site in their 5"end previously described were used to introduce rGRF3 and GRF3 native promoter to generate the pGRF3:rGRF3-GPF and pGRF3:rGRF3-GIF1 fusions.

The miRNA target motif in GRF3 was altered introducing synonymous mutations in the cloned GRF3 wild type genomic fragment (pGEM-T-GRF3) using the QuikChange® Site Directed Mutagenesis Kit (Stratagene).

Digestion of ~1.5 µg pGEM-T-rGRF3 in a 50 µl total volume reaction with KpnI and SalI (Promega) in the appropriate buffer was performed at 37° C. for 4 hour in a water bath. Digestion of ~1.5 µg pGEM-T-pGRF3 in a 50 µl total volume reaction with MunI (Fermentas) and KpnI (Promega) in the appropriate buffer was performed at 37° C. for 4 hours in a water bath.

Approximately 1 µg of pCHF3-GIF1 or pCHF3-GPF was digested with restriction enzymes EcoRI and SalI (Promega) in the appropriate buffer for 4 hour at 37° C. The linearised vector was dephosphorylated by incubation at 37° C. for a further hour with shrimp alkaline phosphatase (SAP, Promega). The linearised vectors were purified with a PCR product purification kit (Promega).

An overnight ligation reaction was performed at 16° C. and contained the rGRF3 and the pGRF3 fragments and the linear pCHF3-GIF1 or pCHF3-GFP vectors at a 3:3:1 ratio respectively. One unit of T4 ligase (Fermentas) was used in the 10 µl ligation. To 50 µl of DH5α competent *E. coli* cells 2 µl of the ligation reaction was added and transformation was carried out by electroporation. The cells were grown in 900 µl of LB medium for 1 hour at 37° C. and shaken at 200 rpm. The cells were centrifuged at 4000 g for 3 minutes, and the cell pellet was spread onto plates of solid LB medium (Sambrook and Russell, 2001) containing appropriate selection and incubated overnight at 37° C.

*E. coli* colonies were screened by direct colony PCR to ensure that they contained pCHF3-pGRF3:rGRF3-GIF1 or pCHF3-pGRF3:rGRF3-GFP. Two PCR positive single colonies were transferred to 10 ml of liquid LB media containing the appropriate selection and incubated at 37° C. shaken 220 rpm overnight. Plasmid DNA was isolated using a mini-prep kit (Promega). The integrity of the constructs pCHF3-pGRF3:rGRF3-GIF1 and pCHF3-pGRF3:rGRF3-GFP was confirmed by enzyme digestion and sequencing of the insertion sites.

The plasmids pCHF3-pGRF3:rGRF3-GIF1 or pCHF3-pGRF3:rGRF3-GFP were transformed into *Agrobacterium tumefaciens* strain ASE by electroporation. Briefly, 100 ng of plasmid DNA were added to 40 µl of electro-competent *A. tumefaciens* cells in a pre-chilled electroporation cuvette with 2 mm electrode separation. The cells were electroporated in a GenePulser (Biorad) with the following settings 2.50 kV, 25 µFD and 400 Ohms. Immediately 900 µl of liquid LB medium was added to recover the cells, these were grown at 28° C., shaken at 180 rpm for 2 hours. The *A. tumefaciens* cultures were spread onto solid LB medium (Sambrook and Russell, 2001) containing appropriate selection and incubated at 28° C. for 48 hours. Single colonies were selected and used to inoculate 10 ml of liquid LB media containing the appropriate antibiotics and incubated at 28° C., shaken at 200 rpm for 48 hours. Glycerol stocks and standard inoculums were prepared and stored at −80° C. The plasmids were checked once again, by enzyme digestion, prior to embarking on the *Arabidopsis* transformation experiments.

Plant Transformation:

*Arabidopsis* transgenic plants were obtained by floral-dip. The *A. tumefaciens* transformed with the pCHF3-pGRF3:rGRF3-GIF1, pCHF3-pGRF3:rGRF3-GFP or pCHF3-GIF1 vectors were streaked onto solid LB medium (Sambrook and Russell, 2001) containing appropriate selection and incubated at 28° C. for 48 hours. A single colony was transferred to 10 ml of liquid LB media containing the appropriate selection and transferred to a 28° C. shaker for 48 hours. A 1 ml aliquot of the resulting bacterial suspension was transferred to 100 ml of LB liquid medium with selection and grown over night in a 28° C. shaker. Overnight cultures were spun down at 3,000 g for 5 minutes at R.T. before being resuspended in 100 ml transformation medium (5% sucrose, 0.02% Silwett). Inflorescences from 35 days old plants were dipped into the suspension of *Agrobacterium* and plants were maintained overnight in darkness. Then plants were maintained in growth rooms at 23° C. with 16 hour day length. Plants were threshed when dry, and seed stored.

Transgenic Selection and Phenotypic Analysis:

Seeds were surface sterilized in 70% ethanol plus 0.05% Tween-20 for 15 minutes and rinsed once in 96% ethanol. Seeds were sown in MS medium (Murashige and Skoog, 1962) supplemented with 50 µg/ml kanamycin to select the primary transformants. Plants were grown in long photoperiods (16 hr light/8 hr dark) at 23° C. for 6 days, after that selected primary transgenic were transferred to soil and maintained under the same conditions of light and temperature. Leaf area was measured by first taking a photograph of detached fully expanded third leaves from 35 days old plants, and then measuring the foliar area with the NIH software ImageJ. For this analysis, leaves from at least 50 independent primary transgenic plants were collected for each vector.

Conclusions:

rGRF3-GFP increases biomass accumulation but the chimera rGRF3-GIF1 is even more efficient causing a larger effect.

Chimeras containing a GIF moiety can be used to enhance the activity of an existing tool to increase plant biomass.

Chimeras containing a GIF moiety can be used to enhance the activity of modified transcription factors, or synthetically generated transcription factors.

| Vector name | Construction | Chromoson: start-end | Binary vector |
|---|---|---|---|
| pJD104 | GRF3:GRF3-GPF | [GRF3:GRF3, 2: 15274101-15270302]-GFP CDS<br>CGC AAC CGT TCA AGA AAG CCT GTG GAA ACT CCA<br>R   N   R   S   R   K   P   V   E   T   F | pCHF3 |
| pJD105 | GRF3:rGRF3-GPF | [GRF3:rGRF3, 2: 15274101-15270302]-GFP CDS<br>CGC AAC CGT TC<u>T</u> AGA AA<u>A</u> CC<u>A</u> GT<u>A</u> GA<u>G</u> ACT CCA<br>R   N   R   S   R   K   P   V   E   T   F | pCHF3 |
| pJD149 | GRF3:GRF3-GIF1 | [GRF3:GRF3, 2: 15274101-15270302]-GIF1 CDS | pCHF3 |
| pJD150 | GRF3:rGRF3-GIF1 | [GRF3:rGRF3, 2: 15274101-15270302]<br>(mutations like JD105)-GIF1 CDS | pCHF3 |

| Vector name | Construction | Chromoson: start-end | Binary vector |
|---|---|---|---|
| pJD155 | GRF3:rGRF3-GRGIF1 | [GRF3:rGRF3, 2: 15274101-15270302]-GR CDS-GIF1 CDS | pCHF3 |
| pJD220 | 35S:STM-GFP | STM CDS-GFP CDS | pCHF3 |
| pJD221 | 35S:STM-GIF1 | STM CDS-GIF1 CDS | pCHF3 |
| pJD222 | 35S:TCP2-GIF1 | TCP2 CDS-GIF1 CDS | pCHF3 |

BIBLIOGRAPHY

Century, K., T. L. Reuber, et al. (2008). "Regulating the regulators: the future prospects for transcription-factor-based agricultural biotechnology products." *Plant Physiol* 147(1): 20-29.

Debernardi, J. M., M. A. Mecchia, et al. (2014). "Post-transcriptional control of GRF transcription factors by microRNA miR396 and GIF co-activator affects leaf size and longevity." *Plant J.*

Debernardi, J. M., R. E. Rodriguez, et al. (2012). "Functional specialization of the plant miR396 regulatory network through distinct microRNA-target interactions." *PLoS Genet* 8(1): e1002419.

Devereux et al. 1984. A comprehensive set of sequence analysis programs for the vax. *Nucl. Acid. Res.* 12, 387-395.

Doebley, J., A. Stec, et al. (1997). "The evolution of apical dominance in maize." *Nature* 386(6624): 485-488.

Gonzalez, N., G. T. Beemster, et al. (2009). "David and Goliath: what can the tiny weed *Arabidopsis* teach us to improve biomass production in crops?" *Curr Opin Plant Biol* 12(2): 157-164.

Gonzalez, N., S. De Bodt, et al. (2010). "Increased leaf size: different means to an end." *Plant Physiol* 153(3): 1261-1279.

Gribskov, M. & Burgess, R. R. Sigma factors from *E. coli, B. subtilis*, phage SPO1 and phage T4 are homologous proteins. *Nucl. Acids Res.* 14, 6745-6763 (1986).

Hake, S., H. M. Smith, et al. (2004). "The role of knox genes in plant development." *Annu Rev Cell Dev Biol* 20: 125-151.

Horiguchi, G., G. T. Kim, et al. (2005). "The transcription factor AtGRF5 and the transcription coactivator AN3 regulate cell proliferation in leaf primordia of *Arabidopsis thaliana*." *Plant J* 43(1): 68-78.

Ikeda, M., K. Miura, et al. (2013). "Genes offering the potential for designing yield-related traits in rice." *Curr Opin Plant Biol* 16(2): 213-220.

Jarvis, P., L. J. Chen, et al. (1998). "An *Arabidopsis* mutant defective in the plastid general protein import apparatus." *Science* 282(5386): 100-103.

Jirschitzka, J., D. J. Mattern, et al. (2013). "Learning from nature: new approaches to the metabolic engineering of plant defense pathways." *Curr Opin Biotechnol* 24(2): 320-328.

Kim, J. H., D. Choi, et al. (2003). "The AtGRF family of putative transcription factors is involved in leaf and cotyledon growth in *Arabidopsis*." *Plant J* 36(1): 94-104.

Kim, J. H. and H. Kende (2004). "A transcriptional coactivator, AtGIF1, is involved in regulating leaf growth and morphology in *Arabidopsis*." *Proc Natl Acad Sci USA* 101(36): 13374-13379.

Kim, J. H. and B. H. Lee (2006). "GROWTH-REGULATING FACTOR4 of *Arabidopsis thaliana* is required for development of leaves, cotyledons, and shoot apical meristem." *Journal of Plant Biology* 49(6): 463-468.

Kim, J. S., J. Mizoi, et al. (2012). "*Arabidopsis* growth-regulating factor7 functions as a transcriptional repressor of abscisic acid- and osmotic stress-responsive genes, including DREB2A." *Plant Cell* 24(8): 3393-3405.

Kosugi, S. and Y. Ohashi (1997). "PCF1 and PGF2 specifically bind to cis elements in the rice proliferating cell nuclear antigen gene." *Plant Cell* 9(9): 1607-1619.

Lee, B. H., J. H. Ko, et al. (2009). "The *Arabidopsis* GRF-INTERACTING FACTOR Gene Family Performs an Overlapping Function in Determining Organ Size as well as Multiple Developmental Properties." *Plant Physiol*.

Liu, D., Y. Song, et al. (2009). "Ectopic expression of miR396 suppresses GRF target gene expression and alters leaf growth in *Arabidopsis*." *Physiol Plant* 136(2): 223-236.

Luo, D., R. Carpenter, et al. (1996). "Origin of floral asymmetry in *Antirrhinum*." *Nature* 383(6603): 794-799.

Murashige T and Skoog F (1962) A revised medium for rapid growth and bio-assays with tobacco tissue cultures. *Physiol Plant* 15(3): 473-497.

Needleman, S. B, and Wunsch, C. D. (1970). A general method applicable to the search for similarities in the amino acid sequence of two proteins. *J. Mol. Biol.* 48:443-53.

Palatnik, J. F., E. Allen, et al. (2003). "Control of leaf morphogenesis by microRNAs." *Nature* 425(6955): 257-263.

Pulido, A. and P. Laufs (2010). "Co-ordination of developmental processes by small RNAs during leaf development." *J Exp Bot* 61(5): 1277-1291.

Rodriguez, R. E., M. A. Mecchia, et al. (2010). "Control of cell proliferation in *Arabidopsis thaliana* by microRNA miR396." *Development* 137(1): 103-112.

Rubio-Somoza, I. and D. Weigel (2011). "MicroRNA networks and developmental plasticity in plants." *Trends Plant Sci* 16(5): 258-264.

Sambrook, J and Russell, D. W. 2001. Molecular Cloning: A Laboratory Manual. Cold Spring Harbour Laboratory Press, Cold Spring Harbour, N.Y.

Schwartz, R. M. and Dayhoff, M. in *Atlas of Protein Sequence and Structure*, Dayhoff, M. (Ed.) *National Biomedical Research Foundation,* 1979. pp. 353-358.

Smith, T. and Waterman, M. (1981), Comparison of biosequences. Advances in Applied Mathematics 2 (1981), p 482-489

Tsiantis, M. and A. Hay (2003). "Comparative plant development: the time of the leaf?" *Nat Rev Genet* 4(3): 169-180.

Van Camp, W. (2005). "Yield enhancement genes: seeds for growth." *Curr Opin Biotechnol* 16(2): 147-153.

van der Knaap, E., J. H. Kim, et al. (2000). "A novel gibberellin-induced gene from rice and its potential regulatory role in stem growth." *Plant Physiol* 122(3): 695-704.

Vercruyssen, L., A. Verkest, et al. (2014). "ANGUSTIFOLIA3 binds to SWI/SNF chromatin remodeling complexes to regulate transcription during *Arabidopsis* leaf development." *Plant Cell* 26(1): 210-229.

Wang, L., X. Gu, et al. (2011). "miR396-targeted AtGRF transcription factors are required for coordination of cell division and differentiation during leaf development in *Arabidopsis.*" *J Exp Bot* 62(2): 761-773.

---

The invention claimed is:

1. A method of enhancing the activity of a transcription factor in a plant, the method comprising expressing in said plant a chimeric protein comprising a GIF1 protein of SEQ ID NO:1 fused to the transcription factor, wherein the chimeric protein has an amino acid sequence selected from the group consisting of SEQ ID NO: 18, SEQ ID NO: 21, SEQ ID NO: 24, SEQ ID NO: 30, and SEQ ID NO: 33, or a sequence having at least 85% sequence identity to SEQ ID NO: 18, SEQ ID NO: 21, SEQ ID NO: 24, SEQ ID NO: 30, or SEQ ID NO: 33 wherein the transcription factor is selected from the group consisting of Growth Regulating Factor 3 (GFR3), GRF3 transgene insensitive to the regulation by microRNA miR396 (rGRF3), SHOOT MERISTEMLESS (STM), and TCP2, being TCP: TEOSINTE BRANCHED1 from *Zea mays*, CYCLOIDEA from *Antirrhinum majus*, and PCF 1 and 2 from *Oryza sativa* 2;

and wherein the enhanced activity of the transcription factor is relative to the activity of the transcription factor not fused to GIF1.

* * * * *